(12) United States Patent
Mikoshiba et al.

(10) Patent No.: US 8,937,091 B2
(45) Date of Patent: Jan. 20, 2015

(54) INHIBITOR OF PROTEIN CROSSLINKING AND USE OF THE SAME

(75) Inventors: Katsuhiko Mikoshiba, Saitama (JP); Kozo Hamada, Saitama (JP); Akiko Terauchi, Saitama (JP); Shouichirou Ozaki, Saitama (JP); Jun-ichi Goto, Saitama (JP); Etsuko Ebisui, Saitama (JP); Akinobu Suzuki, Saitama (JP)

(73) Assignee: Japan Science and Technology Agency, Saitama (JP)

( * ) Notice: Subject to any disclaimer, the term of this patent is extended or adjusted under 35 U.S.C. 154(b) by 109 days.

(21) Appl. No.: 13/508,247

(22) PCT Filed: May 19, 2010

(86) PCT No.: PCT/JP2010/058411
§ 371 (c)(1),
(2), (4) Date: Jul. 20, 2012

(87) PCT Pub. No.: WO2011/055561
PCT Pub. Date: May 12, 2011

(65) Prior Publication Data
US 2012/0277423 A1 Nov. 1, 2012

(30) Foreign Application Priority Data
Nov. 6, 2009 (JP) ................................. 2009-255518

(51) Int. Cl.
| | | |
|---|---|---|
| A61K 31/45 | (2006.01) |
| C07D 295/10 | (2006.01) |
| A61K 31/045 | (2006.01) |
| A61K 31/085 | (2006.01) |
| A61K 31/12 | (2006.01) |
| A61K 31/136 | (2006.01) |
| A61K 31/137 | (2006.01) |
| A61K 31/216 | (2006.01) |
| A61K 31/341 | (2006.01) |
| A61K 31/36 | (2006.01) |

(Continued)

(52) U.S. Cl.
CPC ............. *A61K 31/045* (2013.01); *A61K 31/085* (2013.01); *A61K 31/12* (2013.01); *A61K 31/136* (2013.01); *A61K 31/137* (2013.01); *A61K 31/216* (2013.01); *A61K 31/341* (2013.01); *A61K 31/36* (2013.01); *A61K 31/381* (2013.01); *A61K 31/40* (2013.01); *A61K 31/417* (2013.01); *A61K 31/426* (2013.01); *A61K 31/4402* (2013.01); *A61K 31/4406* (2013.01); *A61K 31/4409* (2013.01); *A61K 31/4439* (2013.01); *A61K 31/444* (2013.01); *A61K 31/4453* (2013.01); *A61K 31/4545* (2013.01); *A61K 31/496* (2013.01); *A61K 31/4965* (2013.01); *A61K 31/5375* (2013.01); *A61K 31/55* (2013.01)

USPC ............ 514/354; 514/355; 546/314; 546/315

(58) Field of Classification Search
USPC ......................... 546/314, 315; 514/354, 355
See application file for complete search history.

(56) References Cited

U.S. PATENT DOCUMENTS 3,859,305 A * 1/1975 Posselt et al. ................ 548/493
3,862,953 A * 1/1975 Berger et al. ............. 546/276.7

(Continued)

FOREIGN PATENT DOCUMENTS

EP    0 399 504 A2    4/1990
JP    54-066640       5/1979

(Continued)

OTHER PUBLICATIONS

Giomi et al. (Tetrahedron (2009), 65(34), 7048-7055).*

(Continued)

*Primary Examiner* — Bruck Kifle
(74) *Attorney, Agent, or Firm* — Foley & Lardner LLP

(57) ABSTRACT

The present invention relates to: a ketone compound having transglutaminase-inhibiting activity, which is represented by the following Formula 1, 2, or 3:

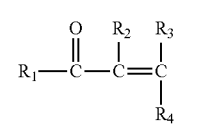

1

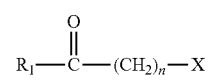

2

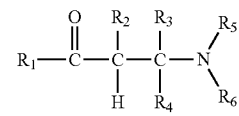

3 wherein $R_1$ is a substituted or unsubstituted aryl or heterocyclyl group, $R_2$, $R_3$, and $R_4$ are hydrogen atoms, n is 2, X is halogen, $R_5$ and $R_6$ independently represent a hydrogen atom or a substituted or unsubstituted C1-C10 alkyl, aryl, or aralkyl group, wherein $R_5$ and $R_6$ are not hydrogen atoms at the same time, or $R_5$ and $R_6$ may be taken together to form a saturated or unsaturated and substituted or unsubstituted heterocyclyl group containing a nitrogen atom (N); an inhibitor of protein crosslinking comprising the compound; and a composition for preventing or treating a protein-crosslinking causative disease, which comprises the compound or the protein crosslinking inhibitor.

3 Claims, No Drawings

(51) Int. Cl.

| | |
|---|---|
| A61K 31/381 | (2006.01) |
| A61K 31/40 | (2006.01) |
| A61K 31/417 | (2006.01) |
| A61K 31/426 | (2006.01) |
| A61K 31/4402 | (2006.01) |
| A61K 31/4406 | (2006.01) |
| A61K 31/4409 | (2006.01) |
| A61K 31/4439 | (2006.01) |
| A61K 31/444 | (2006.01) |
| A61K 31/4453 | (2006.01) |
| A61K 31/4545 | (2006.01) |
| A61K 31/496 | (2006.01) |
| A61K 31/4965 | (2006.01) |
| A61K 31/5375 | (2006.01) |
| A61K 31/55 | (2006.01) |

(56) References Cited

U.S. PATENT DOCUMENTS

| | | |
|---|---|---|
| 4,695,652 A | 9/1987 | Seng et al. |
| 2004/0105875 A1 | 6/2004 | Boulle et al. |
| 2008/0227775 A1 | 9/2008 | Andries et al. |
| 2008/0249095 A1 | 10/2008 | Dorsch et al. |
| 2008/0255116 A1 | 10/2008 | Andries et al. |

FOREIGN PATENT DOCUMENTS

| | | |
|---|---|---|
| JP | 61-91158 | 5/1986 |
| JP | 3-17046 | 1/1991 |
| JP | 5-194236 | 8/1993 |
| JP | 07-291886 A | 11/1995 |
| JP | 09-255726 | 9/1997 |
| JP | 2001-120297 A | 5/2001 |
| JP | 2004-269499 | 9/2004 |
| JP | 2009-503021 | 1/2009 |
| JP | 2009/503024 | 1/2009 |
| JP | 2009-504694 | 2/2009 |
| WO | WO 01/07431 A2 | 2/2001 |
| WO | WO 2008/144933 A1 | 12/2008 |

OTHER PUBLICATIONS

Kano et al. (Chemical & Pharmaceutical Bulletin (1979), 27(10), 2450-5). Abstract.*

JP2009-255518 Japanese Patent Office, Office Action dated Dec. 18, 2012.

International Search Report PCT/JP2010/058411 dated Jun. 22, 2010.

Litina D. Hadjipavlou et al., "Antiinflammatory Activity of Aminoketone Derivatives of 2,4-Disubstituted Thiazoles", Research Communications in Chemical Pathology and Pharmacology, vol. 79, No. 3, Mar. 1993, pp. 355-362.

Dimitra J. Hadjipavlou-Litina et al., "Effect of 2,4-Disubstituted Thiazol-5YL-Aminoketones on Inflammation. In Vitro and In Vivo Biological Studies: A Structure-Activity Approach", Research Communications in Molecular Pathology and Pharmacology, vol. 96, No. 3, Jun. 1997, pp. 307-318.

Shoichiro Ozaki et al., "Potent transglutaminase inhibitors, aryl β-aminoethyl ketones", Bioorganic and Medicinal Chemistry Letters 20 (2010) 1141-1144.

Thung-S Lai et al., "Identification of Chemical Inhibitors to Human Tissue Transglutaminase by Screening Existing Drug Libraries", Chemistry and Biology 15, 969-978, Sep. 22, 2008.

Florence Chung et al., "Design of tRNA$^{Lys}_3$ Ligands: Fragment Evolution and Linker Selection Guided by NMR Spectroscopy", J. Chem. Eur. 2009, 15, 7109-7116.

* cited by examiner

US 8,937,091 B2

INHIBITOR OF PROTEIN CROSSLINKING AND USE OF THE SAME

TECHNICAL FIELD

The present invention relates to a compound having transglutaminase-inhibiting activity or an inhibitor of protein crosslinking and to the use of the same.

More specifically, the present invention relates to a compound having transglutaminase-inhibiting activity, which is a ketone or alcohol, especially a ketone, having a particular structure, to an inhibitor of protein crosslinking and/or an intracellular calcium modulator, and to a composition for preventing or treating protein-crosslinking causative diseases such as Alzheimer's disease, Huntington's disease, Parkinson's disease, Celiac disease, cataract, mad cow disease, congenital lamellar ichthyosis, congenital hemostatic disorder, liver disorder, autoimmune disease, and cerebral infarction.

BACKGROUND ART

Calcium is well known to play various and important roles in living organisms and cells. In the past, the present inventors discovered that 2-APB (2-aminoethyl diphenyl borinate) acts to modulate the intracellular calcium concentration (Non-Patent Literature 1), and then synthesized about 500 different boron compounds analogous to 2-APB and examined calcium concentration modulating activities of these compounds (Patent Literatures 1 to 4). As a result, it was revealed that these compounds function to modulate an intracellular calcium concentration associated with SOCE (store operated calcium entry) or IICR (IP3 induced calcium release). In addition, it was found that some of the compounds have transglutaminase-inhibiting activities, in addition to the above-mentioned activities.

It has been revealed that abnormal crosslinking reactions of certain proteins cause intractable diseases such as Alzheimer's disease, Huntington's disease, Parkinson's disease, Celiac disease, cataract, mad cow disease, congenital lamellar ichthyosis, and congenital hemostatic disorder (Non-Patent Literatures 2 to 4). In particular, an enzyme that is thought to be involved in abnormal protein crosslinking reactions is transglutaminase.

Transglutaminase is an enzyme that is activated in the presence of calcium. Recently, it has been known that transglutaminase is involved in the development of neurological diseases such as Alzheimer's disease, Parkinson's disease, and Huntington's disease. Thus, transglutaminase inhibitors are thought to be effective drugs for treatment of such diseases (Non-Patent Literatures 5 and 6).

The main reaction of the abnormal protein crosslinking is a reaction in which isopeptide bonds are formed from the amide group of glutamine and the amino group of lysine of a protein through deammoniation. The mechanism revealing that inhibitors of the enzyme capable of inducing such reaction (i.e., transglutaminase) would be effective for treatment of the aforementioned diseases or the like has been clarified (Non-Patent Literature 7). Based on these findings, there are increasing researches to develop transglutaminase inhibitors as therapeutic drugs for diseases such as Alzheimer's disease, Huntington's disease, Parkinson's disease, Celiac disease, cataract, mad cow disease, congenital lamellar ichthyosis, congenital hemostatic disorder, liver disorder, autoimmune disease, and cerebral infarction (Non-Patent Literatures 8 to 13).

CITATION LIST

Patent Literatures

Patent Literature 1: WO 03/033002
Patent Literature 2: WO 2007/061074
Patent Literature 3: JP Patent Publication (Kokai) No. 2009-184988 A
Patent Literature 4: JP Patent Publication (Kokai) No. 2007-169272 A

Non-Patent Literatures

Non-Patent Literature 1: Mikoshiba et al., J. Biochem., 1997, 122:498-505
Non-Patent Literature 2: Hartley M D et al., Transglutaminase induces protofibril-like amyloid β-protein assemblies that are protease-resistant and inhibit long-term potentiation, J. Biol. Chem., 2008, 283:16790-16800
Non-Patent Literature 3: Thomas M J et al., Increased levels of γ-glutamylamines in Huntington disease CSF, J. Neurochemistry, 2008 Apr. 1, 106 (1): 7-44
Non-Patent Literature 4: Kim S Y et al., Transglutaminases in disease. Neurochem Int., 2002 January, 40 (1): 85-103
Non-Patent Literature 5: Hoffner G and Djian P, Transglutaminase and diseases of the central nervous system, Front Biosci., 2005 Sep. 1, 10: 3078-3092
Non-Patent Literature 6: Duval E et al., Structure-activity relationship study of novel tissue transglutaminase inhibitors., Bioorg Med Chem. Lett., 2005 Apr. 1, 15 (7): 1885-1889
Non-Patent Literature 7: Mastroberardino P G, et al., Tissue transglutaminase ablation reduce neuronal death and prolongs survival in a mouse model of Huntington's disease, Cell Death Differ., 2002 September, 9 (9): 873-880
Non-Patent Literature 8: Lorand L, Neurodegenerative diseases and transglutaminase, Proc Natl Acad Sci U.S.A., 1996 Dec. 10, 93 (25): 14310-14313
Non-Patent Literature 9: Grierson A J, et al., Three different human tau isoforms and rat neurofilament light, middle and heavy chain proteins are cellular substrates for transglutaminase, Neurosci Lett., 2001 January 26, 298 (1): 9-12
Non-Patent Literature 10: Watts R E, et al., Structure-activity relationship analysis of the selective inhibition of transglutaminase 2 by dihydroisoxazoles, J Med. Chem., 2006 Dec. 14, 49 (25): 7493-7501
Non-Patent Literature 11: Karpuj M V et al., Prolonged survival and decreased abnormal movements in transgenic model of Huntington disease, with administration of the transglutaminase inhibitor cystamine, Nat. Med., 2002 February, 8 (2): 143-149
Non-Patent Literature 12: Thung G L et al., Identification of Chemical Inhibitors to Human Tissue Transglutaminase by Screening Existing Drug Libraries Chemistry & Biology 2008 Sep. 22, 15: 969-978
Non-Patent Literature 13: Tatsukawa H et al., Transglutaminase Cross-links SP1-mediated transcriptional to ethanol-induce liver injury, Gastroenterology 2009. 136 (5): 1783-1795

SUMMARY OF INVENTION

Problem to be Solved by Invention

An object of the present invention is to produce compounds having the action of modulating an intracellular calcium concentration, modulators of transglutaminase activity, and compounds capable of modulating a protein crosslinking reaction. Another object of the present invention is to develop drugs for preventing and/or treating diseases caused by abnormal protein crosslinking.

Means for Solving Problem

In order to achieve the above-mentioned objects, the present inventors attempted to find compounds having the above-mentioned action other than boron compounds previously developed by the present inventors. As a result, the present inventors have now found that ketone compounds having particular structures have the action significantly superior to the boron compounds. This led to the completion of the present invention. It was revealed that such ketone compounds have transglutaminase-inhibiting activities, and that they include compounds that substantially do not inhibit SOCE but strongly inhibit IICR, and compounds inhibiting IICR more strongly than SOCE.

The present invention has the features as described below.

In a first aspect, the present invention provides a ketone compound having transglutaminase-inhibiting activity, which is represented by Formula (1), (2), or (3):

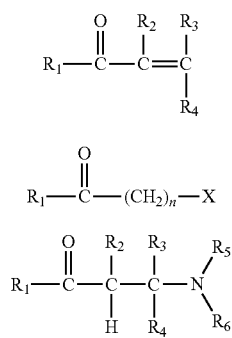

wherein $R_1$ is a substituted or unsubstituted aryl or heterocyclyl group, $R_2$, $R_3$, and $R_4$ are hydrogen atoms, n is 2, X is halogen, $R_5$ and $R_6$ independently represent a hydrogen atom or a substituted or unsubstituted C1-C10 alkyl, aryl, or aralkyl group, wherein $R_5$ and $R_6$ are not hydrogen atoms at the same time, or $R_5$ and $R_6$ may be taken together to form a saturated or unsaturated and substituted or unsubstituted heterocyclyl group containing a nitrogen atom (N).

In one embodiment of the present invention, $R_1$ is a substituted or unsubstituted phenyl, naphthyl, fluorenyl, benzothienyl, pyridyl, pyrazinyl, furyl, thienyl, pyrrolyl, thiazolyl, ferrocenyl, morpholino, or 6- to 7-membered cyclic lactam group.

In another embodiment of the present invention, $R_5$ or $R_6$ is a substituted or unsubstituted benzyl or C1-C6 alkyl group.

In another embodiment of the present invention, a heterocyclyl group formed from $R_5$ and $R_6$ is a substituted or unsubstituted piperadino, piperidino, or pyrrolidino group.

In another embodiment of the present invention, a substituent on $R_1$ is one or more C1-C4 alkyl, halogen, cyano, hydroxy, C1-C4 alkoxy, or substituted or unsubstituted phenyl, phenoxy, or phenylthio groups.

In another embodiment of the present invention, a substituent on $R_5$ or $R_6$ is one or more substituted or unsubstituted C1-C10 alkyl, halogen, cyano, hydroxy, C1-C4 alkoxy, C1-C4 alkylcarbonyl, C1-C4 alkylcarbonyloxy, disulfide, thiol, amino, substituted or unsubstituted mono-C1-C10 alkylamino, substituted or unsubstituted di-C1-C10 alkylamino, carbonyl, substituted or unsubstituted phenyl or phenyl-C1-C4 alkyl, or substituted or unsubstituted aryl or heterocyclyl groups.

In another embodiment of the present invention, the ketone compound represented by Formula (1) is selected from the group consisting of the following compounds (where the numerals in parentheses represent compound ID numbers).
acryloylbenzene (8184)
4-methyl-1-acryloylbenzene (8185)
4-fluoro-1-acryloylbenzene (8186)
1-bromo-6-acryloylnaphthalene (8187)
2-acryloylnaphthalene (8213)
2-acryloylanthracene (8189)
1-acryloylmorpholine (8171)
2-(cinnamoyl)-naphthalene (9195)
1-acryloyl-4-bromobenzene (8266)
2-bromo-4,5-dioxymethylene-1-acryloylbenzene (8200)
4-bromo-2-methoxy-1-acryloylbenzene (8203)
2,5-dimethyl-1-acryloylbenzene (8209)
1-methyl-6-acryloylnaphthalene (8211)
1-methyl-4-crotonoylbenzene (6228)
1-methoxy-4-crotonoylbenzene (8229)
1-methoxy-4-tigloylbenzene (8233)
1-ethyl-4-acryloylbenzene (8237)
3,4-dimethyl-1-acryloylbenzene (8241)
3,4-dimethoxy-1-acryloylbenzene (8243)
1-acryloyldibenzyl (8250)
1-acryloyldiphenylether (8251)
2-methyl-6-acryloylnaphthalene (8256)
1-fluoro-6-acryloylnaphthalene (8257)
Acryloyldiphenylsulfide (9261)
4-chloro-1-acryloylbenzene (8264)
4-acryloylpyridine (8265)
1-chloro-6-acryloylnaphthalene (8268)
Acryloyldiphenylmethane (8269)
Acryloyl-1-phenylnaphthalene (8270)
3-methoxyacryloylbenzene (8294)
1-acryloylnaphthalene (8293)

In another embodiment of the present invention, the ketone compound represented by Formula (2) is selected from the group consisting of the following compounds, (where the numerals in parentheses represent compound ID numbers).
1-(3-chloropropionyl)-4-fluorobenzene (8178)
1-(3-chloropropionyl)-4-methylbenzene (8179)
3-chloropropio-4-bromophenone (8180)

In another embodiment of the present invention, the ketone compound represented by Formula (3) is selected from the group consisting of the following compounds (where the numerals in parentheses represent compound ID numbers).
2-(N-t-butyl-2-hydroxyethyl)aminoethyl-4-pyridylketone (8672)
2-(N-methylbenzyl)aminoethyl-4-pyridylketone (8673)
2-(N-hydroxyethylbutyl)aminoethyl-4-pyridylketone (8674)
2-(hydroxyethylisopropyl)aminoethyl-3-thiophenylketone (8675)
2-(N-isopropylbenzyl)aminoethyl-4-benzylphenylketone (8285)
2-(N-isopropylbenzyl)aminoethyl-4-methylphenylketone (8286)
2-(N-isopropylbenzyl)aminoethyl-2-naphthylketone (8291)
2-(isopropylbenzyl)aminoethylphenylketone (8299)
2-(N-isopropylbenzyl)aminoethyl-4-methoxyphenylketone (8304)
2-(N-isopropylbenzyl)aminoethyl-2-pyridylketone (8305)
2-(N-methylbenzyl)aminoethyl-2-pyridylketone (8310)

2-(N-methylbenzyl)aminoethyl-5-methyl-2-naphthylketone (8315)
2-(N-isopropylbenzyl)aminoethyl-5-methyl-2-naphthylketone (8316)
2-(N-diphenyl)aminoethyl-5-methyl-2-naphthylketone (8317)
1-(N-benzylisopropyl)aminoethyl-1-naphthylketone (8298)
2-(N-isopropylbenzyl)aminoethyl-5-chloro-2-naphthylketone (8323)
2-(N-isopropylbenzyl)aminoethyl-4-phenoxyphenylketone (8324)
2-(N-methylbenzyl)aminoethyl-4-phenoxyphenylketone (8327)
2-(N-2-hydroxy-2-phenylethyl)aminoethyl-4-phenoxyphenylketone (8329)
2-piperidinoethyl-5-chloro-2-naphthylketone (8330)
2-(N-2-hydroxyethylbenzyl)aminoethyl-5-chloro-2-naphthylketone (8331)
2-(N-1,1-dihydroxymethylpropyl)aminoethyl-5-chloro-2-naphthylketone (8332)
2-(N-2-hydroxyethylbutyl)aminoethyl-5-chloro-2-naphthylketone (8333)
2-(N-t-butylbenzyl)aminoethyl-2-pyridylketone (8336)
2-(N-hydroxymethylbenzyl)aminoethyl-2-pyridylketone (8339)
2-(N-methylbenzyl)aminoethyl-2-naphthylketone (8346)
2-(N-methylhydroxyethyl)aminoethyl-2-naphthylketone (8347)
N-benzylethylaminoethyl-3-thiophenylketone (8677)
N,N-bis(2-hydroxyethyl)aminoethyl-2-pyrazylketone (8678)
2-(N-isopropylbenzyl)aminoethyl-4-benzylphenylketone (8361)
2-(N-methylbenzyl)aminoethyl-4-benzylphenylketone (8362)
2-(N-t-butylbenzyl)aminoethyl-4-benzylphenylketone (8363)
2-(N-isopropylbenzyl)aminoethyl-3-pyridylketone (8366)
2-(N-isopropylbenzyl)aminoethyl-4-pyridylketone (8367)
2-(N-butyl-2-hydroxyethyl)aminoethyl-2-pyrazinylketone (8679)
2-(N-isopropylbenzyl)aminoethyl-2-furylketone (8370)
2-(N-ethylbenzyl)aminoethyl-2-pyrazinylketone (8680)
2-(N-mercaptoethyl)aminoethyl-4-phenoxyphenylketone (8375)
2-(N-imidazolylethyl)aminoethyl-4-phenoxyphenylketone (8376)
2-(N-hydroxyethylbutyl)aminoethyl-4-phenoxyphenylketone (8377)
2-(N-furoylpiperazyl)aminoethyl-4-phenoxyphenylketone (8378)
2-(N-diethyl)aminoethyl-4-phenoxyphenylketone (8379)
2-(N-isopropylbenzyl)aminoethyl-2-pyrazylketone (8381)
2-(N-isopropylbenzyl)aminoethyl-2-thiazolylketone (8384)
2-(N-t-butylbenzyl)aminoethyl-2-furylketone (8385)
2-(N-t-butylhydroxyethyl)aminoethyl-2-furylketone (8387)
2-(N-hydroxyethylbenzyl)aminoethyl-2-furylketone (8388)
2-(N-methylbenzyl)aminoethyl-2-thiophenylketone (8389)
2-(N-methylhydroxyethyl)aminoethyl-2-thiophenylketone (8390)
2-hydroxymethylpyrazinylethyl-2-thiophenylketone (8391)
2-(N-benzylhydroxyethyl)aminoethyl-2-pyrazylketone (8397)
2-(N-bis-hydroxyethyl)aminoethyl-2-furylketone (8398)
2-(N-phenylhydroxyethyl)aminoethyl-4-pyridylketone (8402)
2-(N-benzylhydroxyethyl)aminoethyl-4-pyridylketone (8403)
2-(N-benzylhydroxyethyl)aminoethyl-5-methyl-2-furylketone (8404)
2-(N-benzyl-t-butyl)aminoethyl-5-methyl-2-furylketone (8405)
2-(N-dibenzyl)aminoethyl-5-methyl-2-furylketone (8406)
2-(N-benzylhydroxyethyl)aminoethyl-5-methyl-2-furylketone (8407)
2-(N-methylhydroxyethyl)aminoethyl-5-methyl-2-furylketone (8409)
2-(N-benzylethyl)aminoethyl-2-furylketone (8412)
2-(N,N-dihydroxyethyl)aminoethyl-2-thiazolylketone (8682)
2-(N-benzylethyl)aminoethyl-3-pyridylketone (8414)
2-(N-bishydroxyethyl)aminoethyl-5-methyl-2-furylketone (8415)
2-(N-isopropylhydroxyethyl)aminoethyl-5-methyl-2-furylketone (8416)
2-(N-bishydroxyethyl)aminoethyl-2-naphthylketone (8418)
2-(N-dihydroxyethyl)aminoethylthiophenylketone (8420)
2-(N-isopropylhydroxyethyl)aminoethyl-2-pyrazylketone (8422)
2-(N-hydroxyethylisopropyl)aminoethyl-2-furylketone (8424)
2-(N-hydroxyethylisopropyl)aminoethyl-2-pyridylketone (8426)
2-(N-hydroxyethylisopropyl)aminoethyl-4-pyridylketone (8428)
2-(N-hydroxyethylisopropyl)aminoethyl-2-thiazolylketone (8429)
2-(N-isopropylhydroxyethyl)aminoethyl-3'-pyridylketone (8433)
2-(N-hydroxyethylisopropyl)aminoethyl-4-fluorophenylketone (8503)
2-(N-methyl-2-hydroxyethyl)aminoethyl-2-(N-methylpyrrolyl)ketone (8685)
2-(N-isopropylbenzyl)aminomethyl-4-phenylketone (8506)
2-(N-isopropyl-2-hydroxyethyl)aminoethyl-2-(N-methylpyrrolyl)ketone (8686)
2-(N-isopropyl-2-hydroxyethyl)aminoethyl-2-pyrrolylketone (8687)
2-(N-bis(hydroxyethyl))aminoethyl-2-furylketone (8516)
2-(N-2-hydroxyethylbenzyl)aminoethyl-3-pyridylketone (8691)
3-(N-isopropylbenzyl)aminopropylphenylketone (8523)
2-(N-2-hydroxyethylbutyl)aminoethyl-3-pyridylketone (8692)
1-methyl-2-(N-hydroxyethylisopropyl)aminoethyl-2-fluorophenylketone (8525)
1-methyl-2-(N-benzylisopropyl)aminoethyl-2-fluorophenylketone (8526)
2-(N-isopropylbenzyl)aminoethyl-2-thiophenylketone (8651)
2-(N-2-hydroxyethylbenzyl)aminoethyl-3-thiophenylketone (8652)
2-(N-isopropylbenzyl)aminoethyl-2-(3-ethyl)-pyrazylketone (8656)
2-(N-hydroxyethylbenzyl)aminoethyl-2-(3-ethyl)-pyrazylketone (8657)
2-(N-t-butylbenzyl)aminoethyl-2-(3-ethyl)-pyrazylketone (8658)
2-N-adamantane-aminoethyl-2-methylfurylketone (8534)
2-(N-t-butylbenzyl)aminoethyl-2-thiophenylketone (8638)
2-(N-isopropylhydroxyethyl)aminoethyl-2-thiophenylketone (8639)

2-(N-isopropylbenzyl)aminoethyl-1-methyl-2-pyrrylketone (8646)
3-(N-benzylisopropyl)aminopropionylcaprolactam (8563)
2-(N-isopropylbenzyl)aminomethyl-3-(2,5-dichlorothiophenyl)ketone (8659)
2-(N-isopropyl-2-hydroxyethyl)aminomethyl-3-(2,5-dichlorothiophenyl)ketone (8660)
2-(N-2-hydroxyethylbenzyl)aminomethyl-3-(2,5-dichlorothiophenyl)ketone (8661)
2-(N-hydroxyethylisopropyl)aminoethyl-2-naphthylketone (8570)
2-(N-hydroxyethylisopropyl)aminomethylphenylketone (8572)
2-(N-hydroxyethylmethyl)aminoethyl-2-pyrazylketone (8593)
2-(N-ethylbenzyl)aminoethyl-4-pyridylketone (8594)
2-(N-t-butylbenzyl)aminoethyl-4-pyridylketone (8595)
2-(N-2-furylpiperadino)ethyl-4-fluorophenylketone (8596)
2-(N-isopropylbenzyl)aminoethyl-4-fluorophenylketone (8597)
2-(N-2-benzyl-t-butyl)aminoethyl-2-pyrazylketone (8693)
2-(N-2-hydroxyethyl-t-butyl)aminoethyl-2-pyrazylketone (8694)
2-(N-benzylmethyl)aminoethyl-2-pyrazylketone (8695)
N,N-bis(4-pyrizoylethyl)spermidine (8603)
2-hydroxypiperidinoethyl-4-pyridylketone (8604)
2-(N-benzylethyl)aminoethyl-2-florenylketone (8663)
2-(N-benzylisopropyl)aminoethyl-5-(2,4-dimethylthiazolyl)ketone (8666)
2-(N-isopropylbenzyl)aminoethyl-3-thiophenylketone (8625)
2-(N-isopropylbenzyl)aminoethyl-4,5-dimethyl-2-furylketone (8696)
2-(N-2-hydroxyethylethyl)aminoethyl-4,5-dimethyl-2-furylketone (8697)
2-(N-2-hydroxyethylbenzyl)aminoethyl-4,5-dimethyl-2-furylketone (8698)
2-(N-2-hydroxyethylethyl)aminoethyl-2,5-dimethyl-3-thiophenylketone (8699)
2-(N-benzyl-t-butyl)aminoethyl-3-pyridylketone (8702)
2-(N-t-butyl-2-hydroxyethyl)aminoethyl-3-pyridylketone (8703)
2-(N-benzylmethyl)aminoethyl-2-furylketone (8705)
2-(N-2-hydroxyethylbutyl)aminoethyl-2-furylketone (8706)
2-(N-2-hydroxyethylmethyl)aminoethyl-2-furylketone (8707)
2-(N-benzylmethyl)aminoethyl-3-thiophenylketone (8708)
2-(N-2-hydroxyethylbutyl)aminoethyl-3-thiophenylketone (8709)
2-(N-benzyl-t-butyl)aminoethyl-3-thiophenylketone (8710)
2-(N-benzylethyl)aminoethyl-5-methyl-2-furylketone (8711)
2-(N-2-hydroxyethyl-t-butyl)aminoethyl-5-methyl-2-furylketone (8712)
2-(N-benzylmethyl)aminoethyl-5-methyl-2-furylketone (8713)
2-(N-benzylethyl)aminoethyl-2-pyridylketone (8714)
2-(N-bis-2-hydroxyethyl)aminoethyl-2-pyridylketone (8715)
2-(N-t-butyl-2-hydroxyethyl)aminoethyl-2-pyridylketone (8716)
2-(N-benzyl-2-hydroxyethyl)aminoethyl-2-thiophenylketone (8717)
2-(N-t-butyl-2-hydroxyethyl)aminoethyl-2-thiophenylketone (8718)
2-(N-butyl-2-hydroxyethyl)aminoethyl-2-thiophenylketone (8719)
2-(N-benzylmethyl)aminoethyl-3-pyridylketone (8720)
2-(N-bis-2-hydroxyethyl)aminoethyl-4-pyridylketone (8721)
2-(N-2-hydroxyethylbutyl)aminoethyl-4-pyridylketone (8723)
2-(N-methyl-2-hydroxyethyl)aminoethyl-2-pyridylketone (8724)
2-(N-isopropyl-2-hydroxyethyl)aminoethyl-3-ethyl-2-pyrazylketone (8725)
2-(N-benzylethyl)aminoethyl-2-thiophenylketone (8734)
2-(N-2-hydroxyethylmethyl)aminoethyl-3-thiophenylketone (8727)
2-(N-2-hydroxyethylbutyl)aminoethyl-5-methyl-2-furylketone (8728)
2-(N-benzyl-t-butyl)aminoethyl-2-thiazolylketone (8729)
2-(N-benzylmethyl)aminoethyl-2-thiazolylketone (8731)
2-(N-2-hydroxyethylmethyl)aminoethyl-3-pyridylketone (8732)
2-(N-bis-hydroxyethyl)aminoethyl-3-ethyl-2-pyrazylketone (8733)
2-(N-bis-hydroxyethyl)aminoethyl-2-thiophenylketone (8676)
2-(N-2-hydroxyethylmethyl)aminoethyl-4-pyridylketone (8722)
2-(N-benzylisopropyl)aminoethyl-4-methyl-2-thiazolylketone (8738)
2-(N-butyl-2-hydroxyethyl)aminoethyl-4-methyl-2-thiazolylketone (8739)
2-(N-benzylmethyl)aminoethyl-4-methyl-2-thiazolylketone (8740)
2-(N-benzylisopropyl)aminoethyl-5-chloro-2-thiophenylketone (8741)
2-(N-2-hydroxyethylisopropyl)aminoethyl-5-chloro-2-thiophenylketone (8742)
2-(N-benzyl-2-hydroxyethyl)aminoethyl-5-chloro-2-thiophenylketone (8743)
2-(N-t-butylbenzyl)aminoethyl-5-bromo-2-thiophenylketone (8778)
2-(N-1,2-diphenyl-2-hydroxyethyl)aminoethyl-2-furylketone (8748)
N,N-bis(2-pyrazoylethyl)-N-hydroxyethylethylenediamine (8749)
2-(N-1-benzyl-2-hydroxyethyl)aminoethyl-4-pyridylketone (8750)
2-(N-2-hydroxyethyl)aminoethyl-2-furylketone (8751)
N,N-bis(2-pyrazoylethyl)tetramethylenediamine (8752)
2-bis(N-2-hydroxyethyl)aminoethyl-5-chloro-2-thienylketone (8753)
2-(N-ethylbenzyl)aminoethyl-5-chloro-2-thienylketone (8754)
2-(N-methylbenzyl)aminoethyl-5-chloro-2-thienylketone (8755)
2-(N-t-butylbenzyl)aminoethyl-5-chloro-2-thienylketone (8756)
2-(2-hydroxymethylpyrrolidino)ethyl-2-pyrazylketone (8758)
2-(N-isopropylbenzyl)aminoethyl-2-benzothienylketone (8759)
2-(N-isopropyl-2-hydroxyethyl)aminoethyl-2-benzothienylketone (8760)
2-(N-t-butylbenzyl)aminoethyl-2-benzothienylketone (8761)
2-(N-isopropylbenzyl)aminoethylferrocenylketone (8762)
2-(N-isopropyl-2-hydroxyethyl)aminoethylferrocenylketone (8763)
2-bis(N-2-hydroxyethyl)aminoethylferrocenylketone (8764)
2-(N-ethylbenzyl)aminoethyl-2-thiazolylketone (8765)

2-(N-2-hydroxyethylbenzyl)aminoethyl-2-thiazolylketone (8766)
2-(N-2-hydroxyethylmethyl)aminoethyl-2-thiazolylketone (8767)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-isopropylbenzyl)aminoethyl-1-4-biphenylketone (8774)
2-(N-2-hydroxyethylisopropyl)aminoethyl-4-biphenylketone (8775)
2-(N-2-hydroxyethylphenyl)aminoethyl-4-biphenylketone (8776)
2-(N-phenethyl)aminoethyl-2-furylketone (8745)
2-(N-ethylbenzyl)aminoethyl-5-bromo-2-thienylketone (8779)
2-(N-t-butylbenzyl)aminoethyl-4-cyanophenylketone (8789)
4-tolyl(N-benzyl-N-t-butyl)aminoethylketone (8793)
4-cyanophenyl(N-benzyl-N-t-butyl)aminoethylketone (8794)
2-(N-t-butyl-N-benzyl)aminoethyl-4-chlorophenylketone (8799)
2-(N-hydroxyethyl)aminoethyl-5-bromo-2-thienylketone (8802)
2-(N-benzylisopropyl)aminoethyl-4-cyanophenylketone (8803)
2-(N-hydroxylethylisopropyl)aminoethyl-4-cyanophenylketone (8804)
2-(N-benzylisopropyl)aminoethyl-4-chloro-phenylketone (8805)
2-(N-hydroxyethylisopropyl)aminoethyl-4-chloro-phenylketone (8806)
2-(N-hydroxyethylisopropyl)aminoethylphenylketone (8807)
2-(N-benzylethyl)aminoethyl-4-fluorophenylketone (8808)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N-benzyl-t-butyl)aminoethyl-5,6-ethylenedioxy-2-phenylketone (8820)
2-(N-benzylisopropyl)aminoethyl-5-methyl-2-thienylketone (8822)
2-(N-benzylethyl)aminoethyl-5-methyl-2-thienylketone (8823)
2-(N,N-bis-(2-hydroxyethyl)aminoethyl-5-iodo-2-thienylketone (8948)
2-(N-benzylisopropyl)aminoethyl-4-methyl-2-thienylketone (8828)
2-(N-dibenzyl)aminoethyl-4-methyl-2-thienylketone (8829)
2-(N-benzylhydroxyethyl)aminoethyl-4-methyl-2-thienylketone (8830)
2-(N-benzyl-t-butyl)aminoethyl-4-bromophenylketone (8831)
2-(N-dibenzyl)aminoethyl-5-bromo-2-thienylketone (8832)
2-(N-benzylmethyl)aminoethyl-5-bromo-2-thienylketone (8833)
2-(N-benzylhydroxyethyl)aminoethyl-5-bromo-2-thienylketone (8834)
2-(N-hydroxylmethyl)aminoethyl-5-bromo-2-thienylketone (8835)
2-(N-hydroxyethylisopropyl)aminoethyl-5-bromo-2-thienylketone (8836)
2-(N-bishydroxyethyl)aminoethyl-5-bromo-2-thienylketone (8837)
2-(N-2-hydroxyethylethyl)aminoethyl-5-bromo-2-thienylketone (8838)
2-(N-hydroxyethyl-t-butyl)aminoethyl-5-bromo-2-thienylketone (8839)
2-(2-hydroxymethylpyrrolidinyl)aminoethyl-5-bromo-2-thienylketone (8842)
2-(N-2-hydroxyethyl-N-2-aminoethyl)aminoethyl-5-bromo-2-thienylketone (8843)
2-(N-mercaptoethyl)aminoethyl-5-bromo-2-thienylketone (8844)
2-(N-phenyl-N-n-butyl)aminoethyl-5-bromo-2-thienylketone (8847)
2-(N,N-di-n-butyl)aminoethyl-5-bromo-2-thienylketone (8848)
2-(N,N-di-sec-butyl)aminoethyl-5-bromo-2-thienylketone (8849)
N,N-bis(2-(5-bromo-2-thiophenoyl)ethyl)cystamine (8823)
N-2-furoyl-piperadinoethyl-5-bromo-2-thienylketone (8851)
2-(N-2-hydroxy-3-aminopropyl)aminoethyl-5-bromo-2-thienylketone (8853)
2-(N-4-aminobutyl-N-3-aminopropyl)aminoethyl-5-bromo-2-thienylketone (8854)
2-(N-2-hydroxypyrrolidino)aminoethyl-5-bromo-2-thienylketone (8855)
2-(N-hydroxypropyl-N-5-bromo-thienoylethyl)aminoethyl-5-bromo-2-thienylketone (8856)
2-piperidinoethyl-5-bromo-2-thienylketone (8858)
2-(N-hydroxymethylpiperidinoethyl-5-bromo-2-thienylketone (8860)
2-phenethylaminoethyl-5-bromo-2-thienylketone (8861)
2-(N-5-bromothienoylethylaminoethyl-N-hydroxyethyl)aminoethyl-5-bromo-2-thienylketone (8864)
N,N-bis(5-bromo-2-thienoylethyl)tetramethylenediamine (8866)
2-(N-hydroxy-1-benzylethyl)aminoethyl-5-bromo-2-thienylketone (8867)
2-(N-hydroxyethyl)aminoethyl-5-bromo-2-thienylketone (8868)
2-(N-2-hydroxypropyl)aminoethyl-5-bromo-2-thienylketone (8870)
2-(4-hydroxyethylpiperadino)ethyl-5-bromo-2-thienylketone (8871)
2-(N-hydroxymethyl-N-ethyl)aminoethyl-5-bromo-2-thienylketone (8872)
2-(N-methylpiperadino)ethyl-5-bromo-2-thienylketone (8873)
2-(4-imidazolylethyl)aminoethyl-5-bromo-2-thienylketone (8874)
2-(N-1,1-bishydroxymethylpropyl)aminoethyl-5-bromo-2-thienylketone (8875)
N,N-bis(2-(5-chloro-2-thiophenoyl)ethyl)cystamine (8876)
N,N-bis(2-(4-bromo-benzoyl)ethyl)cystamine (8877)
N,N-bis(2-(benzoyl)ethyl)cystamine (8878)
N,N-bis(2-(2-thiophenoyl)ethyl)cystamine (8879)
N,N-bis(2-naphthoylethyl)cystamine (8881)
N,N-bis(3-pyridinoylethyl)cystamine (8882)
N,N-bis(2-furoylethyl)cystamine (8883)
2-(N-butyl-N-benzyl)aminoethyl-5-bromo-2-thienylketone (8884)
2-(N-butyl-N-benzyl)aminoethyl-5-chloro-2-thienylketone (8885)
2-(N-butyl-N-benzyl)aminoethyl-4-bromophenylketone (8886)
2-(N-butyl-N-benzyl)aminoethyl-4-pyridylketone (8887)

2-(N-butyl-N-benzyl)aminoethyl-2-furylketone (8888)
2-(N-butyl-N-benzyl)aminoethyl-2-naphthylketone (8889)
2-(N-2-hydroxyethyl-N-benzyl)aminoethyl-5-iodo-2-thienylketone (8947)
N,N-bis(2-(3-thiophenoyl)ethyl)cystamine (8891)
N,N-bis(2-(2,5-dichloro-3-thiophenoyl)ethyl)cystamine (8892)
2-N-benzylaminoethyl-5-bromo-2-thienylketone (8840)
2-(N,N-dihexyl)aminoethyl-5-bromo-2-thienylketone (8900)
2-(N,N-diisobutyl)aminoethyl-5-bromo-2-thienylketone (8901)
2-(N,N-dihexyl)aminoethyl-5-chloro-2-thienylketone (8902)
N,N-bis(2-(5-bromo-2-thiophenoyl)ethyl)cystinemethylester (8904)
N,N-bis(2-(5-chloro-2-thiophenoyl)ethyl)cystine (8905)
N,N-bis(4-iodobenzoylethyl)cystamine (8906)
N,N-bis(2-thiophenoylethyl)cystinemethylester (8908)
2-(N-isopropyl-N-benzyl)aminoethyl-5-iodo-2-thienyltone (8946)
N,N-bis(2-naphthoylethyl)cystinemethylester (8910)
N,N-bis(2-(4-bromobenzoyl)ethyl)cystinemethylester (8911)
N,N-bis(2-(4-pyridinoyl)ethyl)cystinemethylester (8912)
N,N-bis(2-(benzothiophenoyl)ethyl)cystinemethylester (8913)
2-diisopropylaminoethyl-5-bromo-2-thienylketone (8925)
2-diisopropylaminoethyl-5-chloro-2-thienylketone (8926)
2-diisopropylaminoethyl-4-pyridylketone (8927)
N,N-bis(4-cyanobenzoylethyl)cystamine (8928)
N,N-bis(4-cyanobenzoylethyl)cystinemethylester (8929)
N,N-bis(2-thiazolylethyl)cystinemethylester (8930)
N,N-bis(2-furoylethyl)cystinemethylester (8931)
N,N-bis(2-pyrazinoylethyl)cystinemethylester (8933)
N,N-bis(2-(5-methyl-2-thiophenoyl)ethyl)cystinemethylester (8932)
N,N-bis(2-fluorenylethyl)cystinemethylester (8936)
2-(N-t-butyl-N-benzyl)aminoethyl-5-iodo-2-thienylketone (8937)
N,N-bis(5-iodo-2-thiophenoylethyl)cystinemethylester (8938)
2-(N-t-butyl-N-benzyl)aminoethyl-3-bromo-2-thienylketone (8939)
2-(N-t-butyl-N-benzyl)aminoethyl-3-bromo-2-pyridylketone (8940)
N,N-bis(2-(5-bromo-2-thiophenoyl)ethyl)cystinemethylester (8941)
N,N-bis-(2-(5-iodo-2-thiophenoyl)ethyl)cystamine (8942)
2-(N,N-diisobutyl)aminoethyl-5-iodo-2-thienylketone (8943)
2-(N,N-isobutyl)aminoethyl-6-bromo-2-pyridylketone (8944)
2-(N,N-isobutyl)aminoethyl-3-bromo-2-thienylketone (8945)

In another embodiment of the present invention, the ketone compound further has IICR-inhibiting activity higher than SOCE-inhibiting activity.

Where the SOCE activity is inhibited, store operated calcium entry (SOCE) is inhibited. Meanwhile, where the IICR activity is inhibited, IP3 induced calcium release (IICR) is inhibited. When a compound has an IICR-inhibiting activity higher than SOCE-inhibiting activity, it means that the compound can control IICR and SOCE such that the amount of $Ca^{2+}$ released into the endoplasmic reticulum becomes greater than the amount of $Ca^{2+}$ released from the endoplasmic reticulum. In such case, it is predicted that the $Ca^{2+}$ concentration in cytoplasm surrounding the endoplasmic reticulum would transiently decrease. Since transglutaminase (TG) activity is changed in a $Ca^{2+}$-concentration-dependent manner, a decrease in $Ca^{2+}$ concentration would cause inhibition of TG activity. Therefore, it is thought that a compound that has a high TG-inhibiting activity and also has an IICR-inhibiting activity higher than SOCE-inhibiting activity would be able to inhibit TG with good efficiency. When the IICR-inhibiting activity is compared with the SOCE-inhibiting activity at a compound concentration that allows 50% inhibition, the IICR-inhibiting activity would be, for example, at least 3 times, preferably at least 5 times, more preferably at least 10 times, further preferably at least 50 times as strong as the SOCE-inhibiting activity.

In another embodiment of the present invention, a ketone compound that has an IICR-inhibiting activity higher than SOCE-inhibiting activity is selected from the group consisting of the following compounds (where the numerals in parentheses represent compound ID numbers).

2-(N-methylbenzyl)aminoethyl-4-pyridylketone (8673)
2-(N-isopropylbenzyl)aminoethyl-4-benzylphenylketone (8285)
2-(N-isopropylbenzyl)aminoethyl-2-pyridylketone (8305)
2-(N-isopropylbenzyl)aminoethyl-3-pyridylketone (8366)
2-(N-isopropylbenzyl)aminoethyl-4-pyridylketone (8367)
2-(N-isopropylbenzyl)aminoethyl-2-furylketone (8370)
2-(N-isopropylbenzyl)aminoethyl-2-pyrazylketone (8381)
2-(N-t-butylbenzyl)aminoethyl-2-furylketone (8385)
2-(N-benzylhydroxyethyl)aminoethyl-2-pyrazylketone (8397)
2-(N-benzylhydroxyethyl)aminoethyl-5-methyl-2-furylketone (8404)
2-(N-benzyl-t-butyl)aminoethyl-5-methyl-2-furylketone (8405)
2-(N-benzylethyl)aminoethyl-2-furylketone (8412)
2-(N-hydroxyethylisopropyl)aminoethyl-2-furylketone (8424)
2-(N-isopropylbenzyl)aminoethyl-2-(3-ethyl)-pyrazylketone (8656)
2-(N-t-butylbenzyl)aminoethyl-2-(3-ethyl)-pyrazylketone (8658)
2-(N-t-butylbenzyl)aminoethyl-2-thiophenylketone (8638)
2-(N-isopropylbenzyl)aminomethyl-3-(2,5-dichlorothiophenyl)ketone (8659)
2-(N-benzylisopropyl)aminoethyl-5-(2,4-dimethylthiazolyl)ketone (8666)
2-(N-benzyl-t-butyl)aminoethyl-3-pyridylketone (8702)
2-(N-2-hydroxyethylmethyl)aminoethyl-2-furylketone (8707)
2-(N-benzyl-t-butyl)aminoethyl-2-thiazolylketone (8729)
2-(N-t-butylbenzyl)aminoethyl-5-bromo-2-thiophenylketone (8778)
2-(N-t-butylbenzyl)aminoethyl-5-chloro-2-thienylketone (8756)
2-(N-isopropylbenzyl)aminoethyl-2-benzothienylketone (8759)
2-(N-t-butylbenzyl)aminoethyl-2-benzothienylketone (8761)
2-(N-ethylbenzyl)aminoethyl-2-thiazolylketone (8765)
2-(N-2-hydroxyethylbenzyl)aminoethyl-2-thiazolylketone (8766)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-t-butylbenzyl)aminoethyl-4-cyanophenylketone (8789)

4-cyanophenyl(N-benzyl-N-t-butyl)aminoethylketone (8794)
2-(N-benzylisopropyl)aminoethyl-4-cyanophenylketone (8803)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N,N-di-n-butyl)aminoethyl-5-bromo-2-thienylketone (8848)
2-(N,N-di-sec-butyl)aminoethyl-5-bromo-2-thienylketone (8849)
2-(N-2-hydroxy-3-aminopropyl)aminoethyl-5-bromo-2-thienylketone (8853)

In a second aspect, the present invention provides a transglutaminase activity inhibitor, which comprises at least one member selected from the group consisting of the compounds represented by any of Formulae (1) to (3) and the aforementioned specific compounds.

In a third aspect, the present invention provides an inhibitor of protein crosslinking, which comprises at least one of the compounds represented by any of Formulae (1) to (3) and the aforementioned specific compounds.

In a forth aspect, the present invention provides a calcium concentration modulator, which comprises at least one of the compounds represented by any of Formulae (1) to (3) and the aforementioned specific compounds.

In a fifth aspect, the present invention provides a composition for prevention or treatment of a protein-crosslinking causative disease, which comprises at least one of the compounds represented by any of Formulae (1) to (3) and the aforementioned specific compounds.

In the above aspects of the present invention, the protein-crosslinking causative disease is selected from the group consisting of Alzheimer's disease, Huntington's disease, Parkinson's disease, Celiac disease, cataract, mad cow disease, congenital lamellar ichthyosis, congenital hemostatic disorder, liver disorder, autoimmune disease, and cerebral infarction.

This description includes all or part of the contents as disclosed in the description and/or drawings of Japanese Patent Application No. 2009-255518, from which the present application claims the priority.

Advantageous Effect of Invention

The compounds of the present invention have the action of modulating an intracellular calcium concentration (SOCE and/or IICR) or the action of inhibiting a transglutaminase (TG) activity or a protein crosslinking reaction. In addition, it has now been found that these compounds include therapeutically useful compounds that strongly exhibit the TG-activity-inhibiting action (i.e. the protein-crosslinking-inhibiting action) and also strongly exhibit an IICR-inhibiting activity but almost no SOCE-inhibiting activity. Since the compounds of the present invention have such properties, they are useful for prevention or treatment of diseases caused by abnormal protein crosslinking (e.g., Alzheimer's disease, Huntington's disease, Parkinson's disease, Celiac disease, cataract, mad cow disease, congenital lamellar ichthyosis, congenital hemostatic disorder, liver disorder, autoimmune disease, and cerebral infarction).

MODE FOR CARRYING OUT INVENTION

The present invention provides a ketone compound having transglutaminase-inhibiting activity represented by Formula (1), (2), or (3) above. Such compound has a protein-crosslinking-inhibiting action and thus it can be effectively used for prevention or treatment of a disease caused by an abnormal crosslinking reaction of a certain protein.

In any Formula shown above, $R_1$ is a substituted or unsubstituted C1-C20 alkyl, aryl, or heterocyclyl group, $R_2$, $R_3$, $R_4$, $R_5$, and $R_6$ independently represent a hydrogen atom or a substituted or unsubstituted C1-C10 alkyl, aryl, or aralkyl group, wherein $R_5$ and $R_6$ are not hydrogen atoms at the same time, or $R_5$ and $R_6$ may be taken together to form a saturated or unsaturated and substituted or unsubstituted heterocyclyl group containing a nitrogen atom (N), X is halogen or $NR_5R_6$ (where $R_5$ and $R_6$ have the same meanings as defined above), and n is an integer of 2 to 4, preferably 2.

A preferable example of the compound is a ketone compound having transglutaminase-inhibiting activity of Formula (1), (2) or (3), wherein $R_1$ is a substituted or unsubstituted aryl or heterocyclyl group, $R_2$, $R_3$, and $R_4$ are hydrogen atoms, n is 2, X is halogen, $R_5$ and $R_6$ independently represent a hydrogen atom or a substituted or unsubstituted C1-C10 alkyl, aryl, or aralkyl group, wherein $R_5$ and $R_6$ are not hydrogen atoms at the same time, or $R_5$ and $R_6$ may be taken together to form a saturated or unsaturated and substituted or unsubstituted heterocyclyl group containing a nitrogen atom (N).

The alkyl group is a substituted or unsubstituted C1-C20, preferably C1-C10, more preferably C1-C6, such as C1-C4, linear, branched, or cyclic alkyl group. Examples thereof include methyl, ethyl, n- or iso-propyl, n-, iso- or tert-butyl, n-pentyl, n-hexyl, cyclopentyl, cyclohexyl, and adamantyl.

The aryl group is a substituted or unsubstituted monocyclic or (condensed) polycyclic (preferably bicyclic or tricyclic) aromatic group. Examples thereof include substituted or unsubstituted phenyl, naphthyl, and anthracenyl. Examples of substituted phenyl include ethylenedioxyphenyl, diphenyl, phenoxy-phenyl, benzyl-phenyl, and phenylthio-phenyl.

The aralkyl group is an arylalkyl group. Examples thereof include substituted or unsubstituted phenylalkyl such as benzyl, phenylethyl, and phenylpropyl.

The heterocyclyl group is a cyclic group containing 1 atom or 2 or more different atoms (such as N, O, or S other than C) on its ring. It may be a substituted or unsubstituted and saturated or unsaturated monocyclic heterocyclyl group or condensed heterocyclyl group. Examples thereof include, but are not limited to, pyridyl, pyrimidyl, quinolyl, isoquinolyl, furyl, pyrazyl, pyrazinyl, pyrazolyl, pyrimidyl, pyridazinyl, imidazolyl, thiazolyl, isothiazolyl, imidazolyl, oxazolyl, isooxazolyl, triazolyl, thienyl, pyrrolyl, indolyl, carbazolyl, indazolyl, pyrrolidinyl, pyrrolinyl, imidazolidinyl, pyrazolidinyl, pyrazolinyl, piperazyl, piperidyl, piperazinyl, indolinyl, morpholinyl, benzofuryl, benzothienyl, lactone, lactam, and ferrocenyl.

The halogen is a fluorine atom, a bromine atom, a chlorine atom, or an iodine atom.

The position of the above substituents is not particularly limited.

Examples of the substituents include one or more C1-C10 alkyl (e.g., methyl, ethyl, n- or iso-propyl, or n-, iso- or tert-butyl), C2-C10 alkenyl (e.g., ethenyl or propenyl), C2-C10 alkynyl, halogen (e.g., fluorine, bromine, chlorine, or iodine), C1-C4 alkoxy (e.g., methoxy, ethoxy, or n- or iso-propoxy), methylenedioxy, ethylenedioxy, C1-C4 alkylthio (e.g., methylthio or ethylthio), C1-C4 alkylsulfonyl (e.g., mesyl or ethylsulfonyl), sulfamoyl, carboxy, C1-C4 alkoxy-carbonyl (e.g., methoxycarbonyl or ethoxycarbonyl), C1-C4 alkylcarbonyloxy (e.g., acetoxy or ethylcarbonyloxy), hydroxy, mercapto, alkylthio, amide, acetamide, carbonyl (—C(=O)—), amino, mono- or di-C1-C4 alkylamino (e.g., methylamino, dimethylamino, ethylamino, or diethylamino), hydroxyalkylamino, nitro, cyano, isocyanato, thiocyanato, cycloalkyl (e.g., cyclohexyl or cyclopentyl), disulfide (—S—S—), —NH—, and aryl or heterocyclyl groups that have the same meanings as defined above. However, the substituents are not limited to such examples as long as the compound is imparted with transglutaminase-inhibiting activity.

In an embodiment of the present invention, preferably $R_1$ is a substituted or unsubstituted phenyl, naphthyl, fluorenyl, benzothienyl, pyridyl, pyrazinyl, furyl, thienyl, pyrrolyl, thiazolyl, ferrocenyl, morpholino, or 6- to 7-membered cyclic lactam group.

In another embodiment of the present invention, preferably $R_5$ or $R_6$ is a substituted or unsubstituted benzyl or C1-C6 alkyl group.

In another embodiment of the present invention, a preferable heterocyclyl group formed from $R_5$ and $R_6$ is a substituted or unsubstituted piperadino, piperidino, or pyrrolidino group.

In another embodiment of the present invention, examples of a preferable substituent on $R_1$ include one or more C1-C4 alkyl, halogen, cyano, hydroxy, C1-C4 alkoxy, or substituted or unsubstituted phenyl, phenoxy, or phenylthio groups.

In another embodiment of the present invention, examples of a preferable substituent on $R_5$ or $R_6$ include one or more substituted or unsubstituted C1-C10 alkyl, halogen, cyano, hydroxy, C1-C4 alkoxy, C1-C4 alkylcarbonyl, C1-C4 alkylcarbonyloxy, disulfide, thiol, amino, substituted or unsubstituted mono-C1-C10 alkylamino, substituted or unsubstituted di-C1-C10 alkylamino, carbonyl, substituted or unsubstituted phenyl or phenyl-C1-C4 alkyl, or substituted or unsubstituted aryl or heterocyclyl groups.

Specifically, examples of the compounds of the present invention include, but are not limited to, the following compounds (where the numerals in parentheses represent compound ID numbers).

acryloylbenzene (8184)
4-methyl-1-acryloylbenzene (8185)
4-fluoro-1-acryloylbenzene (8186)
1-bromo-6-acryloylnaphthalene (8187)
2-acryloylnaphthalene (8213)
2-acryloylanthracene (8189)
1-acryloylmorpholine (8171)
1-(3-chloropropionyl)-4-fluorobenzene (8178)
1-(3-chloropropionyl)-4-methylbenzene (8179)
3-chloropropio-4-bromophenone (8180)
2-(cinnamoyl)-naphthalene (9195)
1-acryloyl-4-bromobenzene (8266)
2-bromo-4,5-dioxymethylene-1-acryloylbenzene (8200)
4-bromo-2-methoxy-1-acryloylbenzene (8203)
2,5-dimethyl-1-acryloylbenzene (8209)
1-methyl-6-acryloylnaphthalene (8211)
2-(N-t-butyl-2-hydroxyethyl)aminoethyl-4-pyridylketone (8672)
2-(N-methylbenzyl)aminoethyl-4-pyridylketone (867)
1-methyl-4-crotonoylbenzene (6228)
1-methoxy-4-crotonoylbenzene (8229)
1-methoxy-4-tigloylbenzene (8233)
1-ethyl-4-acryloylbenzene (8237)
3,4-dimethyl-1-acryloylbenzene (8241)
3,4-dimethoxy-1-acryloylbenzene (8243)
1-acryloyldibenzyl (8250)
1-acryloyldiphenylether (8251)
2-methyl-6-acryloylnaphthalene (8256)
1-fluoro-6-acryloylnaphthalene (8257)
2-(N-hydroxyethylbutyl)aminoethyl-4-pyridylketone (8674)
Acryloyldiphenylsulfide (9261)
4-chloro-1-acryloylbenzene (8264)
4-acryloylpyridine (8265)
2-(hydroxyethylisopropyl)aminoethyl-3-thiophenylketone (8675)
1-chloro-6-acryloylnaphthalene (8268)
Acryloyldiphenylmethane (8269)
Acryloyl-1-phenylnaphthalene (8270)
2-(N-isopropylbenzyl)aminoethyl-4-benzylphenylketone (8285)
2-(N-isopropylbenzyl)aminoethyl-4-methylphenylketone (8286)
2-(N-isopropylbenzyl)aminoethyl-2-naphthylketone (8291)
3-methoxyacryloylbenzene (8294)
1-acryloylnaphthalene (8293)
2-(isopropylbenzyl)aminoethylphenylketone (8299)
2-(N-isopropylbenzyl)aminoethyl-4-methoxyphenylketone (8304)
2-(N-isopropylbenzyl)aminoethyl-2-pyridylketone (8305)
2-(N-methylbenzyl)aminoethyl-2-pyridylketone (8310)
2-(N-methylbenzyl)aminoethyl-5-methyl-2-naphthylketone (8315)
2-(N-isopropylbenzyl)aminoethyl-5-methyl-2-naphthylketone (8316)
2-(N-diphenyl)aminoethyl-5-methyl-2-naphthylketone (8317)
1-(N-benzylisopropyl)aminoethyl-1-naphthylketone (8298)
2-(N-isopropylbenzyl)aminoethyl-5-chloro-2-naphthylketone (8323)
2-(N-isopropylbenzyl)aminoethyl-4-phenoxyphenylketone (8324)
2-(N-methylbenzyl)aminoethyl-4-phenoxyphenylketone (8327)
2-(N-2-hydroxy-2-phenylethyl)aminoethyl-4-phenoxyphenylketone (8329)
2-piperidinoethyl-5-chloro-2-naphthylketone (8330)
2-(N-2-hydroxyethylbenzyl)aminoethyl-5-chloro-2-naphthylketone (8331)
2-(N-1,1-dihydroxymethylpropyl)aminoethyl-5-chloro-2-naphthylketone (8332)
2-(N-2-hydroxyethylbutyl)aminoethyl-5-chloro-2-naphthylketone (8333)
2-(N-t-butylbenzyl)aminoethyl-2-pyridylketone (8336)
2-(N-hydroxymethylbenzyl)aminoethyl-2-pyridylketone (8339)
3-acetyl-3-methoxycarbonylpropyl-2-naphthylketone (8341)
2-(N-methylbenzyl)aminoethyl-2-naphthylketone (8346)
2-(N-methylhydroxyethyl)aminoethyl-2-naphthylketone (8347)
N-benzylethylaminoethyl-3-thiophenylketone (8677)
N,N-bis(2-hydroxyethyl)aminoethyl-2-pyrazylketone (8678)
2-(N-isopropylbenzyl)aminoethyl-4-benzylphenylketone (8361)
2-(N-methylbenzyl)aminoethyl-4-benzylphenylketone (8362)
2-(N-t-butylbenzyl)aminoethyl-4-benzylphenylketone (8363)
2-(N-isopropylbenzyl)aminoethyl-3-pyridylketone (8366)
2-(N-isopropylbenzyl)aminoethyl-4-pyridylketone (8367)
2-(N-butyl-2-hydroxyethyl)aminoethyl-2-pyrazinylketone (8679)
2-(N-isopropylbenzyl)aminoethyl-2-furylketone (8370)
2-(N-ethylbenzyl)aminoethyl-2-pyrazinylketone (8680)
2-(N-mercaptoethyl)aminoethyl-4-phenoxyphenylketone (8375)

2-(N-imidazolylethyl)aminoethyl-4-phenoxyphenylketone (8376)
2-(N-hydroxyethylbutyl)aminoethyl-4-phenoxyphenylketone (8377)
2-(N-furoylpiperazyl)aminoethyl-4-phenoxyphenylketone (8378)
2-(N-diethyl)aminoethyl-4-phenoxyphenylketone (8379)
2-(N-isopropylbenzyl)aminoethyl-2-pyrazylketone (8381)
2-(N-isopropylbenzyl)aminoethyl-2-thiazolylketone (8384)
2-(N-t-butylbenzyl)aminoethyl-2-furylketone (8385)
2-(N-t-butylhydroxyethyl)aminoethyl-2-furylketone (8387)
2-(N-hydroxyethylbenzyl)aminoethyl-2-furylketone (8388)
2-(N-methylbenzyl)aminoethyl-2-thiophenylketone (8389)
2-(N-methylhydroxyethyl)aminoethyl-2-thiophenylketone (8390)
2-hydroxymethylpyrazinylethyl-2-thiophenylketone (8391)
2-(N-benzylhydroxyethyl)aminoethyl-2-pyrazylketone (8397)
2-(N-bis-hydroxyethyl)aminoethyl-2-furylketone (8398)
2-(N-phenylhydroxyethyl)aminoethyl-4-pyridylketone (8402)
2-(N-benzylhydroxyethyl)aminoethyl-4-pyridylketone (8403)
2-(N-benzylhydroxyethyl)aminoethyl-5-methyl-2-furylketone (8404)
2-(N-benzyl-t-butyl)aminoethyl-5-methyl-2-furylketone (8405)
2-(N-dibenzyl)aminoethyl-5-methyl-2-furylketone (8406)
2-(N-benzylhydroxyethyl)aminoethyl-5-methyl-2-furylketone (8407)
2-(N-methylhydroxyethyl)aminoethyl-5-methyl-2-furylketone (8409)
2-(N-benzylethyl)aminoethyl-2-furylketone (8412)
2-(N,N-dihydroxyethyl)aminoethyl-2-thiazolylketone (8682)
2-(N-benzylethyl)aminoethyl-3-pyridylketone (8414)
2-(N-bishydroxyethyl)aminoethyl-5-methyl-2-furylketone (8415)
2-(N-isopropylhydroxyethyl)aminoethyl-5-methyl-2-furylketone (8416)
2-(N-bishydroxyethyl)aminoethyl-2-naphthylketone (8418)
2-(N-dihydroxyethyl)aminoethylthiophenylketone (8420)
2-(N-isopropylhydroxyethyl)aminoethyl-2-pyrazylketone (8422)
2-(N-hydroxyethylisopropyl)aminoethyl-2-furylketone (8424)
2-(N-hydroxyethylisopropyl)aminoethyl-2-pyridylketone (8426)
2-(N-hydroxyethylisopropyl)aminoethyl-4-pyridylketone (8428)
2-(N-hydroxyethylisopropyl)aminoethyl-2-thiazolylketone (8429)
2-(N-isopropylhydroxyethyl)aminoethyl-3'-pyridylketone (8433)
2-(N-hydroxyethylisopropyl)aminoethyl-4-fluorophenylketone (8503)
2-(N-methyl-2-hydroxyethyl)aminoethyl-2-(N-methylpyrrolyl)ketone (8685)
2-(N-isopropylbenzyl)aminomethyl-4-phenylketone (8506)
2-(N-isopropyl-2-hydroxyethyl)aminoethyl-2-(N-methylpyrrolyl)ketone (8686)
2-(N-isopropyl-2-hydroxyethyl)aminoethyl-2-pyrrolylketone (8687)
2-(N-bis(hydroxyethyl))aminoethyl-2-furylketone (8516)
2-(N-2-hydroxyethylbenzyl)aminoethyl-3-pyridylketone (8691)
3-(N-isopropylbenzyl)aminopropylphenylketone (8523)
2-(N-2-hydroxyethylbutyl)aminoethyl-3-pyridylketone (8692)
1-methyl-2-(N-hydroxyethylisopropyl)aminoethyl-2-fluorophenylketone (8525)
1-methyl-2-(N-benzylisopropyl)aminoethyl-2-fluorophenylketone (8526)
2-(N-isopropylbenzyl)aminoethyl-2-thiophenylketone (8651)
2-(N-2-hydroxyethylbenzyl)aminoethyl-3-thiophenylketone (8652)
2-(N-isopropylbenzyl)aminoethyl-2-(3-ethyl)-pyrazylketone (8656)
2-(N-hydroxyethylbenzyl)aminoethyl-2-(3-ethyl)-pyrazylketone (8657)
2-(N-t-butylbenzyl)aminoethyl-2-(3-ethyl)-pyrazylketone (8658)
2-N-adamantane-aminoethyl-2-methylfurylketone (8534)
2-(N-t-butylbenzyl)aminoethyl-2-thiophenylketone (8638)
2-(N-isopropylhydroxyethyl)aminoethyl-2-thiophenylketone (8639)
2-(N-isopropylbenzyl)aminoethyl-1-methyl-2-pyrrylketone (8646)
3-(N-benzylisopropyl)aminopropionylcaprolactam (8563)
2-(N-isopropylbenzyl)aminomethyl-3-(2,5-dichlorothiophenyl)ketone (8659)
2-(N-isopropyl-2-hydroxyethyl)aminomethyl-3-(2,5-dichlorothiophenyl)ketone (8660)
2-(N-2-hydroxyethylbenzyl)aminomethyl-3-(2,5-dichlorothiophenyl)ketone (8661)
2-(N-hydroxyethylisopropyl)aminoethyl-2-naphthylketone (8570)
2-(N-hydroxyethylisopropyl)aminomethylphenylketone (8572)
2-(N-hydroxyethylmethyl)aminoethyl-2-pyrazylketone (8593)
2-(N-ethylbenzyl)aminoethyl-4-pyridylketone (8594)
2-(N-t-butylbenzyl)aminoethyl-4-pyridylketone (8595)
2-(N-2-furylpiperadino)ethyl-4-fluorophenylketone (8596)
2-(N-isopropylbenzyl)aminoethyl-4-fluorophenylketone (8597)
2-(N-2-benzyl-t-butyl)aminoethyl-2-pyrazylketone (8693)
2-(N-2-hydroxyethyl-t-butyl)aminoethyl-2-pyrazylketone (8694)
2-(N-benzylmethyl)aminoethyl-2-pyrazylketone (8695)
Bis-N,N-(4-pyrizoylethyl)spermidine (8603)
2-hydroxypiperidinoethyl-4-pyridylketone (8604)
2-(N-benzylethyl)aminoethyl-2-florenylketone (8663)
2-(N-benzylisopropyl)aminoethyl-5-(2,4-dimethylthiazolyl)ketone (8666)
2-(N-isopropylbenzyl)aminoethyl-3-thiophenylketone (8625)
2-(N-isopropylbenzyl)aminoethyl-4,5-dimethyl-2-furylketone (8696)
2-(N-2-hydroxyethylethyl)aminoethyl-4,5-dimethyl-2-furylketone (8697)
2-(N-2-hydroxyethylbenzyl)aminoethyl-4,5-dimethyl-2-furylketone (8698)
2-(N-2-hydroxyethylethyl)aminoethyl-2,5-dimethyl-3-thiophenylketone (8699)
2-(N-benzyl-t-butyl)aminoethyl-3-pyridylketone (8702)
2-(N-t-butyl-2-hydroxyethyl)aminoethyl-3-pyridylketone (8703)
2-(N-benzylmethyl)aminoethyl-2-furylketone (8705)
2-(N-2-hydroxyethylbutyl)aminoethyl-2-furylketone (8706)
2-(N-2-hydroxyethylmethyl)aminoethyl-2-furylketone (8707)
2-(N-benzylmethyl)aminoethyl-3-thiophenylketone (8708)

2-(N-2-hydroxyethylbutyl)aminoethyl-3-thiophenylketone (8709)
2-(N-benzyl-t-butyl)aminoethyl-3-thiophenylketone (8710)
2-(N-benzylethyl)aminoethyl-5-methyl-2-furylketone (8711)
2-(N-2-hydroxyethyl-t-butyl)aminoethyl-5-methyl-2-furylketone (8712)
2-(N-benzylmethyl)aminoethyl-5-methyl-2-furylketone (8713)
2-(N-benzylethyl)aminoethyl-2-pyridylketone (8714)
2-(N-bis-2-hydroxyethyl)aminoethyl-2-pyridylketone (8715)
2-(N-t-butyl-2-hydroxyethyl)aminoethyl-2-pyridylketone (8716)
2-(N-benzyl-2-hydroxyethyl)aminoethyl-2-thiophenylketone (8717)
2-(N-t-butyl-2-hydroxyethyl)aminoethyl-2-thiophenylketone (8718)
2-(N-butyl-2-hydroxyethyl)aminoethyl-2-thiophenylketone (8719)
2-(N-benzylmethyl)aminoethyl-3-pyridylketone (8720)
2-(N-bis-2-hydroxyethyl)aminoethyl-4-pyridylketone (8721)
2-(N-2-hydroxyethylbutyl)aminoethyl-4-pyridylketone (8723)
2-(N-methyl-2-hydroxyethyl)aminoethyl-2-pyridylketone (8724)
2-(N-isopropyl-2-hydroxyethyl)aminoethyl-3-ethyl-2-pyrazylketone (8725)
2-(N-benzylethyl)aminoethyl-2-thiophenylketone (8734)
2-(N-2-hydroxyethylmethyl)aminoethyl-3-thiophenylketone (8727)
2-(N-2-hydroxyethylbutyl)aminoethyl-5-methyl-2-furylketone (8728)
2-(N-benzyl-t-butyl)aminoethyl-2-thiazolylketone (8729)
2-(N-benzylmethyl)aminoethyl-2-thiazolylketone (8731)
2-(N-2-hydroxyethylmethyl)aminoethyl-3-pyridylketone (8732)
2-(N-bis-hydroxyethyl)aminoethyl-3-ethyl-2-pyrazylketone (8733)
2-(N-bis-hydroxyethyl)aminoethyl-2-thiophenylketone (8676)
2-(N-2-hydroxyethylmethyl)aminoethyl-4-pyridylketone (8722)
2-(N-benzylisopropyl)aminoethyl-4-methyl-2-thiazolylketone (8738)
2-(N-butyl-2-hydroxyethyl)aminoethyl-4-methyl-2-thiazolylketone (8739)
2-(N-benzylmethyl)aminoethyl-4-methyl-2-thiazolylketone (8740)
2-(N-benzylisopropyl)aminoethyl-5-chloro-2-thiophenylketone (8741)
2-(N-2-hydroxyethylisopropyl)aminoethyl-5-chloro-2-thiophenylketone (8742)
2-(N-benzyl-2-hydroxyethyl)aminoethyl-5-chloro-2-thiophenylketone (8743)
2-(N-t-butylbenzyl)aminoethyl-5-bromo-2-thiophenylketone (8778)
2-(N-1,2-diphenyl-2-hydroxyethyl)aminoethyl-2-furylketone (8748)
N,N-bis(2-pyrazoylethyl)-N-hydroxyethylethylenediamine (8749)
2-(N-1-benzyl-2-hydroxyethyl)aminoethyl-4-pyridylketone (8750)
2-(N-2-hydroxyethyl)aminoethyl-2-furylketone (8751)
N,N-bis(2-pyrazoylethyl)tetramethylenediamine (8752)
2-bis(N-2-hydroxyethyl)aminoethyl-5-chloro-2-thienylketone (8753)
2-(N-ethylbenzyl)aminoethyl-5-chloro-2-thienylketone (8754)
2-(N-methylbenzyl)aminoethyl-5-chloro-2-thienylketone (8755)
2-(N-t-butylbenzyl)aminoethyl-5-chloro-2-thienylketone (8756)
2-(2-hydroxymethylpyrrolidino)ethyl-2-pyrazylketone (8758)
2-(N-isopropylbenzyl)aminoethyl-2-benzothienylketone (8759)
2-(N-isopropyl-2-hydroxyethyl)aminoethyl-2-benzothienylketone (8760)
2-(N-t-butylbenzyl)aminoethyl-2-benzothienylketone (8761)
2-(N-isopropylbenzyl)aminoethylferrocenylketone (8762)
2-(N-isopropyl-2-hydroxyethyl)aminoethylferrocenylketone (8763)
2-bis(N-2-hydroxyethyl)aminoethylferrocenylketone (8764)
2-(N-ethylbenzyl)aminoethyl-2-thiazolylketone (8765)
2-(N-2-hydroxyethylbenzyl)aminoethyl-2-thiazolylketone (8766)
2-(N-2-hydroxyethylmethyl)aminoethyl-2-thiazolylketone (8767)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-isopropylbenzyl)aminoethyl-1-4-biphenylketone (8774)
2-(N-2-hydroxyethylisopropyl)aminoethyl-4-biphenylketone (8775)
2-(N-2-hydroxyethylphenyl)aminoethyl-4-biphenylketone (8776)
2-(N-phenethyl)aminoethyl-2-furylketone (8745)
2-(N-ethylbenzyl)aminoethyl-5-bromo-2-thienylketone (8779)
2-(N-t-butylbenzyl)aminoethyl-4-cyanophenylketone (8789)
4-tolyl(N-benzyl-N-t-butyl)aminoethylketone (8793)
4-cyanophenyl(N-benzyl-N-t-butyl)aminoethylketone (8794)
2-(N-t-butyl-N-benzyl)aminoethyl-4-chlorophenylketone (8799)
2-(N-hydroxyethyl)aminoethyl-5-bromo-2-thienylketone (8802)
2-(N-benzylisopropyl)aminoethyl-4-cyanophenylketone (8803)
2-(N-hydroxylethylisopropyl)aminoethyl-4-cyanophenylketone (8804)
2-(N-benzylisopropyl)aminoethyl-4-chloro-phenylketone (8805)
2-(N-hydroxyethylisopropyl)aminoethyl-4-chloro-phenylketone (8806)
2-(N-hydroxyethylisopropyl)aminoethylphenylketone (8807)
2-(N-benzylethyl)aminoethyl-4-fluorophenylketone (8808)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N-benzyl-t-butyl)aminoethyl-5,6-ethylenedioxy-2-phenylketone (8820)

2-(N-benzylisopropyl)aminoethyl-5-methyl-2-thienylketone (8822)
2-(N-benzylethyl)aminoethyl-5-methyl-2-thienylketone (8823)
2-(N,N-bis-(2-hydroxyethyl)aminoethyl-5-iodo-2-thienylketone (8948)
2-(N-benzylisopropyl)aminoethyl-4-methyl-2-thienylketone (8828)
2-(N-dibenzyl)aminoethyl-4-methyl-2-thienylketone (8829)
2-(N-benzylhydroxyethyl)aminoethyl-4-methyl-2-thienylketone (8830)
2-(N-benzyl-t-butyl)aminoethyl-4-bromophenylketone (8831)
2-(N-dibenzyl)aminoethyl-5-bromo-2-thienylketone (8832)
2-(N-benzylmethyl)aminoethyl-5-bromo-2-thienylketone (8833)
2-(N-benzylhydroxyethyl)aminoethyl-5-bromo-2-thienylketone (8834)
2-(N-hydroxyethylmethyl)aminoethyl-5-bromo-2-thienylketone (8835)
2-(N-hydroxyethylisopropyl)aminoethyl-5-bromo-2-thienylketone (8836)
2-(N-bishydroxyethyl)aminoethyl-5-bromo-2-thienylketone (8837)
2-(N-2-hydroxyethylethyl)aminoethyl-5-bromo-2-thienylketone (8838)
2-(N-hydroxyethyl-t-butyl)aminoethyl-5-bromo-2-thienylketone (8839)
2-(2-hydroxymethylpyrrolidinyl)aminoethyl-5-bromo-2-thienylketone (8842)
2-(N-2-hydroxyethyl-N-2-aminoethyl)aminoethyl-5-bromo-2-thienylketone (8843)
2-(N-mercaptoethyl)aminoethyl-5-bromo-2-thienylketone (8844)
2-(N-phenyl-N-n-butyl)aminoethyl-5-bromo-2-thienylketone (8847)
2-(N,N-di-n-butyl)aminoethyl-5-bromo-2-thienylketone (8848)
2-(N,N-di-sec-butyl)aminoethyl-5-bromo-2-thienylketone (8849)
N,N-bis(2-(5-bromo-2-thiophenoyl)ethyl)cystamine (8823)
N-2-furoyl-piperadinoethyl-5-bromo-2-thienylketone (8851)
2-(N-2-hydroxy-3-aminopropyl)aminoethyl-5-bromo-2-thienylketone (8853)
2-(N-4-aminobutyl-N-3-aminopropyl)aminoethyl-5-bromo-2-thienylketone (8854)
2-(N-2-hydroxypyrrolidino)aminoethyl-5-bromo-2-thienylketone (8855)
2-(N-hydroxypropyl-N-5-bromo-thienoylethyl)aminoethyl-5-bromo-2-thienylketone (8856)
2-piperidinoethyl-5-bromo-2-thienylketone (8858)
2-(N-hydroxymethylpiperidinoethyl-5-bromo-2-thienylketone (8860)
2-phenethylaminoethyl-5-bromo-2-thienylketone (8861)
2-(N-5-bromothienoylethylaminoethyl-N-hydroxyethyl)aminoethyl-5-bromo-2-thienylketone (8864)
N,N-bis(5-bromo-2-thienoylethyl)tetramethylenediamine (8866)
2-(N-hydroxy-1-benzylethyl)aminoethyl-5-bromo-2-thienylketone (8867)
2-(N-hydroxyethyl)aminoethyl-5-bromo-2-thienylketone (8868)
2-(N-2-hydroxypropyl)aminoethyl-5-bromo-2-thienylketone (8870)
2-(4-hydroxyethylpiperadino)ethyl-5-bromo-2-thienylketone (8871)
2-(N-hydroxymethyl-N-ethyl)aminoethyl-5-bromo-2-thienylketone (8872)
2-(N-methylpiperadino)ethyl-5-bromo-2-thienylketone (8873)
2-(4-imidazolylethyl)aminoethyl-5-bromo-2-thienylketone (8874)
2-(N-1,1-bishydroxymethylpropyl)aminoethyl-5-bromo-2-thienylketone (8875)
N,N-bis(2-(5-chloro-2-thiophenoyl)ethyl)cystamine (8876)
N,N-bis(2-(4-bromo-benzoyl)ethyl)cystamine (8877)
N,N-bis(2-(benzoyl)ethyl)cystamine (8878)
N,N-bis(2-(2-thiophenoyl)ethyl)cystamine (8879)
N,N-bis(2-naphthoylethyl)cystamine (8881)
N,N-bis(3-pyridinoylethyl)cystamine (8882)
N,N-bis(2-furoylethyl)cystamine (8883)
2-(N-butyl-N-benzyl)aminoethyl-5-bromo-2-thienylketone (8884)
2-(N-butyl-N-benzyl)aminoethyl-5-chloro-2-thienylketone (8885)
2-(N-butyl-N-benzyl)aminoethyl-4-bromophenylketone (8886)
2-(N-butyl-N-benzyl)aminoethyl-4-pyridylketone (8887)
2-(N-butyl-N-benzyl)aminoethyl-2-furylketone (8888)
2-(N-butyl-N-benzyl)aminoethyl-2-naphthylketone (8889)
2-(N-2-hydroxyethyl-N-benzyl)aminoethyl-5-iodo-2-thienylketone (8947)
N,N-bis(2-(3-thiophenoyl)ethyl)cystamine (8891)
N,N-bis(2-(2,5-dichloro-3-thiophenoyl)ethyl)cystamine (8892)
2-N-benzylaminoethyl-5-bromo-2-thienylketone (8840)
2-(N,N-dihexyl)aminoethyl-5-bromo-2-thienylketone (8900)
2-(N,N-diisobutyl)aminoethyl-5-bromo-2-thienylketone (8901)
2-(N,N-dihexyl)aminoethyl-5-chloro-2-thienylketone (8902)
N,N-bis(2-(5-bromo-2-thiophenoyl)ethyl)cystinemethylester (8904)
N,N-bis(2-(5-chloro-2-thiophenoyl)ethyl)cystine (8905)
N,N-bis(4-iodobenzoylethyl)cystamine (8906)
N,N-bis(2-thiophenoylethyl)cystinemethylester (8908)
2-(N-isopropyl-N-benzyl)aminoethyl-5-iodo-2-thienylketone (8946)
N,N-bis(2-naphthoylethyl)cystinemethylester (8910)
N,N-bis(2-(4-bromobenzoyl)ethyl)cystinemethylester (8911)
N,N-bis(2-(4-pyridinoyl)ethyl)cystinemethylester (8912)
N,N-bis(2-(benzothiophenoyl)ethyl)cystinemethylester (8913)
2-diisopropylaminoethyl-5-bromo-2-thienylketone (8925)
2-diisopropylaminoethyl-5-chloro-2-thienylketone (8926)
2-diisopropylaminoethyl-4-pyridylketone (8927)
N,N-bis(4-cyanobenzoylethyl)cystamine (8928)
N,N-bis(4-cyanobenzoylethyl)cystinemethylester (8929)
N,N-bis(2-thiazolylethyl)cystinemethylester (8930)
N,N-bis(2-furoylethyl)cystinemethylester (8931)
N,N-bis(2-pyrazinoylethyl)cystinemethylester (8933)
N,N-bis(2-(5-methyl-2-thiophenoyl)ethyl)cystinemethylester (8932)
N,N-bis(2-fluorenylethyl)cystinemethylester (8936)
2-(N-t-butyl-N-benzyl)aminoethyl-5-iodo-2-thienylketone (8937)
N,N-bis(5-iodo-2-thiophenoylethyl)cystinemethylester (8938)

2-(N-t-butyl-N-benzyl)aminoethyl-3-bromo-2-thienylketone (8939)
2-(N-t-butyl-N-benzyl)aminoethyl-3-bromo-2-pyridylketone (8940)
N,N-bis(2-(5-bromo-2-thiophenoyl)ethyl)cystinemethylester (8941)
N,N-bis-(2-(5-iodo-2-thiophenoyl)ethyl)cystamine (8942)
2-(N,N-diisobutyl)aminoethyl-5-iodo-2-thienylketone (8943)
2-(N,N-isobutyl)aminoethyl-6-bromo-2-pyridylketone (8944)
2-(N,N-isobutyl)aminoethyl-3-bromo-2-thienylketone (8945)

The above compounds, and in particular, the compounds represented by Formula (1), include compounds that have high transglutaminase-inhibiting activities. Many such compounds have an acryloyl (—CO—CH=CH$_2$) group and a substituted or unsubstituted aromatic group such as phenyl, naphthalene, or diphenylmethane. Examples of such compounds include the following compounds (where the numerals in parentheses represent compound ID numbers).

Acryloylbenzene (8184)
4-methyl-1-acryloylbenzene (8185)
4-fluoro-1-acryloylbenzene (8186)
2-acryloylnaphthalene (8213)
1-acryloyl-4-bromobenzene (8266)
2-bromo-4,5-dioxymethylene-1-acryloylbenzene (8200)
1-methyl-6-acryloylnaphthalene (8211)
1-fluoro-6-acryloylnaphthalene (8257)
Acryloyldiphenylmethane (8269)
1-acryloylnaphthalene (8293)

Further preferable examples of the compounds of Formula (1) include the following compounds.
acryloylbenzene (8184)
acryloyldiphenylmethane (8269)

Alternatively, other examples of the compound of the present invention include the following compounds represented by Formula (2), wherein X is halogen and n is 2 (where the numerals in parentheses represent compound ID numbers).
1-(3-chloropropionyl)-4-fluorobenzene (8178)
1-(3-chloropropionyl)-4-methylbenzene (8179)
3-chloropropio-4-bromophenone (8180)

Further preferable examples of the compounds of Formula (2) include the following compounds.
1-(3-chloropropionyl)-4-fluorobenzene (8178)

Alternatively, examples of the compounds of the present invention include the following compounds represented by Formula (3) (where the numerals in parentheses represent compound ID numbers).
2-(N-t-butyl-2-hydroxyethyl)aminoethyl-4-pyridylketone (8672)
2-(N-methylbenzyl)aminoethyl-4-pyridylketone (8673)
2-(N-hydroxyethylbutyl)aminoethyl-4-pyridylketone (8674)
2-(hydroxyethylisopropyl)aminoethyl-3-thiophenylketone (8675)
2-(N-isopropylbenzyl)aminoethyl-4-benzylphenylketone (8285)
2-(N-isopropylbenzyl)aminoethyl-4-methylphenylketone (8286)
2-(N-isopropylbenzyl)aminoethyl-2-naphthylketone (8291)
2-(isopropylbenzyl)aminoethylphenylketone (8299)
2-(N-isopropylbenzyl)aminoethyl-4-methoxyphenylketone (8304)
2-(N-isopropylbenzyl)aminoethyl-2-pyridylketone (8305)
2-(N-methylbenzyl)aminoethyl-2-pyridylketone (8310)
2-(N-methylbenzyl)aminoethyl-5-methyl-2-naphthylketone (8315)
2-(N-isopropylbenzyl)aminoethyl-5-methyl-2-naphthylketone (8316)
2-(N-diphenyl)aminoethyl-5-methyl-2-naphthylketone (8317)
1-(N-benzylisopropyl)aminoethyl-1-naphthylketone (8298)
2-(N-isopropylbenzyl)aminoethyl-5-chloro-2-naphthylketone (8323)
2-(N-isopropylbenzyl)aminoethyl-4-phenoxyphenylketone (8324)
2-(N-methylbenzyl)aminoethyl-4-phenoxyphenylketone (8327)
2-(N-2-hydroxy-2-phenylethyl)aminoethyl-4-phenoxyphenylketone (8329)
2-piperidinoethyl-5-chloro-2-naphthylketone (8330)
2-(N-2-hydroxyethylbenzyl)aminoethyl-5-chloro-2-naphthylketone (8331)
2-(N-1,1-dihydroxymethylpropyl)aminoethyl-5-chloro-2-naphthylketone (8332)
2-(N-2-hydroxyethylbutyl)aminoethyl-5-chloro-2-naphthylketone (8333)
2-(N-t-butylbenzyl)aminoethyl-2-pyridylketone (8336)
2-(N-hydroxymethylbenzyl)aminoethyl-2-pyridylketone (8339)
2-(N-methylbenzyl)aminoethyl-2-naphthylketone (8346)
2-(N-methylhydroxyethyl)aminoethyl-2-naphthylketone (8347)
N-benzylethylaminoethyl-3-thiophenylketone (8677)
N,N-bis(2-hydroxyethyl)aminoethyl-2-pyrazylketone (8678)
2-(N-isopropylbenzyl)aminoethyl-4-benzylphenylketone (8361)
2-(N-methylbenzyl)aminoethyl-4-benzylphenylketone (8362)
2-(N-t-butylbenzyl)aminoethyl-4-benzylphenylketone (8363)
2-(N-isopropylbenzyl)aminoethyl-3-pyridylketone (8366)
2-(N-isopropylbenzyl)aminoethyl-4-pyridylketone (8367)
2-(N-butyl-2-hydroxyethyl)aminoethyl-2-pyrazinylketone (8679)
2-(N-isopropylbenzyl)aminoethyl-2-furylketone (8370)
2-(N-ethylbenzyl)aminoethyl-2-pyrazinylketone (8680)
2-(N-mercaptoethyl)aminoethyl-4-phenoxyphenylketone (8375)
2-(N-imidazolylethyl)aminoethyl-4-phenoxyphenylketone (8376)
2-(N-hydroxyethylbutyl)aminoethyl-4-phenoxyphenylketone (8377)
2-(N-furoylpiperazyl)aminoethyl-4-phenoxyphenylketone (8378)
2-(N-diethyl)aminoethyl-4-phenoxyphenylketone (8379)
2-(N-isopropylbenzyl)aminoethyl-2-pyrazylketone (8381)
2-(N-isopropylbenzyl)aminoethyl-2-thiazolylketone (8384)
2-(N-t-butylbenzyl)aminoethyl-2-furylketone (8385)
2-(N-t-butylhydroxyethyl)aminoethyl-2-furylketone (8387)
2-(N-hydroxyethylbenzyl)aminoethyl-2-furylketone (8388)
2-(N-methylbenzyl)aminoethyl-2-thiophenylketone (8389)
2-(N-methylhydroxyethyl)aminoethyl-2-thiophenylketone (8390)
2-hydroxymethylpyrazinylethyl-2-thiophenylketone (8391)
2-(N-benzylhydroxyethyl)aminoethyl-2-pyrazylketone (8397)
2-(N-bis-hydroxyethyl)aminoethyl-2-furylketone (8398)
2-(N-phenylhydroxyethyl)aminoethyl-4-pyridylketone (8402)

2-(N-benzylhydroxyethyl)aminoethyl-4-pyridylketone (8403)
2-(N-benzylhydroxyethyl)aminoethyl-5-methyl-2-furylketone (8404)
2-(N-benzyl-t-butyl)aminoethyl-5-methyl-2-furylketone (8405)
2-(N-dibenzyl)aminoethyl-5-methyl-2-furylketone (8406)
2-(N-benzylhydroxyethyl)aminoethyl-5-methyl-2-furylketone (8407)
2-(N-methylhydroxyethyl)aminoethyl-5-methyl-2-furylketone (8409)
2-(N-benzylethyl)aminoethyl-2-furylketone (8412)
2-(N,N-dihydroxyethyl)aminoethyl-2-thiazolylketone (8682)
2-(N-benzylethyl)aminoethyl-3-pyridylketone (8414)
2-(N-bishydroxyethyl)aminoethyl-5-methyl-2-furylketone (8415)
2-(N-isopropylhydroxyethyl)aminoethyl-5-methyl-2-furylketone (8416)
2-(N-bishydroxyethyl)aminoethyl-2-naphthylketone (8418)
2-(N-dihydroxyethyl)aminoethylthiophenylketone (8420)
2-(N-isopropylhydroxyethyl)aminoethyl-2-pyrazylketone (8422)
2-(N-hydroxyethylisopropyl)aminoethyl-2-furylketone (8424)
2-(N-hydroxyethylisopropyl)aminoethyl-2-pyridylketone (8426)
2-(N-hydroxyethylisopropyl)aminoethyl-4-pyridylketone (8428)
2-(N-hydroxyethylisopropyl)aminoethyl-2-thiazolylketone (8429)
2-(N-isopropylhydroxyethyl)aminoethyl-3'-pyridylketone (8433)
2-(N-hydroxyethylisopropyl)aminoethyl-4-fluorophenylketone (8503)
2-(N-methyl-2-hydroxyethyl)aminoethyl-2-(N-methylpyrrolyl)ketone (8685)
2-(N-isopropylbenzyl)aminomethyl-4-phenylketone (8506)
2-(N-isopropyl-2-hydroxyethyl)aminoethyl-2-(N-methylpyrrolyl)ketone (8686)
2-(N-isopropyl-2-hydroxyethyl)aminoethyl-2-pyrrolylketone (8687)
2-(N-bis(hydroxyethyl))aminoethyl-2-furylketone (8516)
2-(N-2-hydroxyethylbenzyl)aminoethyl-3-pyridylketone (8691)
3-(N-isopropylbenzyl)aminopropylphenylketone (8523)
2-(N-2-hydroxyethylbutyl)aminoethyl-3-pyridylketone (8692)
1-methyl-2-(N-hydroxyethylisopropyl)aminoethyl-2-fluorophenylketone (8525)
1-methyl-2-(N-benzylisopropyl)aminoethyl-2-fluorophenylketone (8526)
2-(N-isopropylbenzyl)aminoethyl-2-thiophenylketone (8651)
2-(N-2-hydroxyethylbenzyl)aminoethyl-3-thiophenylketone (8652)
2-(N-isopropylbenzyl)aminoethyl-2-(3-ethyl)-pyrazylketone (8656)
2-(N-hydroxyethylbenzyl)aminoethyl-2-(3-ethyl)-pyrazylketone (8657)
2-(N-t-butylbenzyl)aminoethyl-2-(3-ethyl)-pyrazylketone (8658)
2-N-adamantane-aminoethyl-2-methylfurylketone (8534)
2-(N-t-butylbenzyl)aminoethyl-2-thiophenylketone (8638)
2-(N-isopropylhydroxyethyl)aminoethyl-2-thiophenylketone (8639)
2-(N-isopropylbenzyl)aminoethyl-1-methyl-2-pyrrylketone (8646)
3-(N-benzylisopropyl)aminopropionylcaprolactam (8563)
2-(N-isopropylbenzyl)aminomethyl-3-(2,5-dichlorothiophenyl)ketone (8659)
2-(N-isopropyl-2-hydroxyethyl)aminomethyl-3-(2,5-dichlorothiophenyl)ketone (8660)
2-(N-2-hydroxyethylbenzyl)aminomethyl-3-(2,5-dichlorothiophenyl)ketone (8661)
2-(N-hydroxyethylisopropyl)aminoethyl-2-naphthylketone (8570)
2-(N-hydroxyethylisopropyl)aminomethylphenylketone (8572)
2-(N-hydroxyethylmethyl)aminoethyl-2-pyrazylketone (8593)
2-(N-ethylbenzyl)aminoethyl-4-pyridylketone (8594)
2-(N-t-butylbenzyl)aminoethyl-4-pyridylketone (8595)
2-(N-2-furylpiperadino)ethyl-4-fluorophenylketone (8596)
2-(N-isopropylbenzyl)aminoethyl-4-fluorophenylketone (8597)
2-(N-2-benzyl-t-butyl)aminoethyl-2-pyrazylketone (8693)
2-(N-2-hydroxyethyl-t-butyl)aminoethyl-2-pyrazylketone (8694)
2-(N-benzylmethyl)aminoethyl-2-pyrazylketone (8695)
Bis-N,N-(4-pyrizoylethyl)spermidine (8603)
2-hydroxypiperidinoethyl-4-pyridylketone (8604)
2-(N-benzylethyl)aminoethyl-2-florenylketone (8663)
2-(N-benzylisopropyl)aminoethyl-5-(2,4-dimethylthiazolyl)ketone (8666)
2-(N-isopropylbenzyl)aminoethyl-3-thiophenylketone (8625)
2-(N-isopropylbenzyl)aminoethyl-4,5-dimethyl-2-furylketone (8696)
2-(N-2-hydroxyethylethyl)aminoethyl-4,5-dimethyl-2-furylketone (8697)
2-(N-2-hydroxyethylbenzyl)aminoethyl-4,5-dimethyl-2-furylketone (8698)
2-(N-2-hydroxyethylethyl)aminoethyl-2,5-dimethyl-3-thiophenylketone (8699)
2-(N-benzyl-t-butyl)aminoethyl-3-pyridylketone (8702)
2-(N-t-butyl-2-hydroxyethyl)aminoethyl-3-pyridylketone (8703)
2-(N-benzylmethyl)aminoethyl-2-furylketone (8705)
2-(N-2-hydroxyethylbutyl)aminoethyl-2-furylketone (8706)
2-(N-2-hydroxyethylmethyl)aminoethyl-2-furylketone (8707)
2-(N-benzylmethyl)aminoethyl-3-thiophenylketone (8708)
2-(N-2-hydroxyethylbutyl)aminoethyl-3-thiophenylketone (8709)
2-(N-benzyl-t-butyl)aminoethyl-3-thiophenylketone (8710)
2-(N-benzylethyl)aminoethyl-5-methyl-2-furylketone (8711)
2-(N-2-hydroxyethyl-t-butyl)aminoethyl-5-methyl-2-furylketone (8712)
2-(N-benzylmethyl)aminoethyl-5-methyl-2-furylketone (8713)
2-(N-benzylethyl)aminoethyl-2-pyridylketone (8714)
2-(N-bis-2-hydroxyethyl)aminoethyl-2-pyridylketone (8715)
2-(N-t-butyl-2-hydroxyethyl)aminoethyl-2-pyridylketone (8716)
2-(N-benzyl-2-hydroxyethyl)aminoethyl-2-thiophenylketone (8717)
2-(N-t-butyl-2-hydroxyethyl)aminoethyl-2-thiophenylketone (8718)
2-(N-butyl-2-hydroxyethyl)aminoethyl-2-thiophenylketone (8719)

2-(N-benzylmethyl)aminoethyl-3-pyridylketone (8720)
2-(N-bis-2-hydroxyethyl)aminoethyl-4-pyridylketone (8721)
2-(N-2-hydroxyethylbutyl)aminoethyl-4-pyridylketone (8723)
2-(N-methyl-2-hydroxyethyl)aminoethyl-2-pyridylketone (8724)
2-(N-isopropyl-2-hydroxyethyl)aminoethyl-3-ethyl-2-pyrazylketone (8725)
2-(N-benzylethyl)aminoethyl-2-thiophenylketone (8734)
2-(N-2-hydroxyethylmethyl)aminoethyl-3-thiophenylketone (8727)
2-(N-2-hydroxyethylbutyl)aminoethyl-5-methyl-2-furylketone (8728)
2-(N-benzyl-t-butyl)aminoethyl-2-thiazolylketone (8729)
2-(N-benzylmethyl)aminoethyl-2-thiazolylketone (8731)
2-(N-2-hydroxyethylmethyl)aminoethyl-3-pyridylketone (8732)
2-(N-bis-hydroxyethyl)aminoethyl-3-ethyl-2-pyrazylketone (8733)
2-(N-bis-hydroxyethyl)aminoethyl-2-thiophenylketone (8676)
2-(N-2-hydroxyethylmethyl)aminoethyl-4-pyridylketone (8722)
2-(N-benzylisopropyl)aminoethyl-4-methyl-2-thiazolylketone (8738)
2-(N-butyl-2-hydroxyethyl)aminoethyl-4-methyl-2-thiazolylketone (8739)
2-(N-benzylmethyl)aminoethyl-4-methyl-2-thiazolylketone (8740)
2-(N-benzylisopropyl)aminoethyl-5-chloro-2-thiophenylketone (8741)
2-(N-2-hydroxyethylisopropyl)aminoethyl-5-chloro-2-thiophenylketone (8742)
2-(N-benzyl-2-hydroxyethyl)aminoethyl-5-chloro-2-thiophenylketone (8743)
2-(N-t-butylbenzyl)aminoethyl-5-bromo-2-thiophenylketone (8778)
2-(N-1,2-diphenyl-2-hydroxyethyl)aminoethyl-2-furylketone (8748)
N,N-bis(2-pyrazoylethyl)-N-hydroxyethylethylenediamine (8749)
2-(N-1-benzyl-2-hydroxyethyl)aminoethyl-4-pyridylketone (8750)
2-(N-2-hydroxyethyl)aminoethyl-2-furylketone (8751)
N,N-bis(2-pyrazoylethyl)tetramethylenediamine (8752)
2-bis(N-2-hydroxyethyl)aminoethyl-5-chloro-2-thienylketone (8753)
2-(N-ethylbenzyl)aminoethyl-5-chloro-2-thienylketone (8754)
2-(N-methylbenzyl)aminoethyl-5-chloro-2-thienylketone (8755)
2-(N-t-butylbenzyl)aminoethyl-5-chloro-2-thienylketone (8756)
2-(2-hydroxymethylpyrrolidino)ethyl-2-pyrazylketone (8758)
2-(N-isopropylbenzyl)aminoethyl-2-benzothienylketone (8759)
2-(N-isopropyl-2-hydroxyethyl)aminoethyl-2-benzothienylketone (8760)
2-(N-t-butylbenzyl)aminoethyl-2-benzothienylketone (8761)
2-(N-isopropylbenzyl)aminoethylferrocenylketone (8762)
2-(N-isopropyl-2-hydroxyethyl)aminoethylferrocenylketone (8763)
2-bis(N-2-hydroxyethyl)aminoethylferrocenylketone (8764)
2-(N-ethylbenzyl)aminoethyl-2-thiazolylketone (8765)
2-(N-2-hydroxyethylbenzyl)aminoethyl-2-thiazolylketone (8766)
2-(N-2-hydroxyethylmethyl)aminoethyl-2-thiazolylketone (8767)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-isopropylbenzyl)aminoethyl-1-4-biphenylketone (8774)
2-(N-2-hydroxyethylisopropyl)aminoethyl-4-biphenylketone (8775)
2-(N-2-hydroxyethylphenyl)aminoethyl-4-biphenylketone (8776)
2-(N-phenethyl)aminoethyl-2-furylketone (8745)
2-(N-ethylbenzyl)aminoethyl-5-bromo-2-thienylketone (8779)
2-(N-t-butylbenzyl)aminoethyl-4-cyanophenylketone (8789)
4-tolyl(N-benzyl-N-t-butyl)aminoethylketone (8793)
4-cyanophenyl(N-benzyl-N-t-butyl)aminoethylketone (8794)
2-(N-t-butyl-N-benzyl)aminoethyl-4-chlorophenylketone (8799)
2-(N-hydroxyethyl)aminoethyl-5-bromo-2-thienylketone (8802)
2-(N-benzylisopropyl)aminoethyl-4-cyanophenylketone (8803)
2-(N-hydroxylethylisopropyl)aminoethyl-4-cyanophenylketone (8804)
2-(N-benzylisopropyl)aminoethyl-4-chloro-phenylketone (8805)
2-(N-hydroxyethylisopropyl)aminoethyl-4-chloro-phenylketone (8806)
2-(N-hydroxyethylisopropyl)aminoethylphenylketone (8807)
2-(N-benzylethyl)aminoethyl-4-fluorophenylketone (8808)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N-benzyl-t-butyl)aminoethyl-5,6-ethylenedioxy-2-phenylketone (8820)
2-(N-benzylisopropyl)aminoethyl-5-methyl-2-thienylketone (8822)
2-(N-benzylethyl)aminoethyl-5-methyl-2-thienylketone (8823)
2-(N,N-bis-(2-hydroxyethyl)aminoethyl-5-iodo-2-thienylketone (8948)
2-(N-benzylisopropyl)aminoethyl-4-methyl-2-thienylketone (8828)
2-(N-dibenzyl)aminoethyl-4-methyl-2-thienylketone (8829)
2-(N-benzylhydroxyethyl)aminoethyl-4-methyl-2-thienylketone (8830)
2-(N-benzyl-t-butyl)aminoethyl-4-bromophenylketone (8831)
2-(N-dibenzyl)aminoethyl-5-bromo-2-thienylketone (8832)
2-(N-benzylmethyl)aminoethyl-5-bromo-2-thienylketone (8833)
2-(N-benzylhydroxyethyl)aminoethyl-5-bromo-2-thienylketone (8834)
2-(N-hydroxyethylmethyl)aminoethyl-5-bromo-2-thienylketone (8835)
2-(N-hydroxyethylisopropyl)aminoethyl-5-bromo-2-thienylketone (8836)

2-(N-bishydroxyethyl)aminoethyl-5-bromo-2-thienylketone (8837)
2-(N-2-hydroxyethylethyl)aminoethyl-5-bromo-2-thienylketone (8838)
2-(N-hydroxyethyl-t-butyl)aminoethyl-5-bromo-2-thienylketone (8839)
2-(2-hydroxymethylpyrrolidinyl)aminoethyl-5-bromo-2-thienylketone (8842)
2-(N-2-hydroxyethyl-N-2-aminoethyl)aminoethyl-5-bromo-2-thienylketone (8843)
2-(N-mercaptoethyl)aminoethyl-5-bromo-2-thienylketone (8844)
2-(N-phenyl-N-n-butyl)aminoethyl-5-bromo-2-thienylketone (8847)
2-(N,N-di-n-butyl)amino ethyl-5-bromo-2-thienylketone (8848)
2-(N,N-di-sec-butyl)aminoethyl-5-bromo-2-thienylketone (8849)
N,N-bis(2-(5-bromo-2-thiophenoyl)ethyl)cystamine (8823)
N-2-furoyl-piperadinoethyl-5-bromo-2-thienylketone (8851)
2-(N-2-hydroxy-3-aminopropyl)aminoethyl-5-bromo-2-thienylketone (8853)
2-(N-4-aminobutyl-N-3-aminopropyl)aminoethyl-5-bromo-2-thienylketone (8854)
2-(N-2-hydroxypyrrolidino)aminoethyl-5-bromo-2-thienylketone (8855)
2-(N-hydroxypropyl-N-5-bromo-thienoylethyl)aminoethyl-5-bromo-2-thienylketone (8856)
2-piperidinoethyl-5-bromo-2-thienylketone (8858)
2-(N-hydroxymethylpiperidinoethyl-5-bromo-2-thienylketone (8860)
2-phenethylaminoethyl-5-bromo-2-thienylketone (8861)
2-(N-5-bromothienoylethylaminoethyl-N-hydroxyethyl)aminoethyl-5-bromo-2-thienylketone (8864)
N,N-bis(5-bromo-2-thienoylethyl)tetramethylenediamine (8866)
2-(N-hydroxy-1-benzylethyl)aminoethyl-5-bromo-2-thienylketone (8867)
2-(N-hydroxyethyl)aminoethyl-5-bromo-2-thienylketone (8868)
2-(N-2-hydroxypropyl)aminoethyl-5-bromo-2-thienylketone (8870)
2-(4-hydroxyethylpiperadino)ethyl-5-bromo-2-thienylketone (8871)
2-(N-hydroxymethyl-N-ethyl)aminoethyl-5-bromo-2-thienylketone (8872)
2-(N-methylpiperadino)ethyl-5-bromo-2-thienylketone (8873)
2-(4-imidazolylethyl)aminoethyl-5-bromo-2-thienylketone (8874)
2-(N-1,1-bishydroxymethylpropyl)aminoethyl-5-bromo-2-thienylketone (8875)
N,N-bis(2-(5-chloro-2-thiophenoyl)ethyl)cystamine (8876)
N,N-bis(2-(4-bromo-benzoyl)ethyl)cystamine (8877)
N,N-bis(2-(benzoyl)ethyl)cystamine (8878)
N,N-bis(2-(2-thiophenoyl)ethyl)cystamine (8879)
N,N-bis(2-naphthoylethyl)cystamine (8881)
N,N-bis(3-pyridinoylethyl)cystamine (8882)
N,N-bis(2-furoylethyl)cystamine (8883)
2-(N-butyl-N-benzyl)aminoethyl-5-bromo-2-thienylketone (8884)
2-(N-butyl-N-benzyl)aminoethyl-5-chloro-2-thienylketone (8885)
2-(N-butyl-N-benzyl)aminoethyl-4-bromophenylketone (8886)
2-(N-butyl-N-benzyl)aminoethyl-4-pyridylketone (8887)
2-(N-butyl-N-benzyl)aminoethyl-2-furylketone (8888)
2-(N-butyl-N-benzyl)aminoethyl-2-naphthylketone (8889)
2-(N-2-hydroxyethyl-N-benzyl)aminoethyl-5-iodo-2-thienylketone (8947)
N,N-bis(2-(3-thiophenoyl)ethyl)cystamine (8891)
N,N-bis(2-(2,5-dichloro-3-thiophenoyl)ethyl)cystamine (8892)
2-N-benzylaminoethyl-5-bromo-2-thienylketone (8840)
2-(N,N-dihexyl)aminoethyl-5-bromo-2-thienylketone (8900)
2-(N,N-diisobutyl)aminoethyl-5-bromo-2-thienylketone (8901)
2-(N,N-dihexyl)aminoethyl-5-chloro-2-thienylketone (8902)
N,N-bis(2-(5-bromo-2-thiophenoyl)ethyl)cystinemethylester (8904)
N,N-bis(2-(5-chloro-2-thiophenoyl)ethyl)cystine (8905)
N,N-bis(4-iodobenzoylethyl)cystamine (8906)
N,N-bis(2-thiophenoylethyl)cystinemethylester (8908)
2-(N-isopropyl-N-benzyl)aminoethyl-5-iodo-2-thienylketone (8946)
N,N-bis(2-naphthoylethyl)cystinemethylester (8910)
N,N-bis(2-(4-bromobenzoyl)ethyl)cystinemethylester (8911)
N,N-bis(2-(4-pyridinoyl)ethyl)cystinemethylester (8912)
N,N-bis(2-(benzothiophenoyl)ethyl)cystinemethylester (8913)
2-diisopropylaminoethyl-5-bromo-2-thienylketone (8925)
2-diisopropylaminoethyl-5-chloro-2-thienylketone (8926)
2-diisopropylaminoethyl-4-pyridylketone (8927)
N,N-bis(4-cyanobenzoylethyl)cystamine (8928)
N,N-bis(4-cyanobenzoylethyl)cystinemethylester (8929)
N,N-bis(2-thiazolylethyl)cystinemethylester (8930)
N,N-bis(2-furoylethyl)cystinemethylester (8931)
N,N-bis(2-pyrazinoylethyl)cystinemethylester (8933)
N,N-bis(2-(5-methyl-2-thiophenoyl)ethyl)cystinemethylester (8932)
N,N-bis(2-fluorenylethyl)cystinemethylester (8936)
2-(N-t-butyl-N-benzyl)aminoethyl-5-iodo-2-thienylketone (8937)
N,N-bis(5-iodo-2-thiophenoylethyl)cystinemethylester (8938)
2-(N-t-butyl-N-benzyl)aminoethyl-3-bromo-2-thienylketone (8939)
2-(N-t-butyl-N-benzyl)aminoethyl-3-bromo-2-pyridylketone (8940)
N,N-bis(2-(5-bromo-2-thiophenoyl)ethyl)cystinemethylester (8941)
N,N-bis-(2-(5-iodo-2-thiophenoyl)ethyl)cystamine (8942)
2-(N,N-diisobutyl)aminoethyl-5-iodo-2-thienylketone (8943)
2-(N,N-isobutyl)aminoethyl-6-bromo-2-pyridylketone (8944)
2-(N,N-isobutyl)aminoethyl-3-bromo-2-thienylketone (8945)

Preferable examples of the compound of Formula (3) are described below (where the numerals in parentheses represent compound ID numbers).

2-(N-methylbenzyl)aminoethyl-4-pyridylketone (8673)
2-(N-hydroxyethylbutyl)aminoethyl-4-pyridylketone (8674)
2-(N-isopropylbenzyl)aminoethyl-4-benzylphenylketone (8285)
2-(N-isopropylbenzyl)aminoethyl-2-pyridylketone (8305)
2-(N-2-hydroxyethylbenzyl)aminoethyl-5-chloro-2-naphthylketone (8331)
2-(N-2-hydroxyethylbutyl)aminoethyl-5-chloro-2-naphthylketone (8333)

2-(N-t-butylbenzyl)aminoethyl-2-pyridylketone (8336)
2-(N-isopropylbenzyl)aminoethyl-3-pyridylketone (8366)
2-(N-isopropylbenzyl)aminoethyl-4-pyridylketone (8367)
2-(N-butyl-2-hydroxyethyl)aminoethyl-2-pyrazinylketone (8679)
2-(N-isopropylbenzyl)aminoethyl-2-furylketone (8370)
2-(N-ethylbenzyl)aminoethyl-2-pyrazinylketone (8680)
2-(N-isopropylbenzyl)aminoethyl-2-pyrazylketone (8381)
2-(N-isopropylbenzyl)aminoethyl-2-thiazolylketone (8384)
2-(N-t-butylbenzyl)aminoethyl-2-furylketone (8385)
2-(N-benzylhydroxyethyl)aminoethyl-2-pyrazylketone (8397)
2-(N-benzylhydroxyethyl)aminoethyl-5-methyl-2-furylketone (8404)
2-(N-benzyl-t-butyl)aminoethyl-5-methyl-2-furylketone (8405)
2-(N-benzylethyl)aminoethyl-2-furylketone (8412)
2-(N-hydroxyethylisopropyl)aminoethyl-2-furylketone (8424)
2-(N-isopropylbenzyl)aminoethyl-2-(3-ethyl)-pyrazylketone (8656)
2-(N-t-butylbenzyl)aminoethyl-2-(3-ethyl)-pyrazylketone (8658)
2-(N-t-butylbenzyl)aminoethyl-2-thiophenylketone (8638)
2-(N-isopropylbenzyl)aminomethyl-3-(2,5-dichlorothiophenyl)ketone (8659)
2-(N-isopropyl-2-hydroxyethyl)aminomethyl-3-(2,5-dichlorothiophenyl)ketone (8660)
2-(N-2-hydroxyethylbenzyl)aminomethyl-3-(2,5-dichlorothiophenyl)ketone (8661)
2-(N-ethylbenzyl)aminoethyl-4-pyridylketone (8594)
2-(N-t-butylbenzyl)aminoethyl-4-pyridylketone (8595)
2-(N-2-furylpiperadino)ethyl-4-fluorophenylketone (8596)
2-(N-isopropylbenzyl)aminoethyl-4-fluorophenylketone (8597)
2-(N-benzylisopropyl)aminoethyl-5-(2,4-dimethylthiazolyl)ketone (8666)
2-(N-isopropylbenzyl)aminoethyl-4,5-dimethyl-2-furylketone (8696)
2-(N-2-hydroxyethylethyl)aminoethyl-4,5-dimethyl-2-furylketone (8697)
2-(N-2-hydroxyethylbenzyl)aminoethyl-4,5-dimethyl-2-furylketone (8698)
2-(N-benzyl-t-butyl)aminoethyl-3-pyridylketone (8702)
2-(N-2-hydroxyethylbutyl)aminoethyl-2-furylketone (8706)
2-(N-2-hydroxyethylmethyl)aminoethyl-2-furylketone (8707)
2-(N-benzylethyl)aminoethyl-5-methyl-2-furylketone (8711)
2-(N-2-hydroxyethyl-t-butyl)aminoethyl-5-methyl-2-furylketone (8712)
2-(N-benzylethyl)aminoethyl-2-pyridylketone (8714)
2-(N-benzylethyl)aminoethyl-2-thiophenylketone (8734)
2-(N-2-hydroxyethylbutyl)aminoethyl-5-methyl-2-furylketone (8728)
2-(N-benzyl-t-butyl)aminoethyl-2-thiazolylketone (8729)
2-(N-benzylmethyl)aminoethyl-2-thiazolylketone (8731)
2-(N-benzylisopropyl)aminoethyl-4-methyl-2-thiazolylketone (8738)
2-(N-benzylisopropyl)aminoethyl-5-chloro-2-thiophenylketone (8741)
2-(N-t-butylbenzyl)aminoethyl-5-bromo-2-thiophenylketone (8778)
2-(N-ethylbenzyl)aminoethyl-5-chloro-2-thienylketone (8754)
2-(N-t-butylbenzyl)aminoethyl-5-chloro-2-thienylketone (8756)
2-(N-isopropylbenzyl)aminoethyl-2-benzothienylketone (8759)
2-(N-t-butylbenzyl)aminoethyl-2-benzothienylketone (8761)
2-(N-isopropylbenzyl)aminoethylferrocenylketone (8762)
2-(N-ethylbenzyl)aminoethyl-2-thiazolylketone (8765)
2-(N-2-hydroxyethylbenzyl)aminoethyl-2-thiazolylketone (8766)
2-(N-2-hydroxyethylmethyl)aminoethyl-2-thiazolylketone (8767)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-t-butylbenzyl)aminoethyl-4-cyanophenylketone (8789)
4-cyanophenyl(N-benzyl-N-t-butyl)aminoethylketone (8794)
2-(N-t-butyl-N-benzyl)aminoethyl-4-chlorophenylketone (8799)
2-(N-benzylisopropyl)aminoethyl-4-cyanophenylketone (8803)
2-(N-benzylisopropyl)aminoethyl-4-chloro-phenylketone (8805)
2-(N-hydroxyethylisopropyl)aminoethyl-4-chloro-phenylketone (8806)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N-benzylisopropyl)aminoethyl-4-methyl-2-thienylketone (8828)
2-(N-benzyl-t-butyl)aminoethyl-4-bromophenylketone (8831)
2-(N-dibenzyl)aminoethyl-5-bromo-2-thienylketone (8832)
2-(N-benzylmethyl)aminoethyl-5-bromo-2-thienylketone (8833)
2-(N-benzylhydroxyethyl)aminoethyl-5-bromo-2-thienylketone (8834)
2-(N,N-di-n-butyl)amino ethyl-5-bromo-2-thienylketone (8848)
2-(N,N-di-sec-butyl)aminoethyl-5-bromo-2-thienylketone (8849)
2-(N-2-hydroxy-3-aminopropyl)aminoethyl-5-bromo-2-thienylketone (8853)
2-(N-hydroxymethylpiperidinoethyl-5-bromo-2-thienylketone (8860)
N,N-bis(2-(benzoyl)ethyl)cystamine (8878)
N,N-bis(2-furoylethyl)cystamine (8883)
2-(N-butyl-N-benzyl)aminoethyl-4-bromophenylketone (8886)
2-(N-butyl-N-benzyl)aminoethyl-2-naphthylketone (8889)
2-diisopropylaminoethyl-4-pyridylketone (8927)
2-(N-t-butyl-N-benzyl)aminoethyl-5-iodo-2-thienylketone (8937)
2-(N-t-butyl-N-benzyl)aminoethyl-3-bromo-2-pyridylketone (8940)
2-(N,N-diisobutyl)aminoethyl-5-iodo-2-thienylketone (8943)

In addition, the compounds shown in table 1 below are characterized in that they strongly exhibit a TG-activity-inhibiting action or protein-crosslinking-inhibiting action and also strongly exhibit an IICR-inhibiting activity but almost no SOCE-inhibiting activity.

TABLE 1

| Example | Compound ID number | Structural Formula | SOCE IC50 (μmol) | IICR IC50 (μmol) | TG IC50 (μmol) |
|---|---|---|---|---|---|
| 153 | 8424 | 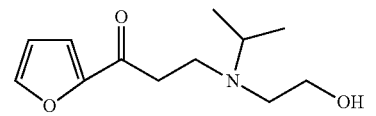 [SMILES: CC(C)N(CCO)CCC(=O)c1ccco1] | 100> | 20 | 0.3 |
| 121 | 8385 | 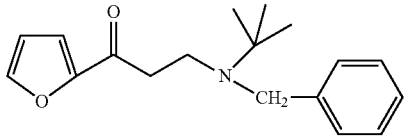 [SMILES: CC(C)(C)N(CCC(=O)c1ccco1)Cc1ccccc1] | 100> | 30 | 0.5 |
| 117 | 8381 | 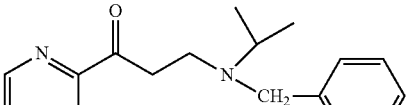 | 100> | 30 | 2 |
| 107 | 8367 | 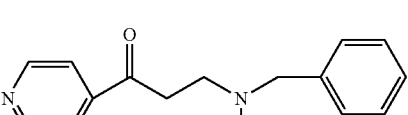 | 100> | 10< | 1.3 |
| 106 | 8366 | 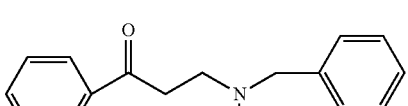 | 100> | 10< | 0.4 |

In addition to the compounds shown in table 1, the following compounds similarly exhibit an excellent activity (where the numerals in parentheses represent compound ID numbers). These compounds also strongly exhibit a TG-activity-inhibiting action or protein-crosslinking-inhibiting action and have an IICR-inhibiting activity higher than SOCE-inhibiting activity.

2-(N-methylbenzyl)aminoethyl-4-pyridylketone (8673)
2-(N-isopropylbenzyl)aminoethyl-4-benzylphenylketone (8285)
2-(N-isopropylbenzyl)aminoethyl-2-pyridylketone (8305)
2-(N-isopropylbenzyl)aminoethyl-2-furylketone (8370)
2-(N-benzylhydroxyethyl)aminoethyl-2-pyrazylketone (8397)
2-(N-benzylhydroxyethyl)aminoethyl-5-methyl-2-furylketone (8404)
2-(N-benzyl-t-butyl)aminoethyl-5-methyl-2-furylketone (8405)
2-(N-benzylethyl)aminoethyl-2-furylketone (8412)
2-(N-isopropylbenzyl)aminoethyl-2-(3-ethyl)-pyrazylketone (8656)
2-(N-t-butylbenzyl)aminoethyl-2-(3-ethyl)-pyrazylketone (8658)
2-(N-t-butylbenzyl)aminoethyl-2-thiophenylketone (8638)
2-(N-isopropylbenzyl)aminomethyl-3-(2,5-dichlorothiophenyl)ketone (8659)
2-(N-benzylisopropyl)aminoethyl-5-(2,4-dimethylthiazolyl)ketone (8666)
2-(N-benzyl-t-butyl)aminoethyl-3-pyridylketone (8702)
2-(N-2-hydroxyethylmethyl)aminoethyl-2-furylketone (8707)
2-(N-benzyl-t-butyl)aminoethyl-2-thiazolylketone (8729)
2-(N-t-butylbenzyl)aminoethyl-5-bromo-2-thiophenylketone (8778)
2-(N-t-butylbenzyl)aminoethyl-5-chloro-2-thienylketone (8756)
2-(N-isopropylbenzyl)aminoethyl-2-benzothienylketone (8759)
2-(N-t-butylbenzyl)aminoethyl-2-benzothienylketone (8761)
2-(N-ethylbenzyl)aminoethyl-2-thiazolylketone (8765)
2-(N-2-hydroxyethylbenzyl)aminoethyl-2-thiazolylketone (8766)
2-(N-isopropylbenzyl)aminoethyl-5-bromo-2-thienylketone (8768)
2-(N-2-hydroxyethylbutyl)aminoethyl-5-bromo-2-thienylketone (8769)
2-(N-t-butylbenzyl)aminoethyl-4-cyanophenylketone (8789)
4-cyanophenyl(N-benzyl-N-t-butyl)aminoethylketone (8794)
2-(N-benzylisopropyl)aminoethyl-4-cyanophenylketone (8803)
2-(N-benzyl-t-butyl)aminoethyl-3-methyl-2-thienylketone (8816)
2-(N-benzyl-t-butyl)aminoethyl-4-methyl-2-thienylketone (8817)
2-(N-benzyl-t-butyl)aminoethyl-5-methyl-2-thienylketone (8818)
2-(N,N-di-n-butyl)aminoethyl-5-bromo-2-thienylketone (8848)
2-(N,N-di-sec-butyl)aminoethyl-5-bromo-2-thienylketone (8849)
2-(N-2-hydroxy-3-aminopropyl)aminoethyl-5-bromo-2-thienylketone (8853)

The compound of the present invention can be obtained by synthesizing compounds using, for example, a variety of reactions described in the Examples below, purifying the compounds, examining the bioactivity (e.g., transglutaminase-inhibiting activity) levels of the compounds, and selecting an optimum compound.

The compounds of the present invention can be produced by the methods described in the following: H. Dannenberg et al., Zur Darstellung von 1,5-Benzindan, Chemiche Ber. (1955) 88:1405; F. Mayer et al., Uber eine Synthese von Indanen, Ber. (1922) 60:2279; A. E. Vanstone et al., A Covenient Preparation of Viny Ketones, J. Chem. Soc. (C) (1966) 1972; F. Golemba. et al., Polymers of Phenyl Vinyl Ketones, Macromoleculeles (1972) 5:212; and WO 2007/136790, for example.

Purification can be carried out by techniques generally used in the art such as salting-out, extraction, evaporation, distillation, crystallization, and chromatography (e.g., silica gel column chromatography, ion-exchange chromatography, hydrophobic interaction chromatography, size-exclusion chromatography, HPLC, gas chromatography, or thin-layer chromatography). In addition, the obtained compounds can be analyzed by NMR, IR, Mass spectrometry, element analysis, or the like.

The above compounds can be synthesized by Friedel-Crafts reactions (I) and (II) and Grignard reaction (III) with the reaction schemes shown in Reaction formulae (I) to (VIII) below. Ketone (1) can be obtained via chromic acid oxidation of alcohol (4) obtained through Grignard reaction (III) (Reaction formula (IV)). Compound (3) can be obtained through Michael addition of amine and ketone (1) which is an acryloyl compound (Reaction formula (V)). Compound (5) can be obtained by allowing paraformaldehyde and amine to react with ketone (8) (Reaction formula (VI); Mannnich Reaction (Arend M et al., Angew. Chem. Int. Ed (1998) 37: 1044)). When compound (5) is in the acidic condition, a reverse reaction of the Michael reaction occurs to give compound (6) (Reaction formula (VII)). In addition, compound (7) can be obtained by reacting halogenated ketone (compound (2)) (X=Cl)) with amine (Reaction formula (VIII)).

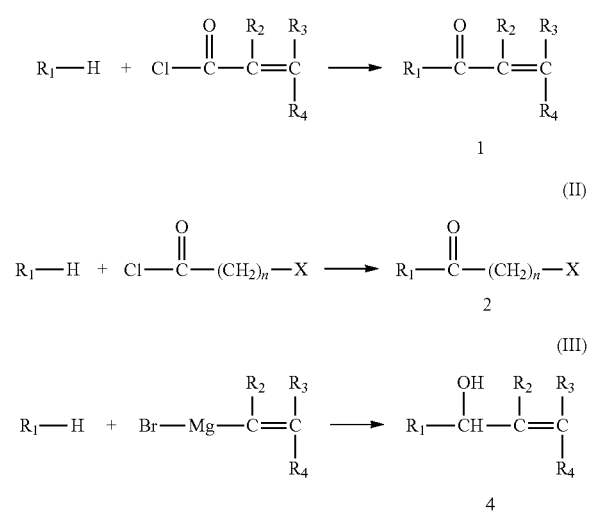
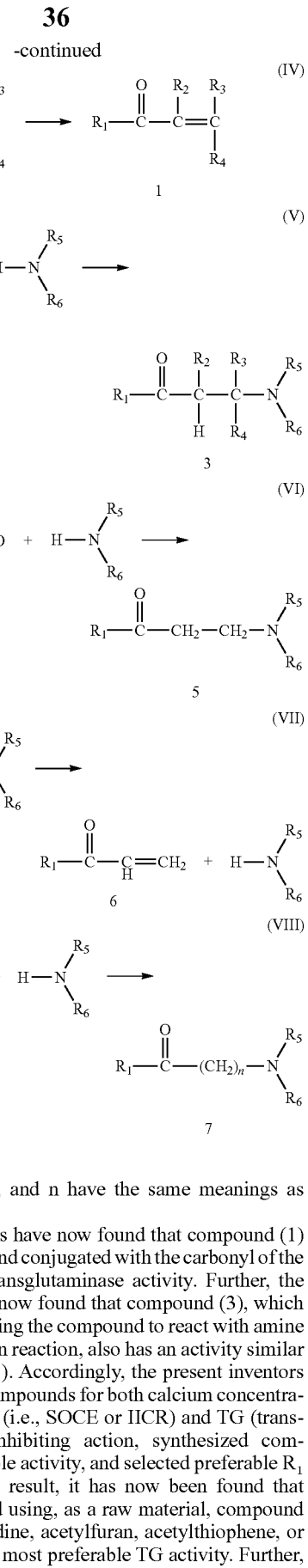

(wherein $R_1$ to $R_6$, X, and n have the same meanings as defined above).

The present inventors have now found that compound (1) comprising a double bond conjugated with the carbonyl of the ketone has a strong transglutaminase activity. Further, the present inventors have now found that compound (3), which is synthesized by allowing the compound to react with amine via the Michael addition reaction, also has an activity similar to that of compound (1). Accordingly, the present inventors assayed the obtained compounds for both calcium concentration modulating action (i.e., SOCE or IICR) and TG (transglutaminase)-activity-inhibiting action, synthesized compounds having preferable activity, and selected preferable $R_1$ to $R_6$, X, and n. As a result, it has now been found that compound (5) obtained using, as a raw material, compound (8), such as acetylpyridine, acetylfuran, acetylthiophene, or acetylpyrazine, has the most preferable TG activity. Further, the present inventors have now found the compounds exemplified above, which are characterized in that they have low levels of or no SOCE-inhibiting activity but high levels of IICR-inhibiting activity, among the above-described compounds.

The compounds of the present invention have TG-activity-inhibiting action, i.e., protein-crosslinking-inhibiting action. As such, they can be used as prophylactic/therapeutic drugs or pharmaceutical compositions for preventing or treating diseases caused by abnormal protein crosslinking reactions. Examples of such diseases include Alzheimer's disease, Huntington's disease, Parkinson's disease, Celiac disease, cataract, mad cow disease, congenital lamellar ichthyosis, congenital hemostatic disorder, liver disorder, autoimmune disease, and cerebral infarction. In addition, the relationship between the diseases exemplified above and abnormal protein crosslinking is as described in "Background Art" above.

In addition, as described above, the compounds of the present invention include compounds characterized in that they have TG-activity-inhibiting action or protein-crosslinking-inhibiting action and have low levels of SOCE-inhibiting activity (and thus do not significantly influence the SOCE function) but high levels of IICR-inhibiting activity. There are known diseases associated with an increase in intracellular calcium concentration. Examples of such diseases include Alzheimer's disease, platelet aggregation, ischemic heart or brain diseases, immunodeficiency, allergic diseases, bronchial asthma, hypertension, cerebral vasoconstriction, a variety of kidney diseases, pancreatitis, autoimmune disease, multiple sclerosis (MS), Crohn's disease, and Sjögren's syndrome. Examples of known diseases caused in connection with the IICR function (i.e., the induction of calcium ion release from calcium ion pools in a cell) include ischemic diseases of the heart or brain, hypertension, cerebral vasoconstriction, and Alzheimer's disease (JP Patent Publication (Kokai) No. 2009-184988 A). The compounds of the present invention can be used as drugs for treating or preventing such diseases.

As used herein, the term "protein crosslinking" refers to a situation in which a new intramolecular or intermolecular protein chain bond (e.g. a covalent bond, ion bond, coordination bond, or hydrogen bond) is formed for crosslinking.

In addition, it is known that when an abnormal protein crosslinking reaction takes place in the brain so as to result in insoluble protein formation or protein aggregation, neurodegenerative diseases such as Alzheimer's disease, Huntington's disease, and Parkinson's disease are developed.

Transglutaminase is an enzyme that is involved in protein crosslinking in the cases of the above diseases. As such, transglutaminase inhibitors are effective for prevention or treatment of the diseases.

According to the present invention, the enzyme-inhibiting action of transglutaminase (TGase) can be determined by assaying enzyme activity using an optionally modified version of the method of Lorand et al. (Lorand, L. et al. (1971) Anal Biochem. 1971 November 44 (1):221-31). Specifically, the methods described in the Examples below can be used.

Alternatively, the therapeutic effects of the compounds of the present invention can be confirmed by administering each of the compounds of the present invention to model animals (e.g. mice) with diseases such as Alzheimer's disease, Huntington's disease, and Parkinson's disease and observing alleviation of the symptoms. Examples of known model animals include Huntington's disease model mice (J Neurol Sci, 231: 57-66 (Apr. 15, 2005)), Alzheimer's disease model mice (J. Clin. Invest., 116 (3): 825-832 (2006)), and Parkinson's disease model mice (PLoS Biol. 3 (8): e303 (2005 August)).

One or more compounds of the present invention (i.e., active substances or active ingredients) formulated in the oral or parenteral dosage form can be systemically or locally administered to subjects (i.e., mammals including humans, and preferably humans). Examples of parenteral administration include intravenous administration, intraarterial administration, intramuscular administration, subcutaneous administration, intradermal administration, intraperitoneal administration, intrarectal administration, intradural administration, intravaginal administration, transmucosal administration, intracerebral/transdural administration, and intraocular administration.

The administration dose would vary depending on the type of compound to be administered, subject's age, sex, weight, and symptoms, expected therapeutic effects, administration methods, and the like. However, in general, the dose for an adult (with a body weight of about 60 kg) is, for example, 10 μg to 1,000 mg per oral administration once or several times per day. Alternatively, it is, for example, 1 μg to 100 mg per oral administration once or several times per day.

Examples of the formulations of the compounds of the present invention include, but are not limited to: tablets, pills, suspensions, solutions, capsules, syrups, elixirs, granules, and powders for oral administration; injections, drugs for external use, suppositories, solutions for external use, ointments, liniments, inhalation, and spray for parenteral administration; and pessaries for intravaginal administration.

The above formulation can comprise a pharmaceutically acceptable carrier (e.g., an excipient or a diluent) and an additive, in combination with the compound of the present invention used as an active ingredient.

Examples of excipients include lactose, mannitol, glucose, microcrystalline cellulose, and starch.

Examples of an additive include a binder (e.g., hydroxypropyl cellulose, polyvinyl pyrrolidone, or magnesium aluminometasilicate), a disintegrant (e.g., calcium carboxymethyl cellulose), a lubricant (e.g., magnesium stearate), a stabilizer (e.g., an amino acid or a sugar), and a solubilizer (e.g., glutamic acid or aspartic acid).

The formulation of the present invention may be coated with a coating agent (e.g. sucrose, gelatin, hydroxypropyl cellulose, or hydroxypropyl methylcellulose phthalate) or it may be coated with at least two layers. As a result of such coating, the formulation of the present invention can be formed into a controlled-release formulation, an enteric formulation, or the like. Further, it may be formed into capsules made of an bioabsorbable material such as gelatin (i.e., soft or hard gelatin).

A solution for oral administration is prepared by dissolving, suspending, or emulsifying at least one active substance in a generally used diluent (e.g., purified water, ethanol, buffer, Ringer's solution, or a mixture thereof). The thus prepared solution may contain a wetting agent, a suspending agent, an emulsifier, a stabilizer, a sweetening agent, a flavor, a fragrance, a preservative, a buffering agent, and the like.

Examples of injections for parenteral administration include solutions, suspensions, emulsions, and injections prepared by dissolving or suspending in a solvent upon use. An injection is prepared by dissolving, suspending, or emulsifying at least one active substance in a solvent. Examples of a solvent include distilled water for injection, physiological saline, vegetable oil, propylene glycol, polyethylene glycol, alcohol such as ethanol, and combinations thereof. Such injection may comprise a stabilizer (e.g., an amino acid such as lysine or methionine, or a sugar such as trehalose), a solubilizer (e.g., glutamic acid, aspartic acid, or polysorbate 80 (registered trademark)), a suspending agent, an emulsifier, a soothing agent, a buffer, a preservative, and the like. The prepared injection is sterilized in the final production step or produced/formulated by an aseptic technique. In addition, it is possible to produce a sterile solid agent such as a freeze-dried product and dissolve the product in sterilized or sterile distilled water for injection, or in a different solvent, before use.

A spray formulation may comprise a stabilizer such as sodium bisulfite and a buffering agent that can impart isotonicity, such as an isotonic agent (e.g., sodium chloride, sodium citrate, or citric acid), in addition to a generally used diluent.

EXAMPLES

The present invention will hereafter be described in more detail with reference to the following examples. It is contemplated, however, that the technical scope of the present invention is not limited to the examples.

Bioactivity Assay:

<Assay of SOCE (Store Operated Calcium Entry)-Inhibiting Action>

The extracellular fluid (i.e., medium) of cultured Chinese hamster ovary (CHO) cells was replaced by BSS containing no calcium. One minute later, a test compound was added. Two minutes later, 1 µM thapsigargin was added to cause depletion of the intracellular calcium store. Nine minutes later, calcium chloride (final concentration: 2 mM) was added to the extracellular fluid. The SOCE-inhibiting action levels at different compound concentrations after the addition of calcium chloride were determined as the percentage of inhibition (%) by evaluating the influence of the compound on the degree of increase in the intracellular calcium concentration.

<Assay of IICR (IP3 Induced Calcium Release)-Inhibiting Action>

The extracellular fluid (i.e., medium) of cultured CHO cells was replaced by BSS containing calcium. One minute later, a test compound was added. Two minutes later, 10 µM ATP was added. The IICR-inhibiting action levels at different compound concentrations after the addition of ATP were determined as the percentage of inhibition (%) by evaluating the influence of the compound on the degree of increase in the intracellular calcium concentration.

<TG (Trans Glutaminase)-Inhibiting Activity Assay>

Inhibition of TG enzyme was determined by assaying the enzyme activity in accordance with an optionally modified version of the method of Lorand et al. (Lorand, L. et al. (1971) Anal Biochem. 44 (1):221-231).

An enzyme reaction solution (0.1 ml) (100 mM HEPES-NaOH, pH 7.5, 1 mM $CaCl_2$, 20 µM monodansyl cadaverine, 0.05 mg/ml N,N-dimethylcasein, 5 µg/ml TGase) was introduced into wells of a 96-well plate (Nunc, 96 Well Black Plate with Clear Bottom). A test compound was added in concentrations of 0.3, 1.0, 3.0, 10, and 30 µM. The solution and the compound were sufficiently mixed while preventing foaming. The plate was set in the fluorescence drug screening system FDSS 3000 (Hamamatsu Photonics K.K.). TGase-inhibiting activity of the compound was calculated by assaying changes in fluorescence wavelength (at 340 nm) per unit time. The assay level at which a fluorescence change was observed with the addition of DMSO (dimethyl sulfoxide) (1 µl) used as a control instead of the test compound was designated as 100. The assay level at which TGase activity decreased by half in the presence of the test compound was designated as TG 50.

Hereafter, the numerals in parentheses written after the TG level, the SOCE level, and the IICR level correspond to the test compound concentrations. The number following the name of each title compound used in the Examples below represents a compound ID number designated arbitrarily by the present inventors.

Example 1

Acryloylbenzene 8184

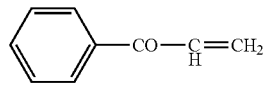

Benzene (1 mL), acryloyl chloride (0.4 mL), and aluminium chloride (0.33 g) were added to dichloromethane (4 mL), followed by stirring at 0° C. for 2 hours. After reaction, 1 N hydrochloric acid and dichlormethane (5 mL) were added in order. The organic phase was concentrated. The obtained residue was applied to a silica gel column to obtain the title compound (120 mg).

NMR ($CDCl_3$) 5.85 (d, 1H), 6.45 (d, 1H), 7.2-8.9 (m, 6H)

TG 46 (1 µmol) 16.8 (3 µmol) 4.8 (10 µmol) 5.9 (30 µmol)

Example 2

4-methyl-1-acryloylbenzene 8185

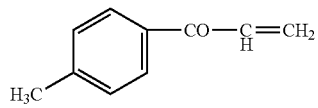

Toluene (0.3 mL), acryloyl chloride (0.23 g), and aluminium chloride (0.33 g) were treated in the same manner as described in Example 1 to obtain the title compound (90 mg).

NMR ($CDCl_3$) 2.85 (s, 3H), 5.85 (d, 1H), 6.45 (d, 1H), 7.0-7.9 (m, 5H)

TG 72.8 (1 µmol) 39.9 (3 µmol) 18 (10 µmol) 5.0 (30 µmol)

Example 3

4-fluoro-1-acryloylbenzene 8186

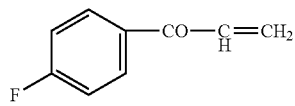

Fluorobenzene (0.5 mL), acryloyl chloride (0.23 g), and aluminium chloride (0.33 g) were treated in the same manner as described in Example 1 to obtain the title compound (90 mg).

NMR ($CDCl_3$) 6.05 (m, 1H), 6.45 (d, 1H), 7.0-8.0 (m, 5H)

TG 72.8 (1 µmol) 39.9 (3 µmol) 18 (10 µmol) 5.0 (30 µmol)

Example 4

1-bromo-6-acryloylnaphthalene 8187

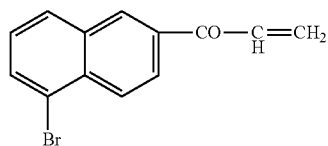

1-bromonaphthalene (0.42 g), acryloyl chloride (0.31 g), and aluminium chloride (0.27 g) were treated in the same manner as described in Example 1 to obtain the title compound (22 mg).

NMR (CDCl$_3$) 5.95 (m, 1H), 6.52 (d, 1H), 7.35-8.20 (m, 5H)

TG 90.5 (1 µmol) 78.17 (3 µmol) 60.7 (10 µmol) 24.4 (30 µmol)

Example 5

2-acryloylnaphthalene 8213

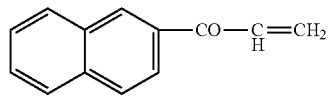

Naphthalene (0.128 g), acryloyl chloride (0.11 g), and aluminium chloride (0.15 g) were treated in the same manner as described in Example 1 to obtain the title compound (75 mg).

NMR (CDCl$_3$) 6.00 (m, 1H), 6.5 (d, 1H), 7.35-8.00 (m, 8H)

TG 44.1 (3 µmol) 11.3 (10 µmol) 0.4 (30 µmol)

Example 6

2-acryloylanthracene 8189

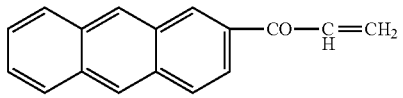

Anthracene (0.156 g), acryloyl chloride (0.11 g), and aluminium chloride (0.15 g) were treated in the same manner as described in Example 1 to obtain the title compound (56 mg).

NMR (CDCl$_3$) 5.95 (m, 1H), 6.45 (d, 1H), 7.00-7.80 (m, 10H)

TG 90.3 (3 µmol) 78.7 (10 µmol) 68.0 (30 µmol)

Example 7

1-acryloylmorpholine 8171

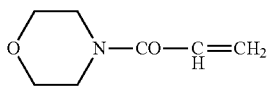

Commercially Available Product
TG 81.3 (1 µmol) 79.0 (3 µmol)

Example 8

2-chloroethyl-2-naphthylketone 8175

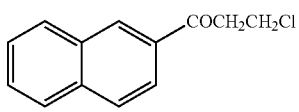

2-chloroethylpropionyl chloride (2.78 g), naphthalene (2.56 g), and aluminium chloride (3.2 g) were reacted in nitrobenzene (9 mL) at 0° C., followed by treatment with hydrochloric acid to obtain the title compound (1.5 g).

NMR (CDCl$_3$) 3.60 (m, 2H), 3.95 (m, 2H), 6.70-8.20 (m, 7H)

TG 59.1 (3 µmol) 39.2 (10 µmol) 0.1 (30 µmol)

Example 9

2-chloroethyl-2-anthranilketone 8176

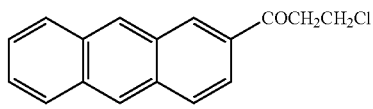

2-chloroethylpropionyl chloride (0.63 g), anthracene (0.89 g), and aluminium chloride (0.8 g) were reacted in nitrobenzene (2.3 mL) at 0° C., followed by treatment with hydrochloric acid to obtain the title compound (1.5 g).

NMR (CDCl$_3$) 3.50 (m, 2H), 4.4 (m, 2H), 7.20-8.10 (m, 9H)

TG 59.1 (3 µmol) 39.2 (10 µmol) 0.1 (30 µmol)

Example 10

3-chloropropiophenone 8177

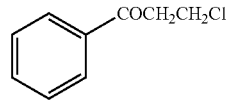

Commercially Available Product
TG 100 (3 µmol) 100 (10 µmol) 96.9 (30 µmol)

Example 11

1-(3-chloropionyl)-4-fluorobenzene 8178

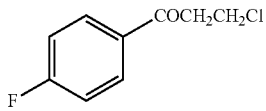

2-chloroethylpropionyl chloride (0.63 g), fluorobenzene (0.48 g), and aluminium chloride (0.8 g) were reacted in nitrobenzene (2.3 mL) at 0° C., followed by treatment with hydrochloric acid to obtain the title compound (0.2 g).

NMR (CDCl$_3$) 3.5 (m, 2H), 4.3 (m, 2H), 7.2-8.1 (m, 4H)

TG 49.6 (3 μmol) 22.4 (10 μmol) 5.6 (30 μmol)

Example 12

1-(3-chloropropionyl)-4-methylbenzene 8179

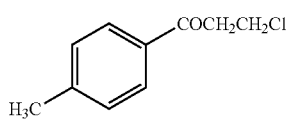

2-chloroethylpropionyl chloride (0.63 g), toluene (0.885 g), and aluminium chloride (0.8 g) were reacted in nitrobenzene (1 mL) at 0° C., followed by treatment with hydrochloric acid to obtain the title compound (0.25 g).

NMR (CDCl$_3$) 2.1 (s, 3H) 3.5 (m, 2H), 4.1 (m, 2H), 6.8-8.2 (m, 4H)

TG 89.5 (3 μmol) 50.7 (10 μmol) 3.7 (30 μmol)

Example 13

3-chloropropio-4-bromophenone 8180

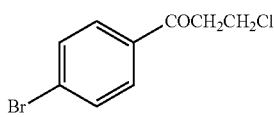

2-chloroethylpropionyl chloride (0.63 g), bromobenzene (0.46 g), and aluminium chloride (0.8 g) were reacted in nitrobenzene (1 mL) at 0° C., followed by treatment with hydrochloric acid to obtain the title compound (0.25 g).

NMR (CDCl$_3$) 3.55 (m, 2H), 4.15 (m, 2H), 6.82-8.24 (m, 4H)

TG 90.2 (3 μmol) 52.5 (10 μmol) 7.8 (30 μmol)

Example 14

MethAcryloylbenzene 8192

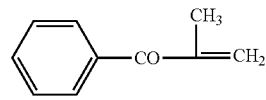

Benzene (1 mL), methacryloyl chloride (0.156 mg), and aluminium chloride (199 mg) were reacted in carbon disulfide (2 mL) at from 0° C. to room temperature for 2 hours. The resultant was treated in the same manner as described in Example 1 to obtain the title compound (106 mg).

NMR (CDCl$_3$) 2.16 (m, 3H), 5.62 (m, 1H), 6.20 (d, 1H), 7.2-7.7 (m, 5H)

TG 95.2 (3 μmol) 98.4 (10 μmol) 88.7 (30 μmol)

Example 15 methacryloylnaphthalene 8193

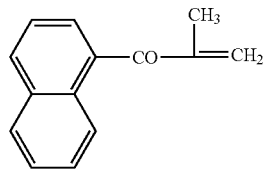

Naphthalene (128 mg), methacryloyl chloride (0.156 mg), and aluminium chloride (199 mg) were reacted in carbon disulfide (2 mL) at from 0° C. to room temperature for 2 hours. The resultant was treated in the same manner as described in Example 1 to obtain the title compound (65 mg).

NMR (CDCl$_3$) 1.95 (m, 3H), 5.65 (m, 1H), 6.20 (d, 1H)), 7.3-8.0 (m, 7H)

TG 88.3 (3 μmol) 93.0 (10 μmol) 86.7 (30 μmol)

Example 16

Cinnamoylbenzene 8194

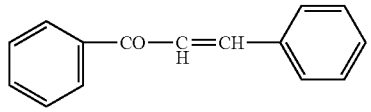 [SMILES: O=C(C=Cc1ccccc1)c1ccccc1]

Benzene (1 mL), cinnamoyl chloride (0.160 mg), and aluminium chloride (150 mg) were reacted in carbon disulfide (5 mL) at from 0° C. to room temperature for 2 hours. The resultant was treated in the same manner as described in Example 1 to obtain the title compound (35 mg).

NMR (CDCl$_3$) 6.45 (d, 1H), 6.60 (d, 1H), 7.4-8.0 (m, 10H)

TG 95.4 (3 μmol) 95.4 (10 μmol) 90.7 (30 μmol)

Example 17

2-(cinnamoyl)-naphthalene 9195

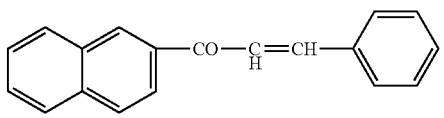 [SMILES: O=C(C=Cc1ccccc1)c1ccc2ccccc2c1]

Naphthalene (128 mg), cinnamoyl chloride (0.160 mg), and aluminium chloride (150 mg) were reacted in carbon disulfide (5 mL) at from 0° C. to room temperature. The resultant was treated in the same manner as described in Example 1 to obtain the title compound (35 mg).

NMR (CDCl$_3$) 6.65 (s, 1H), 6.68 (a1H) 7.4-8.0 (m, 12H)

TG 96.0 (3 μmol) 95.9 (10 μmol) 86.3 (30 μmol)

Example 18 p-methacryloyl toluene 8197

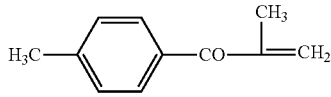

Toluene (1 mL), cinnamoyl chloride (100 mg), and aluminium chloride (150 mg) were reacted in carbon disulfide (5 mL) at from 0° C. to room temperature for 2 hours. The resultant was treated in the same manner as described in Example 1 to obtain the title compound (35 mg).

NMR (CDCl$_3$) 2.05 (s, 3H), 5.50 (s, 1H), 5.84 (s, 1H), 7.20-7.95 (m, 4H)

TG 100 (3 μmol) 98.5 (10 μmol) 86.7 (30 μmol)

Example 19

1-methacryloyl-4-fluorobenzene 8198

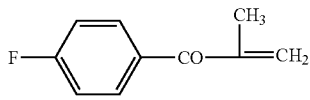

Fluorobenzene (1 mL), cinnamoyl chloride (100 mg), and aluminium chloride (150 mg) were reacted in carbon disulfide (5 mL) at from 0° C. to room temperature for 2 hours. The resultant was treated in the same manner as described in Example 1 to obtain the title compound (52 mg).

NMR (CDCl$_3$) 6.65 (s, 1H), 6.68 (a1H), 7.4-8.0 (m, 12H)

TG 99.1 (3 μmol) 100 (10 μmol) 100 (30 μmol)

Example 20

1-acryloyl-4-bromobenzene 8266

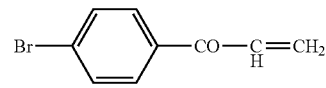

Bromobenzene (0.5 mL), acryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (1207.0 mg).

NMR (CDCl$_3$) 7.00-7.95 (m, 7H)

TG 32.2 (3 μmol) 31.0 (10 μmol) 6.6 (30 μmol)

Example 21

2-bromo-4,5-dioxymethylene-1-acryloylbenzene 8200

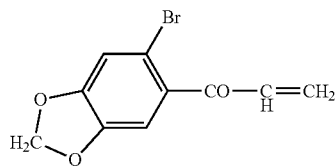

Bromobenzene (0.5 mL), acryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (1207 mg).

NMR (CDCl$_3$) 7.00-7.95 (m, 7H)

TG 32.2 (3 μmol) 31.0 (10 μmol) 6.6 (30 μmol)

Example 22

4-bromo-2-methoxy-1-acryloylbenzene 8203

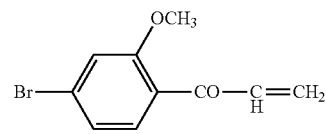

3-methoxybromobenzene (0.5 mL), acryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (8.0 mg).

NMR (CDCl$_3$) 3.7 (s, 3H), 5.8 (m, 1H), 6.3 (m, 1H), 6.8-7.5 (m, 4H)

TG 81.2 (3 μmol) 73.6 (10 μmol) 57.0 (30 μmol)

Example 23

4-bromo-1-methacryloylbenzene 8205

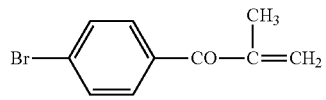

Bromobenzene (0.5 mL), methacryloyl chloride (110 mg), and aluminium chloride (150 mg) were reacted in dichloromethane (1.5 mL) at from −20° C. to room temperature for 4 hours. The resultant was treated in the same manner as described in Example 1 to obtain the title compound (1207 mg).

NMR (CDCl$_3$) 2.0 (m, 3H), 5.57 (s, 1H), 6.25 (m, 1H), 7.2-7.5 (m, 5H)

TG 90.0 (3 μmol) 99 (10 μmol) 100 (30 μmol)

Example 24

4-bromo-2-methoxy-1-methacryloylbenzene 8206

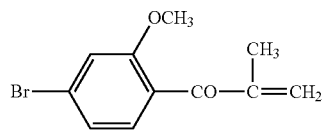

3-methoxybromobenzene (238 mg), methacryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (120 mg).

NMR (CDCl$_3$) 3.8 (m, 3H), 5.62 (m, 1H), 5.93 (m, 1H), 6.8-7.4 (m, 3H)

TG 86 (3 μmol) 97 (10 μmol) 100 (30 μmol)

Example 25

2-bromo-4,5-dioxymethylene-1-methacryloylbenzene 8207

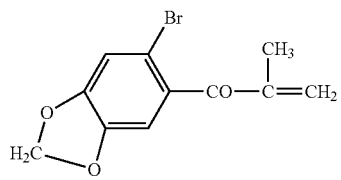

3,4-dimethoxymethylene bromobenzene (201 mg), methacryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (110 mg).

NMR (CDCl$_3$) 2.15 (m, 3H), 5.62 (m, 1H), 5.8 (m, 2H), 5.9 (m, 1H), 6.2 (m, 1H), 6.7-7.4 (m, 2H)

TG 94 (3 μmol) 90 (10 μmol) 93 (30 μmol)

Example 26

2,5-dimethyl-1-methacryloylbenzene 8208

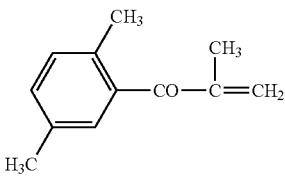

Paraxylene (1 mL), methacryloyl chloride (110 mg), and aluminium chloride (160 mg) were reacted in dichloromethane (1.5 mL) at from 0° C. to room temperature for 4 hours. The resultant was treated in the same manner as described in Example 1 to obtain the title compound (140 mg).

NMR (CDCl$_3$) 2.3-2.4 (m, 6H), 5.77 (m; 1H), 5.95 (m, 1H), 6.9-7.2 (m, 3H)

TG 86 (3 μmol) 96 (10 μmol) 87 (30 μmol)

Example 27

2,5-dimethyl-1-acryloylbenzene 8209

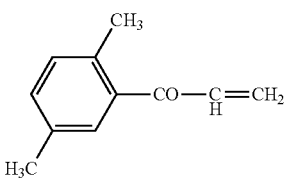

Paraxylene (0.5 mL), methacryloyl chloride (110 mg), and aluminium chloride (150 mg) were reacted in dichloromethane (1.5 mL) at from 0° C. to room temperature for 4 hours. The resultant was treated in the same manner as described in Example 1 to obtain the title compound (89 mg).

NMR (CDCl$_3$) 2.3-2.6 (m, 6H), 6.8-7.4 (m, 5H)

TG 100 (3 μmol) 66 (10 μmol) 12.9 (30 μmol)

Example 28

1-methyl-6-methacryloylnaphthalene 8212

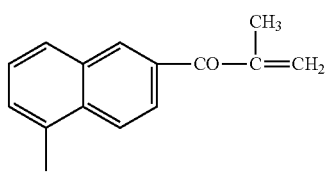 [SMILES: C=C(C)C(=O)c1ccc2c(C)cccc2c1]

1-methylnaphthalene (142 mg), methacryloyl chloride (110 mg), and aluminium chloride (160 mg) were reacted in dichloromethane (1.5 mL) at from −30° C. to room temperature for 4 hours. The resultant was treated in the same manner as described in Example 1 to obtain the title compound (122 mg).

NMR (CDCl₃) 2.8-2.9 (m, 6H), 5.3 (m, 1H), 6.9 (m, 1H), 7.2-8.0 (m, 6H)
TG 100 (3 μmol) 100 (10 μmol) 88 (30 μmol)

Example 29

1-methyl-6-acryloylnaphthalene 8211

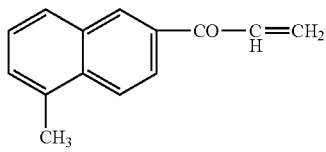

1-methylnaphthalene (142 mg), acryloyl chloride (100 mg), and aluminium chloride (150 mg) were reacted in carbon disulfide (0.5 mL) at from −20° C. to room temperature for 1 hour. The resultant was treated in the same manner as described in Example 1 to obtain the title compound (169 mg) in a viscous liquid form.

NMR (CDCl₃) 6.0 (m, 1H), 6.27 (m, 1H), 6.95 (m, 1H), 7.2-8.0 (m, 6H)
TG 85.1 (0.3 μmol) 64.1 (1 μmol) 22.2 (3 μmol) 9.8 (10 μmol) 4.9 (30 μmol)

Example 30

2-(N-t-butyl-2-hydroxyethyl)aminoethyl-4-pyridylketone 8672

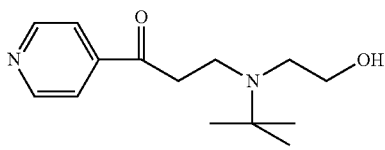 [SMILES: CC(C)(C)N(CCO)CCC(=O)c1ccncc1]

4-acetylpyridine (121 mg), t-butyl-2-hydroxyethyl amine (117 mg), and paraformaldehyde (36 mg) were reacted in dioxane (0.2 ml) at 130° C. for 2 hours.

NMR (CDCl₃) 1.05 (s, 9H), 2.6-2.8 (m, 4H), 3.6 (m, 2H), 8.81 (s, 2H)
TG 75.9 (3 μmol) 12.8 (30 μmol)
SOCE 0 (10 μmol) 0 (30 μmol) 0 (100 μmol)
IICR 20 (10 μmol) 10 (30 μmol) 10 (100 μmol)

Example 31

2-(N-methylbenzyl)aminoethyl-4-pyridylketone 8673

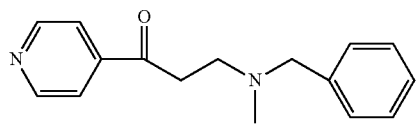 [SMILES: CN(CCC(=O)c1ccncc1)Cc1ccccc1]

4-acetylpyridine (121 mg), methylbenzylamine (121 mg), and paraformaldehyde (36 mg) were reacted in dioxane (0.2 ml) at 130° C. for 2 hours.

NMR (CDCl₃) 2.1 (s, 3H), 2.6 (m, 2H), 2.8 (m, 2H), 3.4 (m, 2H)
TG 27.4 (3 μmol) 0.5 (30 μmol)
SOCE 0 (10 μmol) 0 (30 μmol) 0 (100 μmol)
IICR 40 (10 μmol) 60 (30 μmol) 80 (100 μmol)

Example 32

Tigloylbenzene 8222

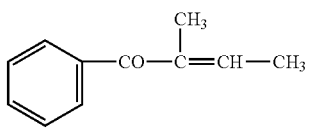

Benzene (1 mL), tigloyl chloride (236 mg), and aluminium chloride (160 mg) were reacted in dichloromethane (1.5 mL) at from 0° C. to room temperature for 4 hours. The resultant was treated in the same manner as described in Example 1 to obtain the title compound (126 mg).

NMR (CDCl₃) 1.9-2.0 (m, 6H), 5.9 (m, 1H), 6.8-7.0 (m, 5H)
TG 100 (3 μmol) 100 (10 μmol) 100 (30 μmol)

Example 33

Crotonoylbenzene 6223

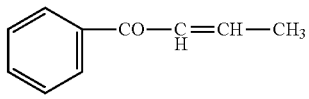

Benzene (1 mL), crotonoyl chloride (236 mg), and aluminium chloride (280 mg) were reacted in dichloromethane (1.5 mL) at from −30° C. to room temperature for 16 hours. The resultant was treated in the same manner as described in Example 1 to obtain the title compound (66 mg).

NMR (CDCl₃) 1.9-2.0 (m, 3H), 5.8 (m, 2H), 6.9-7.0 (m, 5H)
TG 100 (3 μmol) 100 (10 μmol) 100 (30 μmol)

Example 34

Crotonoylnaphthalene 8227

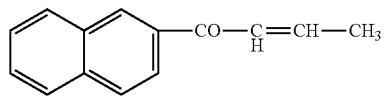

Naphthalene (128 mg), crotonoyl chloride (124 mg), and aluminium chloride (180 mg) were reacted in dichloromethane (1.5 mL) at from −20° C. to room temperature for 4 hours. The resultant was treated in the same manner as described in Example 1 to obtain the title compound (126 mg).

NMR (CDCl₃) 2.0 (m, 3H), 5.9 (m, 1H), 6.6 (m, 1H), 6.8-8.2 (m, 7H)
TG 100 (3 μmol) 100 (10 μmol) 88 (30 μmol)

Example 35

1-methyl-4-crotonoylbenzene 6228

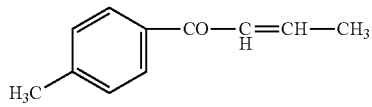

Benzene (1 mL), crotonoyl chloride (236 mg), and aluminium chloride (160 mg) were reacted in dichloromethane (1.5 mL) at from 0° C. to room temperature for 4 hours. The resultant was treated in the same manner as described in Example 1 to obtain the title compound (126 mg).

NMR (CDCl$_3$) 1.9-2.0 (m, 6H), 5.9 (m, 1H), 6.8-7.0 (m, 5H)

TG 90 (3 µmol) 85 (10 µmol) 57 (30 µmol)

Example 36

1-methoxy-4-crotonoylbenzene 8229

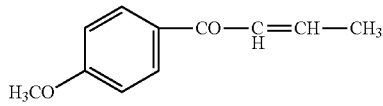

Anisole (0.3 mL), crotonoyl chloride (24 mg), and aluminium chloride (160 mg) were reacted in dichloromethane (1.5 mL) at from −50° C. to room temperature for 4 hours. The resultant was treated in the same manner as described in Example 1 to obtain the title compound (75 mg).

NMR (CDCl$_3$) 1.95 (m, 3H), 3.9 (m, 3H), 6.96 (m, 2H), 7.06 (m, 1H), 7.25 (m, 1H), 7.95 (m, 2H)

TG 96 (3 µmol) 74 (10 µmol) 67 (30 µmol)

Example 37

2-methoxy-6-crotonoylnaphthalene 8230

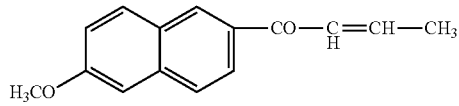 [SMILES: CC=CC(=O)c1ccc2cc(OC)ccc2c1]

2-methoxynaphthalene (158 mg), crotonoyl chloride (124 mg), and aluminium chloride (150 mg) were reacted in dichloromethane (1.5 mL) at from 0° C. to room temperature for 4 hours. The resultant was treated in the same manner as described in Example 1 to obtain the title compound (156 mg).

NMR (CDCl$_3$) 1.9-2.0 (m, 3H), 3.9 (m, 3H), 5.9 (m, 1H), 5.6 (m, 1H), 7.2-7.9 (m, 6H)

TG 100 (3 µmol) 100 (10 µmol) 100 (30 µmol)

Example 38

1-methoxy-4-acryloylbenzene 3231

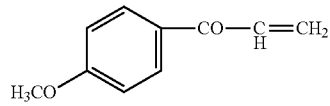

Anisole (108 mg), acryloyl chloride (154 mg), and aluminium chloride (199 mg) were reacted in dichloromethane (1.5 mL) at from −20° C. to room temperature for 4 hours. The resultant was treated in the same manner as described in Example 1 to obtain the title compound (160 mg).

NMR (CDCl$_3$) 3.95 (m, 3H), 6.48-8.00 (m, 7H)

TG 100 (3 µmol) 100 (10 µmol) 93 (30 µmol)

Example 39

1-methoxy-4-tigloylbenzene 8233

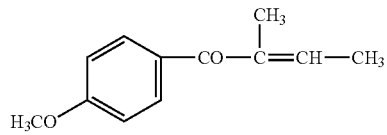

Anisole (128 mg), tigloyl chloride (140 mg), and aluminium chloride (155 mg) were reacted in dichloromethane (1.5 mL) at from 0° C. to room temperature for 4 hours. The resultant was treated in the same manner as described in Example 1 to obtain the title compound (63 mg).

NMR (CDCl$_3$) 1.9 (d, 3H), 2.9 (d, 3H) 3.8 (m, 3H), 5.13 (m, 1H), 6.9-76 (m, 4H)

TG 63 (3 µmol) 26 (10 µmol) 8.2 (30 µmol)

Example 40

4-chlorobutyrylbenzene 8236

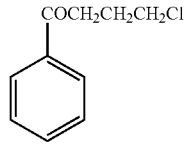

Benzene (0.5 mg), 4-chlorobutyryl chloride (141 mg), and aluminium chloride (170 mg) were reacted in dichloromethane (1.5 mL) at from 0° C. to room temperature for 4 hours. The resultant was treated in the same manner as described in Example 1 to obtain the title compound (10.3 mg).

NMR (CDCl$_3$) 2.30 (m, 2H), 3.20 (m, 2H), 3.93 (m, 2H), 7.45-8.10 (m, 5H)

TG 85 (3 µmol) 92 (10 µmol) 83 (30 µmol)

Example 41

1-ethyl-4-acryloylbenzene 8237

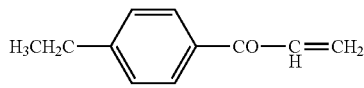

Ethylbenzene (0.5 mL), acryloyl chloride (120 mg), and aluminium chloride (199 mg) were reacted in dichloromethane (1.5 mL) at from 0° C. to room temperature for 4 hours. The resultant was treated in the same manner as described in Example 1 to obtain the title compound (110 mg).

NMR (CDCl$_3$) 1.2 (m, 3H), 2.62 (m, 2H), 5.93 (m, 1H), 6.4 (m, 1H), 7.0-7.9 (m, 5H)

TG 71 (3 μmol) 55 (10 μmol) 21 (30 μmol)

Example 42

2,4-dimethyl-1-acryloylbenzene 8239

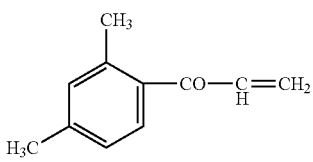

Metaxylene (128 mg), acryloyl chloride (154 mg), and aluminium chloride (160 mg) were reacted in dichloromethane (1.5 mL) at from 0° C. to room temperature for 4 hours. The resultant was treated in the same manner as described in Example 1 to obtain the title compound (31 mg).

NMR (CDCl$_3$) 2.42 (m, 6H), 7.0-7.8 (m, 4H)

TG 88 (3 μmol) 93 (10 μmol) 85 (30 μmol)

Example 43

Chloroacetyl benzene 8240

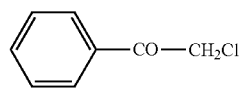

Benzene (0.5 mL), chloroacetyl chloride (120 mg), and aluminium chloride (180 mg) were reacted in dichloromethane (1.5 mL) at from −40° C. to room temperature for 2 hours. The resultant was treated in the same manner as described in Example 1 to obtain the title compound (11 mg).

NMR (CDCl$_3$) 4.7 (s, 2H), 7.45 (m, 2H), 7.2 (m, 1H), 7.86 (m, 2H)

TG 59 (3 μmol) 28 (10 μmol) 12 (30 μmol)

Example 44

3,4-dimethyl-1-acryloylbenzene 8241

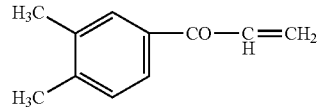

Orthoxylene (0.5 mL), acryloyl chloride (120 mg), and aluminium chloride (150 mg) were reacted in dichloromethane (1.5 mL) at from 0° C. to room temperature for 4 hours. The resultant was treated in the same manner as described in Example 1 to obtain the title compound (160 mg).

NMR (CDCl$_3$) 2.20-2.25 (m, 6H), 5.58 (d, 1H), 6.42 (d, 1H), 7.0-7.5 (m, 4H)

TG 51 (3 μmol) 30 (10 μmol) 10 (30 μmol)

Example 45

2,6-dimethyl-4-t-butyl-1-acryloylbenzene 8242

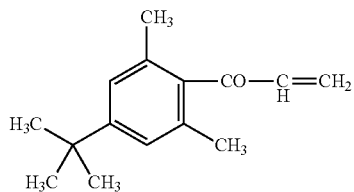 [SMILES: C=CC(=O)c1c(C)cc(C(C)(C)C)cc1C]

5-t-butylmetaxylene (0.5 mL), acryloyl chloride (120 mg), and aluminium chloride (150 mg) were reacted in dichloromethane (1.5 mL) at from −40° C. to room temperature for 2 hours. The resultant was treated in the same manner as described in Example 1 to obtain the title compound (120 mg).

NMR (CDCl$_3$) 1.2 (s, 9H), 2.22 (m, 6H), 6.5-6.6 (m, 2H)

TG 86 (3 μmol) 97 (10 μmol) 99 (30 μmol)

Example 46

3,4-dimethoxy-1-acryloylbenzene 8243

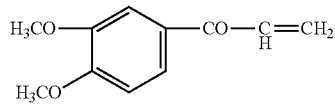

1,2-dimethoxybenzene (135 mg), acryloyl chloride (118 mg), and aluminium chloride (199 mg) were reacted in dichloromethane (1.5 mL) at from −40° C. to room temperature for 2 hours. The resultant was treated in the same manner as described in Example 1 to obtain the title compound (55 mg).

NMR (CDCl$_3$) 3.8 (m, 6H), 6.4 (m, 1H), 5.75 (m, 1H), 6.7-7.5 (m, 4H)

TG 87 (3 μmol) 79 (10 μmol) 47 (30 μmol)

Example 47

1-acryloyldibenzyl 8250

Diphenyl (154 mg), acryloyl chloride (220 mg), and aluminium chloride (319 mg) were reacted in dichloromethane (5 mL) at from 0° C. to room temperature for 4 hours. The resultant was treated in the same manner as described in Example 1 to obtain the title compound (240 mg).

NMR (CDCl$_3$) 5.95 (m, 1H), 6.48 (m, 1H), 7.3-8.0 (m, 7H)

TG 88 (3 μmol) 52 (10 μmol) 15 (30 μmol)

Example 48

1-acryloyldiphenylether 8251

Diphenylether (170 mg), acryloyl chloride (220 mg), and aluminium chloride (319 mg) were reacted in dichloromethane (6 mL) at from 0° C. to room temperature for 4 hours. The resultant was treated in the same manner as described in Example 1 to obtain the title compound (390 mg).

NMR (CDCl$_3$) 5.91 (m, 1H), 6.5 (m, 1H), 6.9-8.2 (m, 10H)

TG 88 (3 μmol) 52 (10 μmol) 15 (30 μmol)

Example 49

2-methyl-6-acryloylnaphthalene 8256

Diphenylether (170 mg), acryloyl chloride (220 mg), and aluminium chloride (319 mg) were reacted in dichloromethane (6 mL) at from 0° C. to room temperature for 4 hours. The resultant was treated in the same manner as described in Example 1 to obtain the title compound (390 mg).

NMR (CDCl$_3$) 5.91 (m, 1H), 6.5 (m, 1H), 6.9-8.2 (m, 10H)

TG 88 (3 μmol) 52 (10 μmol) 15 (30 μmol)

Example 50

1-fluoro-6-acryloylnaphthalene 8257

1-fluoronaphthalene (146 mg), acryloyl chloride (110 mg), and aluminium chloride (150 mg) were reacted in dichloromethane (1 mL) at from −15° C. to room temperature for 2 hours. The resultant was treated in the same manner as described in Example 1 to obtain the title compound (390 mg).

NMR (CDCl$_3$) 5.80 (m, 1H), 6.3 (m, 1H), 6.5 (m, 1H), 6.9-8.8 (m, 7H)

TG 46 (3 μmol) 18 (10 μmol) 7 (30 μmol)

Example 51

2-(N-hydroxyethylbutyl)aminoethyl-4-pyridylketone 8674

4-acetylpyridine (124 mg), 2-hydroxyethylbutyl amine (117 mg), and paraformaldehyde (36 mg) were reacted in dioxane (0.2 ml) at 130° C. for 2 hours.

NMR (CDCl$_3$) 0.8 (s, 3H), 1.1-1.5 (m, 4H), 2.42 (m, 2H), 2.6 (m, 2H), 2.9 (m, 2H), 3.8 (m, 2H), 3.5 (m, 2H), 4.4 (m, 2H), 7.8 (m, 2H), 8.8 (m, 2H)

TG 42.7 (3 μmol) 3.4 (30 μmol)

SOCE 0 (10 μmol) 0 (30 μmol) 0 (100 μmol)

IICR 0 (10 μmol) 20 (30 μmol) 100 (100 μmol)

Example 52

Acryloyldinaphthylether 8260

Diphenylether (170 mg), acryloyl chloride (220 mg), and aluminium chloride (319 mg) were reacted in dichloromethane (6 mL) at from 0° C. to room temperature for 4 hours. The resultant was treated in the same manner as described in Example 1 to obtain the title compound (390 mg).

NMR (CDCl$_3$) 5.9 (m, 1H), 6.5 (m, 1H), 7.0-8.1 (m, 14H)

TG 102 (3 μmol) 92 (10 μmol) 61 (30 μmol)

Example 53

Acryloyldiphenylsulfide 9261

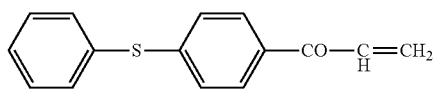 [SMILES: C=CC(=O)c1ccc(Sc2ccccc2)cc1]

Phenyl sulfide (188 mg), acryloyl chloride (300 mg), and aluminium chloride (440 mg) were reacted in dichloromethane (2 mL) at from −40° C. to room temperature for 2 hours. The resultant was treated in the same manner as described in Example 1 to obtain the title compound (390 mg).

NMR (CDCl$_3$) 5.9 (m, 1H), 6.5 (m, 1H), 7.29-7.90 (m, 10H)

TG 97 (3 µmol) 88 (10 µmol) 34 (30 µmol)

Example 54

4-chloro-1-acryloylbenzene 8264

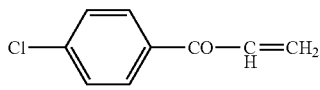

Chlorobenzene (0.3 mL), acryloyl chloride (120 mg), and aluminium chloride (115 mg) were reacted in dichloromethane (1 mL) at from 0° C. to room temperature for 4 hours. The resultant was treated in the same manner as described in Example 1 to obtain the title compound (390 mg).

NMR (CDCl$_3$) 5.91 (m, 1H), 6.4 (m, 1H), 7.2-7.9 (m, 5H)

TG 27 (3 µmol) 10 (10 µmol) 7.9 (30 µmol)

Example 55

4-acryloylpyridine 8265

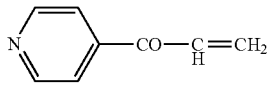

Pyridine (0.5 mL), acryloyl chloride (120 mg), and aluminium chloride (150 mg) were reacted in dichloromethane (1 mL) at from 0° C. to room temperature for 2 hours. The resultant was treated in the same manner as described in Example 1 to obtain the title compound (37.9 mg).

NMR (CDCl$_3$) 5.9 (m, 1H), 6.6 (m, 1H), 6.0-8.2 (m, 5H)

TG 78 (3 µmol) 75 (10 µmol) 52 (30 µmol)

Example 56

2-(hydroxyethylisopropyl)aminoethyl-3-thiophenylketone 8675

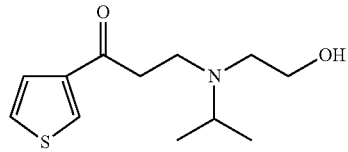 [SMILES: CC(C)N(CCO)CCC(=O)c1ccsc1]

3-acetylthiophene (121 mg), isopropyl-2-hydroxyethyl amine (126 mg), and paraformaldehyde (36 mg) were reacted in dioxane (0.2 ml) at 130° C. for 2 hours.

NMR (CDCl$_3$) 1.05 (m, 6H), 2.4 (m, 4H), 2.9 (m, 2H), 3.8 (m, 2H), 4.3 (m, 2H), 7.3 (s, 1H), 7.9 (s, 1H), 8.0 (s, 1H)

TG 70.9 (3 µmol) 0.2 (30 µmol)

SOCE 0 (10 µmol) 0 (30 µmol) 0 (100 µmol)

IICR 0 (10 µmol) 0 (30 µmol) 50 (100 µmol)

Example 57

Methyl vinylketone 8267

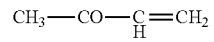

Commercially Available Product

TG 84 (3 µmol) 94 (10 µmol) 37 (30 µmol)

Example 58

1-chloro-6-acryloylnaphthalene 8268

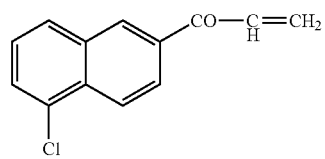

1-chloronaphthalene (183 mg), acryloyl chloride (120 mg), and aluminium chloride (150 mg) were reacted in dichloromethane (1.5 mL) at from −40° C. to room temperature for 2 hours. The resultant was treated in the same manner as described in Example 1 to obtain the title compound (277 mg).

NMR (CDCl$_3$) 6.0 (d, 1H), 6.9 (m, 1H), 7.3-8.5 (m, 6H)

TG 15.1 (3 µmol) 4.8 (10 µmol) 2.6 (30 µmol)

Example 59

Acryloyldiphenylmethane 8269

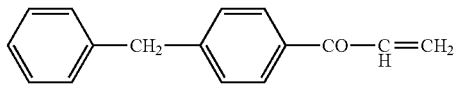 [SMILES: C=CC(=O)c1ccc(Cc2ccccc2)cc1]

Diphenylmethane (168 mg), acryloyl chloride (200 mg), and aluminium chloride (280 mg) were reacted in dichloromethane (2 mL) at from −40° C. to room temperature for 2 hours. The resultant was treated in the same manner as described in Example 1 to obtain the title compound (190 mg).

NMR (CDCl$_3$) 6.0 (m, 1H), 6.5 (m, 1H), 6.4 (m, 1H), 7.5-8.2 (m, 8H)

TG 6.7, 14.1 (3 μmol) 1.7, 4.8 (10 μmol) 0.6, 3.0 (30 μmol)

Example 60

Acryloyl-1-phenylnaphthalene 8270

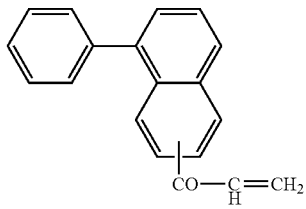

1-phenylnaphthalene (204 mg), acryloyl chloride (200 mg), and aluminium chloride (290 mg) were reacted in dichloromethane (1.5 mL) at from −40° C. to room temperature for 2 hours. The resultant was treated in the same manner as described in Example 1 to obtain the title compound (323 mg).

NMR (CDCl$_3$) 5.95 (d, 1H), 6.1 (d, 1H), 6.5-8.0 (m, 11H)

TG 70.6 (3 μmol) 41.1 (10 μmol) 19.1 (30 μmol)

Example 61

Vinylphenylcarbinol 8272

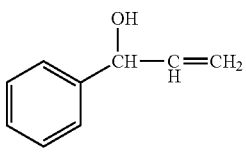

Benzaldehyde (342 mg) was mixed with THF (4 ml) and further mixed with vinylmagnesium bromide (1 N solution) (4 mL), followed by stirring for 12 hours to obtain the title compound (320 mg).

NMR (CDCl$_3$) 5.42 (d, 1H), 5.23 (m, 1H), 6.1 (m, 1H), 7.3-7.4 (m, 5H)

TG 100 (3 μmol) 100 (10 μmol) 62 (30 μmol)

Example 62

Vinyl-4-methoxy phenylcarbinol 8273

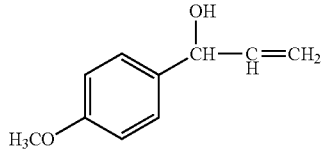

p-anisaldehyde (136 mg) was mixed with THF (4 ml) and further mixed with vinylmagnesium bromide (1 N solution) (4 mL), followed by stirring for 12 hours to obtain the title compound (195 mg).

NMR (CDCl$_3$) 3.80 (s, 3H), 5.2 (m, 1H), 6.1 (d, 1H), 6.2 (s, 1H), 6.95 (m, 2H), 7.3 (m, 2H)

TG100 (3 μmol) 100 (10 μmol) 82 (30 μmol)

Example 63

Vinyl-2-naphthylcarbinol 8274

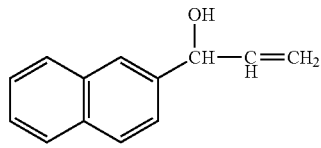

2-naphthylaldehyde (300 mg) was mixed with THF (4 ml) and further mixed with vinylmagnesium bromide (1 N solution) (4 mL), followed by stirring for 12 hours to obtain the title compound (352 mg).

NMR (CDCl$_3$) 5.25 (m, 1H), 5.39 (m, 1H), 6.14 (d, 1H), 7.5 (m, 3H), 7.85 (m, 4H)

TG 100 (3 μmol) 89 (10 μmol) 71.5 (30 μmol)

Example 64

2-(N-isopropylbenzyl)aminoethyl-4-benzylphenylketone 8285

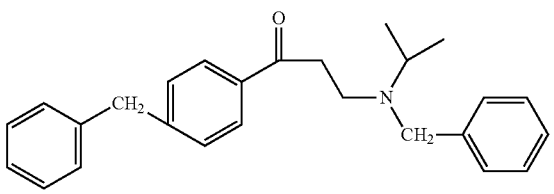 [SMILES: CC(C)N(CCC(=O)c1ccc(Cc2ccccc2)cc1)Cc1ccccc1]

Acryloyldiphenylmethane (22 mg), isopropylbenzylamine (14.9 mg), and diisopropylethyl amine (5 mg) were reacted in dichlormethane (0.2 ml) at 50° C. for 2 hours.

NMR (CDCl$_3$) 1.05 (m, 6H), 2.5 (m, 2H), 3.0 (m, 2H), 3.5 (m, 2H), 3.6 (m, 2H), 7.5 (m, 3H), 7.85 (m, 4H).

TG 45.8 (3 μmol) 17.5 (10 μmol) 8.7 (30 μmol)

SOCE 0 (10 μmol) 0 (30 μmol) 30 (100 μmol)

IICR 50 (10 μmol) 70 (30 μmol) 96 (100 μmol)

Example 65

2-(N-isopropylbenzyl)aminoethyl-4-methylphenylketone 8286

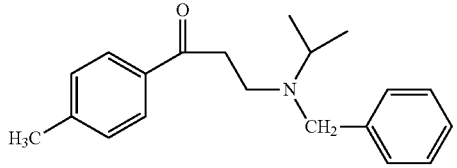 [SMILES: Cc1ccc(C(=O)CCN(Cc2ccccc2)C(C)C)cc1]

Acryloyl toluene (15 mg), isopropylbenzylamine (14.9 mg), and diisopropylethyl amine (5 mg) were reacted in dichlormethane (0.2 ml) at 50° C. for 2 hours.

NMR (CDCl$_3$) 1.05 (m, 6H), 2.5 (m, 4H), 3.0 (m, 2H), 3.0 (m, 1H), 3.7 (m, 2H), 6.8-7.8 (m, 9H)

TG 88.8 (3 µmol) 62 (10 µmol) 16.3 (30 µmol)
SOCE 0 (10 µmol) 0 (30 µmol) 30 (100 µmol)
IICR 30 (10 µmol) 10 (30 µmol) 30 (100 µmol)

Example 66

2-(N-isopropylbenzyl)aminoethyl-2-naphthylketone 8291

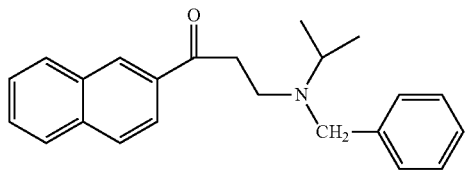 [SMILES: CC(C)N(CCC(=O)c1ccc2ccccc2c1)Cc1ccccc1]

2-acetonaphthone (17 mg), isopropylbenzylamine (149 mg), and paraformaldehyde (39 mg) were reacted in dioxane (0.2 ml) at 150° C. for 2 hours.

NMR (CDCl$_3$) 1.05 (m, 6H), 2.5 (m, 2H), 3.0 (m, 2H), 3.0 (m, 1H), 3.7 (m, 2H), 7.1-7.9. (m, 12H)

TG 80.2 (3 µmol) 62.4 (10 µmol) 17.5 (30 µmol)
SOCE 0 (10 µmol) 0 (30 µmol) 0 (100 µmol)
IICR 10 (10 µmol) 10 (30 µmol) 70 (100 µmol)

Example 67

3-methoxyacryloylbenzene 8294

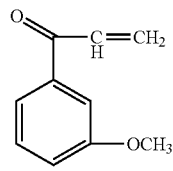

Vinyl-4-methoxy phenylcarbinol (172 mg) was oxidized with pyridinium chlorochromate (230 mg).

NMR (CDCl$_3$) 2.9 (m, 3H), 5.7 (m, 1H), 6.3 (m, 1H), 7.2 (m, 1H), 7.7 (m, 4H)

TG 83.9 (3 µmol) 53.6 (10 µmol) 16.8 (30 µmol)
SOCE 0 (10 µmol) 0 (30 µmol) 0 (100 µmol)
IICR 40 (10 µmol) 40 (30 µmol) 70 (100 µmol)

Example 68

1-acryloylnaphthalene 8293

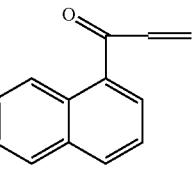

Vinyl-1-naphthylcarbinol (184 mg) was oxidized with pyridinium chlorochromate (214 mg).

NMR (CDCl$_3$) 5.25 (m, 1H), 6.05 (m, 1H), 6.14 (d, 1H), 7.2-8.3 (m, 7H)

TG 33.1 (3 µmol) 7.8 (10 µmol) 0.8 (30 µmol)
SOCE 0 (10 µmol) 10 (30 µmol) 70 (100 µmol)
IICR 80 (10 µmol) 90 (30 µmol) 95 (100 µmol)

Example 69

2-(isopropylbenzyl)aminoethylphenylketone 8299

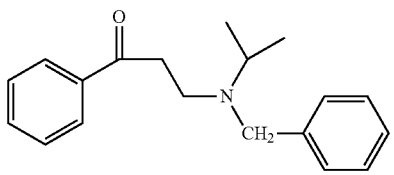 [SMILES: CC(C)N(CCC(=O)c1ccccc1)Cc1ccccc1]

Acetophenone (17 mg), isopropylbenzylamine (149 mg), and paraformaldehyde (39 mg) were reacted in dioxane (0.2 ml) at 150° C. for 2 hours reaction.

NMR (CDCl$_3$) 1.05 (m, 6H), 2.5 (m, 2H), 3.0 (m, 2H), 3.0 (m, 1H), 3.7 (m, 2H), 6.5 (1H), 7.0-7.9 (m, 10H)

TG 68.4 (3 µmol) 40.2 (10 µmol) 3.4 (30 µmol)
SOCE 0 (10 µmol) 10 (30 µmol) 20 (100 µmol)
IICR 20 (10 µmol) 20 (30 µmol) 90 (100 µmol)

Example 70

2-N-diphenylaminoethyl naphthylketone 8301

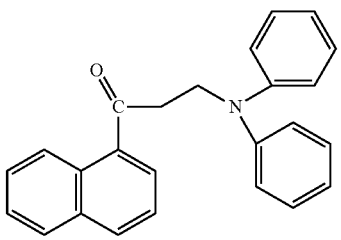 [SMILES: O=C(CCN(c1ccccc1)c1ccccc1)c1cccc2ccccc12]

1-acetonaphthone (170 mg), diphenyl amine (169 mg), and paraformaldehyde (39 mg) were reacted in dioxane (0.2 ml) at 150° C. for 2 hours.

NMR (CDCl$_3$) 2.8 (m, 2H), 3.2 (m, 2H), 7.0-8.05 (m, 17H)

TG 100 (3 µmol) 91 (10 µmol) 74 (30 µmol)
SOCE 0 (10 µmol) 10 (30 µmol) 20 (100 µmol)
IICR 10 (10 µmol) 0 (30 µmol) 40 (100 µmol)

Example 71

2-(N-methylbenzyl)aminoethyl naphthylketone 8303

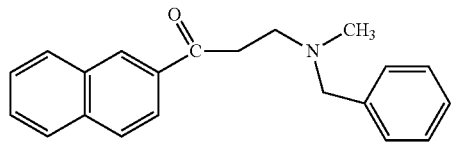 [SMILES: CN(CCC(=O)c1ccc2ccccc2c1)Cc1ccccc1]

2-acetonaphthone (170 mg), methylbenzylamine (121 mg), and paraformaldehyde (39 mg) were reacted in dioxane (0.2 ml) at 150° C. for 2 hours.

NMR (CDCl$_3$) 2.3 (m, 2H), 2.8 (m, 2H), 3.8 (m, 5H), 7.4-80 (m, 12H)
TG 92.9 (3 μmol) 82.7 (10 μmol) 31.8 (30 μmol)
SOCE 0 (10 μmol) 0 (30 μmol) 0 (100 μmol)
IICR 0 (10 μmol) 0 (30 μmol) 0 (100 μmol)

Example 72

2-(N-isopropylbenzyl)aminoethyl-4-methoxyphenylketone 8304

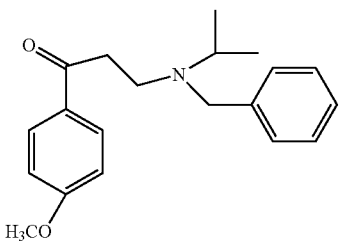 [SMILES: COc1ccc(C(=O)CCN(Cc2ccccc2)C(C)C)cc1]

4-methoxyacetophenone (150 mg), isopropylbenzylamine (149 mg), and paraformaldehyde (39 mg) were reacted in dioxane (0.2 ml) at 150° C. for 2 hours.

NMR (CDCl$_3$) 1.05 (m, 6H), 2.5 (m, 2H), 3.0 (m, 2H), 3.0 (m, 1H), 3.7 (m, 2H), 3.9 (s, 3H), 6.9-8.0 (m, 9H)
TG 93.6 (3 μmol) 87.5 (10 μmol) 43.1 (30 μmol)
SOCE 0 (10 μmol) 10 (30 μmol) 20 (100 μmol)
IICR 20 (10 μmol) 20 (30 μmol) 70 (100 μmol)

Example 73

2-(N-isopropylbenzyl)aminoethyl-2-pyridylketone 8305

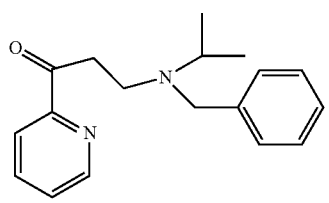 [SMILES: CC(C)N(CCC(=O)c1ccccn1)Cc1ccccc1]

2-acetylpyridine (121 mg), isopropylbenzylamine (149 mg), and paraformaldehyde (39 mg) were reacted in dioxane (0.2 ml) at 150° C. for 2 hours.

NMR (CDCl$_3$) 1.05 (m, 6H), 2.5 (m, 2H), 3.0 (m, 2H), 3.0 (m, 1H), 3.7 (m, 2H), 7.0-8.1 (m, 9H)
TG 84 (0.3 μmol) 52 (1 μmol) 16.9 (3 μmol) 9.5 (10 μmol) 4.4 (30 μmol)
SOCE 0 (10 μmol) 0 (30 μmol) 10 (100 μmol)
IICR 70 (10 μmol) 100 (30 μmol) 90 (100 μmol)

Example 74

2-(N-methylbenzyl)aminoethyl-1-naphthylketone 8306

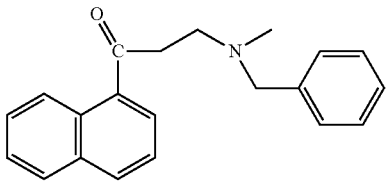 [SMILES: CN(CCC(=O)c1cccc2ccccc12)Cc1ccccc1]

1-acetonaphthone (170 mg), methylbenzylamine (121 mg), and paraformaldehyde (39 mg) were reacted in dioxane (0.2 ml) at 150° C. for 2 hours.

NMR (CDCl$_3$) 2.2 (m, 3H), 2.7 (m, 2H), 3.0 (m, 2H), 3.7 (m, 2H), 7.3-8.0 (m, 12H)
TG 96.1 (3 μmol) 89 (10 μmol) 65 (30 μmol)
SOCE 0 (10 μmol) 10 (30 μmol) 30 (100 μmol)
IICR 30 (10 μmol) 50 (30 μmol) 70 (100 μmol)

Example 75

2-(N-diphenyl)aminoethyl-2-naphthylketone 8307

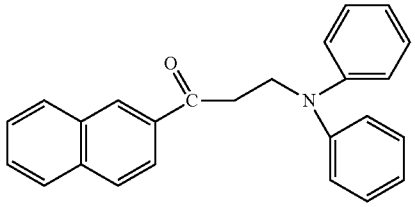 [SMILES: O=C(CCN(c1ccccc1)c1ccccc1)c1ccc2ccccc2c1]

2-acetonaphthone (170 mg), dibenzyl amine (169 mg), and paraformaldehyde (39 mg) were reacted in dioxane (0.2 ml) at 150° C. for 2 hours.

NMR (CDCl$_3$) 2.5 (m, 2H), 3.7 (m, 2H), 6.7-8.0 (m, 17H)
TG 91.4 (3 μmol) 66.1 (10 μmol) 35.1 (30 μmol)
SOCE 0 (10 μmol) 0 (30 μmol) 0 (100 μmol)
IICR 0 (10 μmol) 0 (30 μmol) 0 (100 μmol)

Example 76

2-(N-methylbenzyl)aminoethyl-4-methoxyphenylketone 8309

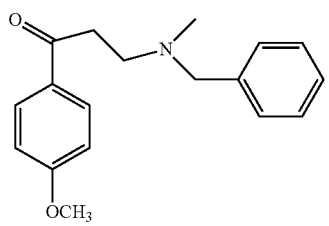 [SMILES: COc1ccc(C(=O)CCN(C)Cc2ccccc2)cc1]

1-4-methoxyacetophenone (150 mg), methylbenzylamine (121 mg), and paraformaldehyde (39 mg) were reacted in dioxane (0.2 ml) at 150° C. for 2 hours.

NMR (CDCl$_3$) 2.2 (m, 3H), 2.5 (m, 2H), 3.7 (m, 2H), 3.9 (m, 5H), 6.9-8.0 (9H)

TG 93.5 (3 μmol) 82 (10 μmol) 57 (30 μmol)
SOCE 0 (10 μmol) 10 (30 μmol) 20 (100 μmol)
IICR 0 (10 μmol) 10 (30 μmol) 30 (100 μmol)

Example 77

2-(N-methylbenzyl)aminoethyl-2-pyridylketone 8310

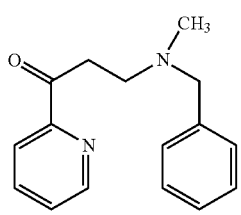 [SMILES: CN(CCC(=O)c1ccccn1)Cc1ccccc1]

2-acetylpyridine (150 mg), methylbenzylamine (121 mg), and paraformaldehyde (39 mg) were reacted in dioxane (0.2 ml) at 150° C. for 2 hours reaction.

NMR (CDCl$_3$) 2.27 (s, 3H), 2.5 (m, 2H), 3.0 (m, 2H), 3.7 (m, 2H), −8.0 (9H)

TG 85.2 (3 μmol) 71.2 (10 μmol) 23.4 (30 μmol)
SOCE 0 (10 μmol) 20 (30 μmol) 30 (100 μmol)
IICR 0 (10 μmol) 10 (30 μmol) 30 (100 μmol)

Example 78

2-(N-methylbenzyl)aminoethyl-5-methyl-2-naphthylketone 8315

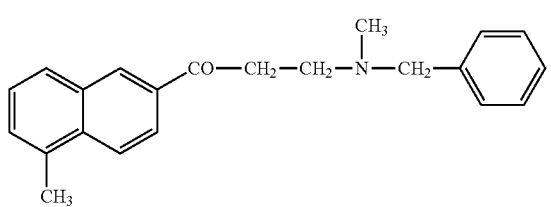 [SMILES: Cc1cccc2cc(C(=O)CCN(C)Cc3ccccc3)ccc12]

5-methylacryloylnaphthalene (14.8 mg) and methylbenzylamine (9.1 mg) were reacted at 50° C. for 5 hours.

NMR (CDCl$_3$) 2.2 (s, 3H), 2.5 (m, 2H), 3.0 (m, 2H), 3.7 (m, 2H), 3.9 (s, 3H), 7.2-8.1 (m, 11H)

TG 87.9 (3 μmol) 62.7 (10 μmol) 8.2 (30 μmol)
SOCE 10 (10 μmol) 20 (30 μmol) 50 (100 μmol)
IICR 20 (10 μmol) 70 (30 μmol) 90 (100 μmol)

Example 79

2-(N-isopropylbenzyl)aminoethyl-5-methyl-2-naphthylketone 8316

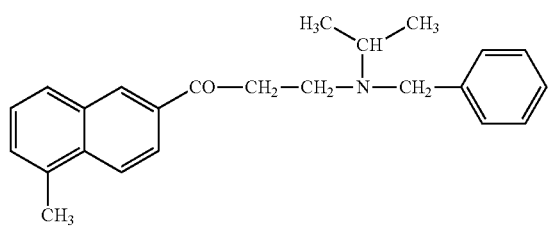 [SMILES: Cc1cccc2cc(C(=O)CCN(Cc3ccccc3)C(C)C)ccc12]

5-methylacryloylnaphthalene (14.8 mg) and isopropylbenzylamine (9.1 mg) were reacted at 50° C. for 5 hours.

NMR (CDCl$_3$) 1.05 (m, 6H), 2.5 (m, 2H), 3.0 (m, 2H), 3.0 (m, 1H), 3.7 (m, 2H), 3.9 (s, 3H), 7.2-8.1 (m, 11H)

TG 64.4 (3 μmol) 28.1 (10 μmol) 1.8 (30 μmol)
SOCE 10 (10 μmol) 30 (30 μmol) 70 (100 μmol)
IICR 70 (10 μmol) 90 (30 μmol) 90 (100 μmol)

Example 80

2-(N-diphenyl)aminoethyl-5-methyl-2-naphthylketone 8317

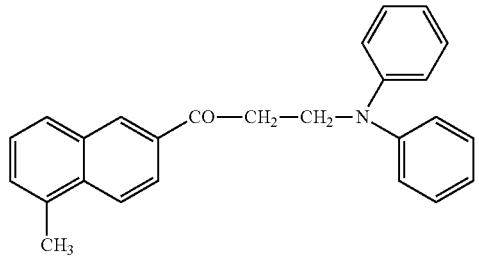 [SMILES: Cc1cccc2cc(C(=O)CCN(c3ccccc3)c3ccccc3)ccc12]

5-methylacryloylnaphthalene (14.8 mg) and diphenyl amine (9.1 mg) were reacted at 50° C. for 5 hours.

NMR (CDCl$_3$) 2.7 (m, 2H), 3.4 (m, 2H), 4.2 (s, 3H) 6.9-8.0 (16H)

TG 72.2 (3 μmol) 54.9 (10 μmol) 10.8 (30 μmol)
SOCE 10 (10 μmol) 30 (30 μmol) 50 (100 μmol)
IICR 10 (10 μmol) 50 (30 μmol) 90 (100 μmol)

Example 81

2-piperidinoethyl-5-methyl-2-naphthylketone 8318

5-methylacryloylnaphthalene (21.8 mg) and piperidine (9.1 mg) were reacted at 50° C. for 5 hours.

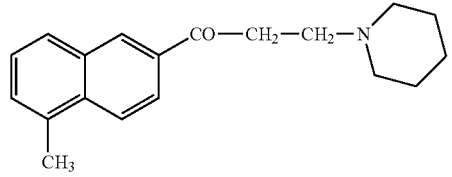 [SMILES: Cc1cccc2cc(C(=O)CCN3CCCCC3)ccc12]

NMR (CDCl₃) 1.4-1.8 (m, 6H), 2.5 (m, 2H), 2.8 (m, 6H), 3.2 (s, 3H), 7.0-8.0 (6H)
TG 89.2 (3 μmol) 99 (10 μmol) 69.4 (30 μmol)
SOCE 0 (10 μmol) 10 (30 μmol) 40 (100 μmol)
IICR 0 (10 μmol) 10 (30 μmol) 30 (100 μmol)

Example 82

1-(N-benzylisopropyl)aminoethyl-1-naphthylketone 8298

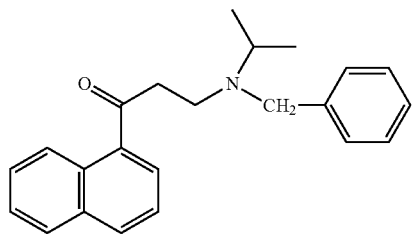 [SMILES: CC(C)N(CCC(=O)c1cccc2ccccc12)Cc1ccccc1]

1-acetonaphthone (170 mg), isopropylbenzylamine (149 mg), and paraformaldehyde (39 mg) were reacted in dioxane (0.2 mol) at 140° C. for 2 hours.
NMR (CDCl₃) 1.05 (m, 6H), 2.7 (m, 2H), 3.05 (m, 1H), 3.10 (m, 2H), 3.60 (m, 2H), 7.1-8.0 (m, 12H)
TG 90.3 (3 μmol) 57 (10 μmol) 6.5 (30 μmol)
SOCE 0 (10 μmol) 0 (30 μmol) 20 (100 μmol)
IICR 50 (10 μmol) 70 (30 μmol) 100 (100 μmol)

Example 83

N-methylpiperazinylpropyl-1-thiophenylketone 8576

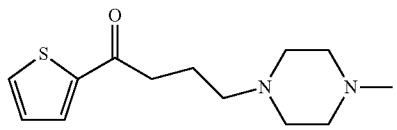 [SMILES: CN1CCN(CCCC(=O)c2cccs2)CC1]

2-(4-chlorobutanoyl)thiophene (188 mg), N-methylpiperidine (100 mg), and diisopropylethyl amine (128 mg) were heated at 100° C. for 1 hour.
NMR (CDCl₃) 1.3 (m, 2H), 2.20 (m, 2H), 2.40 (m, 2H), 2.9 (m, 4H), 3.6 (m, 2H), 4.2 (s, 2H), 6.8 (s, 1H), 7.7 (s. 1H), 7.7 (s, 1H)
TG 100 (3 μmol) 100 (10 μmol) 88 (30 μmol)

Example 84

2-(N-isopropylbenzyl)aminoethyl-5-chloro-2-naphthylketone 8323

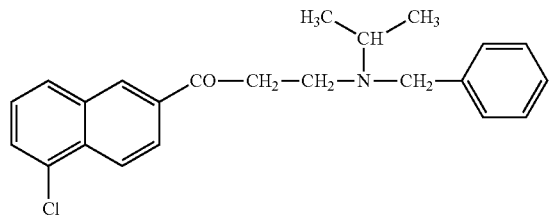 [SMILES: CC(C)N(CCC(=O)c1ccc2c(Cl)cccc2c1)Cc1ccccc1]

Vinyl-5-chloro-2-naphthylketone (18.5 mg) and isopropylbenzylamine (12.7 mg) were reacted in dichloromethane (0.5 mL).
NMR (CDCl₃) 1.05 (m, 6H), 2.5 (m, 2H), 3.0 (m, 2H), 3.0 (m, 1H), 3.7 (m, 2H), 7.0-8.9 (11H)
TG 34.5 (3 μmol) 11.6 (10 μmol) 1.4 (30 μmol)
SOCE 20 (10 μmol) 30 (30 μmol) 70 (100 μmol)
IICR 90 (10 μmol) 100 (30 μmol) 100 (100 μmol)

Example 85

2-(N-isopropylbenzyl)aminoethyl-4-phenoxyphenylketone 8324

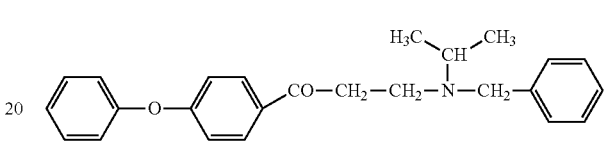

Vinyl-4-phenoxyphenylketone (15.9 mg) and isopropylbenzylamine (10.6 mg) were reacted in dichloromethane (0.3 mL).
NMR (CDCl₃) 1.05 (m, 6H), 2.5 (m, 2H), 3.0 (m, 2H), 3.0 (m, 1H), 3.7 (m, 2H), 6.9-7.9 (14H)
TG 73.7 (3 μmol) 61.8 (10 μmol) 16.9 (30 μmol)
SOCE 10 (10 μmol) 20 (30 μmol) 30 (100 μmol)
IICR 50 (10 μmol) 50 (30 μmol) 95 (100 μmol)

Example 86

2-(N-methylbenzyl)aminoethyl-4-phenoxyphenylketone 8327

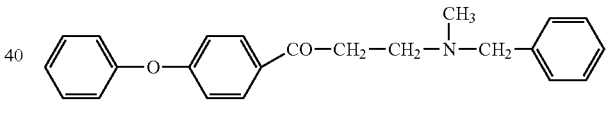

Vinyl-4-phenoxyphenylketone (18.9 mg) and methylbenzylamine (10.3 mg) were reacted in dichloromethane (0.3 mL).
NMR (CDCl₃) 2.5 (m, 2H), 3.0 (m, 2H), 3.7 (m, 2H), 3.9 (m, 3H), 6.9-7.9 (m, 14H)
TG 89.3 (3 μmol) 72.6 (10 μmol) 28.7 (30 μmol)
SOCE 0 (10 μmol) 20 (30 μmol) 50 (100 μmol)
IICR 30 (10 μmol) 70 (30 μmol) 95 (100 μmol)

Example 87

2-(N-2-hydroxy-2-phenylethyl)aminoethyl-4-phenoxyphenylketone 8329

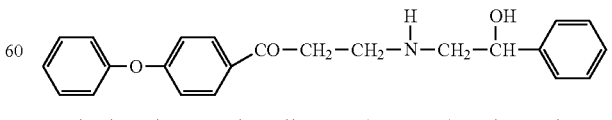

Vinyl-4-phenoxyphenylketone (10.4 mg) and 2-amino-1-phenyl ethanol amine (10.3 mg) were reacted in dichloromethane (0.3 mL).
NMR (CDCl₃) 3.2 (m, 2H), 3.4 (m, 2H), 3.7 (m, 2H), 6.8-8.0 (m, 14H)

TG 61.7 (3 μmol) 41.7 (10 μmol) 8.7 (30 μmol)
SOCE 0 (10 μmol) 0 (30 μmol) 20 (100 μmol)
IICR 10 (10 μmol) 10 (30 μmol) 90 (100 μmol)

Example 88

2-piperidinoethyl-5-chloro-2-naphthylketone 8330

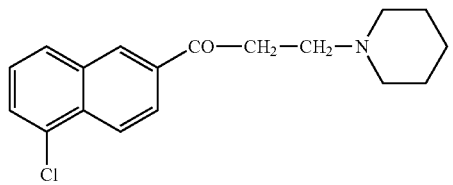 [SMILES: O=C(CCN1CCCCC1)c1ccc2c(Cl)cccc2c1]

Vinyl-5-chloro-2-naphthylketone (21.4 mg) and piperidine (8.4 mg) were reacted in dichloromethane (0.3 mL).
NMR (CDCl$_3$) 1.4-1.8 (m, 6H), 2.5 (m, 2H), 2.8 (m, 6H), 7.0-8.0 (6H)
TG 69.9 (3 μmol) 52.2 (10 μmol) 10.2 (30 μmol)
SOCE 0 (10 μmol) 0 (30 μmol) 20 (100 μmol)
IICR 10 (10 μmol) 10 (30 μmol) 100 (100 μmol)

Example 89

2-(N-2-hydroxyethylbenzyl)aminoethyl-5-chloro-2-naphthylketone 8331

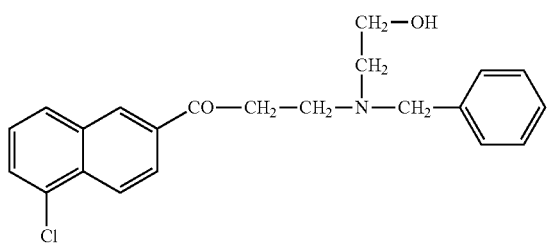 [SMILES: O=C(CCN(CCO)Cc1ccccc1)c1ccc2c(Cl)cccc2c1]

Vinyl-5-chloro-2-naphthylketone (14.8 mg) and benzylethanol amine (10.3 mg) were reacted in dichloromethane (0.3 mL).
NMR (CDCl$_3$) 2.6 (m, 2H), 2.8 (m, 2H), 3.0 (m, 2H), 3.2 (m, 2H), 4.2 (m, 2H), 7.2-8.0 (11H)
TG 27.6 (3 μmol) 11.2 (10 μmol) 11.2 (30 μmol)
SOCE 0 (10 μmol) 10 (30 μmol) 80 (100 μmol)
IICR 30 (10 μmol) 80 (30 μmol) 100 (100 μmol)

Example 90

2-(N-1,1-dihydroxymethylpropyl)aminoethyl-5-chloro-2-naphthylketone 8332

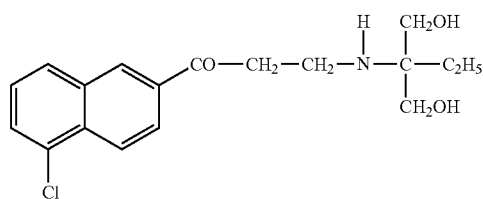 [SMILES: CCC(CO)(CO)NCCC(=O)c1ccc2c(Cl)cccc2c1]

Vinyl-5-chloro-2-naphthylketone (28.4 mg) and 2-amino-2-ethyl-1,3-propanediol (11.4 mg) were reacted in dichloromethane (0.3 mL).
NMR (CDCl$_3$) 0.9 (m, 3H), 1.6 (m, 2H), 3.05 (m, 2H), 3.2 (m, 2H), 3.4 (m, 2H), 3.6 (m, 2H), 7.4-8.3 (6H)

TG 64.5 (3 μmol) 44.5 (10 μmol) 11.7 (30 μmol)
SOCE 0 (10 μmol) 10 (30 μmol) 30 (100 μmol)
IICR 10 (10 μmol) 20 (30 μmol) 100 (100 μmol)

Example 91

2-(N-2-hydroxyethylbutyl)aminoethyl-5-chloro-2-naphthylketone 8333

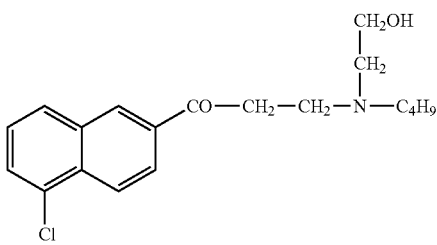

Vinyl-5-chloro-2-naphthylketone (19.1 mg) and N-n-butylethanol amine (9.9 mg) were reacted in dichloromethane (0.3 mL).
NMR (CDCl$_3$) 0.9 (m, 3H), 1.4 (m, 4H), 2.6 (m, 2H), 3.05 (m, 2H), 3.2 (m, 2H), 3.6 (m, 2H), 3.9 (m, 2H), 7.6-8.4 (6H)
TG 31.8 (3 μmol) 14.4 (10 μmol) 18.5 (30 μmol)
SOCE 0 (10 μmol) 10 (30 μmol) 90 (100 μmol)
IICR 20 (10 μmol) 90 (30 μmol) 100 (100 μmol)

Example 92

Allyl-2-naphthylketone 8334

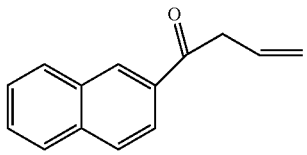

Allyl-2-naphthylcarbinol 205 mg obtained by reacting naphthylaldehyde (960 mg) and 1N allylmagnesium bromide (6.3 ml) and pyridinium chlorochromate (230 mg) were reacted in dichloromethane (2 mL) at room temperature for 4 hours.
TG 82.2 (3 μmol) 67.4 (10 μmol) 52.2 (30 μmol)
SOCE 0 (10 μmol) 0 (30 μmol) 0 (100 μmol)
IICR 0 (10 μmol) 0 (30 μmol) 30 (100 μmol)

Example 93

Allyl-1-naphthylketone 8335

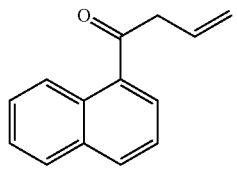

Allyl-1-naphthylcarbinol (205 mg) and pyridinium chlorochromate (230 mg) were reacted in dichloromethane (2 mL) at room temperature for 4 hours.
TG 71 (3 μmol) 69 (10 μmol) 46 (30 μmol)
SOCE 0 (10 μmol) 0 (30 μmol) 30 (100 μmol)
IICR 20 (10 μmol) 70 (30 μmol) 90 (100 μmol)

Example 94

2-(N-t-butylbenzyl)aminoethyl-2-pyridylketone 8336

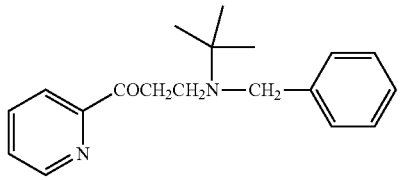

Acetylpyridine (121 mg), N-t-butylbenzylamine (163 mg), and paraformaldehyde (36 mg) were reacted in dioxane (0.2 ml) at 150° C. for 2 hours.
NMR (CDCl$_3$) 1.2 (m, 9H), 2.7 (m, 2H), 3.0 (m, 2H), 3.2 (m, 2H), 7.0-7.9 (m, 9H)
TG 27.3 (3 µmol) 16.0 (10 µmol) 12.2 (30 µmol)
SOCE 0 (10 µmol) 0 (30 µmol) 0 (100 µmol)
IICR 30 (10 µmol) 90 (30 µmol) 100 (100 µmol)

Example 95

2-piperidinoethyl-2-pyridylketone 8338

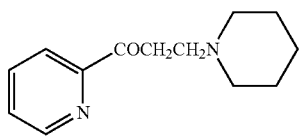

2-acetylpyridine (121 mg), piperidine (65 mg), and paraformaldehyde (36 mg) were reacted in dioxane (0.2 ml) at 150° C. for 2 hours.
NMR (CDCl$_3$) 1.4 (m, 6H), 2.5 (m, 4H), 2.6 (m, 2H), 2.8 (m, 2H), 7.4-8.7 (m, 4H)
TG 89.0 (3 µmol) 76.9 (10 µmol) 69.2 (30 µmol)
SOCE 0 (10 µmol) 0 (30 µmol) 0 (100 µmol)
IICR 0 (10 µmol) 10 (30 µmol) 10 (100 µmol)

Example 96

2-(N-hydroxymethylbenzyl)aminoethyl-2-pyridylketone 8339

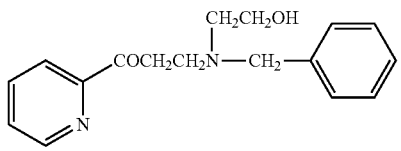

Acetylpyridine (121 mg), N-benzylethanol amine (151 mg), and paraformaldehyde (36 mg) were reacted in dioxane (0.2 ml) at 150° C. for 2 hours.
NMR (CDCl$_3$) 2.7 (m, 2H), 3.0 (m, 2H), 3.7 (m, 2H), 3.8 (m, 2H), 3.6 (m, 2H), 7.2-8.0 (m, 9H)
TG 56.9 (3 µmol) 41.8 (10 µmol) 15.6 (30 µmol)
SOCE 0 (10 µmol) 0 (30 µmol) 0 (100 µmol)
IICR 20 (10 µmol) 30 (30 µmol) 100 (100 µmol)

Example 97

3-acetyl-3-methoxycarbonylpropyl-2-naphthylketone 8341

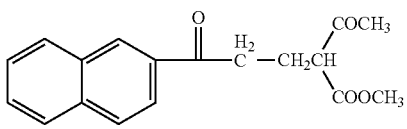

Acryloylnaphthalene (11.9 mg) and acetoacetic acid methyl ester (7.6 mg) were heated with a small amount of sodium ethylate at 45° C. for 5 hours.
NMR (CDCl$_3$) 1.6 (m, 2H), 2.6 (m, 3H), 3.6 (m, 2H), 3.8 (m, 3H), 7.4-8.3 (7H)
TG 100 (3 µmol) 77.5 (10 µmol) 47.6 (30 µmol)
SOCE 0 (10 µmol) 10 (30 µmol) 90 (100 µmol)
IICR 0 (10 µmol) 10 (30 µmol) 70 (100 µmol)

Example 98

3-propionyl-3-methoxycarbonylpropyl-2-naphthylketone 8342

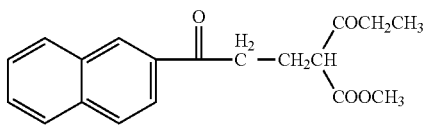

2-acryloylnaphthalene (9.9 mg) and 3-ketovaleric acid methyl ester (7.1 mg) were heated with a small amount of sodium ethylate at 45° C. for 5 hours.
NMR (CDCl$_3$) 1.1 (m, 3H), 1.3 (m, 2H), 2.3 (m, 2H), 2.6 (m, 2H), 3.8 (m, 3H), 7.4-8.3 (7H)
TG 100 (3 µmol) 92.2 (10 µmol) 77.2 (30 µmol)
SOCE 0 (10 µmol) 10 (30 µmol) 60 (100 µmol)
IICR 0 (10 µmol) 0 (30 µmol) 0 (100 µmol)

Example 99

2-(N-methylbenzyl)aminoethyl-2-naphthylketone 8346

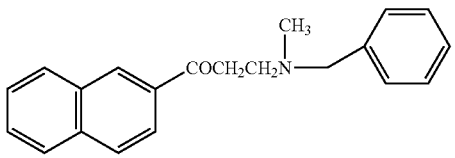

2-acryloylnaphthalene (17.2 mg) and N-methylbenzylamine (7.1 mg) were heated at 45° C. for 15 hours.
NMR (CDCl$_3$) 2.5 (m, 2H), 3.0 (m, 2H), 3.7 (m, 2H), 3.9 (m, 3H), 7.2-78.0 (m, 12H)
TG 100 (3 µmol) 84 (10 µmol) 35 (30 µmol)
SOCE 0 (10 µmol) 0 (30 µmol) 30 (100 µmol)
IICR 0 (10 µmol) 20 (30 µmol) 60 (100 µmol)

Example 100

2-(N-methylhydroxyethyl)aminoethyl-2-naphthylketone 8347

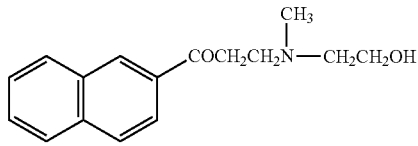

2-acryloylnaphthalene (9.8 mg) and N-methylethanol amine (4.1 mg) were heated at 45° C. for 15 hours.

NMR (CDCl$_3$) 2.5 (m, 2H), 2.6 (m, 2H), 3.1 (m, 2H), 3.6 (m, 2H), 3.7 (m, 3H), 6.9-7.9 (m, 7H)

TG 92.5 (3 µmol) 57.6 (30 µmol)
SOCE 0 (10 µmol) 0 (30 µmol) 20 (100 µmol)
IICR 0 (10 µmol) 0 (30 µmol) 60 (100 µmol)

Example 101

N-benzylethylaminoethyl-3-thiophenylketone 8677

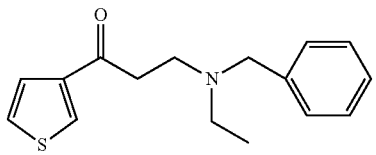 [SMILES: CCN(CCC(=O)c1ccsc1)Cc1ccccc1]

2-acetylthiophene (126 mg), ethylbenzylamine (135 mg), and paraformaldehyde (39 mg) were reacted in dioxane (0.2 ml) at 130° C. for 2 hours.

NMR (CDCl$_3$) 1.0 (s, 3H), 2.2-3.2 (m, 6H), 3.6-3.8 (m, 2H), 7.1-8.0 (m, 8H)

TG 80.5 (3 µmol) 13.4 (30 µmol)
SOCE 10 (10 µmol) 20 (30 µmol) 40 (100 µmol)
IICR 30 (10 µmol) 70 (30 µmol) 100 (100 µmol)

Example 102

N,N-bis(2-hydroxyethyl)aminoethyl-2-pyrazylketone 8678

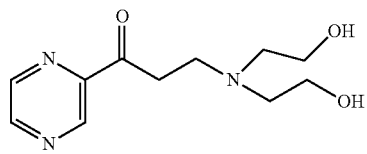 [SMILES: O=C(CCN(CCO)CCO)c1cnccn1]

1-acetylpyrazine (122 mg), diethanol amine (105 mg), and paraformaldehyde (39 mg) were reacted in dioxane (0.2 ml) at 130° C. for 2 hours.

NMR (CDCl$_3$) 2.5-2.8 (m, 4H), 3.4-3.8 (m, 8H), 7.6 (s, 1H), 8.7 (s, 1H), 9.2 (s, 1H)

TG 57.8 (1 µmol) 19.8 (3 µmol) 1.1 (30 µmol)
SOCE 0 (10 µmol) 0 (30 µmol) 0 (100 µmol)
IICR 0 (10 µmol) 20 (30 µmol) 100 (100 µmol)

Example 103

2-(N-isopropylbenzyl)aminoethyl-4-benzylphenylketone 8361

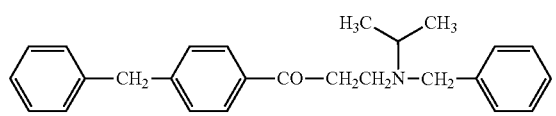

Vinyl-4-benzylphenylketone (15.3 mg) and isopropylbenzylamine (10.2 mg) were heated at 45° C. for 5 hours.

NMR (CDCl$_3$) 1.05 (m, 6H), 2.4 (m, 2H), 2.7 (m, 2H), 2.9 (m, 1H), 3.7 (m, 2H), 4.0 (s, 2H), 7.2-7.8 (m, 14H)

TG 79.3 (3 µmol) 46.3 (10 µmol) 18.5 (30 µmol)
SOCE 10 (10 µmol) 50 (30 µmol) 60 (100 µmol)
IICR 80 (10 µmol) 80 (30 µmol) 100 (100 µmol)

Example 104

2-(N-methylbenzyl)aminoethyl-4-benzylphenylketone 8362

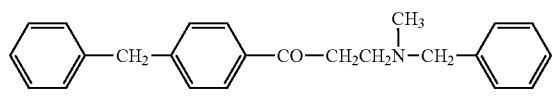

Vinyl-4-benzylphenylketone (15.3 mg) and methylbenzylamine (8.2 mg) were heated at 45° C. for 5 hours.

NMR (CDCl$_3$) 2.4 (m, 2H), 2.7 (m, 2H), 3.7 (m, 2H), 3.8 (m, 3H), 4.0 (m, 2H), 7.1-7.8 (m, 14H)

TG 95 (3 µmol) 82 (10 µmol) 44 (30 µmol)
SOCE 0 (10 µmol) 10 (30 µmol) 70 (100 µmol)
IICR 40 (10 µmol) 20 (30 µmol) 90 (100 µmol)

Example 105

2-(N-t-butylbenzyl)aminoethyl-4-benzylphenylketone 8363

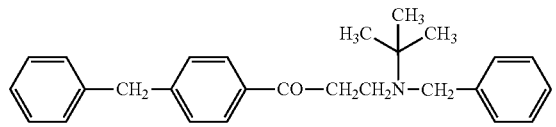

Vinyl-4-benzylphenylketone (15.3 mg) and t-butylbenzylamine (12.2 mg) were heated at 45° C. for 5 hours.

NMR (CDCl$_3$) 1.25 (s, 9H), 2.4 (m, 2H), 2.7 (m, 2H), 3.7 (m, 2H), 4.0 (m, 2H), 7.1-7.8 (m, 14H)

TG 63.3 (3 µmol) 36.2 (10 µmol) 23.6 (30 µmol)
SOCE 0 (10 µmol) 20 (30 µmol) 40 (100 µmol)
IICR 40 (10 µmol) 70 (30 µmol) 90 (100 µmol)

Example 106

2-(N-isopropylbenzyl)aminoethyl-3-pyridylketone
8366

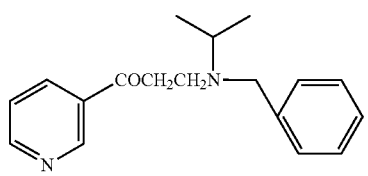

Acetylpyridine (121 mg), propylbenzylamine (149 mg), and paraformaldehyde (36 mg) were reacted in dioxane (0.2 ml) at 150° C. for 2 hours.

NMR (CDCl$_3$) 1.05 (m, 6H), 2.6 (m, 2H), 2.7 (m, 2H), 2.9 (m, 1H), 3.7 (m, 2H), 7.0-9.1 (m, 9H)

TG 57.4 (0.3 μmol), 19.4 (1 μmol) 23.4 (3 μmol) 8.7 (10 μmol) 6.0 (30 μmol)

SOCE 0 (10 μmol) 0 (30 μmol) 0 (100 μmol)

IICR 90 (10 μmol) 90 (30 μmol) 100 (100 μmol)

Example 107

2-(N-isopropylbenzyl)aminoethyl-4-pyridylketone
8367

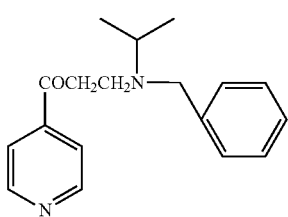

Acetylpyridine (121 mg), isopropylbenzylamine (163 mg), and paraformaldehyde (36 mg) were reacted in dioxane (0.2 ml) at 150° C. for 2 hours.

NMR (CDCl$_3$) 1.05 (m, 6H), 2.5-2.7 (m, 2H), 2.8 (m, 2H), 3.0 (m, 1H), 3.7 (m, 2H), 7.1-7.6 (7H), 7.8 (2H)

TG 10.4 (3 μmol) 6.5 (10 μmol) 6.3 (30 μmol)

SOCE 0 (10 μmol) 20 (30 μmol) 30 (100 μmol)

IICR 30 (10 μmol) 90 (30 μmol) 90 (100 μmol)

Example 108

2-(N-butyl-2-hydroxyethyl)aminoethyl-2-pyrazinylketone 8679

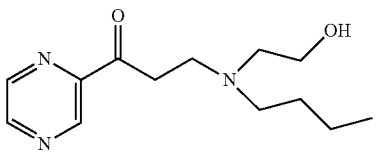 [SMILES: CCCCN(CCO)CCC(=O)c1cnccn1]

Acetylpyrazine (122 mg), 2-hydroxyethylbutyl amine (105 mg), and paraformaldehyde (36 mg) were reacted in dioxane (0.2 ml) at 150° C. for 2 hours.

NMR (CDCl$_3$) 0.8 (s, 3H), 1.5 (m, 4H), 2.4 (m, 2H), 2.7 (m, 2H), 2.9 (m, 2H), 3.5 (m, 2H), 3.7 (m, 2H), 8.72 (s, 1H), 8.75 (s, 1H), 9.21 (m, 1H)

TG 29.6 (3 μmol) 2.6 (30 μmol)

SOCE 0 (10 μmol) 0 (30 μmol) 0 (100 μmol)

IICR 0 (10 μmol) 10 (30 μmol) 80 (100 μmol)

Example 109

2-(N-isopropylbenzyl)aminoethyl-2-furylketone
8370

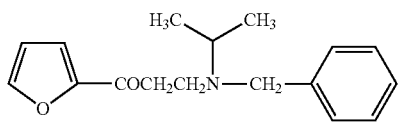

Acetylfuran (121 mg), isopropylbenzylamine (163 mg), and paraformaldehyde (36 mg) were reacted in dioxane (0.2 ml) at 150° C. for 2 hours.

NMR (CDCl$_3$) 0.9-1.1 (m, 6H), 2.45 (m, 2H), 2.8 (m, 2H), 2.9 (m, 1H), 3.7 (m, 2H), 7.0-7.6 (m, 8H)

TG 71 (0.3 μmol) 40 (1 μmol) 13.8 (3 μmol) 14.5 (10 μmol) 17.5 (30 μmol)

SOCE 0 (10 μmol) 0 (30 μmol) 10 (100 μmol)

IICR 20 (10 μmol) 90 (30 μmol) 70 (100 μmol)

Example 110

2-(N-isopropylbenzyl)aminoethyl-2-pyrroleketone
8372

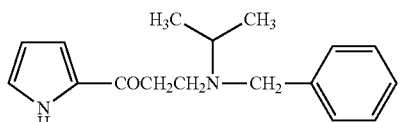

Acetyl pyrrole (109 mg), N-isopropylbenzylamine (149 mg), and paraformaldehyde (36 mg) were reacted in dioxane (0.2 ml) at 140° C. for 2 hours.

NMR (CDCl$_3$) 1.05 (m, 6H), 2.4 (m, 2H), 2.9 (m, 3H), 3.7 (m, 2H), 7.0-8.0 (m, 8H)

TG 92 (3 μmol) 91.2 (10 μmol) 85.9 (30 μmol)

SOCE 0 (10 μmol) 0 (30 μmol) 0 (100 μmol)

IICR 20 (10 μmol) 40 (30 μmol) 100 (100 μmol)

Example 111

2-(N-ethylbenzyl)aminoethyl-2-pyrazinylketone
8680

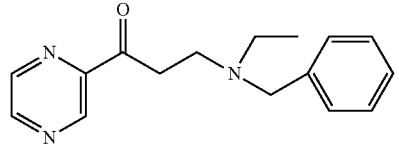 [SMILES: CCN(CCC(=O)c1cnccn1)Cc1ccccc1]

Acetylpyrazine (122 mg), ethylbenzylamine (135 mg), and paraformaldehyde (36 mg) were reacted in dioxane (0.2 ml) at 140° C. for 2 hours.

NMR (CDCl₃) 0.8 (s, 3H), 2.5-2.7 (m, 2H), 3.3 (m, 2H), 3.6 (m, 2H), 6.9-7.1 (m, 6H), 8.6 (s, 1H), 9.1 (s, 1H)
TG 14 (3 μmol) 4.2 (30 μmol)
SOCE 0 (10 μmol) 0 (30 μmol) 0 (100 μmol)
IICR 30 (10 μmol) 80 (30 μmol) 95 (100 μmol)

Example 112

2-(N-mercaptoethyl)aminoethyl-4-phenoxyphenylketone 8375

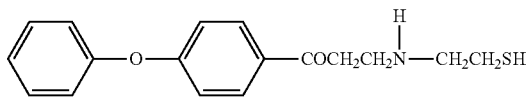

1-acryloyldiphenylether (12.3 mg) and cysteamine (4.3 mg) were reacted at 50° C. for 5 hours.
NMR (CDCl₃) 2.9-3.2 (m, 4H), 3.3 (m, 2H), 3.4 (m, 2H), 6.8-8.0 (9H)
TG 71.4 (3 μmol) 47.1 (10 μmol) 20.3 (30 μmol)
SOCE 0 (10 μmol) 0 (30 μmol) 30 (100 μmol)
IICR 20 (10 μmol) 30 (30 μmol) 40 (100 μmol)

Example 113

2-(N-imidazolylethyl)aminoethyl-4-phenoxyphenylketone 8376

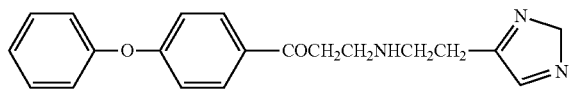

1-acryloyldiphenylether (11.3 mg) and histamine (5.6 mg) were reacted at 50° C. for 5 hours.
NMR (CDCl₃) 2.9-3.2 (m, 2H), 3.5 (m, 2H), 3.7 (m, 2H), 3.8 (m, 2H), 6.8-8.0 (m, 11H)
TG 72.6 (3 μmol) 34.2 (10 μmol) 4.0 (30 μmol)
SOCE 0 (10 μmol) 10 (30 μmol) 40 (100 μmol)
IICR 70 (10 μmol) 90 (30 μmol) 100 (100 μmol)

Example 114

2-(N-hydroxyethylbutyl)aminoethyl-4-phenoxyphenylketone 8377

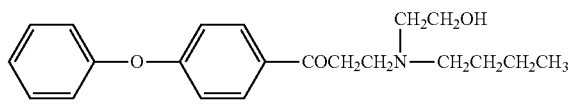

1-acryloyldiphenylether (12.3 mg) and butylethanol amine (6.63 mg) were reacted at 50° C. for 5 hours.
NMR (CDCl₃) 1.4-1.7 (m, 7H), 2.4 (m, 2H), 2.7 (m, 2H), 3.02 (m, 2H), 3.7 (m, 2H), 7.4-8.3 (m, 9H)
TG 73.9 (3 μmol) 44.4 (10 μmol) 3.7 (30 μmol)
SOCE 0 (10 μmol) 10 (30 μmol) 40 (100 μmol)
IICR 70 (10 μmol) 100 (30 μmol) 30 (100 μmol)

Example 115

2-(N-furoylpiperazyl)aminoethyl-4-phenoxyphenylketone 8378

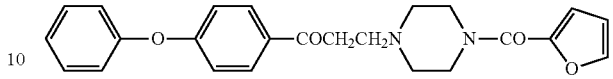

1-acryloyldiphenylether (12.3 mg) and furoylpiperazine (10 mg) were reacted at 50° C. for 5 hours.
NMR (CDCl₃) 12.5 (m, 2H), 3.1 (m, 2H), 3.8 (m, 8H), 6.5-8.0 (12H)
TG 84 (3 μmol) 89 (10 μmol) 28.8 (30 μmol)
SOCE 0 (10 μmol) 0 (30 μmol) 30 (100 μmol)
IICR 20 (10 μmol) 20 (30 μmol) 20 (100 μmol)

Example 116

2-(N-diethyl)aminoethyl-4-phenoxyphenylketone 8379

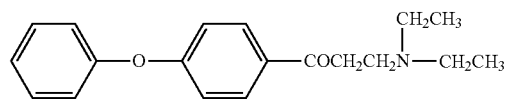

1-acryloyldiphenylether (12.3 mg) and diethyl amine (4.3 mg) were reacted at 50° C. for 5 hours.
NMR (CDCl₃) 1.50 (m, 6H), 3.0 (m, 4H), 3.4 (m, 2H), 7.0-8.0 (m, 9H)
TG 84.8 (3 μmol) 65.1 (10 μmol) 14.1 (30 μmol)
SOCE 0 (10 μmol) 0 (30 μmol) 20 (100 μmol)
IICR 20 (10 μmol) 20 (30 μmol) 70 (100 μmol)

Example 117

2-(N-isopropylbenzyl)aminoethyl-2-pyrazylketone 8381

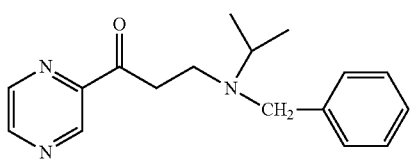 [SMILES: CC(C)N(CCC(=O)c1cnccn1)Cc1ccccc1]

Acetylpyrazine (61 mg), N-isopropylbenzylamine (75 mg), and paraformaldehyde (20 mg) were reacted in dioxane (0.2 ml) at 150° C. for 2 hours.
NMR (CDCl₃) 1.05 (m, 6H), 2.7 (m, 2H), 2.9 (m, 2H), 2.9 (m, 1H), 3.7 (m, 2H), 7.0-8.8 (m, 8H)
TG 32.9 (3 μmol) 12.4 (10 μmol) 0.7 (30 μmol)
SOCE 0 (10 μmol) 0 (30 μmol) 0 (100 μmol)
IICR 20 (10 μmol) 50 (30 μmol) 90 (100 μmol)

Example 118

2-(N-aminobutyl)aminoethyl-2-naphthylketone 8382

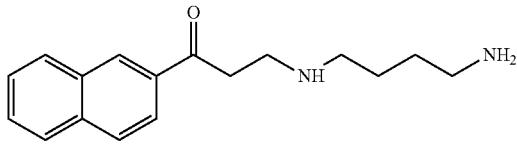 [SMILES: NCCCCNCCC(=O)c1ccc2ccccc2c1]

Acetyl naphthalene (170 mg), diaminobutane (88 mg), and paraformaldehyde (36 mg) were reacted in dioxane (0.2 ml) at 150° C. for 2 hours.

NMR (CDCl$_3$) 1.3 (m, 4H), 1.8 (m, 4H), 3.0 (m, 2H), 3.0 (m, 1H), 3.7 (m, 2H), 6.5 (1H), 7.1 (1H), 7.2 (1H)
TG 100 (3 μmol) 88.6 (10 μmol) 56.1 (30 μmol)
SOCE 0 (10 μmol) 0 (30 μmol) 0 (100 μmol)
IICR 0 (10 μmol) 0 (30 μmol) 0 (100 μmol)

Example 119

2-(N-aminopropylaminobutyl)aminoethyl-2-naphthylketone 8383

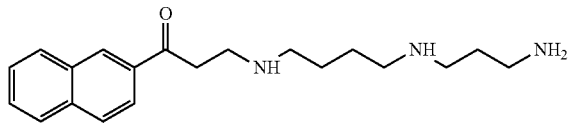 [SMILES: NCCCNCCCCNCCC(=O)c1ccc2ccccc2c1]

Acetyl naphthalene (170 mg), spermidine (145 mg), and paraformaldehyde (36 mg) were reacted in dioxane (0.2 ml) at 150° C. for 2 hours.

NMR (CDCl$_3$) 1.60 (m, 4H), 2.54 (m, 4H), 2.6 (m, 2H), 2.8 (m, 2H), 3.2 (m, 2H), 3.4 (m, 2H), 3.6 (m, 2H), 7.5-8.2 (7H)
TG 100 (3 μmol) 72.4 (10 μmol) 31.7 (30 μmol)
SOCE 0 (10 μmol) 0 (30 μmol) 0 (100 μmol)
IICR 0 (10 μmol) 0 (30 μmol) 0 (100 μmol)

Example 120

2-(N-isopropylbenzyl)aminoethyl-2-thiazolylketone 8384

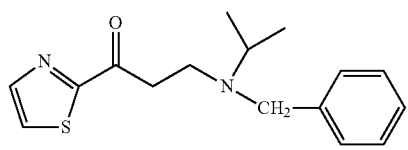 [SMILES: CC(C)N(CCC(=O)c1nccs1)Cc1ccccc1]

Acetyl thiazole (64 mg), N-isopropylbenzylamine (75 mg), and paraformaldehyde (18 mg) were reacted in dioxane (0.2 ml) at 150° C. for 2 hours.

NMR (CDCl$_3$) 1.05 (m, 6H), 2.4 (m, 2H), 2.7 (m, 2H), 2.9 (m, 1H), 3.7 (m, 2H), 7.0-8.0 (m, 7H)
TG 47.5 (3 μmol) 23.5 (10 μmol) 1.7 (30 μmol)
SOCE 0 (10 μmol) 0 (30 μmol) 20 (100 μmol)
IICR 10 (10 μmol) 90 (30 μmol) 100 (100 μmol)

Example 121

2-(N-t-butylbenzyl)aminoethyl-2-furylketone 8385

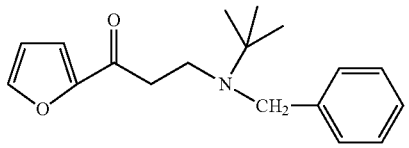

Acetylfuran (110 mg), N-t-butylbenzylamine (163 mg), and paraformaldehyde (36 mg) were reacted in dioxane (0.2 ml) at 150° C. for 2 hours.

NMR (CDCl$_3$) 1.2 (m, 9H), 2.4 (m, 2H), 2.7 (m, 2H), 3.7 (m, 2H), 7.0-8.0 (m, 8H)
TG 70 (0.3 μmol) 38 (1 μmol) 13.3 (3 μmol) 0.2 (10 μmol) 1.7 (30 μmol)
SOCE 0 (10 μmol) 0 (30 μmol) 0 (100 μmol)
IICR 10 (10 μmol) 50 (30 μmol) 100 (100 μmol)

Example 122

2-(N-t-butylhydroxyethyl)aminoethyl-2-thiazolylketone 8681

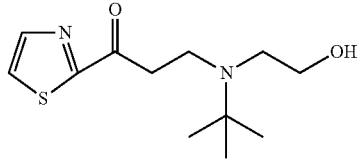 [SMILES: CC(C)(C)N(CCO)CCC(=O)c1nccs1]

Acetyl thiazole (127 mg), N-t-butylethanol amine (117 mg), and paraformaldehyde (36 mg) were reacted in dioxane (0.2 ml) at 130° C. for 2 hours.

NMR (CDCl$_3$) 1.0 (m, 9H), 3.0 (m, 2H), 3.6 (m, 4H), 6.8 (m, 1H), 8.2 (m, 1H)
TG 102 (3 μmol) 68 (30 μmol)
SOCE 0 (10 μmol) 0 (30 μmol) 0 (100 μmol)
IICR 0 (10 μmol) 0 (30 μmol) 0 (100 μmol)

Example 123

2-(N-t-butylhydroxyethyl)aminoethyl-2-furylketone 8387

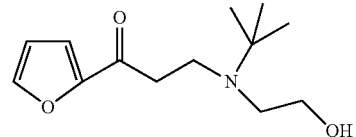 [SMILES: CC(C)(C)N(CCO)CCC(=O)c1ccco1]

Acetylfuran (110 mg), N-t-butylethanol amine (117 mg), and paraformaldehyde (36 mg) were reacted in dioxane (0.2 ml) at 150° C. for 2 hours.

NMR (CDCl$_3$) 1.05 (m, 6H), 2.5 (m, 2H), 3.0 (m, 2H), 3.0 (m, 2H), 3.6 (m, 2H), 6.6 (1H), 7.2 (1H), 7.6 (1H)

TG 57.9 (3 µmol) 25.5 (10 µmol) 9.2 (30 µmol)
SOCE 0 (10 µmol) 10 (30 µmol) 20 (100 µmol)
IICR 20 (10 µmol) 20 (30 µmol) 70 (100 µmol)

Example 124

2-(N-hydroxyethylbenzyl)aminoethyl-2-furylketone 8388

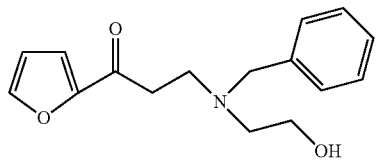 [SMILES: O=C(CCN(CCO)Cc1ccccc1)c1ccco1]

Acetylfuran (110 mg), benzylethanol amine (151 mg), and paraformaldehyde (36 mg) were reacted in dioxane (0.2 ml) at 150° C. for 2 hours.
NMR (CDCl$_3$) 2.5 (m, 2H), 3.0 (m, 2H), 3.7 (m, 2H), 3.8 (m, 2H), 4.2 (m, 2H), 6.6 (1H), 7.2 (1H), 7.1-7.6. (1H), 7.2-7.4 (5H)
TG 31.6 (3 µmol) 23 (10 µmol) 6.8 (30 µmol)
SOCE 0 (10 µmol) 0 (30 µmol) 0 (100 µmol)
IICR 20 (10 µmol) 20 (30 µmol) 70 (100 µmol)

Example 125

2-(N-methylbenzyl)aminoethyl-2-thiophenylketone 8389

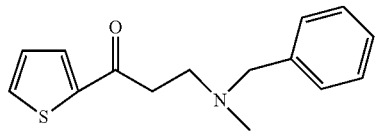 [SMILES: CN(CCC(=O)c1cccs1)Cc1ccccc1]

Acetylthiophene (126 mg), methylbenzylamine (121 mg), paraformaldehyde (36 mg) were reacted in dioxane (0.2 ml) at 150° C. for 2 hours.
NMR (CDCl$_3$) 2.2 (m, 3H), 2.5 (m, 2H), 3.1 (m, 2H), 3.7 (m, 2H), 7.0-7.7 (8H)
TG 78.9 (3 µmol) 62.2 (10 µmol) 19.0 (30 µmol)
SOCE 0 (10 µmol) 0 (30 µmol) 0 (100 µmol)
IICR 0 (10 µmol) 30 (30 µmol) 70 (100 µmol)

Example 126

2-(N-methylhydroxyethyl)aminoethyl-2-thiophenylketone 8390

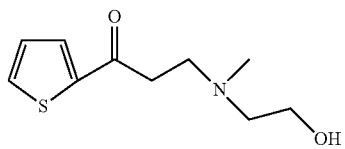

Acetylthiophene (126 mg), methylethanol amine (75 mg), and paraformaldehyde (36 mg) were reacted in dioxane (0.2 ml) at 150° C. for 2 hours.

NMR (CDCl$_3$) 2.5 (s, 3H), 2.7 (m, 2H), 3.7 (m, 2H), 3.8 (m, 2H), 7.2 (1H), 6.5 (1H), 6.7 (1H)
TG 57 (3 µmol) 30 (10 µmol) 4.8 (30 µmol)
SOCE 0 (10 µmol) 0 (30 µmol) 0 (100 µmol)
IICR 20 (10 µmol) 20 (30 µmol) 70 (100 µmol)

Example 127

2-hydroxymethylpyrazinylethyl-2-thiophenylketone 8391

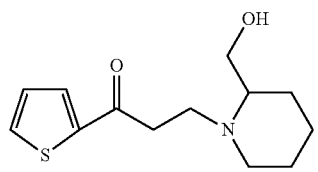 [SMILES: O=C(CCN1CCCCC1CO)c1cccs1]

Acetylthiophene (126 mg), 2-piperidine methanol (115 mg), and paraformaldehyde (36 mg) were reacted in dioxane (0.2 ml) at 150° C. for 2 hours.
NMR (CDCl$_3$) 1.5 (m, 6H), 2.3 (m, 4H), 2.6 (m, 2H), 3.0 (m, 2H), 3.6 (m, 2H), 7.2 (H), 7.6-7.7 (2H)
TG 67.7 (3 µmol) 25.7 (10 µmol) 3.4 (30 µmol)
SOCE 0 (10 µmol) 0 (30 µmol) 10 (100 µmol)
IICR 20 (10 µmol) 20 (30 µmol) 50 (100 µmol)

Example 128

2-(2-mercaptophenyl)aminoethylthiophenylketone 8392

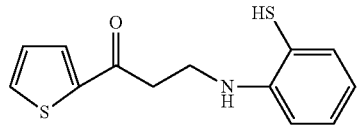 [SMILES: O=C(CCNc1ccccc1S)c1cccs1]

Acetylthiophene (126 mg), aminothiophenol (125 mg), and paraformaldehyde (36 mg) were reacted in dioxane (0.2 ml) at 150° C. for 2 hours.
NMR (CDCl$_3$) 2.5 (m, 2H), 2.7 (m, 2H), 7.1 (1H), 7.6 (1H), 7.7 (1H))
TG 91.5 (3 µmol) 86.3 (10 µmol) 70.5 (30 µmol)
SOCE 0 (10 µmol) 0 (30 µmol) 20 (100 µmol)
IICR 0 (10 µmol) 30 (30 µmol) 10 (100 µmol)

Example 129

2-(N-benzylhydroxyethyl)aminoethyl-2-pyrazylketone 8397

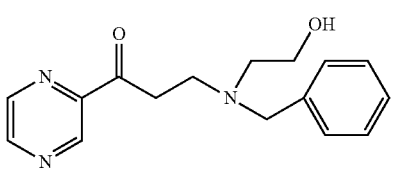 [SMILES: O=C(CCN(CCO)Cc1ccccc1)c1cnccn1]

Acetylpyrazine (122 mg), benzylethanol amine (157 mg), and paraformaldehyde (36 mg) were reacted in dioxane (0.2 ml) at 150° C. for 2 hours.

NMR (CDCl$_3$) 2.6 (m, 2H), 3.0 (m, 2H), 3.7 (m, 2H), 3.8 (m, 2H), 7.2-7.4 (5H), 8.6 (s, 1H), 8.7 (s, 1H), 9.2 (s, 1H))
TG 68 (1 μmol) 37.3 (3 μmol) 8.0 (10 μmol) 10.8 (30 μmol)
SOCE 0 (10 μmol) 0 (30 μmol) 0 (100 μmol)
IICR 0 (10 μmol) 50 (30 μmol) 90 (100 μmol)

Example 130

2-(N-bis-hydroxyethyl)aminoethyl-2-furylketone 8398

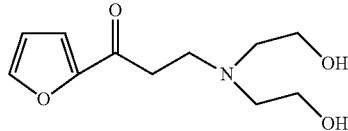 [SMILES: O=C(CCN(CCO)CCO)c1ccco1]

Acetylfuran (110 mg), diethanol amine (105 mg), and paraformaldehyde (36 mg) were reacted in dioxane (0.2 ml) at 150° C. for 2 hours.
NMR (CDCl$_3$) 2.4-2.6 (m, 4H), 2.8 (m, 2H), 3.4-3.7 (m, 4H), 3.7 (m, 2H), 6.5 (1H), 7.1 (1H), 7.5 (1H)
TG 60 (1 μmol) 16.8 (3 μmol) 6.4 (10 μmol) 1.9 (30 μmol)
SOCE 0 (10 μmol) 0 (30 μmol) 0 (100 μmol)
IICR 20 (10 μmol) 20 (30 μmol) 50 (100 μmol)

Example 131

2-(N-methylpiperazyl)ethylphenylketone 8399

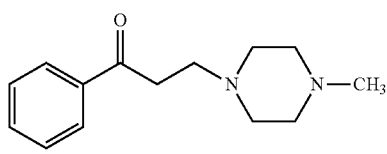 [SMILES: CN1CCN(CCC(=O)c2ccccc2)CC1]

Acetophenone (120 mg), N-methylpiperazine (100 mg), and paraformaldehyde (36 mg) were reacted in dioxane (0.2 ml) at 150° C. for 2 hours.
NMR (CDCl$_3$) 2.5 (m, 2H), 3.0 (m, 4H), 3.0 (m, 2H), 3.6 (m, 2H), 6.6 (1H), 6.5 (1H), 7.1-7.2.0 (7H)
TG 100 (3 μmol) 92.2 (10 μmol) 83.1 (30 μmol)
SOCE 0 (10 μmol) 0 (30 μmol) 0 (100 μmol)
IICR 30 (10 μmol) 20 (30 μmol) 50 (100 μmol)

Example 132

2-(N-phenylhydroxyethyl)aminoethyl-2-furylketone 8400

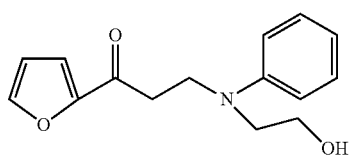 [SMILES: O=C(CCN(CCO)c1ccccc1)c1ccco1]

Acetylfuran (110 mg), anilinoethanol (137 mg), and paraformaldehyde (36 mg) were reacted in dioxane (0.2 ml) at 150° C. for 2 hours.

NMR (CDCl$_3$) 2.5 (m, 2H), 3.0 (m, 4H), 3.0 (m, 2H), 3.6 (m, 2H), 6.6 (1H), 6.5 (1H), 7.1-7.2.0 (7H)
TG 100 (3 μmol) 99 (10 μmol) 67 (30 μmol)
SOCE 0 (10 μmol) 0 (30 μmol) 0 (100 μmol)
IICR 10 (10 μmol) 20 (30 μmol) 20 (100 μmol)

Example 133

2-(N-phenylhydroxyethyl)aminoethylphenylketone 8401

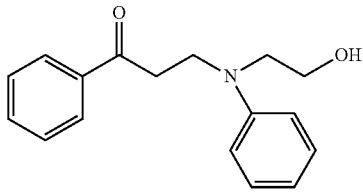 [SMILES: O=C(CCN(CCO)c1ccccc1)c1ccccc1]

Acetophenone (111 mg), 2-anilinoethanol (137 mg), and paraformaldehyde (36 mg) were reacted in dioxane (0.2 ml) at 150° C. for 2 hours.
NMR (CDCl$_3$) 2.5 (m, 2H), 3.0 (m, 4H), 3.0 (m, 2H), 3.6 (m, 2H), 6.6 (1H), 6.5 (1H), 7.1-7.2.0 (7H).
TG 100 (3 μmol) 92.2 (10 μmol) 90 (30 μmol)
SOCE 0 (10 μmol) 0 (30 μmol) 0 (100 μmol)
IICR 20 (10 μmol) 20 (30 μmol) 30 (100 μmol)

Example 134

2-(N-phenylhydroxyethyl)aminoethyl-4-pyridylketone 8402

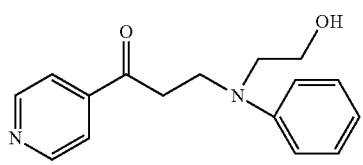 [SMILES: O=C(CCN(CCO)c1ccccc1)c1ccncc1]

Acetylpyridine (121 mg), 2-anilinoethanol (146 mg), and paraformaldehyde (36 mg) were reacted in dioxane (0.2 ml) at 150° C. for 2 hours.
NMR (CDCl$_3$) 2.5 (m, 2H), 3.0 (m, 4H), 3.0 (m, 2H), 3.6 (m, 2H), 6.6 (1H), 6.5 (1H), 7.1-7.2.0 (7H)
TG 63.6 (3 μmol) 42.0 (10 μmol) 10.9 (30 μmol)
SOCE 0 (10 μmol) 0 (30 μmol) 0 (100 μmol)
IICR 20 (10 μmol) 20 (30 μmol) 30 (100 μmol)

Example 135

2-(N-benzylhydroxyethyl)aminoethyl-4-pyridylketone 8403

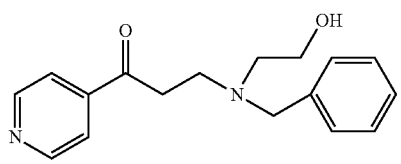 [SMILES: O=C(CCN(CCO)Cc1ccccc1)c1ccncc1]

4-acetylpyridine (243 mg), benzylhydroxyethyl amine (302 mg), and paraformaldehyde (80 mg) were reacted in dioxane (0.4 ml) at 130° C. for 2 hours.

NMR (CDCl$_3$) 2.60 (m, 2H), 3.0 (m, 2H), 3.6 (m, 2H), 4.3 (m, 2H), 7.1 (m, 1H), 7.3 (m, 5H), 7.7 (s, 1H), 8.8 (s, 1H)

TG 64 (3 µmol) 42 (10 µmol) 11 (30 µmol)
SOCE 0 (10 µmol) 0 (30 µmol) 0 (100 µmol)
IICR 20 (10 µmol) 10 (30 µmol) 0 (100 µmol)

Example 136

2-(N-benzylhydroxyethyl)aminoethyl-5-methyl-2-furylketone 8404

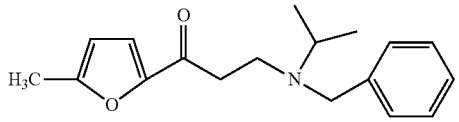 [SMILES: Cc1ccc(C(=O)CCN(Cc2ccccc2)C(C)C)o1]

4-methyl-acetylfuran (124 mg), isopropylbenzylamine (144 mg), and paraformaldehyde (36 mg) were reacted in dioxane (0.2 ml) at 150° C. for 2 hours.

NMR (CDCl$_3$) 1.05 (m, 6H), 2.1 (m, 2H), 2.8 (m, 2H), 3.0 (m, 1H), 3.7 (m, 2H), 6.1 (1H), 7.1-7.5 (m, 7H)

TG 13.6 (3 µmol) 11.0 (10 µmol) 0 (30 µmol)
SOCE 0 (10 µmol) 0 (30 µmol) 20 (100 µmol)
IICR 50 (10 µmol) 60 (30 µmol) 80 (100 µmol)

Example 137

2-(N-benzyl-t-butyl)aminoethyl-5-methyl-2-furylketone 8405

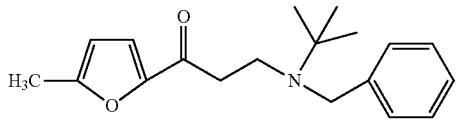 [SMILES: Cc1ccc(C(=O)CCN(Cc2ccccc2)C(C)(C)C)o1]

4-methyl-acetylfuran (124 mg), N-t-butylbenzylamine (163 mg), and paraformaldehyde (36 mg) were reacted in dioxane (0.2 ml) at 150° C. for 2 hours.

NMR (CDCl$_3$) 1.1 (m, 9H), 2.1 (s, 3H), 2.5 (m, 2H), 2.8 (m, 2H), 3.7 (m, 2H), 6.1 (1H), 7.0-7.2 (6H)

TG 42.8 (3 µmol) 16.4 (10 µmol) 5.8 (30 µmol)
SOCE 0 (10 µmol) 0 (30 µmol) 0 (100 µmol)
IICR 40 (10 µmol) 50 (30 µmol) 50 (100 µmol)

Example 138

2-(N-dibenzyl)aminoethyl-5-methyl-2-furylketone 8406

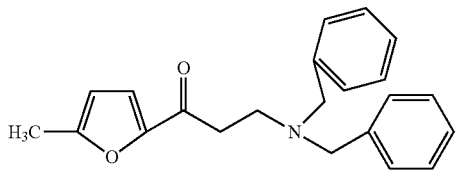 [SMILES: Cc1ccc(C(=O)CCN(Cc2ccccc2)Cc2ccccc2)o1]

4-methyl-acetylfuran (124 mg), dibenzylamine (198 mg), and paraformaldehyde (36 mg) were reacted in dioxane (0.2 ml) at 150° C. for 2 hours.

NMR (CDCl$_3$) 2.1 (m, 3H), 2.5 (m, 2H), 3.4 (m, 2H), 3.7 (m, 4H), 7.3-7.5 (m, 12H)

TG 77.3 (3 µmol) 46.1 (10 µmol) 17.4 (30 µmol)
SOCE 0 (10 µmol) 10 (30 µmol) 20 (100 µmol)
IICR 0 (10 µmol) 0 (30 µmol) 10 (100 µmol)

Example 139

2-(N-benzylhydroxyethyl)aminoethyl-5-methyl-2-furylketone 8407

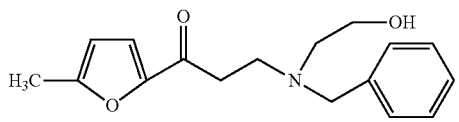 [SMILES: Cc1ccc(C(=O)CCN(CCO)Cc2ccccc2)o1]

4-methyl-acetylfuran (124 mg), hydroxyethylbenzylamine (154 mg), and paraformaldehyde (36 mg) were reacted in dioxane (0.2 ml) at 150° C. for 2 hours.

NMR (CDCl$_3$) 2.1 (m, 3H), 2.5 (m, 2H), 2.9 (m, 2H), 3.7 (m, 2H), 3.8 (m, 2H), 4.3 (m, 2H), 6.2 (s, 1H), 7.1 (m, 1H), 7.2-7.5 (m, 5H)

TG 68.6 (3 µmol) 31.7 (10 µmol) 5.6 (30 µmol)
SOCE 0 (10 µmol) 0 (30 µmol) 0 (100 µmol)
IICR 20 (10 µmol) 20 (30 µmol) 30 (100 µmol)

Example 140

2-(N-methylhydroxyethyl)aminoethyl-5-methyl-2-furylketone 8409

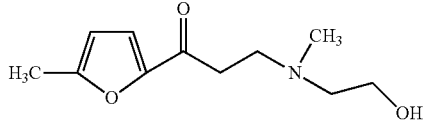

4-methyl-acetylfuran (124 mg), hydroxyethylmethyl amine (76 mg), and paraformaldehyde (36 mg) were reacted in dioxane (0.2 ml) at 150° C. for 2 hours.

NMR (CDCl$_3$) 2.1 (m, 3H), 2.3 (m, 2H), 3.0 (m, 2H), 3.6 (m, 2H), 6.6 (1H), 7.0 (1H)

TG 67 (1 µmol) 32.3 (3 µmol) 11.9 (10 µmol) 4.4 (30 µmol)
SOCE 0 (10 µmol) 0 (30 µmol) 0 (100 µmol)
IICR 20 (10 µmol) 20 (30 µmol) 30 (100 µmol)

Example 141

2-(N-methyl-1,1-dihydroxymethylpropyl)aminoethyl-1-naphthylketone 8410

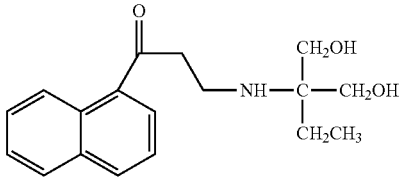 [SMILES: CCC(CO)(CO)NCCC(=O)c1cccc2ccccc12]

1-acetyl naphthalene (170 mg), 2-amino-2-ethyl-1,3-propanediol (161 mg), and paraformaldehyde (36 mg) were reacted in dioxane (0.2 ml) at 150° C. for 2 hours.

NMR (CDCl₃) 0.9 (m, 3H), 2.5 (m, 2H), 3.6 (m, 2H), 3.7 (m, 2H), 4.4 (m, 4H), 7.4-8.0 (7H)
TG 81.5 (3 μmol) 80.2 (10 μmol) 61.6 (30 μmol)
SOCE 0 (10 μmol) 0 (30 μmol) 0 (100 μmol)
IICR 20 (10 μmol) 20 (30 μmol) 20 (100 μmol)

Example 142

2-(N-benzylethyl)aminoethyl-2-furylketone 8412

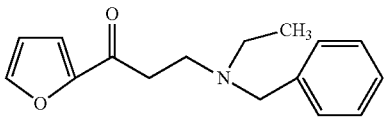 [SMILES: CCN(CCC(=O)c1ccco1)Cc1ccccc1]

2-acetylfuran (121 mg), ethylbenzylamine (140 mg), and paraformaldehyde (36 mg) were reacted in dioxane (0.2 ml) at 150° C. for 2 hours.
NMR (CDCl₃) 1.05 (m, 3H), 2.5 (m, 2H), 2.9 (m, 2H), 3.5 (m, 2H), 3.7 (m, 2H), 6.5 (1H), 7.2-7.2 (7H)
TG 24.8 (3 μmol) 10.8 (10 μmol) 6.9 (30 μmol)
SOCE 0 (10 μmol) 0 (30 μmol) 0 (100 μmol)
IICR 40 (10 μmol) 50 (30 μmol) 80 (100 μmol)

Example 143

2-(N,N-dihydroxyethyl)aminoethyl-2-thiazolylketone 8682

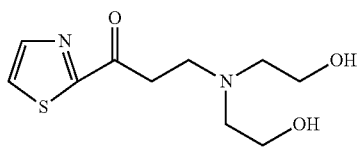 [SMILES: O=C(CCN(CCO)CCO)c1nccs1]

2-acetyl thiazole (50 mg), diethanol amine (44 mg), and paraformaldehyde (10 mg) were reacted at 130° C. for 1 hour.
NMR (CDCl₃) 2.5-2.8 (m, 6H), 3.5-3.9 (m, 6H), 7.6-8.1 (m, 2H)
TG 66 (3 μmol) 10 (30 μmol)
SOCE 0 (10 μmol) 0 (30 μmol) 10 (100 μmol)
IICR 0 (10 μmol) 50 (30 μmol) 90 (100 μmol)

Example 144

2-(N-benzylethyl)aminoethyl-3-pyridylketone 8414

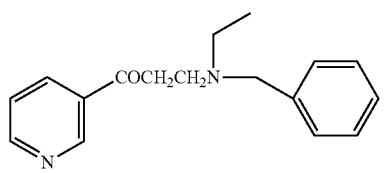

3-acetylpyridine (121 mg), ethylbenzylamine (135 mg), and paraformaldehyde (36 mg) were reacted in dioxane (0.2 ml) at 150° C. for 2 hours.
NMR (CDCl₃) 0.9-1.0 (m, 3H), 2.3-2.8 (m, 4H), 3.4 (m, 2H), 3.7 (m, 2H), 7.0-7.8 (m, 8H), 8.8 (1H)

TG 32.6 (3 μmol) 10.2 (10 μmol) 10.4 (30 μmol)
SOCE 0 (10 μmol) 0 (30 μmol) 0 (100 μmol)
IICR 30 (10 μmol) 40 (30 μmol) 50 (100 μmol)

Example 145

2-(N-bishydroxyethyl)aminoethyl-5-methyl-2-furylketone 8415

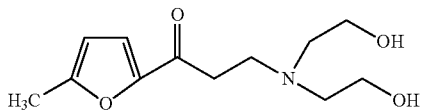 [SMILES: Cc1ccc(C(=O)CCN(CCO)CCO)o1]

4-methyl-acetylfuran (124 mg), bishydroxyethyl amine (125 mg), and paraformaldehyde (36 mg) were reacted in dioxane (0.2 ml) at 150° C. for 2 hours.
NMR (CDCl₃) 2.15-2.4 (m, 4H), 2.4-2.4 (m, 2H), 3.5-3.9 (m, 4H), 4.2 (m, 2H), 6.1 (1H), 7.2 (1H)
TG 62.9 (3 μmol) 45.3 (10 μmol) 13.1 (30 μmol)
SOCE 0 (10 μmol) 10 (30 μmol) 20 (100 μmol)
IICR 50 (10 μmol) 30 (30 μmol) 30 (100 μmol)

Example 146

2-(N-isopropylhydroxyethyl)aminoethyl-5-methyl-2-furylketone 8416

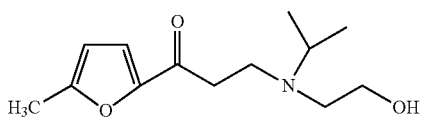 [SMILES: Cc1ccc(C(=O)CCN(CCO)C(C)C)o1]

4-methyl-acetylfuran (124 mg), isopropylaminoethanol (106 mg), paraformaldehyde (36 mg) were reacted in dioxane (0.2 ml) at 150° C. for 2 hours.
NMR (CDCl₃) 0.96 (m, 6H), 2.4 (m, 4H), 3.0 (m, 2H), 3.6 (m, 2H), 6.6 (1H), 7.1-7.2.0 (1H)
TG 36 (3 μmol) 15 (10 μmol) 5 (30 μmol)
SOCE 0 (10 μmol) 0 (30 μmol) 0 (100 μmol)
IICR 50 (10 μmol) 30 (30 μmol) 90 (100 μmol)

Example 147

2-(N-bishydroxyethyl)aminoethyl-2-naphthylketone 8418

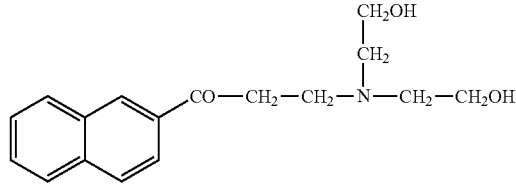 [SMILES: O=C(CCN(CCO)CCO)c1ccc2ccccc2c1]

2-acetyl naphthalene (167 mg), diethanol amine (102 mg), and paraformaldehyde (36 mg) were reacted in dioxane (0.2 ml) at 150° C. for 2 hours.

NMR (CDCl$_3$) 2.6 (m, 4H), 3.0 (m, 2H), 3.6 (m, 2H), 3.8 (m, 2H), 7.6-8.1 (7H)
TG 76.2 (3 µmol) 63.3 (10 µmol) 30.3 (30 µmol)
SOCE 0 (10 µmol) 0 (30 µmol) 0 (100 µmol)
IICR 20 (10 µmol) 60 (30 µmol) 90 (100 µmol)

Example 148

2-(N-bishydroxyethyl)aminoethyl-4-methoxyphenylketone 8419

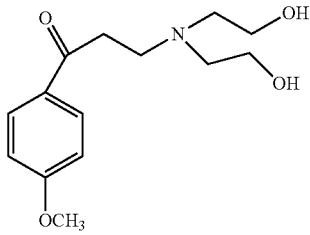 [SMILES: COc1ccc(C(=O)CCN(CCO)CCO)cc1]

4-methoxyacetophenone (171 mg), diethanol amine (102 mg), and paraformaldehyde (36 mg) were reacted in dioxane (0.2 ml) at 150° C. for 2 hours.
NMR (CDCl$_3$) 2.4-2.6 (m, 4H), 2.8 (m, 2H), 3.4-3.7 (m, 4H), 3.7 (s, 3H), 7.0 (m, 2H), 7.95 (m, 2H)
TG 115 (3 µmol) 105 (10 µmol) 58 (30 µmol)
SOCE 0 (10 µmol) 0 (30 µmol) 0 (100 µmol)
IICR 20 (10 µmol) 30 (30 µmol) 90 (100 µmol)

Example 149

2-(N-dihydroxyethyl)aminoethylthiophenylketone 8420

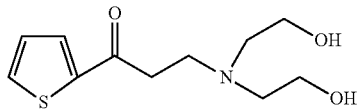 [SMILES: O=C(CCN(CCO)CCO)c1cccs1]

Acetylthiophene (134 mg), diethanol amine (112 mg), and paraformaldehyde (36 mg) were reacted in dioxane (0.2 ml) at 150° C. for 2 hours.
NMR (CDCl$_3$) 2.4-2.6 (m, 4H), 2.8 (m, 2H), 3.4-3.7 (m, 4H), 3.7 (m, 2H), 6.5 (1H), 7.1 (1H), 7.2 (1H)
TG 84.1 (3 µmol) 60.6 (10 µmol) 24.3 (30 µmol)
SOCE 0 (10 µmol) 0 (30 µmol) 0 (100 µmol)
IICR 20 (10 µmol) 20 (30 µmol) 80 (100 µmol)

Example 150

2-(N-bishydroxyethyl)aminoethyl-3-pyridylketone 8421

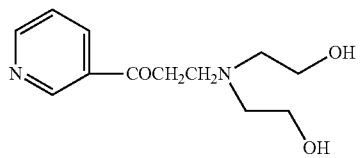

3-acetylpyridine (126 mg), diethanol amine (114 mg), and paraformaldehyde (36 mg) were reacted in dioxane (0.2 ml) at 150° C. for 2 hours.

NMR (CDCl$_3$) 2.5 (m, 2H), 2.8 (m, 4H), 3.6 (m, 4H), 4.0 (m, 2H), 7.4 (1H) 8.2 (1H), 8.6-9.2 (2H)
TG 103.4 (3 µmol) 83.4 (10 µmol) 57.4 (30 µmol)
SOCE 0 (10 µmol) 0 (30 µmol) 10 (100 µmol)
IICR 30 (10 µmol) 20 (30 µmol) 50 (100 µmol)

Example 151

2-(N-isopropylhydroxyethyl)aminoethyl-2-pyrazylketone 8422

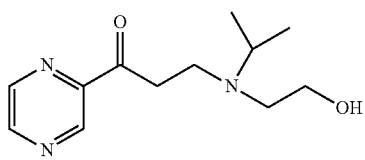 [SMILES: CC(C)N(CCO)CCC(=O)c1cnccn1]

Acetylpyrazine (122 mg), isopropylethanol amine (111 mg), and paraformaldehyde (36 mg) were reacted in dioxane (0.2 ml) at 150° C. for 2 hours.
NMR (CDCl$_3$) 1.1-1.2 (m, 6H), 2.1 (m, 2H), 2.7 (m, 4H), 3.8 (m, 2H), 8.6-9.3 (m, 3H)
TG 64.0 (3 µmol) 46.9 (10 µmol) 18.0 (30 µmol)
SOCE 0 (10 µmol) 0 (30 µmol) 0 (100 µmol)
IICR 20 (10 µmol) 20 (30 µmol) 50 (100 µmol)

Example 152

2-(N-benzyl)aminoethyl-5-methyl-2-furylketone 8423

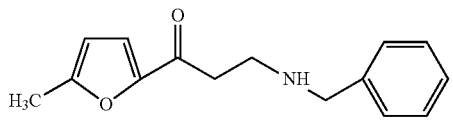 [SMILES: Cc1ccc(C(=O)CCNCc2ccccc2)o1]

4-methyl-acetylfuran (124 mg), benzylamine (107 mg), and paraformaldehyde (36 mg) were reacted in dioxane (0.2 ml) at 150° C. for 2 hours.
NMR (CDCl$_3$) 2.2-2.5 (m, 5H), 3.4 (m, 2H), 3.6 (m, 2H), 6.1 (1H), 7.1-7.5 (6H)
TG 83.3 (3 µmol) 86.4 (10 µmol) 81.4 (30 µmol)
SOCE 0 (10 µmol) 10 (30 µmol) 30 (100 µmol)
IICR 20 (10 µmol) 10 (30 µmol) 30 (100 µmol)

Example 153

2-(N-hydroxyethylisopropyl)aminoethyl-2-furylketone 8424

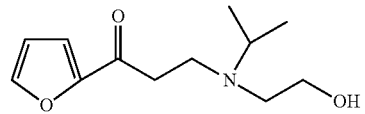 [SMILES: CC(C)N(CCO)CCC(=O)c1ccco1]

Acetylfuran (110 mg), isopropylethanol amine (111 mg), and paraformaldehyde (36 mg) were reacted in dioxane (0.2 ml) at 150° C. for 2 hours.
NMR (CDCl$_3$) 1.05 (m, 6H), 2.5 (m, 2H), 2.9 (m, 2H), 3.9 (m, 2H), 4.2 (m, 2H), 6.6 (1H), 6.5 (1H), 7.1-7.2 (1H)
TG 25.1 (3 µmol) 6.4 (10 µmol) 8.3 (30 µmol)

SOCE 0 (10 μmol) 0 (30 μmol) 10 (100 μmol)
IICR 50 (20 μmol) 60 (30 μmol) 80 (100 μmol)

Example 154

2-(N-hydroxyethylisopropyl)aminoethyl-2-py-ridylketone 8426

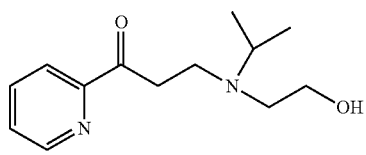 [SMILES: CC(C)N(CCO)CCC(=O)c1ccccn1]

Acetylpyridine (121 mg), isopropylethanol amine (111 mg), and paraformaldehyde (36 mg) were reacted in dioxane (0.2 ml) at 150° C. for 2 hours.
NMR (CDCl$_3$) 1.05 (m, 6H), 2.6 (m, 2H), 2.7 (m, 2H), 3.4 (m, 2H), 3.8 (m, 2H), 7.5 (1H), 7.9 (1H), 8.0 (1H), 8.7 (m, 1H)
TG 60.6 (3 μmol) 44.5 (10 μmol) 12.9 (30 μmol)
SOCE 0 (10 μmol) 0 (30 μmol) 0 (100 μmol)
IICR 40 (10 μmol) 20 (30 μmol) 80 (100 μmol)

Example 155

2-(N-hydroxyethylisopropyl)aminoethyl-4-py-ridylketone 8428

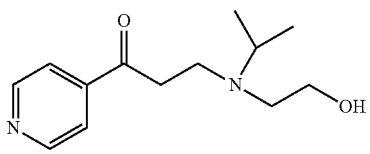 [SMILES: CC(C)N(CCO)CCC(=O)c1ccncc1]

4-acetylpyridine (121 mg), isopropylethanol amine (111 mg), and paraformaldehyde (36 mg) were reacted in dioxane (0.2 ml) at 150° C. for 2 hours.
NMR (CDCl$_3$) 1.1 (m, 6H), 2.6 (m, 4H), 2.8 (m, 2H), 3.6 (m, 2H), 7.2 (2H), 7.8 (2H)
TG 60 (3 μmol) 37 (10 μmol) 9.4 (30 μmol)
SOCE 0 (10 μmol) 0 (30 μmol) 0 (100 μmol)
IICR 20 (10 μmol) 50 (30 μmol) 80 (100 μmol)

Example 156

2-(N-hydroxyethylisopropyl)aminoethyl-2-thiaz-olylketone 8429

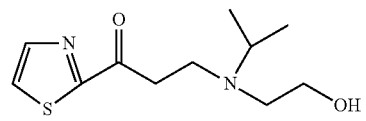 [SMILES: CC(C)N(CCO)CCC(=O)c1nccs1]

Acetyl thiazole (63 mg), isopropylethanol amine (52 mg), and paraformaldehyde (20 mg) were reacted in dioxane (0.2 ml) at 150° C. for 2 hours.
NMR (CDCl$_3$), 0.9-1.2 (m, 6H), 2.7 (m, 2H), 3.0 (m, 4H), 3.4 (m, 1H), 3.8 (m, 2H), 7.7 (1H), 8.1 (1H).

TG 80.9 (3 μmol) 68.4 (10 μmol) 26.0 (30 μmol)
SOCE 0 (10 μmol) 10 (30 μmol) 20 (100 μmol)
IICR 20 (10 μmol) 30 (30 μmol) 60 (100 μmol)

Example 157

1-methyl-2-(N-hydroxyethylisopropyl)aminoethyl-4-fluorophenylketone 8431

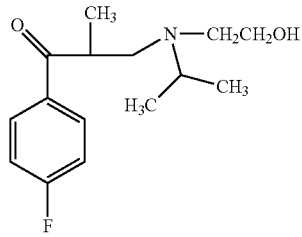

4-fluoropropiophenone (152 mg), isopropylethanol amine (103 mg), and paraformaldehyde (36 mg) were reacted in dioxane (0.2 ml) at 150° C. for 2 hours.
NMR (CDCl$_3$) 1.05 (m, 6H), 1.2 (m, 3H), 2.0-2.5 (m, 2H), 2.8-3.0 (m, 3H), 3.5-3.6 (m, 2H), 6.5 (1H), 7.2 (2H), 7.9. (2H)
TG 104.6 (3 μmol) 107.1 (10 μmol) 84.8 (30 μmol)
SOCE 0 (10 μmol) 0 (30 μmol) 0 (100 μmol)
IICR 0 (10 μmol) 0 (30 μmol) 0 (100 μmol)

Example 158

2-(N-isopropylhydroxyethyl)aminoethyl-3'-py-ridylketone 8433

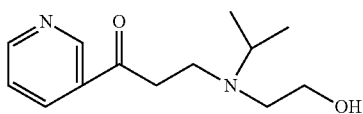 [SMILES: CC(C)N(CCO)CCC(=O)c1cccnc1]

3-acetylpyridine (363 mg), isopropylethanol amine (309 mg), and paraformaldehyde (110 mg) were reacted in dioxane (0.6 ml) at 150° C. for 2 hours.
NMR (CDCl$_3$) 1.05 (m, 6H), 2.5 (m, 4H), 3.0 (m, 2H), 3.0 (m, 1H), 3.7 (m, 2H), 6.5 (1H), 6.8 (1H), 8.6 (1H), 9.0 (1H).
TG 92 (3 μmol) 55 (10 μmol) 11.4 (30 μmol)
SOCE 0 (10 μmol) 0 (30 μmol) 0 (100 μmol)
IICR 30 (10 μmol) 20 (30 μmol) 20 (100 μmol)

Example 159

2-(N-hydroxyethylbenzyl)amino-1-methylethyl-4-fluorophenylketone 8436

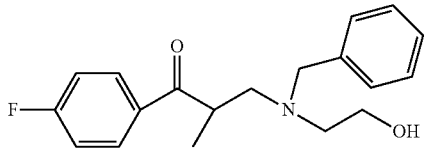 [SMILES: CC(CN(CCO)Cc1ccccc1)C(=O)c1ccc(F)cc1]

4-fluoropropiophenone (152 mg), benzylethanol amine (103 mg), and paraformaldehyde (36 mg) were reacted in dioxane (0.2 ml) at 150° C. for 2 hours.

NMR (CDCl₃) 1.28 (m, 3H), 2.5 (m, 2H), 3.4 (m, 2H), 3.5 (m, 2H), 4.0 (m, 2H), 7.1-7.2.0 (7H), 8.0 (m, 2H)
TG 100 (3 µmol) 100 (10 µmol) 92 (30 µmol)
SOCE 0 (10 µmol) 0 (30 µmol) 20 (100 µmol)
IICR 0 (10 µmol) 0 (30 µmol) 20 (100 µmol)

Example 160

2-(N-bis(hydroxyethyl))amino-1-methylethyl-4-fluorophenylketone 8439

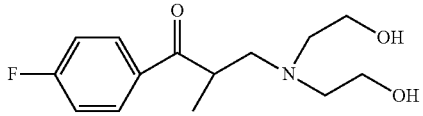 [SMILES: CC(CN(CCO)CCO)C(=O)c1ccc(F)cc1]

4-fluoropropiophenone (152 mg), diethanol amine (105 mg), paraformaldehyde (36 mg) were reacted in dioxane (0.2 ml) at 150° C. for 2 hours.
NMR (CDCl₃) 1.25 (m, 3H), 2.5 (m, 2H), 3.0 (m, 4H), 3.0 (m, 2H), 3.6-3.7 (m, 4H), 6.9-7.2 (2H), 7.9-8.1 (2H)
TG 92 (3 µmol) 113 (10 µmol) 103 (30 µmol)
SOCE 0 (10 µmol) 20 (30 µmol) 60 (100 µmol)
IICR 0 (10 µmol) 0 (30 µmol) 20 (100 µmol)

Example 161

2-(N-hydroxyethyl-t-butyl)amino-1-methylethyl-4-fluorophenylketone 8444

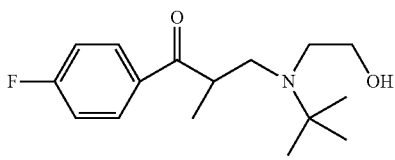 [SMILES: CC(CN(CCO)C(C)(C)C)C(=O)c1ccc(F)cc1]

4-fluoropropiophenone (152 mg), t-butylethanol amine (103 mg), and paraformaldehyde (36 mg) were reacted in dioxane (0.2 ml) at 150° C. for 2 hours.
NMR (CDCl₃) 1.05 (m, 6H), 2.5 (m, 2H), 3.0 (m, 2H), 3.0 (m, 1H), 3.7 (m, 2H), 6.5 (1H), 7.1 (1H), 7.2.0 (1H)
TG 100 (3 µmol) 106 (10 µmol) 88 (30 µmol)
SOCE 0 (10 µmol) 0 (30 µmol) 20 (100 µmol)
IICR 0 (10 µmol) 0 (30 µmol) 20 (100 µmol)

Example 162

2-(N-t-butylbenzyl)amino-1-methylethyl-4-fluorophenylketone 8445

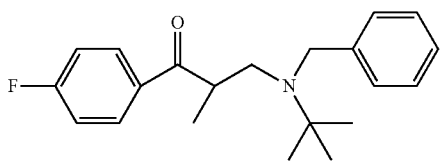 [SMILES: CC(CN(Cc1ccccc1)C(C)(C)C)C(=O)c1ccc(F)cc1]

4-fluoropropiophenone (152 mg), t-butylbenzylamine (163 mg), and paraformaldehyde (36 mg) were reacted in dioxane (0.2 ml) at 150° C. for 2 hours.

NMR (CDCl₃) 1.2 (m, 9H), 1.3 (m, 3H), 2.0 (m, 2H), 3.8 (m, 2H), 6.8-8.1 (9H)
TG 100 (3 µmol) 104 (10 µmol) 87 (30 µmol)
SOCE 0 (10 µmol) 0 (30 µmol) 40 (100 µmol)
IICR 0 (10 µmol) 0 (30 µmol) 0 (100 µmol)

Example 163

2-(N-hydroxyethylmethyl)amino-1-methylethyl-4-fluorophenylketone 8446

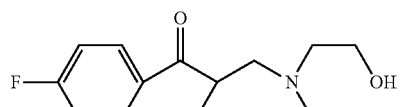

4-fluoropropiophenone (152 mg), methylethanol amine (73 mg), and paraformaldehyde (40 mg) were reacted in dioxane (0.2 ml) at 150° C. for 2 hours.
NMR (CDCl₃) 1.3 (m, 3H), 2.3 (m, 3H), 2.5 (2H), 3.0 (m, 2H), 3.6 (m, 2H), 6.6 (2H), 7.1-7.20 (2H)
TG 100 (3 µmol) 100 (10 µmol) 91 (30 µmol)
SOCE 0 (10 µmol) 0 (30 µmol) 20 (100 µmol)
IICR 0 (10 µmol) 0 (30 µmol) 0 (100 µmol)

Example 164

2-(N-benzyl-2-hydroxyethyl)aminoethyl-2-(N-methylpyrrolyl)ketone 8683

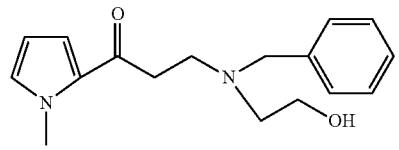 [SMILES: Cn1cccc1C(=O)CCN(CCO)Cc1ccccc1]

2-acetyl-1-methylpyrrole (62 mg), hydroxyethylbenzylamine (76 mg), paraformaldehyde (18 mg) were reacted in dioxane (0.1 ml) at 150° C. for 2 hours.
NMR (CDCl₃) 2.7 (m, 2H), 3.0 (m, 2H), 3.6-3.8 (m, 6H), 4.3 (s, 3H), 7.2 (m, 5H)
TG 107 (3 µmol) 91.3 (30 µmol)
SOCE 0 (10 µmol) 0 (30 µmol) 10 (100 µmol)
IICR 0 (10 µmol) 0 (30 µmol) 40 (100 µmol)

Example 165

2-(N-benzyl-t-butyl)aminoethyl-2-(N-methylpyrrolyl)ketone 8684

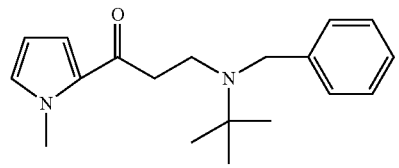 [SMILES: Cn1cccc1C(=O)CCN(Cc1ccccc1)C(C)(C)C]

2-acetyl-1-methylpyrrole (62 mg), t-butylbenzylamine (81 mg), and paraformaldehyde (18 mg) were reacted in dioxane (0.2 ml) at 150° C. for 2 hours.

NMR (CDCl$_3$) 1.0 (s, 9H), 2.33 (m, 2H), 3.64 (m, 2H), 3.83 (m, 2H), 6.0 (s, 1H), 6.6 (s, H), 6.7 (s, 1H), 7.24 (m, 5H)
TG 114 (3 μmol) 100 (30 μmol)
SOCE 0 (10 μmol) 0 (30 μmol) 0 (100 μmol)
IICR 0 (10 μmol) 0 (30 μmol) 0 (100 μmol)

Example 166

2-(N-hydroxyethylisopropyl)aminoethyl-4-fluorophenylketone 8503

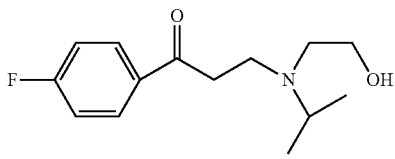

4-fluoroacetophenone (138 mg), hydroxyethylisopropylamine (103 mg), and paraformaldehyde (36 mg) were reacted in dioxane (0.2 ml) at 150° C. for 2 hours.
NMR (CDCl$_3$) 1.05 (m, 6H), 2.5 (m, 4H), 3.0 (m, 2H), 3.0 (m, 1H), 3.7 (m, 2H), 7.2 (2H), 8.0 (2H)
TG 97 (3 μmol) 67 (10 μmol) 35.5 (30 μmol)
SOCE 0 (10 μmol) 0 (30 μmol) 20 (100 μmol)
IICR 0 (10 μmol) 0 (30 μmol) 0 (100 μmol)

Example 167

2-(N-methyl-2-hydroxyethyl)aminoethyl-2-(N-methylpyrrolyl)ketone 8685

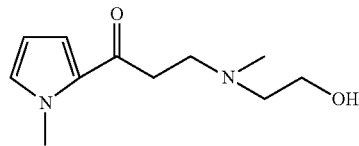

2-acetyl-1-methylpyrrole (62 mg), hydroxyethylmethyl amine (41 mg), and paraformaldehyde (18 mg) were reacted in dioxane (0.1 ml) at 150° C. for 2 hours.
NMR (CDCl$_3$) 2.4-2.8 (m, 6H), 3.8-4.1 (m, 5H), 6.0 (s, 1H), 6.6-6.7 (m, 2H),
TG 104 (3 μmol) 100 (30 μmol)
SOCE 0 (10 μmol) 0 (30 μmol) 0 (100 μmol)
IICR 0 (10 μmol) 0 (30 μmol) 0 (100 μmol)

Example 168

2-(N-isopropylbenzyl)aminomethyl-4-phenylketone 8506

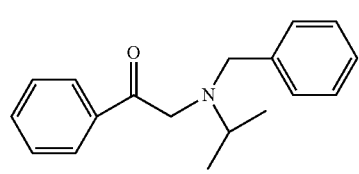 [SMILES: CC(C)N(CC(=O)c1ccccc1)Cc1ccccc1]

Phenacyl chloride (154 mg), isopropylbenzylamine (149 mg), and diisopropylethyl amine (128 mg) were reacted in dioxane (0.1 ml) at 100° C. for 2 hours.
NMR (CDCl$_3$) 1.05 (m, 6H), 2.5 (m, 2H), 3.0 (m, 1H), 3.7 (m, 2H), 7.2-8.0 (10H)
TG 77 (3 μmol) 41.6 (10 μmol) 10.6 (30 μmol)
SOCE 0 (10 μmol) 0 (30 μmol) 50 (100 μmol)
IICR 0 (10 μmol) 0 (30 μmol) 70 (100 μmol)

Example 169

2-(N-isopropyl-2-hydroxyethyl)aminoethyl-2-(N-methylpyrrolyl)ketone 8686

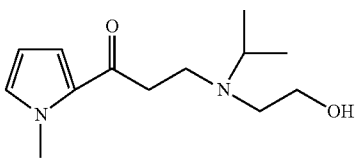 [SMILES: CC(C)N(CCO)CCC(=O)c1cccn1C]

2-acetyl-1-methylpyrrole (62 mg), hydroxyethylisopropylamine (53 mg), and paraformaldehyde (20 mg) were reacted in dioxane (0.1 ml) at 150° C. for 2 hours.
NMR (CDCl$_3$) 10 (m, 6H), 2.4 (m, 2H), 2.9 (m, 2H), 3.9 (m, 2H), 4.0 (m, 3H), 4.3 (m, 2H), 5.15, 6.8, 6.95
TG 107 (3 μmol) 95 (30 μmol)
SOCE 0 (10 μmol) 0 (30 μmol) 0 (100 μmol)
IICR 0 (10 μmol) 0 (30 μmol) 0 (100 μmol)

Example 170

2-(N-isopropyl-2-hydroxyethyl)aminoethyl-2-pyrrolylketone 8687

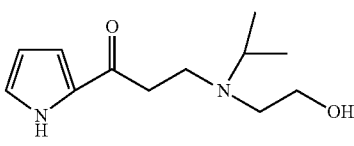 [SMILES: CC(C)N(CCO)CCC(=O)c1ccc[nH]1]

2-acetyl pyrrole (109 mg), hydroxyethylisopropylamine (107 mg), and paraformaldehyde (40 mg) were reacted in dioxane (0.1 ml) at 150° C. for 2 hours.
NMR (CDCl$_3$) 1.60 (m, 6H), 2.35 (m, 2H), 2.83 (m, 2H), 3.78 (m, 2H), 4.23 (m, 2H), 6.16, 6.84, 6.97
TG 103 (3 μmol) 85.2 (30 μmol)
SOCE 0 (10 μmol) 0 (30 μmol) 0 (100 μmol)
IICR 0 (10 μmol) 0 (30 μmol) 0 (100 μmol)

Example 171

2-furyl vinylketone 8512

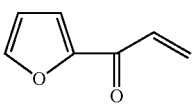

Acryloyl chloride (0.45 g), furan (0.34 g), and AlCl$_3$ (0.66 g) were reacted in CH$_2$Cl$_2$ at −60° C.

NMR (CDCl₃) 5.2 (m, 1H), 5.4 (m, 1H), 6.0 (m, 1H), 6.2-6.5 (m, 1H), 7.2 (m, 1H) 7.5 (m, 1H)
TG 96 (3 µmol) 97 (10 µmol) 7.4 (30 µmol)
SOCE 0 (10 µmol) 10 (30 µmol) 30 (100 µmol)
IICR 0 (10 µmol) 0 (30 µmol) 0 (100 µmol)

Example 172

2-(N-isopropylhydroxyethyl)aminoethyl-2-furylketone 8513

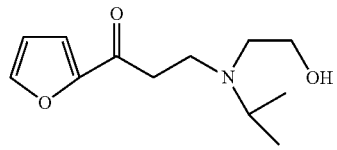 [SMILES: CC(C)N(CCO)CCC(=O)c1ccco1]

2-furyl vinylketone (36 mg) and isopropylhydroxyethyl amine (30 mg) were mixed with dichlormethane (0.5 mL). The resultant was left for 2 hours.
NMR (CDCl₃) 1.4 (m, 6H), 2.2 (m, 2H), 2.8 (m, 2H), 3.4 (m, 2H), 3.8 (m, 2H), 6.5 (1H), 7.1 (1H), 7.2 (1H)
TG 70.6 (3 µmol) 104 (10 µmol) 77.7 (30 µmol)
SOCE 0 (10 µmol) 0 (30 µmol) 0 (100 µmol)
IICR 0 (10 µmol) 0 (30 µmol) 0 (100 µmol)

Example 173

2-(N-benzylhydroxyethyl)aminoethyl-2-pyrrolylketone 8688

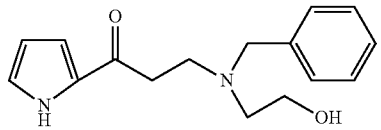 [SMILES: O=C(CCN(CCO)Cc1ccccc1)c1ccc[nH]1]

2-acetyl pyrrole (109 mg), hydroxyethylbenzylamine (151 mg), and paraformaldehyde (40 mg) were reacted in dioxane (0.2 ml) at 150° C. for 2 hours.

NMR (CDCl₃) 2.42 (m, 2H), 2.73 (m, 2H), 2.97 (m, 2H), 3.70-90 (m, 4H), 4.31 (2H), 5.29 (m, 1H), 6.24 (m, 1H), 7.0 (m, 1H), 7.31 (m, 5H)
TG 107 (3 µmol) 91.3 (30 µmol)
SOCE 0 (10 µmol) 0 (30 µmol) 0 (100 µmol)
IICR 0 (10 µmol) 50 (30 µmol) 80 (100 µmol)

Example 174

2-(N-bis(hydroxyethyl))aminoethyl-2-furylketone 8516

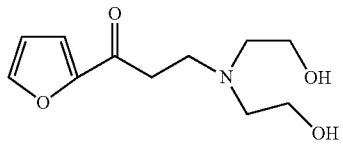 [SMILES: O=C(CCN(CCO)CCO)c1ccco1]

2-acryloylfuran (29 mg) and diethanol amine (24 mg) were reacted in dioxane (0.2 ml) at 50° C. for 2 hours.

NMR (CDCl₃) 3.0 (m, 4H), 3.7 (m, 4H), 3.8 (m, 2H), 6.2 (1H), 6.4 (1H), 7.1-7.2 (1H)
TG 88 (3 µmol) 79.0 (10 µmol) 51.6 (30 µmol)
SOCE 0 (10 µmol) 0 (30 µmol) 0 (100 µmol)
IICR 0 (10 µmol) 0 (30 µmol) 0 (100 µmol)

Example 175

2-(N-benzylmethyl)aminoethyl-2-pyrrolylketone 8689

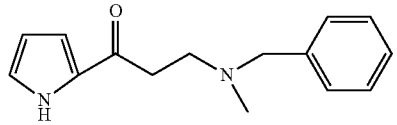 [SMILES: CN(CCC(=O)c1ccc[nH]1)Cc1ccccc1]

2-acetyl pyrrole (112 mg), benzylmethyl amine (125 mg), and paraformaldehyde (40 mg) were reacted in dioxane (0.2 ml) at 130° C. for 2 hours.
NMR (CDCl₃) 2.12 (m, 2H), 2.40 (m, 2H), 8.8 (m, 5H), 6.10 (s, 1H), 7.60 (s, 1H), 7.3 (m, 5H)
TG 99.9 (3 µmol) 108 (30 µmol)
SOCE 0 (10 µmol) 0 (30 µmol) 0 (100 µmol)
IICR 10 (10 µmol) 10 (30 µmol) 20 (100 µmol)

Example 176

2-(1-imidazolylethyl)aminoethyl-3-pyridylketone 8690

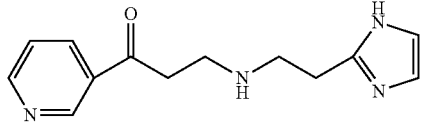 [SMILES: O=C(CCNCCc1ncc[nH]1)c1cccnc1]

3-acetylpyridine (6.5 mg), histamine (6 mg), and paraformaldehyde (2 mg) were reacted in dioxane (0.1 ml) at 150° C. for 2 hours.
NMR (CDCl₃) 2.10 (m, 2H), 2.18 (m, 2H), 3.50 (m, 2H), 3.60 (m, 2H), 7.0-7.8 (m, 61-1)
TG 100 (3 µmol) 88 (30 µmol)
SOCE 0 (10 µmol) 0 (30 µmol) 0 (100 µmol)
IICR 10 (10 µmol) 30 (30 µmol) 50 (100 µmol)

Example 177

2-(N-2-hydroxyethylbenzyl)aminoethyl-3-pyridylketone 8691

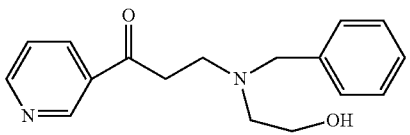 [SMILES: O=C(CCN(CCO)Cc1ccccc1)c1cccnc1]

3-acetylpyridine (121 mg), hydroxyethylbenzylamine (156 mg), and paraformaldehyde (40 mg) were reacted in dioxane (0.2 ml) at 130° C. for 2 hours.
NMR (CDCl₃) 2.6 (m, 2H), 3.6 (m, 2H), 3.7 (m, 2H), 3.9 (m, 2H), 4.3 (m, 2H), 7.2 (s, 1H), 7.4 (m, 5H), 8.2 (s, H), 8.8 (s, 1H), 9.1 (s, 1H)

TG 84.6 (3 μmol) 8.8 (30 μmol)
SOCE 0 (10 μmol) 0 (30 μmol) 0 (100 μmol)
IICR 0 (10 μmol) 0 (30 μmol) 50 (100 μmol)

Example 178

3-(N-isopropylhydroxyethyl)aminopropylphenylketone 8522

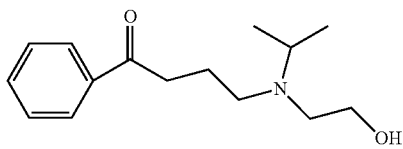 [SMILES: CC(C)N(CCO)CCCC(=O)c1ccccc1]

Chlorobutyrophenone (10.9 mg), hydroxyethylisopropylamine (3.8 mg), and diisopropylethyl amine (4 mg) were reacted in dioxane (0.2 ml) at 50° C. for 2 hours.
NMR (CDCl$_3$) 2.5 (m, 2H), 3.0 (m, 4H), 3.0 (m, 2H), 3.6 (m, 2H), 6.6 (1H), 6.5 (1H), 7.1-7.2.0 (7H)
TG 107 (3 μmol) 100 (10 μmol) 60.3 (30 μmol)
SOCE 0 (10 μmol) 0 (30 μmol) 0 (100 μmol)
IICR 0 (10 μmol) 0 (30 μmol) 0 (100 μmol)

Example 179

3-(N-isopropylbenzyl)aminopropylphenylketone 8523

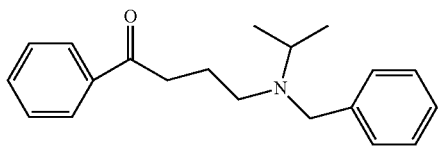 [SMILES: CC(C)N(CCCC(=O)c1ccccc1)Cc1ccccc1]

4-chlorobutyrophenone (10 mg), isopropylbenzylamine (3.8 mg), and diisopropylethanol amine (4.7 mg) at 100° C. for 1.5 hours.
NMR (CDCl$_3$) 1.05 (m, 6H), 2.3 (m, 4H), 3.2 (m, 2H), 3.0 (m, 1H), 3.7 (m, 2H), 6.5 (1H), 7.5-80 (10H)
TG 107 (3 μmol) 100 (10 μmol) 75 (30 μmol)
SOCE 0 (10 μmol) 0 (30 μmol) 0 (100 μmol)
IICR 0 (10 μmol) 0 (30 μmol) 0 (100 μmol)

Example 180

2-(N-2-hydroxyethylbutyl)aminoethyl-3-pyridylketone 8692

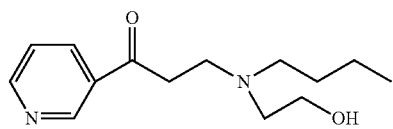

3-acetylpyridine (122 mg), hydroxyethylbutyl amine (115 mg), and paraformaldehyde (40 mg) were reacted in dioxane (0.2 ml) at 150° C. for 2 hours.

NMR (CDCl$_3$) 0.95 (s, 3H), 1.4 (m, 4H), 2.5 (m, 2H), 2.7 (m, 2H), 2.9 (m, 2H), 3.8 (m, 2H), 4.3 (m, 2H) 7.5, 8.2, 8.9, 9.1 (s, 1H)
TG 39.7 (3 μmol) 6.6 (10 μmol) −4.8 (30 μmol)
SOCE 0 (10 μmol) 0 (30 μmol) 0 (100 μmol)
IICR 0 (10 μmol) 0 (30 μmol) 50 (100 μmol)

Example 181

1-methyl-2-(N-hydroxyethylisopropyl)aminoethyl-2-fluorophenylketone 8525

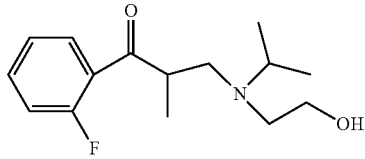 [SMILES: CC(CN(CCO)C(C)C)C(=O)c1ccccc1F]

2-fluoropropylphenone (152 mg), hydroxyethylisopropylamine (103 mg), and paraformaldehyde (40 mg) were reacted in dioxane (0.2 ml) at 150° C. for 2 hours.
NMR (CDCl$_3$) 1.2 (m, 6H), 1.7 (m, 3H), 3.0 (m, 4H), 3.4 (m, 2H), 3.6 (m, 2H), 6.6 (1H), 7.0-7.8 (4H)
TG 108 (3 μmol) 91.3 (10 μmol) 67 (30 μmol)
SOCE 20 (10 μmol) 40 (30 μmol) 80 (100 μmol)
IICR 0 (10 μmol) 10 (30 μmol) 20 (100 μmol)

Example 182

1-methyl-2-(N-benzylisopropyl)aminoethyl-2-fluorophenylketone 8526

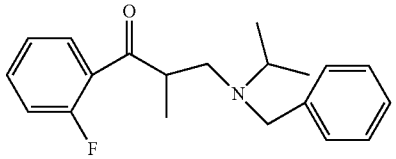 [SMILES: CC(CN(Cc1ccccc1)C(C)C)C(=O)c1ccccc1F]

2-fluoropropylphenone (152 mg), benzylisopropylamine (149 mg), and paraformaldehyde (40 mg) were reacted in dioxane (0.2 ml) at 150° C. for 2 hours.
NMR (CDCl$_3$) 1.1 (m, 6H), 1.4 (m, 3H), 2.8 (m, 2H), 3.0 (m, 1H), 3.7 (m, 2H), 7.1-7.5 (m, 9H)
TG 100 (3 μmol) 96 (10 μmol) 74 (30 μmol)
SOCE 10 (10 μmol) 50 (30 μmol) 80 (100 μmol)
IICR 0 (10 μmol) 0 (30 μmol) 50 (100 μmol)

Example 183

2-(N-isopropylbenzyl)aminoethyl-2-thiophenylketone 8651

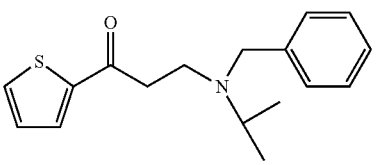 [SMILES: CC(C)N(CCC(=O)c1cccs1)Cc1ccccc1]

2-acetylthiophene (126 mg), benzylisopropylamine (149 mg), and paraformaldehyde (40 mg) were reacted in dioxane (0.2 ml) at 130° C. for 2 hours.

NMR (CDCl₃) 1.1 (m, 6H), 2.6 (m, 2H), 2.9 (m, 2H), 3.6-3.8 (m, 3H), 7.0-7.8 (m, 8H)
TG 27.5 (3 µmol) 5.4 (10 µmol) 68.0 (30 µmol)
SOCE 0 (10 µmol) 0 (30 µmol) 20 (100 µmol)
IICR 0 (10 µmol) 0 (30 µmol) 50 (100 µmol)

Example 184

2-(N-2-hydroxyethylbenzyl)aminoethyl-3-thiophenylketone 8652

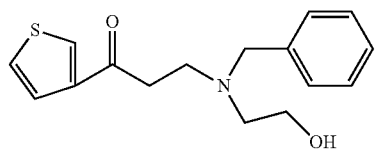 [SMILES: O=C(CCN(CCO)Cc1ccccc1)c1ccsc1]

2-acetylthiophene (126 mg), benzylhydroxyethyl amine (151 mg), and paraformaldehyde (40 mg) were reacted in dioxane (0.2 ml) at 130° C. for 2 hours.
NMR (CDCl₃) 2.55 (m, 2H), 3.0 (m, 2H), 3.7 (m, 2H), 3.8 (m, 2H), 4.35 (m, 2H), 7.1 (m, 6H), 7.55 (s, 1H), 8.0 (s, 1H)
TG 76.5 (3 µmol) 36.8 (10 µmol) 7.3 (30 µmol)
SOCE 0 (10 µmol) 0 (30 µmol) 0 (100 µmol)
IICR 30 (10 µmol) 50 (30 µmol) 60 (100 µmol)

Example 185

2-(N,N-diphenyl)aminoethyl-2-pyridylketone 8337

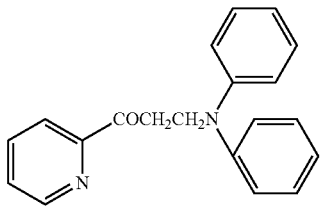

2-acetylpyridine (121 mg), diphenyl amine (169 mg), and paraformaldehyde (40 mg) were reacted in dioxane (0.2 ml) at 130° C. for 2 hours.
NMR (CDCl₃) 2.8 (m, 4H), 6.8-7.4 (m, 10H), 7.4 (1H), 7.8. (1H), 8.1 (m, 1H), 8.7 (m, 1H)
TG 97.1 (3 µmol) 114.6 (10 µmol) 106.2 (30 µmol)
SOCE 0 (10 µmol) 10 (30 µmol) 20 (100 µmol)
IICR 0 (10 µmol) 10 (30 µmol) 20 (100 µmol)

Example 186

2-(N-isopropylbenzyl)aminoethyl-2-(3-ethyl)-pyrazylketone 8656

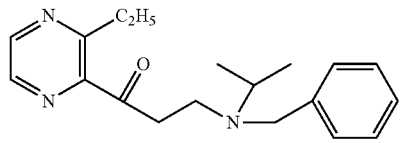 [SMILES: CCc1nccnc1C(=O)CCN(Cc1ccccc1)C(C)C]

2-acetyl-3-ethylpyrazine (151 mg), benzylisopropylamine (149 mg), and paraformaldehyde (40 mg) were reacted in dioxane (0.2 ml) at 130° C. for 2 hours.
NMR (CDCl₃) 1.1-1.2 (m, 6H), 2.7 (m, 1H), 3.1 (m, 4H), 3.7 (m, 2H), 7-7.2 (m, 1H)
TG 29 (3 µmol) 16 (10 µmol) 14 (30 µmol)
SOCE 0 (10 µmol) 0 (30 µmol) 10 (100 µmol)
IICR 70 (10 µmol) 90 (30 µmol) 100 (100 µmol)

Example 187

2-(N-hydroxyethylbenzyl)aminoethyl-2-(3-ethyl)-pyrazylketone 8657

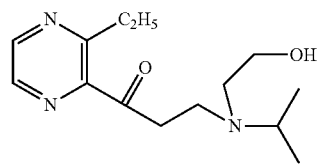 [SMILES: CCc1nccnc1C(=O)CCN(CCO)C(C)C]

2-acetyl-3-ethylpyrazine (150 mg), hydroxyethylisopropylamine (149 mg), and paraformaldehyde (40 mg) were reacted in dioxane (0.2 ml) at 130° C. for 2 hours.
NMR (CDCl₃) 1.3 (m, 3H), 2.6 (m, 4H), 3.2 (m, 4H), 8.6 (s, 1H), 8.7 (s, 1H)
TG 90.3 (3 µmol) 73 (10 µmol) 30 (30 µmol)
SOCE 0 (10 µmol) 0 (30 µmol) 10 (100 µmol)
IICR 20 (10 µmol) 10 (30 µmol) 100 (100 µmol)

Example 188

2-(N-t-butylbenzyl)aminoethyl-2-(3-ethyl)-pyrazylketone 8658

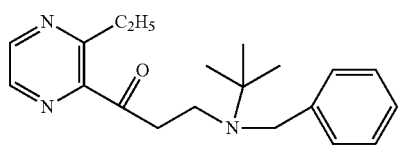 [SMILES: CCc1nccnc1C(=O)CCN(Cc1ccccc1)C(C)(C)C]

2-acetyl-3-ethylpyrazine (151 mg), benzyl-t-butyl amine (149 mg), and paraformaldehyde (40 mg) were reacted in dioxane (0.2 ml) at 130° C. for 2 hours.
NMR (CDCl₃) 1.1 (m, 9H), 2.7 (m, 1H), 3.1 (m, 4H), 3.7 (m, 2H), 7-7.1 (m, 1H), 8.5-8.6 (m, 1H)
TG 42 (3 µmol) 22 (10 µmol) 10 (30 µmol)
SOCE 0 (10 µmol) 0 (30 µmol) 20 (100 µmol)
IICR 50 (10 µmol) 90 (30 µmol) 100 (100 µmol)

Example 189

2-N-adamantaneaminoethylphenylketone 8533

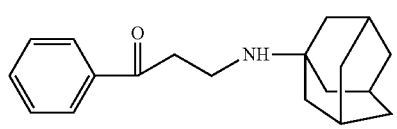 [SMILES: O=C(CCNC12CC3CC(CC(C3)C1)C2)c1ccccc1]

Acetophenone (120 mg), aminoadamantane HCl (187 mg), and paraformaldehyde (36 mg) were reacted in dioxane (0.2 ml) at 110° C. for 2 hours.

NMR (CDCl$_3$) 1.8-2.1 (m, 12H), 3.4 (m, 2H), 3.95 (m, 2H), 7.2-9.4 (5H)

TG 116 (3 µmol) 105 (10 µmol) 83 (30 µmol)
SOCE 0 (10 µmol) 10 (30 µmol) 10 (100 µmol)
IICR 0 (10 µmol) 0 (30 µmol) 0 (100 µmol)

Example 190

2-N-adamantane-aminoethyl-2-methylfurylketone 8534

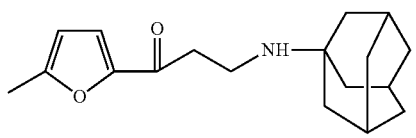 [SMILES: Cc1ccc(C(=O)CCNC23CC4CC(CC(C4)C2)C3)o1]

5-Methyl-2-acetylfuran (124 mg), aminoadamantane HCl (187 mg), and paraformaldehyde (120 mg) were reacted in 110° C. for 2 hours.

NMR (CDCl$_3$) 1.7-2.2 (m, 16H), 3.4 (m, 2H), 3.6 (m, 2H), 6.1 (1H), 7.3 (1H)

TG 106 (3 µmol) 87.3 (10 µmol) 35.9 (30 µmol)
SOCE 0 (10 µmol) 10 (30 µmol) 50 (100 µmol)
IICR 0 (10 µmol) 10 (30 µmol) 50 (100 µmol)

Example 191

1-methyl-2-(N-adamantane)aminoethyl-2-fluorophenylketone 8535

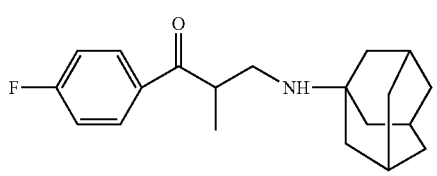 [SMILES: CC(CNC12CC3CC(CC(C3)C1)C2)C(=O)c1ccc(F)cc1]

The title compound was synthesized in the manner as described in Example 189.

NMR (CDCl$_3$) 1.8 (m, 3H), 2.2 (m, 13H), 3.0 (m, 2H), 6.5 (2H), 7.1-8.2 (2H)

TG 111 (3 µmol) 124.4 (10 µmol) 113.1 (30 µmol)
SOCE 0 (10 µmol) 0 (30 µmol) 0 (100 µmol)
IICR 0 (10 µmol) 0 (30 µmol) 0 (100 µmol)

Example 192

3-chloropropyl-4-pyridylketone 8537

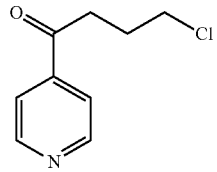 [SMILES: O=C(CCCCl)c1ccncc1]

The title compound was synthesized from chlorobutyryl chloride (141 mg), pyridine (2 ml), and AlCl$_3$ (260 mg).

NMR (CDCl$_3$) 2.1 (m, 2H), 2.2 (m, 2H), 2.6 (m, 2H), 3.7 (m, 2H), 7.7 (2H), 8.6 (2H)

TG 117 (3 µmol) 93 (10 µmol) 49 (30 µmol)
SOCE 0 (10 µmol) 10 (30 µmol) 20 (100 µmol)
IICR 0 (10 µmol) 0 (30 µmol) 0 (100 µmol)

Example 193

2-(N-t-butylbenzyl)aminoethyl-2-thiophenylketone 8638

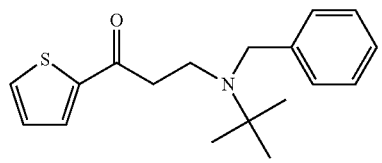 [SMILES: CC(C)(C)N(CCC(=O)c1cccs1)Cc1ccccc1]

2-acetylthiophene (127 mg), benzyl-t-butyl amine (169 mg), and paraformaldehyde (40 mg) were reacted in dioxane (0.2 ml) at 130° C. for 2 hours.

NMR (CDCl$_3$) 1.1 (m, 9H), 2.7 (m, 2H), 3.0 (m, 2H), 3.8 (m, 2H), 7.0-7.4 (5H), 7.7 (2H)

TG 51.5 (0.3 µmol) 18.5 (1.0 µmol) 4.3 (3 µmol) –14.6 (10 µmol) –15.6 (30 µmol)
SOCE 0 (10 µmol) 0 (30 µmol) 0 (100 µmol)
IICR 70 (10 µmol) 95 (30 µmol) 100 (100 µmol)

Example 194

2-(N-isopropylhydroxyethyl)aminoethyl-2-thiophenylketone 8639

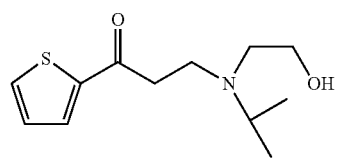 [SMILES: CC(C)N(CCO)CCC(=O)c1cccs1]

2-acetylthiophene (126 mg), 2-hydroxyethylisopropylamine (121 mg), and paraformaldehyde (40 mg) were reacted in dioxane (0.2 ml) at 130° C. for 2 hours.

NMR (CDCl$_3$) 1.05 (m, 6H), 2.5 (m, 2H), 3.0 (m, 4H), 3.0 (m, 2H), 3.6 (m, 2H), 6.6 (1H), 6.5 (1H), 7.1-7.2.0 (7H)

TG 80.5 (3 µmol) 38.3 (10 µmol) –4.3 (30 µmol)
SOCE 0 (10 µmol) 0 (30 µmol) 10 (100 µmol)
IICR 0 (10 µmol) 0 (30 µmol) 0 (100 µmol)

Example 195

2-(N-isopropylbenzyl)aminoethyl-1-methyl-2-pyrrylketone 8646

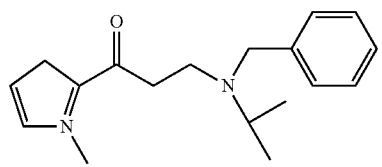

2-acetyl-1-methylpyrrole (123 mg), isopropylbenzylamine (149 mg), and paraformaldehyde (36 mg) were reacted at 70° C. for 10 minutes.

NMR (CDCl₃) 1.05 (m, 6H), 2.5 (m, 2H), 3.0 (m, 3H), 3.5-3.8 (m, 2H), 3.7 (m, 2H), 7.0-7.5 (m, 6H), 7.7-8.0 (2H)
TG 73 (3 µmol) 62.6 (10 µmol) 6.4 (30 µmol)
SOCE 0 (10 µmol) 0 (30 µmol) 10 (100 µmol)
IICR 0 (10 µmol) 0 (30 µmol) 0 (100 µmol)

Example 196

1-(N-benzylisopropyl)aminomethyl-4-fluorophenylketone 8559

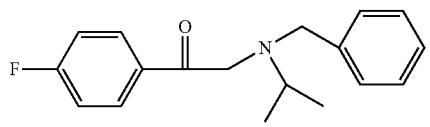

4-fluorobromoacetophenone (217 mg), benzylisopropylamine (149 mg), paraformaldehyde (40 mg), and diisopropylethyl amine (128 mg) were reacted in dioxane (0.2 ml) at 130° C. for 2 hours.
NMR (CDCl₃) 1.05 (m, 6H), 3.2 (m, 2H), 3.2 (m, 1H), 3.6 (m, 2H), 6.2-7.6 (9H)
TG 108 (3 µmol) 98 (10 µmol) 77.6 (30 µmol)
SOCE 0 (10 µmol) 20 (30 µmol) 40 (100 µmol)
IICR 0 (10 µmol) 10 (30 µmol) 30 (100 µmol)

Example 197

2-(N-hydroxyethylisopropyl)aminoethylmethylketone 8560

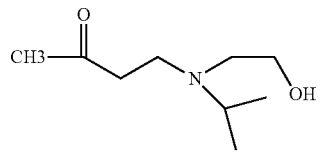

Methyl vinylketone (106 mg) and isopropyl-2-hydroxyethyl amine (156 mg) were heated in hexane (0.5 ml) at 80° C. for 2 hours.
NMR (CDCl₃) 1.1 (m, 6H), 2.1 (s, 3H), 2.6 (m, 2H), 2.8 (m, 2H), 2.9 (m, 1H), 3.5 (m, 2H), 3.85 (m, 2H)
TG 97 (3 µmol) 79 (10 µmol) 35.9 (30 µmol)
SOCE 0 (10 µmol) 0 (30 µmol) 0 (100 µmol)
IICR 0 (10 µmol) 0 (30 µmol) 0 (100 µmol)

Example 198

2-(N-benzylisopropyl)aminoethylmethylketone 8561

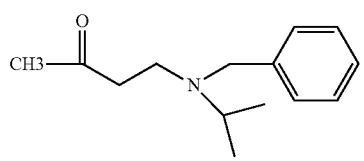 [SMILES: CC(=O)CCN(Cc1ccccc1)C(C)C]

Methyl vinylketone (117 mg) and isopropylbenzylamine (246 mg) were heated in hexane (0.5 ml) at 30° C. for 2 hours.

NMR (CDCl₃) 1.05 (m, 6H), 2.0 (m, 3H), 2.5 (m, 2H), 2.8 (m, 2H), 2.85 (m, 1H), 3.6 (m, 2H), 7.3 (5H)
TG 87 (3 µmol) 66 (10 µmol) 29.2 (30 µmol)
SOCE 0 (10 µmol) 0 (30 µmol) 0 (100 µmol)
IICR 0 (10 µmol) 0 (30 µmol) 0 (100 µmol)

Example 199

2-(N-isopropylhydroxyethyl)aminoethyl-1-imidazolylketone 8630

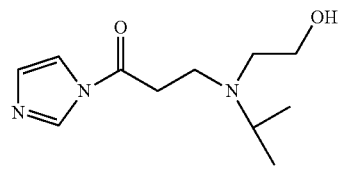 [SMILES: CC(C)N(CCO)CCC(=O)n1ccnc1]

3-acetyl imidazole (110 mg), hydroxyethylisopropylamine (103 mg), and paraformaldehyde (40 mg) were reacted in dioxane (0.2 ml) at 130° C. for 2 hours.
NMR (CDCl₃) 1.05 (m, 6H), 2.2 (m, 2H), 2.8 (m, 2H), 3.0 (m, 2H), 3.7 (m, 2H), 6.9 (1H), 7.1-7.6 (2H)
TG 104.9 (3 µmol) 127.1 (10 µmol) 132.2 (30 µmol)
SOCE 0 (10 µmol) 0 (30 µmol) 0 (100 µmol)
IICR 10 (10 µmol) 20 (30 µmol) 0 (100 µmol)

Example 200

3-(N-benzylisopropyl)aminopropionylcaprolactam 8563

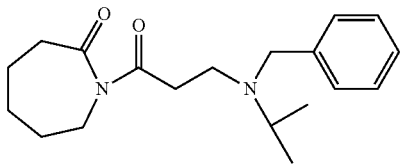 [SMILES: CC(C)N(CCC(=O)N1CCCCCC1=O)Cc1ccccc1]

N-acetylcaprolactam (153 mg), benzylisopropylamine (149 mg), and paraformaldehyde (40 mg) were reacted in dioxane (0.2 ml) at 130° C. for 2 hours.
NMR (CDCl₃) 1.05 (m, 6H), 1.7 (m, 6H), 2.0 (m, 2H), 2.5 (m, 2H), 2.8 (m, 2H), 2.85 (m, 2H), 3.8 (m, 2H), 7.2 (5H)
TG 101.2 (3 µmol) 83.7 (10 µmol) 47.9 (30 µmol)
SOCE 0 (10 µmol) 0 (30 µmol) 10 (100 µmol)
IICR 0 (10 µmol) 0 (30 µmol) 20 (100 µmol)

Example 201

3-(N-hydroxyethylisopropyl)aminopropionylcaprolactam 8564

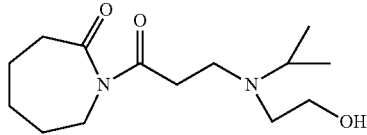 [SMILES: CC(C)N(CCO)CCC(=O)N1CCCCCC1=O]

N-acetylcaprolactam (153 mg), isopropyl-2-hydroxyethyl amine (149 mg), and paraformaldehyde (40 mg) were reacted in dioxane (0.2 ml) at 130° C. for 2 hours.

NMR (CDCl₃) 1.05 (m, 6H), 1.7 (m, 6H), 2.0 (m, 2H), 2.5 (m, 2H), 2.8 (m, 2H), 2.85 (m, 2H), 3.3 (m, 2H), 4.0 (m, 2H)

TG 103.2 (3 μmol) 97.9 (10 μmol) 65.3 (30 μmol)
SOCE 0 (10 μmol) 0 (30 μmol) 0 (100 μmol)
IICR 0 (10 μmol) 0 (30 μmol) 0 (100 μmol)

Example 202

2-(N-isopropylbenzyl)aminomethyl-3-(2,5-dichlorothiophenyl)ketone 8659

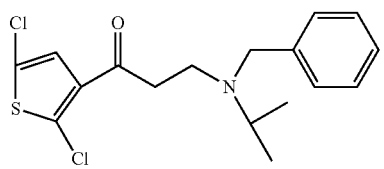 [SMILES: CC(C)N(CCC(=O)c1cc(Cl)sc1Cl)Cc1ccccc1]

3-acetyl-2,5-dichlorothiophene (195 mg), benzylisopropylamine (149 mg), and paraformaldehyde (40 mg) were reacted in dioxane (0.2 ml) at 130° C. for 2 hours.

NMR (CDCl₃) 1.0-1.2 (m, 6H), 2.0 (m, H), 2.6 (m, 2H), 2.8-2.9 (m, 2H), 3.4-3.8 (m, 2H), 7-7.5 (m, 6H)

TG 17.8 (3 μmol) 10.5 (10 μmol) −1.1 (30 μmol)
SOCE 0 (10 μmol) 20 (30 μmol) 50 (100 μmol)
IICR 50 (10 μmol) 80 (30 μmol) 100 (100 μmol)

Example 203

2-(N-isopropyl-2-hydroxyethyl)aminomethyl-3-(2,5-dichlorothiophenyl)ketone 8660

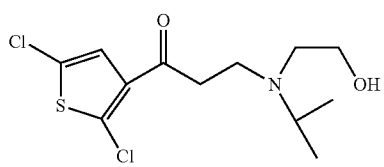 [SMILES: CC(C)N(CCO)CCC(=O)c1cc(Cl)sc1Cl]

3-acetyl-2,5-dichlorothiophene (195 mg), 2-hydroxyethylisopropylamine (103 mg) and paraformaldehyde (40 mg) were reacted in dioxane (0.2 ml) at 130° C. for 2 hours.

NMR (CDCl₃) 11.9-1.1 (m, 6H), 2.3 (m, 2H), 2.7 (m, 2H), 3.6 (m, 2H), 3.8 (m, 2H), 7.2 (s, 1H)

TG 35 (3 μmol) 13 (10 μmol) 2.5 (30 μmol)
SOCE 50 (10 μmol) 20 (30 μmol) 10 (100 μmol)
IICR 40 (10 μmol) 90 (30 μmol) 100 (100 μmol)

Example 204

2-(N-2-hydroxyethylbenzyl)aminomethyl-3-(2,5-dichlorothiophenyl)ketone 8661

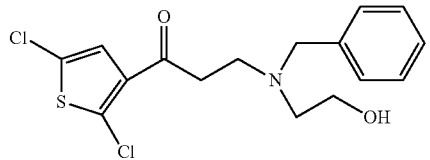 [SMILES: O=C(CCN(CCO)Cc1ccccc1)c1cc(Cl)sc1Cl]

3-acetyl-2,5-dichlorothiophene (195 mg), benzyl-2-hydroxyethyl amine (151 mg), and paraformaldehyde (40 mg) were reacted in dioxane (0.2 ml) at 130° C. for 2 hours.

NMR (CDCl₃) 2.5 (m, 2H), 2.9 (m, 2H), 3.6-3.7 (m, 4H), 4.2 (m, 2H), 7.0-7.5 (m, 6H)

TG 49.1 (3 μmol) 17.6 (10 μmol) 7.7 (30 μmol)
SOCE 0 (10 μmol) 0 (30 μmol) 50 (100 μmol)
IICR 0 (10 μmol) 40 (30 μmol) 70 (100 μmol)

Example 205

2-(N-hydroxyethylisopropyl)aminoethyl-2-naphthylketone 8570

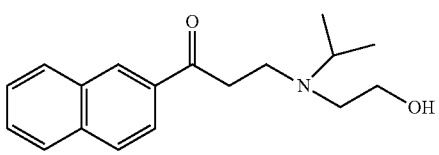 [SMILES: CC(C)N(CCO)CCC(=O)c1ccc2ccccc2c1]

2-acetyl naphthalene (170 mg), 2-hydroxyethylisopropylamine (103 mg), and paraformaldehyde (40 mg) were reacted in dioxane (0.2 ml) at 130° C. for 2 hours reaction.

NMR (CDCl₃) 1.05 (m, 6H), 2.7 (m, 2H), 2.9 (m, 1H), 3.7 (m, 2H), 3.85 (m, 2H), 4.3 (m, 2H), 7.6-8.4 (m, 7H)

TG 82.5 (3 μmol) 62.4 (10 μmol) 28.3 (30 μmol)
SOCE 0 (10 μmol) 0 (30 μmol) 0 (100 μmol)
IICR 0 (10 μmol) 0 (30 μmol) 0 (100 μmol)

Example 206

2-(N-hydroxyethylisopropyl)aminomethylphenylketone 8572

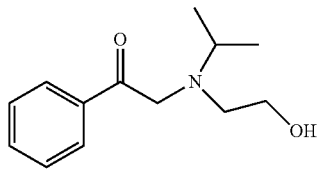 [SMILES: CC(C)N(CCO)CC(=O)c1ccccc1]

Chloroacetophenone (154 mg), 2-hydroxyethylisopropylamine (103 mg), and diisopropylethyl amine (128 mg) were reacted in dioxane (0.2 ml) at 130° C. for 2 hours.

NMR (CDCl₃) 1.05 (m, 6H), 3.1 (m, 2H), 3.6 (m, 1H), 3.6 (m, 2H), 4.0 (m, 2H), 7.1-7.2 (m, 5H)

TG 67.6 (3 μmol) 63.6 (10 μmol) 27.4 (30 μmol)
SOCE 0 (10 μmol) 0 (30 μmol) 0 (100 μmol)
IICR 0 (10 μmol) 0 (30 μmol) 40 (100 μmol)

Example 207

3-(N-hydroxyethylisopropyl)aminopropylphenylketone 8573

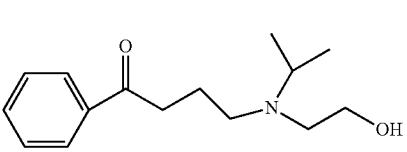 [SMILES: CC(C)N(CCO)CCCC(=O)c1ccccc1]

4-chlorobutyrophenone (269 mg), 2-hydroxyethylisopropylamine (152 mg), and diisopropylethyl amine (187 mg) were reacted at 120° C. for 2 hours.

NMR (CDCl$_3$) 1.4 (m, 6H), 2.5 (m, 2H), 3.05 (m, 4H), 3.0 (m, 2H), 3.6 (m, 2H), 6.6 (1H), 6.5 (1H), 7.1-7.2.0 (7H)
TG 95.2 (3 μmol) 92.5 (10 μmol) 82.9 (30 μmol)
SOCE 0 (10 μmol) 0 (30 μmol) 30 (100 μmol)
IICR 20 (10 μmol) 20 (30 μmol) 20 (100 μmol)

Example 208

2-(N-hydroxyethylmethyl)aminoethyl-2-pyrazylketone 8593

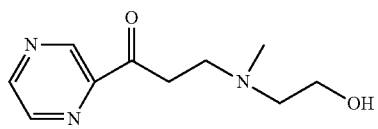

2-acetylpyrazine (122 mg), methylhydroxyethyl amine (75 mg), and paraformaldehyde (40 mg) were reacted at 130° C. for 2 hours.

NMR (CDCl$_3$) 1.8-2.8 (m, 7H), 3.0 (m, 2H), 3.2 (m, 2H), 7.5-8.1 (3H)
TG 99.0 (3 μmol) 53.6 (10 μmol) 11.0 (30 μmol)
SOCE 0 (10 μmol) 10 (30 μmol) 20 (100 μmol)
IICR 20 (10 μmol) 30 (30 μmol) 30 (100 μmol)

Example 209

2-(N-ethylbenzyl)aminoethyl-4-pyridylketone 8594

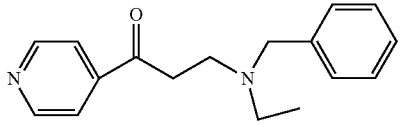

Acetylpyridine (121 mg), benzylethyl amine (135 mg), and paraformaldehyde (40 mg) were reacted in dioxane (0.2 ml) at 130° C. for 2 hours.

NMR (CDCl$_3$) 1.05 (m, 3H), 1.8 (m, 2H), 1.9 (m, 2H), 2.6 (m, 2H), 3.5 (m, 2H), 7.-8.5 (91-1)
TG 100 (3 μmol) 85.9 (10 μmol) 46.0 (30 μmol)
SOCE 0 (10 μmol) 20 (30 μmol) 60 (100 μmol)
IICR 20 (10 μmol) 20 (30 μmol) 50 (100 μmol)

Example 210

2-(N-t-butylbenzyl)aminoethyl-4-pyridylketone 8595

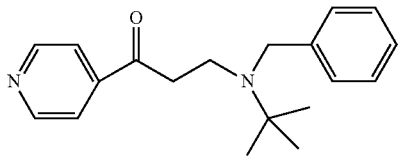 [SMILES: CC(C)(C)N(CCC(=O)c1ccncc1)Cc1ccccc1]

4-acetylpyridine (121 mg), benzyl-t-butyl amine (149 mg), and paraformaldehyde (40 mg) were reacted in dioxane (0.2 ml) at 130° C. for 2 hours.

NMR (CDCl$_3$) 1.05 (m, 9H), 2.5 (m, 2H), 3.4 (m, 2H), 3.8 (m, 2H), 7.5 (5H), 7.9 (2H), 8.3 (2H)

TG 102 (3 μmol) 96 (10 μmol) 69 (30 μmol)
SOCE 0 (10 μmol) 10 (30 μmol) 30 (100 μmol)
IICR 0 (10 μmol) 20 (30 μmol) 0 (100 μmol)

Example 211

2-(N-2-furylpiperadino)ethyl-4-fluorophenylketone 8596

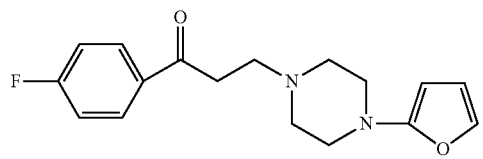 [SMILES: O=C(CCN1CCN(c2ccco2)CC1)c1ccc(F)cc1]

4-fluoroacetophenone (138 mg), acetyl piperazine (180 mg), and paraformaldehyde (40 mg) were reacted in dioxane (0.2 ml) at 130° C. for 2 hours.

NMR (CDCl$_3$) 2.5 (m, 2H), 3.0 (m, 4H), 3.0 (m, 2H), 3.6 (m, 2H), 6.5 (2H), 6.5 (1H), 7.1-7.2 (4H), 8.0 (m, 2H)
TG 100 (3 μmol) 91.0 (10 μmol) 49.7 (30 μmol)
SOCE 0 (10 μmol) 10 (30 μmol) 30 (100 μmol)
IICR 30 (10 μmol) 20 (30 μmol) 20 (100 μmol)

Example 212

2-(N-isopropylbenzyl)aminoethyl-4-fluorophenylketone 8597

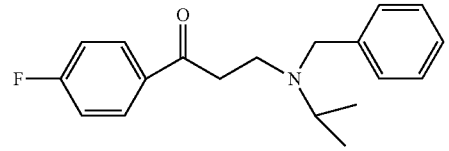 [SMILES: CC(C)N(CCC(=O)c1ccc(F)cc1)Cc1ccccc1]

4-fluoroacetophenone (138 mg), benzylisopropylamine (149 mg), and paraformaldehyde (40 mg) were reacted in dioxane (0.2 ml) at 130° C. for 2 hours.

NMR (CDCl$_3$) 1.05 (m, 6H), 2.5 (m, 4H), 2.9 (m, 1H), 3.9 (m, 2H), 7.0-7.5 (7H), 8.0 (2H)
TG 104 (3 μmol) 82 (10 μmol) 37 (30 μmol)
SOCE 0 (10 μmol) 30 (30 μmol) 50 (100 μmol)
IICR 20 (10 μmol) 80 (30 μmol) 30 (100 μmol)

Example 213

2-(N-2-benzyl-t-butyl)aminoethyl-2-pyrazylketone 8693

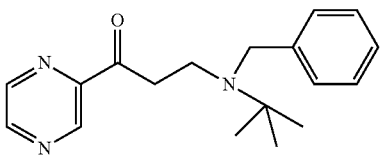 [SMILES: CC(C)(C)N(CCC(=O)c1cnccn1)Cc1ccccc1]

2-acetylpyrazine (122 mg), t-butylbenzylamine (162 mg), and paraformaldehyde (40 mg) were reacted at 130° C. for 2 hours.

NMR (CDCl$_3$) 1.2 (m, 6H), 2.7 (m, 2H), 3.1 (m, 2H), 3.7 (m, 2H), 7.0 (m, 1H), 7.3 (m, 5H), 8.5 (m, 1H), 9.1 (m, 1H)

TG 10.1 (3 μmol) 2.7 (10 μmol) 0.4 (30 μmol)
SOCE 0 (10 μmol) 0 (30 μmol) 10 (100 μmol)
IICR 20 (10 μmol) 80 (30 μmol) 90 (100 μmol)

Example 214

2-(N-2-hydroxyethyl-t-butyl)aminoethyl-2-pyrazylketone 8694

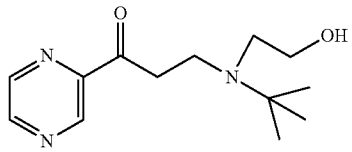 [SMILES: CC(C)(C)N(CCO)CCC(=O)c1cnccn1]

2-acetylpyrazine (122 mg), t-butyl-2-hydroxyethyl amine (117 mg), and paraformaldehyde (40 mg) were reacted in dioxane (0.2 ml) at 130° C. for 2 hours.
NMR (CDCl$_3$) 1.10 (s, 9H), 2.60 (m, 2H), 2.45 (m, 2H), 3.9 (m, 2H), 4.25 (m, 2H), 8.71 (s, 1H), 8.8 (s, 1H), 9.21 (s, 1H)
TG 45.8 (3 μmol) 7.1 (30 μmol)
SOCE 10 (10 μmol) 0 (30 μmol) 0 (100 μmol)
IICR 0 (10 μmol) 0 (30 μmol) 0 (100 μmol)

Example 215

2-(N-benzylmethyl)aminoethyl-2-pyrazylketone 8695

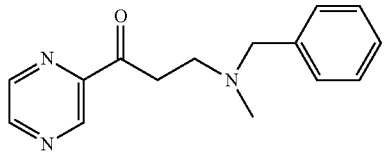 [SMILES: CN(CCC(=O)c1cnccn1)Cc1ccccc1]

2-acetylpyrazine (122 mg), methylbenzylamine (121 mg), and paraformaldehyde (40 mg) were reacted in dioxane (0.2 ml) at 130° C. for 2 hours.
NMR (CDCl$_3$) 2.15 (m, 2H), 3.0 (m, 2H), 3.4 (m, 2H), 3.7 (m, 3H),
TG 24.5 (3 μmol) −1.3 (10 μmol) −3.1 (30 μmol)
SOCE 0 (10 μmol) 0 (30 μmol) 0 (100 μmol)
IICR 0 (10 μmol) 0 (30 μmol) 50 (100 μmol)

Example 216

N,N-bis(4-pyrizoylethyl)spermidine 8603

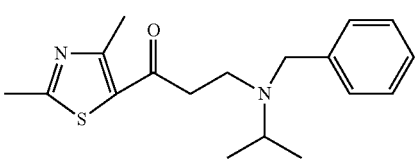

2-acetylpyridine (121 mg), spermidine (87 mg), and paraformaldehyde (40 mg) were reacted in dioxane (0.2 ml) at 130° C. for 2 hours.
NMR (CDCl$_3$) 1.7-2.4 (6H), 2.6 (m, 4H), 3.4-3.6 (m, 8H), 3.8 (2H), 7.4-8.4 (8H)
TG 106.8 (3 μmol) 87.0 (10 μmol) 45.3 (30 μmol)
SOCE 0 (10 μmol) 10 (30 μmol) 10 (100 μmol)
IICR 0 (10 μmol) 0 (30 μmol) 30 (100 μmol)

Example 217

2-hydroxypiperidinoethyl-4-pyridylketone 8604

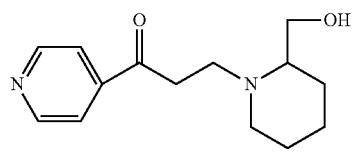 [SMILES: O=C(CCN1CCCCC1CO)c1ccncc1]

2-acetylpyridine (121 mg), piperidine methanol (115 mg), and paraformaldehyde (40 mg) were reacted in dioxane (0.2 ml) at 130° C. for 2 hours.
NMR (CDCl$_3$) 1.2-2.2 (6H), 2.6 (m, 4H), 3.4-4.0 (m, 6H), 7.4-8.2 (4H)
TG 107 (3 μmol) 93.5 (10 μmol) 81.2 (30 μmol)
SOCE 10 (10 μmol) 0 (30 μmol) 20 (100 μmol)
IICR 0 (10 μmol) 20 (30 μmol) 50 (100 μmol)

Example 218

2-(N-benzylethyl)aminoethyl-2-florenylketone 8663

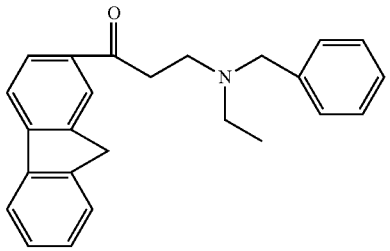 [SMILES: CCN(CCC(=O)c1ccc2c(c1)Cc1ccccc1-2)Cc1ccccc1]

2-acetylfluorene (208 mg), ethylbenzylamine (135 mg), and paraformaldehyde (40 mg) were reacted in dioxane (0.2 ml) at 130° C. for 2 hours.
NMR (CDCl$_3$) 1.0 (m, 3H), 2.2 (m, m, 2H), 2.5 (m, 2H), 2.8 (m, m, 2H), 2.9 (m, 2H), 7.1-8.1 (m, 7H)
TG 100 (3 μmol) 73.6 (10 μmol) 28.5 (30 μmol)
SOCE 20 (10 μmol) 60 (30 μmol) 70 (100 μmol)
IICR 10 (10 μmol) 40 (30 μmol) 70 (100 μmol)

Example 219

2-(N-benzylisopropyl)aminoethyl-5-(2,4-dimethylthiazolyl)ketone 8666

5-acetyl-2,4-dimethylthiazole (155 mg), isopropylbenzylamine (162 mg), and paraformaldehyde (40 mg) were reacted in dioxane (0.2 ml) at 130° C. for 2 hours.

Example 220

2-(N-2-hydroxyaminoethyl)aminoethyl-5-(2,4-dimethylthiazolyl)ketone 8668

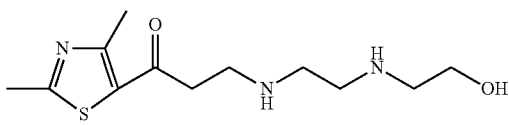 [SMILES: Cc1nc(C)c(C(=O)CCNCCNCCO)s1]

5-acetyl-2,4-dimethylthiazole (155 mg), hydroxyethylethyl amine (104 mg), and paraformaldehyde (40 mg) were reacted in dioxane (0.2 ml) at 130° C. for 2 hours.

NMR (CDCl$_3$) 2.55 (m, 2H), 2.65 (m, 10H), 3.5-3.7 (m, 4H), 5. (m, 4H)
TG 103 (3 µmol) 70 (30 µmol)
SOCE 0 (10 µmol) 0 (30 µmol) 0 (100 µmol)
IICR 0 (10 µmol) 40 (30 µmol) 40 (100 µmol)

Example 221

2-(N-benzylisopropyl)aminoethyl-3-(2,5-dimethylfuryl)ketone 8669

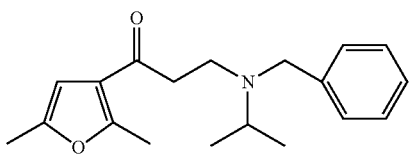 [SMILES: Cc1cc(C(=O)CCN(Cc2ccccc2)C(C)C)c(C)o1]

3-acetyl-2,5-dimethylfuran (155 mg), isopropylbenzylamine (49 mg), and paraformaldehyde (40 mg) were reacted in dioxane (0.2 ml) at 130° C. for 2 hours.

NMR (CDCl$_3$) 1.05 (m, 6H), 1.25 (m, 6H), 2.2 (m, 2H), 2.4 (m, 2H), 3.6 (m, 2H), 3.8 (m 1H), 7.2 (m, 6H)
TG 98 (3 µmol) 44.5 (30 µmol)
SOCE 0 (10 µmol) 0 (30 µmol) 0 (100 µmol)
IICR 0 (10 µmol) 0 (30 µmol) 0 (100 µmol)

Example 222

2-(N-isopropylbenzyl)aminoethyl-3-thiophenylketone 8625

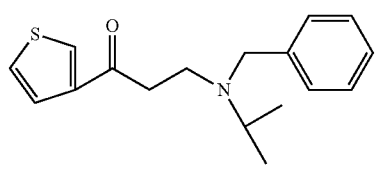 [SMILES: CC(C)N(CCC(=O)c1ccsc1)Cc1ccccc1]

3-acetylthiophene (126 mg), N-isopropylbenzylamine (149 mg), and paraformaldehyde (36 mg) were reacted in dioxane (0.2 ml) at 130° C. for 2 hours.

NMR (CDCl$_3$) 1.0-1.2 (m, 12H), 2.55 (m, 2H), 2.6-2.7 (m, 6H), 2.8 (m, m, 2H), 3.6 (m, 2H)
TG 36 (3 µmol) −2.5 (30 µmol)
SOCE 0 (10 µmol) 0 (30 µmol) 0 (100 µmol)
IICR 20 (10 µmol) 90 (30 µmol) 100 (100 µmol)

Example 223

2-(N-phenethyl)aminoethyl-3-thiophenylketone 8626

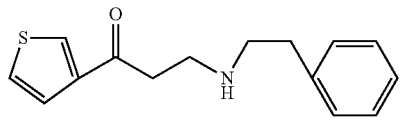

3-acetylthiophene (126 mg), phenylethyl amine (121 mg), and paraformaldehyde (40 mg) were reacted in dioxane (0.2 ml) at 130° C. for 2 hours.

NMR (CDCl$_3$) 2.5 (m, 2H), 2.7 (m, 2H), 3.4 (m, 2H), 3.8 (m, 2H), 7.1-7.2. (5H), 7.5 (m, 2H), 8.0 (m, 2H)
TG 113.3 (3 µmol) 108.7 (10 µmol) 104.4 (30 µmol)
SOCE 0 (10 µmol) 10 (30 µmol) 20 (100 µmol)
IICR 0 (10 µmol) 0 (30 µmol) 0 (100 µmol)

Example 224

2-(N-isopropylbenzyl)aminoethyl-1-imidazolylketone 8629

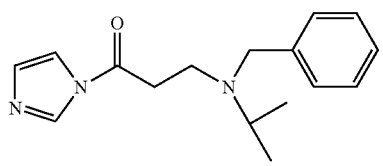 [SMILES: CC(C)N(CCC(=O)n1ccnc1)Cc1ccccc1]

3-acetylimidazole (70 mg), benzylisopropylamine (140 mg), and paraformaldehyde (40 mg) were reacted in dioxane (0.2 ml) at 130° C. for 2 hours.

NMR (CDCl$_3$) 1.05 (m, 6H), 2.5 (m, 2H), 3.0 (m, 2H), 3.0 (m, 1H), 3.7 (m, 2H), 5.9 (1H), 6.8-7.4 (6H), 8.0 (1H)
TG 112 (3 µmol) 122 (10 µmol) 144.9 (30 µmol)
SOCE 0 (10 µmol) 0 (30 µmol) 20 (100 µmol)
IICR 20 (10 µmol) 20 (30 µmol) 0 (100 µmol)

Example 225

2-(N-isopropylbenzyl)aminoethyl-4,5-dimethyl-2-furylketone 8696

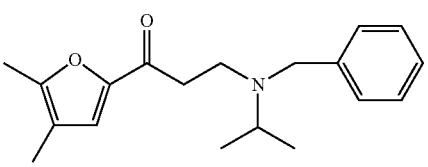 [SMILES: Cc1cc(C(=O)CCN(Cc2ccccc2)C(C)C)oc1C]

3-acetyl-2,3-dimethylfuran (136 mg), benzylisopropylamine (149 mg), and paraformaldehyde (40 mg) were reacted in dioxane (0.2 ml) at 130° C. for 2 hours.

NMR (CDCl$_3$) 1.0 (m, 6H), 1.9 (m, 3H), 2.3 (m, 3H), 2.4 (m, 2H), 2.8 (m, 2H), 3.6 (m, 2H), 7.0 (m, 6H)
TG 34.8 (3 μmol) 6.0 (10 μmol) −13.9 (30 μmol)
SOCE 10 (10 μmol) 30 (30 μmol) 70 (100 μmol)
IICR 20 (10 μmol) 30 (30 μmol) 90 (100 μmol)

Example 226

2-(N-2-hydroxyethylethyl)aminoethyl-4,5-dimethyl-2-furylketone 8697

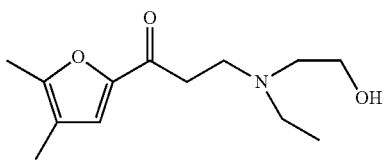 [SMILES: CCN(CCO)CCC(=O)c1cc(C)c(C)o1]

3-acetyl-2,3-dimethylfuran (136 mg), 2-ethylaminoethanol (89 mg), and paraformaldehyde (40 mg) were reacted in dioxane (0.2 ml) at 130° C. for 2 hours.
NMR (CDCl$_3$) 1.0 (m, 3H), 2.0 (m, 6H), 2.2 (m, 4H), 2.6 (m, 4H), 2.6 (m, 2H), 7.0 (s, 1H)
TG 61.7 (3 μmol) 11.4 (10 μmol) −5.9 (30 μmol)
SOCE 0 (10 μmol) 0 (30 μmol) 0 (100 μmol)
IICR 0 (10 μmol) 0 (30 μmol) 50 (100 μmol)

Example 227

2-(N-2-hydroxyethylbenzyl)aminoethyl-4,5-dimethyl-2-furylketone 8698

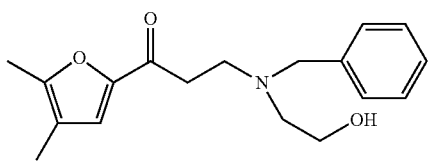 [SMILES: Cc1cc(C(=O)CCN(CCO)Cc2ccccc2)oc1C]

3-acetyl-2,3-dimethylfuran (136 mg), benzylaminoethanol (151 mg), and paraformaldehyde (40 mg) were reacted in dioxane (0.2 ml) at 130° C. for 2 hours.
NMR (CDCl$_3$) 2.0 (m, 3H), 2.15 (m, 2H), 2.5 (m, 2H), 2.8 (m, 2H), 4.1 (m, 2H), 7.1 (m, 6H)
TG 76.6 (3 μmol) 43.8 (10 μmol) 2.5 (30 μmol)
SOCE 0 (10 μmol) 0 (30 μmol) 0 (100 μmol)
IICR 20 (10 μmol) 0 (30 μmol) 20 (100 μmol)

Example 228

2-(N-2-hydroxyethylethyl)aminoethyl-2,5-dimethyl-3-thiophenylketone 8699

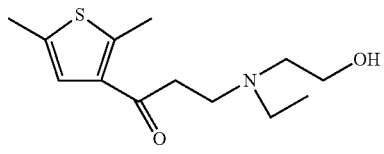 [SMILES: CCN(CCO)CCC(=O)c1cc(C)sc1C]

3-acetyl-2,3-dimethylthiophene (154 mg), ethylethanol amine (89 mg), and paraformaldehyde (40 mg) were reacted in dioxane (0.2 ml) at 130° C. for 2 hours.

NMR (CDCl$_3$) 1.0 (m, 3H), 2.4 (m, 8H), 2.6 (m, 4H), 2.9 (m, 2H), 6.9 (s, 1H)
TG 96.3 (3 μmol) 75.1 (10 μmol) 30.9 (30 μmol)
SOCE 0 (10 μmol) 0 (30 μmol) 20 (100 μmol)
IICR 20 (10 μmol) 0 (30 μmol) 20 (100 μmol)

Example 229

2-(N,N-bis-2-hydroxyethyl)aminoethyl-2,5-dimethyl-3-thiophenylketone 8700

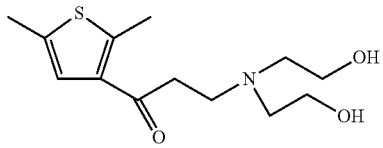 [SMILES: Cc1cc(C(=O)CCN(CCO)CCO)c(C)s1]

3-acetyl-2,3-dimethylthiophene (154 mg), diethanol amine (105 mg), and paraformaldehyde (40 mg) were reacted in dioxane (0.2 ml) at 130° C. for 2 hours.
NMR (CDCl$_3$) 2.4 (m, 3H), 2.5 (m, 3H), 2.6 (m, 2H), 2.7 (m, 2H), 2.9 (m, 2H), 3.0 (m, 2H), 3.7 (m, 2H), 3.7 (m, 2H), 4.3 (m, 2H), 7.0 (s, 1H)
TG 107 (3 μmol) 107 (10 μmol) 77 (30 μmol)
SOCE 0 (10 μmol) 0 (30 μmol) 0 (100 μmol)
IICR 0 (10 μmol) 0 (30 μmol) 0 (100 μmol)

Example 230

2-(N-2-hydroxyethylisopropyl)aminoethyl-2,5-dimethyl-3-thiophenylketone 9701

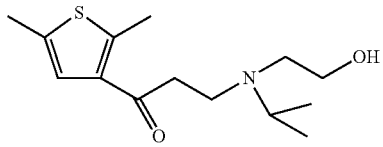 [SMILES: Cc1cc(C(=O)CCN(CCO)C(C)C)c(C)s1]

3-acetyl-2,3-dimethylthiophene (154 mg), isopropylethanol amine (103 mg), and paraformaldehyde (40 mg) were reacted in dioxane (0.2 ml) at 130° C. for 2 hours.
NMR (CDCl$_3$) 1.0 (m, 6H), 2.15 (m, 6H), 2.2 (m, 2H), 2.8 (m, 2H), 3.8 (m, 2H), 4.1 (m, 2H), 7.0 (s, 1H)
TG 102 (3 μmol) 99 (10 μmol) 87.1 (30 μmol)
SOCE 0 (10 μmol) 0 (30 μmol) 0 (100 μmol)
IICR 0 (10 μmol) 0 (30 μmol) 20 (100 μmol)

Example 231

2-(N-benzyl-t-butyl)aminoethyl-3-pyridylketone 8702

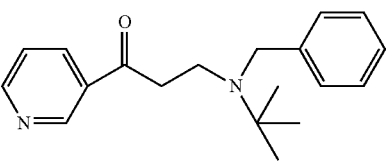 [SMILES: CC(C)(C)N(CCC(=O)c1cccnc1)Cc1ccccc1]

3-acetylpyridine (242 mg), t-butylbenzylamine (326 mg), and paraformaldehyde (80 mg) were reacted in dioxane (0.4 ml) at 130° C. for 2 hours.

NMR (CDCl$_3$) 1.17 (s, 9H), 2.64 (m, 2H), 3.02 (m, 2H), 3.72 (m, 2H), 7.2-9.1 (m, 9H)
TG 4.8 (3 µmol) 1.0 (10 µmol) 0.5 (30 µmol)
SOCE 0 (10 µmol) 0 (30 µmol) 0 (100 µmol)
IICR 20 (10 µmol) 90 (30 µmol) 100 (100 µmol)

Example 232

2-(N-t-butyl-2-hydroxyethyl)aminoethyl-3-pyridylketone 8703

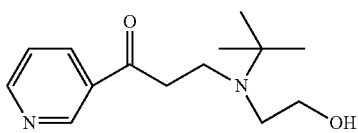 [SMILES: CC(C)(C)N(CCO)CCC(=O)c1cccnc1]

3-acetylpyridine (280 mg), t-butylethanol amine (272 mg), and paraformaldehyde (80 mg) were reacted in dioxane (0.4 ml) at 130° C. for 2 hours.
NMR (CDCl$_3$) 1.13 (s, 9H), 2.66 (m, 2H), 2.90 (m, 2H), 3.83 (m, 2H), 4.39 (m, 2H), 7.45, 8.26, 8.80, 9.17
TG 85.5 (3 µmol) 49.0 (10 µmol) 7.5 (30 µmol)
SOCE 0 (10 µmol) 0 (30 µmol) 0 (100 µmol)
IICR 0 (10 µmol) 10 (30 µmol) 10 (100 µmol)

Example 233

2-(N-benzylmethyl)aminoethyl-2-furylketone 8705

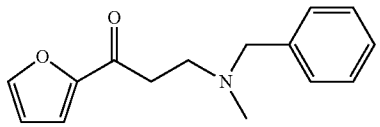 [SMILES: CN(CCC(=O)c1ccco1)Cc1ccccc1]

2-acetylfuran (220 mg), benzylmethyl amine (242 mg), and paraformaldehyde (40 mg) were reacted at 130° C. for 2 hours.
NMR (CDCl$_3$) 2.16 (m, 3H), 2.49 (m, 2H), 2.89 (m, 2H), 3.55 (m, 2H), 6.5-7.7 (m, 8H)
TG 96.3 (3 µmol) 75.1 (10 µmol) 30.9 (30 µmol)
SOCE 0 (10 µmol) 0 (30 µmol) 10 (100 µmol)
IICR 30 (10 µmol) 70 (30 µmol) 80 (100 µmol)

Example 234

2-(N-2-hydroxyethylbutyl)aminoethyl-2-furylketone 8706

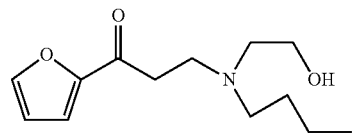 [SMILES: CCCCN(CCO)CCC(=O)c1ccco1]

2-acetylfuran (220 mg), butylethanol amine (134 mg), and paraformaldehyde (78 mg) were reacted at 130° C. for 2 hours.

NMR (CDCl$_3$) 0.90 (m, 3H), 1.3 (m, 4H), 2.5 (m, 2H) 2.90 (m, 2H), 3.54 (m, 2H), 3.76 (2H), 6.53 (s, 1H), 7.21 (1H), 7.6 (1H)
TG 25.0 (3 µmol) 2.9 (10 µmol) −2.5 (30 µmol)
SOCE 0 (10 µmol) 0 (30 µmol) 10 (100 µmol)
IICR 0 (10 µmol) 70 (30 µmol) 80 (100 µmol)

Example 235

2-(N-2-hydroxyethylmethyl)aminoethyl-2-furylketone 8707

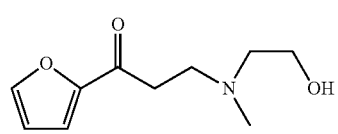

2-acetylfuran (220 mg), methylethanol amine (155 mg), and paraformaldehyde (78 mg) were reacted at 130° C. for 2 hours.
NMR (CDCl$_3$) 2.2-2.5 (m, 7H), 3.6-3.9 (m, 4H), 6.56, 7.21, 7.61
TG 16.5 (3 µmol) 2.8 (10 µmol) 0.5 (30 µmol)
SOCE 0 (10 µmol) 0 (30 µmol) 0 (100 µmol)
IICR 0 (10 µmol) 90 (30 µmol) 80 (100 µmol)

Example 236

2-(N-benzylmethyl)aminoethyl-3-thiophenylketone 8708

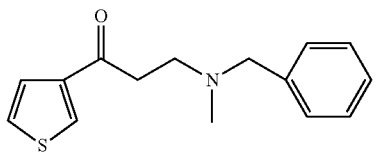 [SMILES: CN(CCC(=O)c1ccsc1)Cc1ccccc1]

3-acetylthiophene (252 mg), methylbenzylamine (244 mg), and paraformaldehyde (78 mg) were reacted at 130° C. for 2 hours.
NMR (CDCl$_3$) 2.16 (m, 3H), 2.23 (m, 2H), 3.04 (m, 2H), 3.63 (m, 2H), 7.1-8.0 (m, 8H)
TG 102 (3 µmol) 79.0 (10 µmol) 37.3 (30 µmol)
SOCE 0 (10 µmol) 0 (30 µmol) 20 (100 µmol)
IICR 10 (10 µmol) 10 (30 µmol) 80 (100 µmol)

Example 237

2-(N-2-hydroxyethylbutyl)aminoethyl-3-thiophenylketone 8709

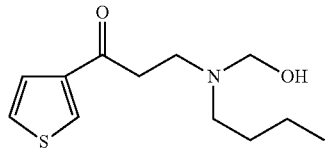 [SMILES: CCCCN(CO)CCC(=O)c1ccsc1]

3-acetylthiophene (252 mg), butylethanol amine (234 mg), and paraformaldehyde (78 mg) were reacted at 130° C. for 2 hours.
NMR (CDCl₃) 0.90 (m, 3H), 1.4 (m, 4H), 2.56 (m, 2H), 2.95 (m, 2H), 3.78 (m, 2H), 7.5-8.1 (m, 3H)
TG 83.6 (3 μmol) 57.6 (10 μmol) 15.2 (30 μmol)
SOCE 0 (10 μmol) 0 (30 μmol) 0 (100 μmol)
IICR 20 (10 μmol) 10 (30 μmol) 70 (100 μmol)

Example 238

2-(N-benzyl-t-butyl)aminoethyl-3-thiophenylketone 8710

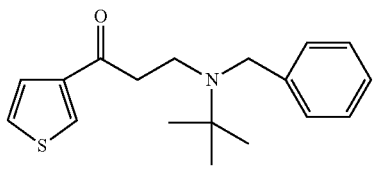 [SMILES: CC(C)(C)N(CCC(=O)c1ccsc1)Cc1ccccc1]

2-acetylthiophene (252 mg), benzyl-t-butyl amine (234 mg), and paraformaldehyde (78 mg) were reacted at 130° C. for 2 hours.
NMR (CDCl₃) 1.12 (m, 9H), 2.34 (m, 2H), 2.94 (m, 2H), 3.84 (m, 2H), 7.5-8.0 (m, 8H)
TG 83.7 (3 μmol) 55.3 (10 μmol) 11.8 (30 μmol)
SOCE 0 (10 μmol) 0 (30 μmol) 0 (100 μmol)
IICR 10 (10 μmol) 0 (30 μmol) 0 (100 μmol)

Example 239

2-(N-benzylethyl)aminoethyl-5-methyl-2-furylketone 8711

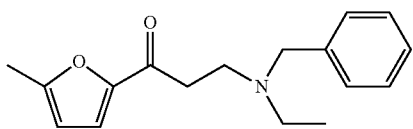 [SMILES: CCN(CCC(=O)c1ccc(C)o1)Cc1ccccc1]

2-acetyl-5-methylfuran (248 mg), ethylbenzylamine (270 mg), and paraformaldehyde (78 mg) were reacted at 130° C. for 2 hours.
NMR (CDCl₃) 1.09 ((m, 3H), 2.40 (m, 2H), 2.91 (m, 2H), 3.50 (m, 2H), 3.60 (m, 2H), 6.10 (m, 1H), 7.20 (m, 6H)
TG 51.7 (3 μmol) 2.2 (10 μmol) 4.3 (30 μmol)
SOCE 0 (10 μmol) 0 (30 μmol) 10 (100 μmol)
IICR 0 (10 μmol) 50 (30 μmol) 80 (100 μmol)

Example 240

2-(N-2-hydroxyethyl-t-butyl)aminoethyl-5-methyl-2-furylketone 8712

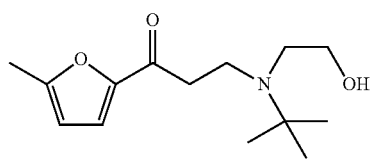 [SMILES: Cc1ccc(C(=O)CCN(CCO)C(C)(C)C)o1]

2-acetyl-5-methylfuran (248 mg), t-butylethanol amine (234 mg), and paraformaldehyde (78 mg) were reacted at 130° C. for 2 hours.
NMR (CDCl₃) 2.24 (m, 3H), 2.48 (m, 3H), 2.85 (m, 2H), 3.55 (m, 2H), 6.1 (s, 1H), 7.0-7.4 (m, 7H)
TG 4.5 (3 μmol) 1.1 (10 μmol) 0 (30 μmol)
SOCE 0 (10 μmol) 0 (30 μmol) 0 (100 μmol)
IICR 10 (10 μmol) 30 (30 μmol) 50 (100 μmol)

Example 241

2-(N-benzylmethyl)aminoethyl-5-methyl-2-furylketone 8713

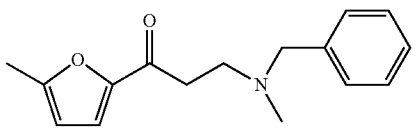 [SMILES: Cc1ccc(C(=O)CCN(C)Cc2ccccc2)o1]

2-acetyl-5-methylfuran (248 mg), benzylmethyl amine (242 mg), and paraformaldehyde (78 mg) were reacted at 130° C. for 2 hours.
NMR (CDCl₃) 2.24 (m, 3H), 2.48 (m, 3H), 2.85 (m, 2H), 3.55 (m, 2H), 6.1 (s, 1H), 7.0-7.4 (m, 6H)
TG 55.9 (3 μmol) 22.6 (10 μmol) 3.6 (30 μmol)
SOCE 0 (10 μmol) 0 (30 μmol) 10 (100 μmol)
IICR 0 (10 μmol) 0 (30 μmol) 70 (100 μmol)

Example 242

2-(N-benzylethyl)aminoethyl-2-pyridylketone 8714

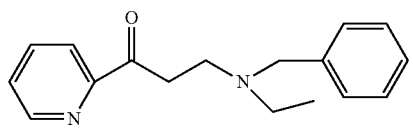 [SMILES: CCN(CCC(=O)c1ccccn1)Cc1ccccc1]

2-acetylpyridine (242 mg), ethylbenzylamine (270 mg), and paraformaldehyde (78 mg) were reacted at 130° C. for 2 hours.
NMR (CDCl₃) 0.88 (m, 3H), 2.41 (m, 2H), 2.61 (m, 2H), 2.93 (m, 2H), 3.48 (m, 2H), 3.69 (m, 2H), 7.1-8.3 (m, 9H)
TG 43.2 (3 μmol) 8.1 (10 μmol) 3.0 (30 μmol)
SOCE 0 (10 μmol) 0 (30 μmol) 0 (100 μmol)
IICR 30 (10 μmol) 80 (30 μmol) 90 (100 μmol)

Example 243

2-(N-bis-2-hydroxyethyl)aminoethyl-2-pyridylketone 8715

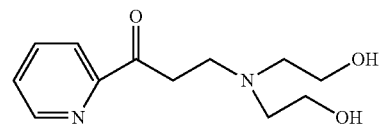 [SMILES: O=C(CCN(CCO)CCO)c1ccccn1]

2-acetylpyridine (242 mg), diethanol amine (210 mg), and paraformaldehyde (78 mg) were reacted at 130° C. for 2 hours.
NMR (CDCl₃) 2.74 (m, 2H), 3.06 (m, 2H), 3.65 (m, 2H), 3.78 (m, 4H), 4.32 (m, 2H), 7.7, 7.9, 8.1, 8.6
TG 42.6 (10 μmol) 10.1 (30 μmol)
SOCE 0 (10 μmol) 0 (30 μmol) 0 (100 μmol)
IICR 0 (10 μmol) 0 (30 μmol) 50 (100 μmol)

Example 244

2-(N-t-butyl-2-hydroxyethyl)aminoethyl-2-pyridylketone 8716

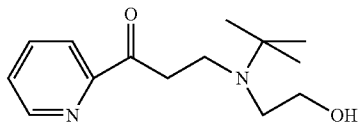 [SMILES: CC(C)(C)N(CCO)CCC(=O)c1ccccn1]

2-acetylpyridine (242 mg), t-butylethanol amine (234 mg), and paraformaldehyde (78 mg) were reacted at 130° C. for 2 hours.

NMR (CDCl$_3$) 1.12 (ms, 9H), 2.70 (m, 2H), 2.95 (m, 2H), 3.84 (m, 2H), 4.18 (m, 2H), 7.48, 7.85, 9.03, 8.69
TG 96.3 (3 μmol) 75.1 (10 μmol) 30.9 (30 μmol)
SOCE 0 (10 μmol) 0 (30 μmol) 0 (100 μmol)
IICR 0 (10 μmol) 0 (30 μmol) 0 (100 μmol)

Example 245

2-(N-benzyl-2-hydroxyethyl)aminoethyl-2-thiophenylketone 8717

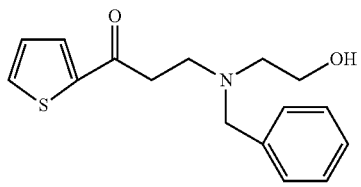 [SMILES: O=C(CCN(CCO)Cc1ccccc1)c1cccs1]

2-acetylthiophene (252 mg), benzylethanol amine (302 mg), and paraformaldehyde (78 mg) were reacted at 130° C. for 2 hours.

NMR (CDCl$_3$) 2.64 (m, 2H), 2.95 (m, 2H), 3.7-3.8 (m, 4H), 4.3 (m, 2H), 7.0-7.7 (m, 7H)
TG 100.2 (3 μmol) 69.4 (10 μmol) 24.3 (30 μmol)
SOCE 0 (10 μmol) 0 (30 μmol) 0 (100 μmol)
IICR 0 (10 μmol) 0 (30 μmol) 0 (100 μmol)

Example 246

2-(N-t-butyl-2-hydroxyethyl)aminoethyl-2-thiophenylketone 8718

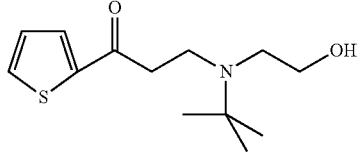 [SMILES: CC(C)(C)N(CCO)CCC(=O)c1cccs1]

2-acetylthiophene (252 mg), t-butylethanol amine (234 mg), and paraformaldehyde (78 mg) were reacted at 130° C. for 2 hours.

NMR (CDCl$_3$) 1.1 (s, 9H), 2.2 (m, 4H), 2.95 (m, 2H), 3.85 (m, 2H), 7.2, 7.8, 7.85
TG 64.7 (3 μmol) 31.3 (10 μmol) 5.8 (30 μmol)
SOCE 0 (10 μmol) 0 (30 μmol) 0 (100 μmol)
IICR 10 (10 μmol) 0 (30 μmol) 0 (100 μmol)

Example 247

2-(N-butyl-2-hydroxyethyl)aminoethyl-2-thiophenylketone 8719

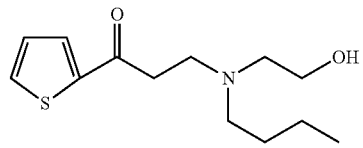 [SMILES: CCCCN(CCO)CCC(=O)c1cccs1]

2-acetylthiophene (252 mg), butylethanol amine (234 mg), and paraformaldehyde (78 mg) were reacted at 130° C. for 2 hours.

NMR (CDCl$_3$) 0.9 (m, 3H), 1.4 (m, 4H), 2.2 (m, 2H), 2.35 (m, 2H), 3.8 (m, 2H), 7.2, 7.8, 7.9
TG 89.5 (3 μmol) 76.5 (10 μmol) 36.6 (30 μmol)
SOCE 0 (10 μmol) 0 (30 μmol) 0 (100 μmol)
IICR 10 (10 μmol) 0 (30 μmol) 0 (100 μmol)

Example 248

2-(N-benzylmethyl)aminoethyl-3-pyridylketone 8720

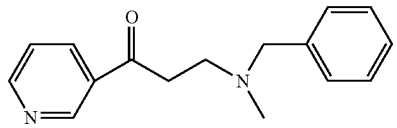 [SMILES: CN(CCC(=O)c1cccnc1)Cc1ccccc1]

2-acetylpyridine (242 mg), benzylmethyl amine (242 mg), and paraformaldehyde (78 mg) were reacted at 130° C. for 2 hours.

NMR (CDCl$_3$) 2.2 (m, 3H), 2.2 (m, 2H), 2.6 (m, 2H), 3.6 (m, 2H), 7.7 (m, 2H), 8.5 (m, 2H)
TG 55.7 (3 μmol) 23.8 (10 μmol) 6.0 (30 μmol)
SOCE 0 (10 μmol) 0 (30 μmol) 0 (100 μmol)
IICR 0 (10 μmol) 10 (30 μmol) 80 (100 μmol)

Example 249

2-(N-bis-2-hydroxyethyl)aminoethyl-4-pyridylketone 8721

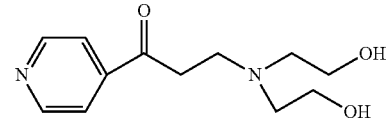 [SMILES: O=C(CCN(CCO)CCO)c1ccncc1]

4-acetylpyridine (242 mg), diethanol amine (210 mg), and paraformaldehyde (78 mg) were reacted at 130° C. for 2 hours.

NMR (CDCl$_3$) 1.9 (m, 2H), 2.1 (m, 2H), 2.6 (m, 2H), 2.7 (m, 2H), 3.5-3.7 (m, 4H), 7.0-9.2 (m, m, 4H)
TG 56.2 (3 μmol) 13.6 (10 μmol) 12 (30 μmol)

SOCE 0 (10 μmol) 0 (30 μmol) 20 (100 μmol)
IICR 0 (10 μmol) 60 (30 μmol) 80 (100 μmol)

Example 250

2-(N-2-hydroxyethylbutyl)aminoethyl-4-pyridylketone 8723

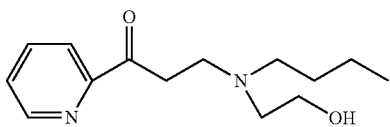 [SMILES: CCCCN(CCO)CCC(=O)c1ccccn1]

4-acetylpyridine (242 mg), butylethanol amine (234 mg), and paraformaldehyde (78 mg) were reacted at 130° C. for 2 hours.
NMR (CDCl$_3$) 0.9 (m, 3H), 1.4-1.4 (m, 4H), 2.5 (m, 2H), 2.6 (m, 2H), 2.9 (m, 2H), 3.7 (m, 2H), 4.1 (m, 2H), 7.5, 7.8, 8.1, 8.7
TG 97.3 (3 μmol) 63.2 (10 μmol) 27.0 (30 μmol)
SOCE 0 (10 μmol) 0 (30 μmol) 0 (100 μmol)
IICR 0 (10 μmol) 10 (30 μmol) 20 (100 μmol)

Example 251

2-(N-methyl-2-hydroxyethyl)aminoethyl-2-pyridylketone 8724

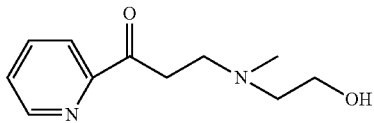

2-acetylpyridine (242 mg), methylethanol amine (150 mg), and paraformaldehyde (78 mg) were reacted at 130° C. for 2 hours.
NMR (CDCl$_3$) 2.35 (m, 2H), 2.7 (m, 3H), 2.9 (m, 2H), 3.7 (m, 2H), 7.5, 7.8, 8.1, 8.4
TG 81.4 (3 μmol) 80.8 (10 μmol) 53.1 (30 μmol)
SOCE 0 (10 μmol) 0 (30 μmol) 0 (100 μmol)
IICR 0 (10 μmol) 0 (30 μmol) 0 (100 μmol)

Example 252

2-(N-isopropyl-2-hydroxyethyl)aminoethyl-3-ethyl-2-pyrazylketone 8725

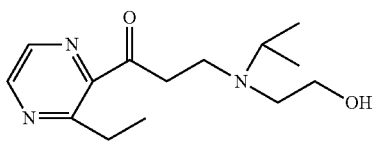 [SMILES: CCc1nccnc1C(=O)CCN(CCO)C(C)C]

2-acetyl-3-ethylpyrazine (150 mg), isopropylethanol amine (103 mg), and paraformaldehyde (38 mg) were reacted at 130° C. for 2 hours.
NMR (CDCl$_3$) 1.30 (m, 6H), 2.73 (m, 2H), 3.14 (m, 2H), 3.9 (m, 2H), 4.25 (m, 2H), 8.4, 8.5

TG 75.4 (3 vitriol) 42.9 (10 μmol) 17.7 (30 μmol)
SOCE 0 (10 μmol) 0 (30 μmol) 0 (100 μmol)
IICR 0 (10 vitriol) 0 (30 μmol) 80 (100 μmol)

Example 253

2-(N-benzylethyl)aminoethyl-2-thiophenylketone 8734

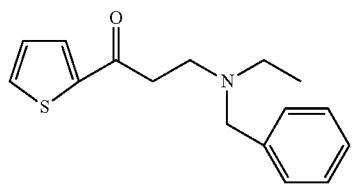 [SMILES: CCN(CCC(=O)c1cccs1)Cc1ccccc1]

2-acetylthiophene (240 mg), ethylbenzylamine (270 mg), and paraformaldehyde (78 mg) were reacted at 130° C. for 2 hours.
NMR (CDCl$_3$) 1.0 (m, 3H), 2.5 (m, 2H), 3.0 (m, 2H), 3.6 (m, 4H), 7.0-7.8 (m, 8H)
TG 39.1 (3 μmol) 3.3 (10 μmol) 0.4 (30 μmol)
SOCE 0 (10 μmol) 10 (30 μmol) 40 (100 μmol)
IICR 20 (10 μmol) 0 (30 μmol) 20 (100 μmol)

Example 254

2-(N-2-hydroxyethylmethyl)aminoethyl-3-thiophenylketone 8727

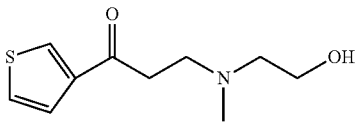

3-acetylthiophene (252 mg), methylethanol amine (150 mg), and paraformaldehyde (78 mg) at 130° C. for 2 hours.
NMR (CDCl$_3$) 2.15 (m, 2H), 2.2 (m, 5H), 2.8 (m, 2H), 3.7 (m, 2H), 6.7 (1H), 6.6 (1H), 8.0 (1H)
TG 85.3 (3 μmol) 64.3 (10 μmol) 19.0 (30 μmol)
SOCE 0 (10 μmol) 0 (30 μmol) 0 (100 μmol)
IICR 0 (10 μmol) 30 (30 μmol) 40 (100 μmol)

Example 255

2-(N-2-hydroxyethylbutyl)aminoethyl-5-methyl-2-furylketone 8728

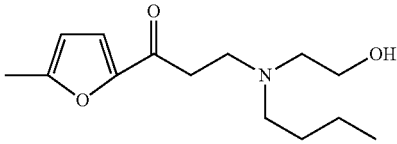 [SMILES: CCCCN(CCO)CCC(=O)c1ccc(C)o1]

2-acetyl-5-methylfuran (248 mg), butylethanol amine (234 mg), and paraformaldehyde (78 mg) were reacted at 130° C. for 2 hours.

NMR (CDCl$_3$) 1.90 (m, 3H), 1.40 (m, 4H), 2.4-2.8 (m 4H), 3.3 (m, 2H), 3.7 (m, 2H), 6.15, 7.15
TG 11.6 (3 µmol) −6.1 (10 µmol) −7.9 (30 µmol)
SOCE 0 (10 µmol) 0 (30 µmol) 0 (100 µmol)
IICR 0 (10 µmol) 30 (30 µmol) 50 (100 µmol)

Example 256

2-(N-benzyl-t-butyl)aminoethyl-2-thiazolylketone 8729

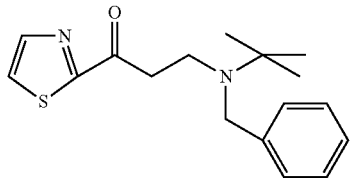 [SMILES: CC(C)(C)N(CCC(=O)c1nccs1)Cc1ccccc1]

2-acetyl thiazole (32 mg), t-butylbenzylamine (34 mg), and paraformaldehyde (10 mg) were reacted at 130° C. for 2 hours.
NMR (CDCl$_3$) 1.00 (s, 9H), 2.70 (m, 2H), 2.95 (m, 2H), 3.7 (m, 2H), 7.0-7.7 (m, 8H)
TG 19.1 (3 µmol) 5.8 (10 µmol) −0.3 (30 µmol)
SOCE 0 (10 µmol) 0 (30 µmol) 10 (100 µmol)
IICR 50 (10 µmol) 90 (30 µmol) 80 (100 µmol)

Example 257

2-(N-isopropyl-2-hydroxyethyl)aminoethyl-2,4-dimethyl-5-thiazolylketone 8730

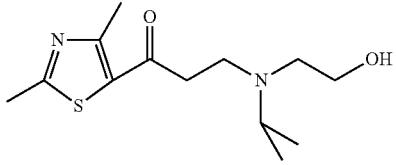 [SMILES: Cc1nc(C)c(C(=O)CCN(CCO)C(C)C)s1]

5-acetyl-2,4-dimethylthiazole (82.5 mg), isopropylethanol amine (55 mg), and paraformaldehyde (78 mg) were reacted at 130° C. for 2 hours.
NMR (CDCl$_3$) 1.00 (m, s, 6H), 2.9 (m, 2H), 2.6 (m, 3H), 2.8 (m, 2H), 2.97 (m, 1H), 3.8 (m, 2H)
TG 101 (3 µmol) 91.4 (10 µmol) 60.6 (30 µmol)
SOCE 0 (10 µmol) 0 (30 µmol) 0 (100 µmol)
IICR 0 (10 µmol) 0 (30 µmol) 20 (100 µmol)

Example 258

2-(N-benzylmethyl)aminoethyl-2-thiazolylketone 8731

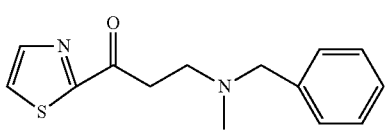 [SMILES: CN(CCC(=O)c1nccs1)Cc1ccccc1]

2-acetyl thiazole (33 mg), benzylmethyl amine (32 mg), and paraformaldehyde (10 mg) were reacted at 130° C. for 2 hours.

NMR (CDCl$_3$) 2.2 (m, 3H), 2.4 (m, 2H), 2.5 (m, 2H), 3.6-3.7 (m, 2H), 7.0, 8.0 (m, 8H)
TG 48.5 (3 µmol) 19.6 (10 µmol) 0.4 (30 µmol)
SOCE 0 (10 µmol) 0 (30 µmol) 0 (100 µmol)
IICR 20 (10 µmol) 0 (30 µmol) 20 (100 µmol)

Example 259

2-(N-2-hydroxyethylmethyl)aminoethyl-3-pyridylketone 8732

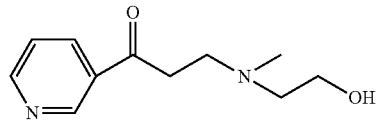

2-acetylpyridine (248 mg), methylethanol amine (150 mg), and paraformaldehyde (78 mg) were reacted at 130° C. for 2 hours.
NMR (CDCl$_3$) 1.50 (m, 2H), 1.75 (m, 2H), 2.80 (m, 2H), 3.4 (m, 2H), 6.9 (m, 2H), 7.9 (m, 2H)
TG 53.7 (3 µmol) 19.9 (10 µmol) 3.4 (30 µmol)
SOCE 0 (10 µmol) 0 (30 µmol) 0 (100 µmol)
IICR 0 (10 µmol) 0 (30 µmol) 20 (100 µmol)

Example 260

2-(N-bis-hydroxyethyl)aminoethyl-3-ethyl-2-pyrazylketone 8733

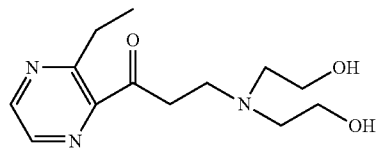 [SMILES: CCc1nccnc1C(=O)CCN(CCO)CCO]

2-acetyl-3-ethylpyrazine (148 mg), diethanol amine (119 mg), and paraformaldehyde (40 mg) were reacted at 130° C. for 2 hours.
NMR (CDCl$_3$) 1.31 (t, 3H), 2.75 (m, 43H), 3.25 (m, 2H), 3.71 (m, 2H), 3.80 (M, 2H), 4.0 (m, 2H), 8.2 (s, 1H), 8.25 (s, 1H)
TG 76.3 (3 µmol) 45.2 (10 µmol) 10.2 (30 µmol)
SOCE 0 (10 µmol) 0 (30 µmol) 0 (100 µmol)
IICR 20 (10 µmol) 0 (30 µmol) 20 (100 µmol)

Example 261

2-(N-bis-hydroxyethyl)aminoethyl-2-thiophenylketone 8676

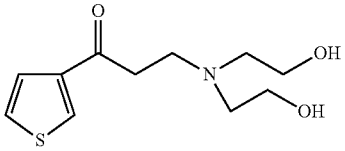 [SMILES: O=C(CCN(CCO)CCO)c1ccsc1]

Acetylthiophene (126 mg), diethanol amine (105 mg), and paraformaldehyde (40 mg) were reacted at 130° C. for 2 hours.

NMR (CDCl₃) 2.5 (m, 2H), 2.6 (m, 2H), 2.8 (m, 2H), 3.6 (m, 4H), 4.2 (m, 2H), 6.6, 7.7, 8.0
TG 87 (3 μmol) 22 (30 μmol)
SOCE 0 (10 μmol) 0 (30 μmol) 0 (100 μmol)
IICR 10 (10 μmol) 20 (30 μmol) 20 (100 μmol)

Example 262

2-(N-2-hydroxyethylmethyl)aminoethyl-4-pyridylketone 8722

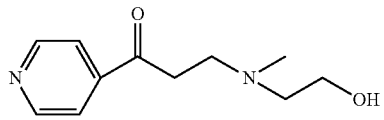

4-acetylpyridine (242 mg), methylethanol amine (150 mg), and paraformaldehyde (78 mg) were reacted at 130° C. for 2 hours.
NMR (CDCl₃) 2.69 (m, 2H), 2.89 (m, 2H), 3.69 (m, 3H), 7.8 (m, 2H), 8.7 (m, 2H)
TG 75 (3 μmol) 8.6 (30 μmol)
SOCE 0 (10 μmol) 0 (30 μmol) 0 (100 μmol)
IICR 0 (10 μmol) 0 (30 μmol) 70 (100 μmol)

Example 263

2-(N-benzylisopropyl)aminoethyl-4-methyl-2-thiazolylketone 8738

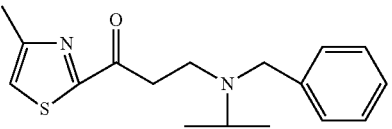 [SMILES: Cc1csc(C(=O)CCN(Cc2ccccc2)C(C)C)n1]

2-acetyl-4-methylthiazole (152 mg), isopropylbenzylamine (134 mg), and paraformaldehyde (78 mg) were reacted at 130° C. for 2 hours.
NMR (CDCl₃) 0.9-1.1 (m, 6H), 2.3-2.9 (m, 3H), 3.4-3.8 (m, 4H), 7.0-7.4 (m, 6H)
TG 26 (3 μmol) 8.6 (30 μmol) 5.6 (10 μmol) 0.2 (30 μmol)
SOCE 0 (10 μmol) 0 (30 μmol) 30 (100 μmol)
IICR 0 (10 μmol) 0 (30 μmol) 70 (100 μmol)

Example 264

2-(N-butyl-2-hydroxyethyl)aminoethyl-4-methyl-2-thiazolylketone 8739

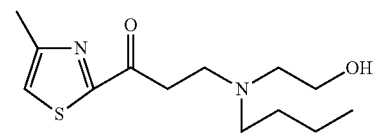 [SMILES: CCCCN(CCO)CCC(=O)c1nc(C)cs1]

2-acetyl-4-methylthiazole, n-butyl-2-hydroxyethyl amine, and paraformaldehyde were reacted at 130° C. for 2 hours.
NMR (CDCl₃) 0.6-0.95 (m, 3H), 1.1-1.5 (m, 4H), 2.5-2.6 (m, 6H), 2.9 (m, 2H), 3.5-3.8 (m, 4H), 7.25 (s, 1H)
TG 40 (3 μmol) 9.9 (10 μmol) 2.6 (30 μmol)
SOCE 0 (10 μmol) 0 (30 μmol) 10 (100 μmol)
IICR 0 (10 μmol) 0 (30 μmol) 70 (100 μmol)

Example 265

2-(N-benzylmethyl)aminoethyl-4-methyl-2-thiazolylketone 8740

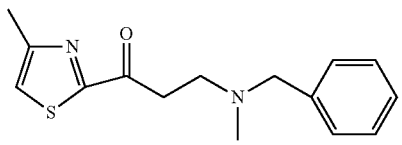 [SMILES: Cc1csc(C(=O)CCN(C)Cc2ccccc2)n1]

2-acetyl-4-methylthiazole, methylbenzylamine, and paraformaldehyde were reacted at 130° C. for 2 hours.
NMR (CDCl₃) 2.1-3.6 (m, 5H), 2.4-3.1 (m, 2H), 3.4-3.7 (m, 2H), 7.0-7.2 (m, 6H)
TG 33 (3 μmol) 7.1 (10 μmol) (130 μmol)
SOCE 10 (10 μmol) 10 (30 μmol) 10 (100 μmol)
IICR 0 (10 μmol) 0 (30 μmol) 70 (100 μmol)

Example 266

2-(N-benzylisopropyl)aminoethyl-5-chloro-2-thiophenylketone 8741

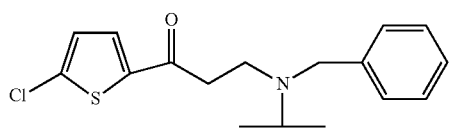 [SMILES: CC(C)N(CCC(=O)c1ccc(Cl)s1)Cc1ccccc1]

2-acetyl-5-chlorothiophene (320 mg), isopropylbenzylamine (298 mg), and paraformaldehyde (78 mg) were reacted at 130° C. for 2 hours.
NMR (CDCl₃) 0.9-1.2 (m, 6H), 2.50 (m, 2H), 2.7-3.0 (m, 3H), 3.5-3.7 (m, 2H), 6.8-7.2 (m, 7H)
TG 2.6 (3 μmol) 4.7 (10 μmol) −4.7 (30 μmol)
SOCE 0 (10 μmol) 20 (30 μmol) 40 (100 μmol)
IICR 0 (10 μmol) 0 (30 μmol) 70 (100 μmol)

Example 267

2-(N-2-hydroxyethylisopropyl)aminoethyl-5-chloro-2-thiophenylketone 8742

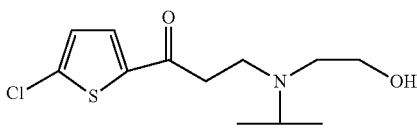 [SMILES: CC(C)N(CCO)CCC(=O)c1ccc(Cl)s1]

2-acetyl-5-chlorothiophene, 2-hydroxyethylisopropylamine, and paraformaldehyde were reacted at 130° C. for 2 hours.
NMR (CDCl₃) 2.69 (m, 2H), 2.89 (m, 2H), 3.69 (m, 3H), 7.8 (m, 2H), 8.7 (m, 2H)
TG 58 (3 μmol) 27 (10 μmol) 7.9 (30 μmol)
SOCE 0 (10 μmol) 0 (30 μmol) 0 (100 μmol)
IICR 0 (10 μmol) 0 (30 μmol) 70 (100 μmol)

Example 268

2-(N-benzyl-2-hydroxyethyl)aminoethyl-5-chloro-2-thiophenylketone 8743

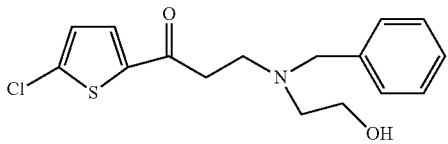 [SMILES: O=C(CCN(CCO)Cc1ccccc1)c1ccc(Cl)s1]

2-acetyl-5-chlorothiophene, 2-hydroxyethylbenzylamine, and paraformaldehyde were reacted at 130° C. for 2 hours.

NMR (CDCl$_3$) 2.69 (m, 2H), 2.89 (m, 2H), 3.69 (m, 3H), 7.8 (m, 2H), 8.7 (m, 2H)

TG 32 (3 µmol) 28 (10 µmol) 6.3 (30 µmol)
SOCE 10 (10 µmol) 0 (30 µmol) 10 (100 µmol)
IICR 0 (10 µmol) 0 (30 µmol) 70 (100 µmol)

Example 269

2-(N-t-butylbenzyl)aminoethyl-5-bromo-2-thiophenylketone 8778

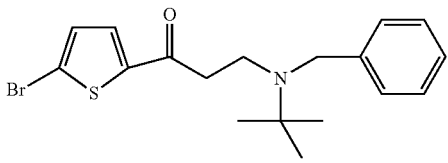 [SMILES: CC(C)(C)N(CCC(=O)c1ccc(Br)s1)Cc1ccccc1]

2-acetyl-5-bromothiophene (410 mg), t-butylbenzylamine (326.5 mg), and paraformaldehyde (78 mg) were heated in dioxane (0.4 ml) at 130° C. for 30 minutes.

NMR (CDCl$_3$) 1.20 (s, 9H), 2.64 (t, 2H), 2.97 (t, 2H), 3.73 (m, 2H), 7.1 (s, 1H), 7.4-7.6 (m, 6H)

TG 15 (0.3 µmol) 12 (1 µmol) 4.7 (3 µmol) 4.5 (10 µmol) 3.1 (30 µmol)

Example 270

2-(N-hydroxypropyl)aminoethyl-2-pyrazylketone 8746

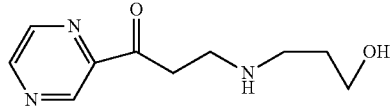 [SMILES: O=C(CCNCCCO)c1cnccn1]

NMR (CDCl$_3$) 1.88 (m, 2H), 2.75 (m, 2H), 3.78 (m, 4H), 4.37 (m, 2H), 8.78 (m, 2H), 9.21 (1H)

TG 106 (3 µmol) 71.7 (30 µmol)
SOCE 10 (30 µmol) 30 (100 µmol)
IICR 20 (10 µmol) 0 (30 µmol) 10 (100 µmol)

Example 271

2-(N-benzyl)aminoethyl-4-pyridylketone 8747

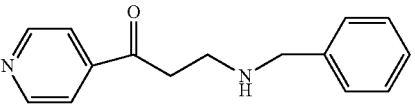

NMR (CDCl$_3$) 2.64 (m, 2H), 3.42 (m, 2H), 3.86 (m, 2H), 7.28 (m, 5H), 8.24 (m, 1H), 8.79 (m, 1H), 9.17 (m, 1H)

TG 108 (3 µmol) 88.5 (30 µmol)
SOCE 0 (30 µmol) 10 (100 µmol)
IICR 10 (10 µmol) 0 (30 µmol) 40 (100 µmol)

Example 272

2-(N-1,2-diphenyl-2-hydroxyethyl)aminoethyl-2-furylketone 8748

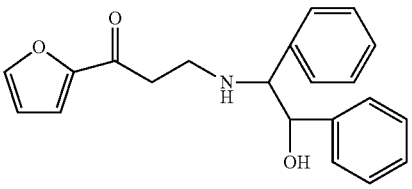 [SMILES: O=C(CCNC(c1ccccc1)C(O)c1ccccc1)c1ccco1]

NMR (CDCl$_3$) 2.48 (m, 2H), 3.70 (m, 1H), 5.29 (m, 1H), 6.54 (m, 1H), 6.9-7.4 (m, 6H)

TG 95.7 (3 µmol) 40.0 (30 µmol)
SOCE 20 (30 µmol) 40 (100 µmol)
IICR 40 (10 µmol) 20 (30 µmol) 20 (100 µmol)

Example 273

N,N-bis(2-pyrazoylethyl)-N-hydroxyethylethylenediamine 8749

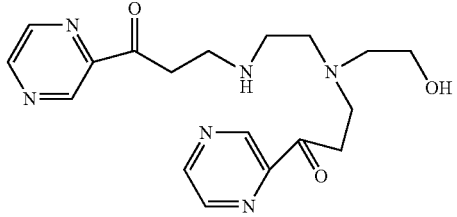 [SMILES: O=C(CCNCCN(CCO)CCC(=O)c1cnccn1)c1cnccn1]

NMR (CDCl$_3$) 2.75 (m, 2H), 2.85 (m, 2H), 3.60 (m, 2H), 3.70 (m, 2H), 5.31 (m, 2H), 8.17 (1H), 8.53 (s, 1H), 8.68 (s, 1H), 9.23 (s, 1H)

TG 90.6 (3 µmol) 25.6 (30 µmol)
SOCE 0 (30 µmol) 10 (100 µmol)
IICR 40 (10 µmol) 30 (30 µmol) 20 (100 µmol)

Example 274

2-(N-1-benzyl-2-hydroxyethyl)aminoethyl-4-pyridylketone 8750

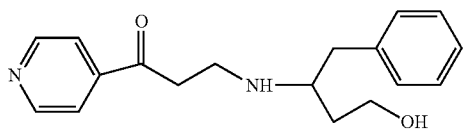 [SMILES: O=C(CCNC(CCO)Cc1ccccc1)c1ccncc1]

NMR (CDCl$_3$) 2.64 (m, 2H), 3.35 (m, 2H), 3.7 (m, 2H), 4.37 (m, 2H), 7.24 (m, 5H), 7.73 (m, 2H), 8.82 (m, 2H).
TG 99.0 (3 µmol) 51.5 (30 µmol)
SOCE 0 (30 µmol) 0 (100 µmol)
IICR 20 (10 µmol) 20 (30 µmol) 80 (100 µmol)

Example 275

2-(N-2-hydroxyethyl)aminoethyl-2-furylketone 8751

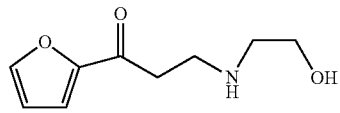 [SMILES: O=C(CCNCCO)c1ccco1]

NMR (CDCl$_3$) 2.46 (m, 2H), 2.65 (m, 2H), 3.14 (m, 2H), 3.67 (m, 2H), 5.30 (s 1H), 6.54 (1H), 7.14 (1H), 7.57 (1H)
TG 106 (3 µmol) 60.6 (30 µmol)
SOCE 0 (30 µmol) 0 (100 µmol)
IICR 30 (10 µmol) 30 (30 µmol) 30 (100 µmol)

Example 276

N,N-bis(2-pyrazoylethyl)tetramethylenediamine 8752

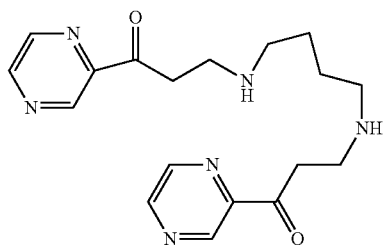 [SMILES: O=C(CCNCCCCNCCC(=O)c1cnccn1)c1cnccn1]

2-acetylpyrazine (244 mg), tetramethylenediamine (88 mg), and paraformaldehyde (80 mg) were reacted at 130° C. for 2 hours.
NMR (CDCl$_3$) 1.66 (m, 4H), 2.74 (m, 2H), 3.35 (m, 2H), 3.62 (m, 2H), 7.60 (m, 2H), 8.76 (s, 1H)
TG 102 (3 µmol) 45.2 (30 µmol)
SOCE 0 (30 µmol) 0 (100 µmol)
IICR 0 (10 µmol) 0 (30 µmol) 20 (100 µmol)

Example 277

2-bis(N-2-hydroxyethyl)aminoethyl-5-chloro-2-thienylketone 8753

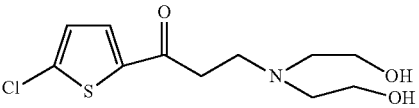 [SMILES: O=C(CCN(CCO)CCO)c1ccc(Cl)s1]

NMR (CDCl$_3$) 2.52 (m, 2H), 2.72 (m, 2H), 3.00 (m, 2H), 3.73 (m, 2H), 4.38 (m, 4H), 6.91 (1H), 7.48 (1H)
TG 37.8 (3 µmol) 4.7 (10 µmol) 3.7 (30 µmol)
SOCE 0 (30 µmol) 0 (100 µmol)
IICR 0 (10 µmol) 0 (30 µmol) 20 (100 µmol)

Example 278

2-(N-ethylbenzyl)aminoethyl-5-chloro-2-thienylketone 8754

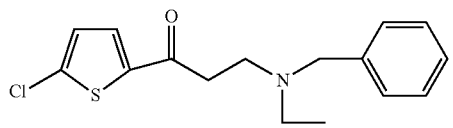 [SMILES: CCN(CCC(=O)c1ccc(Cl)s1)Cc1ccccc1]

NMR (CDCl$_3$) 0.95 (m, 3H), 2.51 (m, 2H), 2.90 (m, 2H), 3.55 (m, 4H), 6.8-7.6 (m, 7H)
TG 7.4 (3 µmol) 4.0 (30 µmol)
SOCE 30 (30 µmol) 40 (100 µmol)
IICR 30 (10 µmol) 20 (30 µmol) 60 (100 µmol)

Example 279

2-(N-methylbenzyl)aminoethyl-5-chloro-2-thienylketone 8755

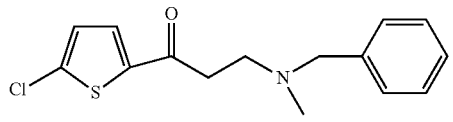 [SMILES: CN(CCC(=O)c1ccc(Cl)s1)Cc1ccccc1]

NMR (CDCl$_3$) 2.23 (m, 2H), 2.51 (m, 2H), 2.85 (m, 2H), 3.55-3.6 (m, 3H) 6.95-7.5 (m, 7H)
TG 26.2 (3 µmol) 7.1 (30 µmol)
SOCE 30 (30 µmol) 40 (100 µmol)
IICR 20 (10 µmol) 0 (30 µmol) 40 (100 µmol)

Example 280

2-(N-t-butylbenzyl)aminoethyl-5-chloro-2-thienylketone 8756

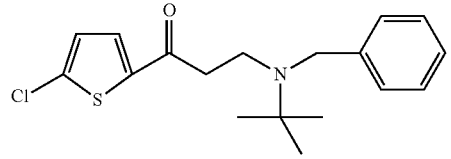 [SMILES: CC(C)(C)N(CCC(=O)c1ccc(Cl)s1)Cc1ccccc1]

NMR (CDCl$_3$) 1.17 (s, 9H), 2.64 (m, 2H), 2.97 (m, 2H), 3.72 (m, 2H), 6.9-7.7 (m, 7H)
TG −3.1 (3 μmol) 3.5 (30 μmol)
SOCE 0 (30 μmol) 30 (100 μmol)
IICR 50 (10 μmol) 60 (30 μmol) 70 (100 μmol)

Example 281

2-(N-2-hydroxypropyl)aminoethyl-2-pyrazylketone 8757

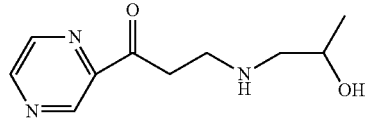

NMR (CDCl$_3$) 1.24 (m, 3H), 2.55 (m, 1H), 2.74 (m, 2H), 3.70 (m, 2H), 8.79 (1H), 9.05 (1H), 9.22 (1H)
TG 101.0 (3 μmol) 80.0 (30 μmol)
SOCE 0 (30 μmol) 0 (100 μmol)
IICR 20 (10 μmol) 20 (30 μmol) 50 (100 μmol)

Example 282

2-(2-hydroxymethylpyrrolidino)ethyl-2-pyrazylketone 8758

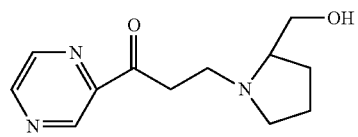

NMR (CDCl$_3$) 1.77 (m, 4H), 2.11 (m, 2H), 2.73 (m, 2H), 3.37 (m, 2H), 3.46 (m, 2H), 3.70 (m, 2H), 8.6-8.7 (m, 2H), 8.24 (s, 1H)
TG 84.9 (3 μmol) 21.2 (30 μmol)
SOCE 0 (30 μmol) 0 (100 μmol)
IICR 0 (10 μmol) 20 (30 μmol) 50 (100 μmol)

Example 283

2-(N-isopropylbenzyl)aminoethyl-2-benzothienylketone 8759

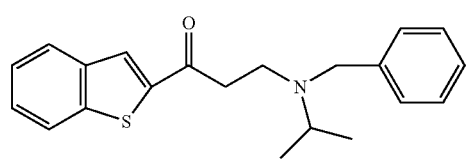 [SMILES: CC(C)N(CCC(=O)c1cc2ccccc2s1)Cc1ccccc1]

2-acetylbenzothiophene (352 mg), isopropylbenzylamine (298 mg), and paraformaldehyde (76 mg) were reacted at 130° C. for 2 hours.
NMR (CDCl$_3$) 1.05 (m, 9H), 2.65 (m, 2H), 2.95 (m, 1H), 3.54-3.6 (m, 2H), 7.15-7.66 (m, 10H)
TG 11.1 (3 μmol) 1.1 (30 μmol)
SOCE 0 (30 μmol) 40 (100 μmol)
IICR 50 (10 μmol) 80 (30 μmol) 50 (100 μmol)

Example 284

2-(N-isopropyl-2-hydroxyethyl)aminoethyl-2-benzothienylketone 8760

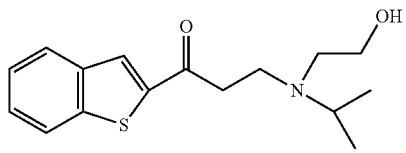 [SMILES: CC(C)N(CCO)CCC(=O)c1cc2ccccc2s1]

NMR (CDCl$_3$) 1.10 (m, 6H), 2.65 (m, 2H), 2.85 (m, 2H), 3.86 (m, 2H), 7.4-7.9 (m, 5H)
TG 71.6 (3 μmol) 7.8 (30 μmol)
SOCE 0 (30 μmol) 0 (100 μmol)
IICR 0 (10 μmol) 0 (30 μmol) 40 (100 μmol)

Example 285

2-(N-t-butylbenzyl)aminoethyl-2-benzothienylketone 8761

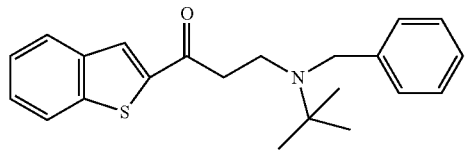 [SMILES: CC(C)(C)N(CCC(=O)c1cc2ccccc2s1)Cc1ccccc1]

NMR (CDCl$_3$) 1.18 (ms, 9H), 2.84 (m, 2H), 3.04 (m, 2H), 3.74 (m, 2H), 7.2-7.9 (m, 10H)
TG 2.3 (3 μmol) −1.5 (30 μmol)
SOCE 0 (30 μmol) 50 (100 μmol)
IICR 50 (10 μmol) 80 (30 μmol) 60 (100 μmol)

Example 286

2-(N-isopropylbenzyl)aminoethylferrocenylketone 8762

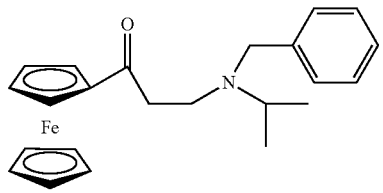

2-acetylferrocene (228 mg), isopropylbenzylamine (148 mg), and paraformaldehyde (40 mg) were reacted at 130° C. for 2 hours.
NMR (CDCl$_3$) 1.18 (m, 6H), 2.84 (m, 2H), 3.04 (m, 2H), 3.74 (m, 2H), 7.3-7.9 (m, 10H)
TG 99.2 (3 μmol) 54.2 (30 μmol)
SOCE 0 (30 μmol) 0 (100 μmol)
IICR 50 (10 μmol) 80 (30 μmol) 50 (100 μmol)

Example 287

2-(N-isopropyl-2-hydroxyethyl)aminoethylferrocenylketone 8763

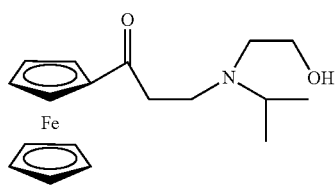

NMR (CDCl$_3$) 2.08 (m, 6H), 2.97 (m, 2H), 3.5 (m, 2H), 3.9 (m, 2H), 4.21 (m, 2H), 7.4-8.0 (m, 8H)

TG 100 (3 μmol) 60.8 (30 μmol)

SOCE 0 (30 μmol) 10 (100 μmol)

IICR 20 (10 μmol) 40 (30 μmol) 40 (100 μmol)

Example 288

2-bis(N-2-hydroxyethyl)aminoethylferrocenylketone 8764

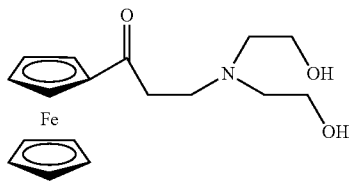

NMR (CDCl$_3$) 1.75 (m, 2H), 2.36 (m, 2H), 2.83 (m, 4H), 3.76 (m, 4H), 4.52 (s, 4H), 4.78 (s, 4H)

TG 94.9 (3 μmol) 44.1 (30 μmol)

SOCE 10 (30 μmol) 40 (100 μmol)

IICR 40 (10 μmol) 50 (30 μmol) 60 (100 μmol)

Example 289

2-(N-ethylbenzyl)aminoethyl-2-thiazolylketone 8765

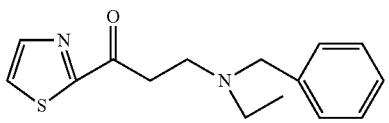 [SMILES: CCN(CCC(=O)c1nccs1)Cc1ccccc1]

NMR (CDCl$_3$) 1.0 (m, 3H), 2.4 (m, 2H), 2.5 (m, 1H), 2.7 (m, 2H), 3.6 (m, 2H), 7-7.5 (m, 5H), 7.66 (s, 1H), 7.7 (s, 1H)

TG 46.9 (3 μmol) 8.1 (30 μmol)

SOCE 0 (30 μmol) 10 (100 μmol)

IICR 40 (10 μmol) 80 (30 μmol) 100 (100 μmol)

Example 290

2-(N-2-hydroxyethylbenzyl)aminoethyl-2-thiazolylketone 8766

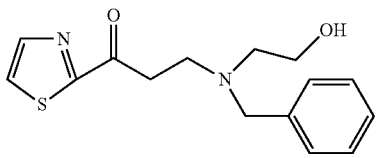 [SMILES: O=C(CCN(CCO)Cc1ccccc1)c1nccs1]

NMR (CDCl$_3$) 2.08 (m, 1H), 2.74 (m, 2H), 2.79 (m, 2H), 3.73 (m, 2H), 3.81 (m, 2H), 7.35 (m, 5H), 7.68 (s, 1H), 8.01 (s, 1H)

TG 71.4 (3 μmol) 14.9 (30 μmol)

SOCE 0 (30 μmol) 0 (100 μmol)

IICR 40 (10 μmol) 60 (30 μmol) 90 (100 μmol)

Example 291

2-(N-2-hydroxyethylmethyl)aminoethyl-2-thiazolylketone 8767

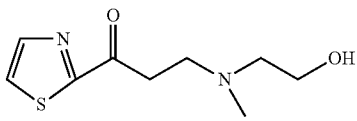

NMR (CDCl$_3$) 2.26 (m, 2H), 2.44 (m, 2H), 2.72 (m, 2H), 7.65 (m, 2H), 7.99 (2H)

TG 61.8 (3 μmol) 14.3 (30 μmol)

SOCE 0 (10 μmol) 0 (30 μmol) 0 (100 μmol)

IICR 40 (10 μmol) 70 (30 μmol) 100 (100 μmol)

Example 292

2-(N-isopropylbenzyl)aminoethyl-5-bromo-2-thienylketone 8768

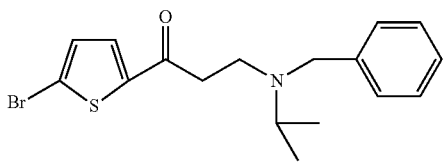 [SMILES: CC(C)N(CCC(=O)c1ccc(Br)s1)Cc1ccccc1]

NMR (CDCl$_3$) 1.0 (m, 6H), 2.5 (m, 2H), 2.8-9 (m, 2H), 3.5 (m, 2H), 7.0-7.5 (m, 7H)

TG −0.3 (3 μmol) −3.8 (30 μmol)

SOCE 0 (10 μmol) 20 (30 μmol) 40 (100 μmol)

IICR 50 (10 μmol) 80 (30 μmol) 90 (100 μmol)

Example 293

2-(N-2-hydroxyethylbutyl)aminoethyl-5-bromo-2-thienylketone 8769

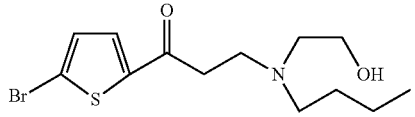 [SMILES: CCCCN(CCO)CCC(=O)c1ccc(Br)s1]

NMR (CDCl$_3$) 0.9 (t, 3H), 1.44 (m, 2H), 1.49 (m, 2H), 2.2 (m, 2H), 2.9 (m, 2H), 3.7 (m, 2H), 7.1 (1H), 7.49 (1H) 1.0 (m, 3H), 2.4 (m, 2H), 2.5 (m, 1H), 2.7 (m, 2H), 3.6 (m, 2H), 7-7.5 (m, 5H), 7.6 (s, 1H), 7.7 (s, 1H)

TG 35.5 (3 μmol) 5.3 (30 μmol)
SOCE 0 (10 μmol) 0 (30 μmol) 10 (100 μmol)
IICR 80 (10 μmol) 50 (30 μmol) 90 (100 μmol)

Example 294

2-(N-2-hydroxyethyl-t-butyl)aminoethyl-5-bromo-2-thienylketone 8770

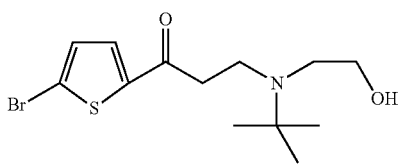 [SMILES: CC(C)(C)N(CCO)CCC(=O)c1ccc(Br)s1]

NMR (CDCl$_3$) 1.1 (m, 9H), 2.5 (m, 2H), 2.9 (m, 2H), 3.8 (m, 2H), 4.4 (m, 2H), 7.11 (m, 2H), 7.44 (m, 2H).

TG 102 (3 μmol) 104 (30 μmol)
SOCE 0 (10 μmol) 0 (30 μmol) 10 (100 μmol)
IICR 70 (10 μmol) 40 (30 μmol) 50 (100 μmol)

Example 295

2-(N-isopropylbenzyl)aminoethyl-1-benzotriazoketone 8771

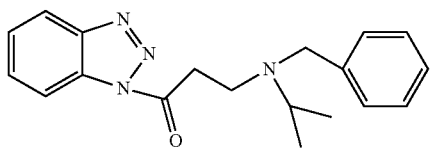 [SMILES: CC(C)N(CCC(=O)n1nnc2ccccc21)Cc1ccccc1]

2-acetyl-1H-benzotriazole (80 mg), isopropylbenzylamine (74.5 mg), and paraformaldehyde (40 mg) were reacted at 130° C. for 2 hours.

NMR (CDCl$_3$) 2.0 (m, 6H), 3.0 (m, 2H), 3.5-3.74 (m, 4H), 4.1 (m, 2H), 7.2-8.0 (m, 9H).

TG 102 (3 μmol) 107 (30 μmol)
SOCE 0 (10 μmol) 0 (30 μmol) 0 (100 μmol)
IICR 80 (10 μmol) 70 (30 μmol) 60 (100 μmol)

Example 296

2-bis(N-2-hydroxyethyl)aminoethyl-1-benzotriazoketone 8773

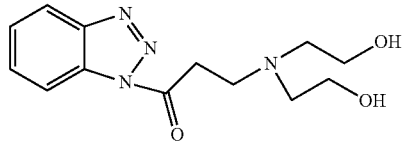 [SMILES: O=C(CCN(CCO)CCO)n1nnc2ccccc21]

NMR (CDCl$_3$) 2.1 (m, 2H), 2.8 (m, 2H), 3.0 (m, 2H), 3.6 (m, 2H), 4.15 (m, 2H), 6.6 (m, 2H), 7.5 (m, 4H)

TG 105 (3 μmol) 107 (30 μmol)
SOCE 0 (10 μmol) 0 (30 μmol) 20 (100 μmol)
IICR 0 (10 μmol) 50 (30 μmol) 60 (100 μmol)

Example 297

2-(N-isopropylbenzyl)aminoethyl-4-biphenylketone 8774

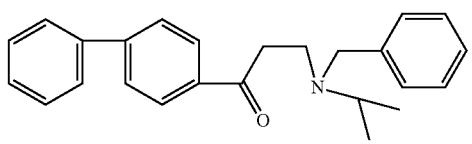 [SMILES: CC(C)N(CCC(=O)c1ccc(-c2ccccc2)cc1)Cc1ccccc1]

4-acetyl biphenyl (392 mg), isopropylbenzylamine (298 mg), and paraformaldehyde (80 mg) were reacted at 130° C. for 2 hours.

NMR (CDCl$_3$) 0.95 (m, 6H), 2.6 (m, 2H), 3.06 (m, 2H), 3.67 (m, 2H), 7-8.1 (m, 14H)

TG 75.7 (3 μmol) 7.1 (30 μmol)
SOCE 20 (10 μmol) 50 (30 μmol) 60 (100 μmol)
IICR 50 (10 μmol) 50 (30 μmol) 90 (100 μmol)

Example 298

2-(N-2-hydroxyethylisopropyl)aminoethyl-4-biphenylketone 8775

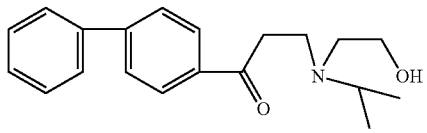 [SMILES: CC(C)N(CCO)CCC(=O)c1ccc(-c2ccccc2)cc1]

NMR (CDCl$_3$) 1.09 (m, 5H), 2.6 (m, 2H), 2.85 (m, 2H), 3.67 (m, 2H), 3.83 (m, 2H), 3.83 (m, 2H), 7.4-8.0 (m, 7H)

TG 95.1 (3 μmol) 64.9 (30 μmol)
SOCE 20 (10 μmol) 40 (30 μmol) 50 (100 μmol)
IICR 60 (10 μmol) 50 (30 μmol) 60 (100 μmol)

Example 299

2-(N-2-hydroxyethylphenyl)aminoethyl-4-biphenylketone 8776

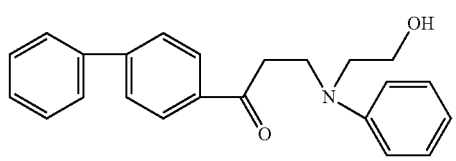 [SMILES: O=C(CCN(CCO)c1ccccc1)c1ccc(-c2ccccc2)cc1]

NMR (CDCl$_3$) 2.6 (m, 2H), 3.38 (m, 2H), 4.13 (m, 2H), 4.85 (m, 2H), 7.3-8.1 (m, 14H)

TG 96.4 (3 µmol) 84.3 (30 µmol)

SOCE 20 (10 µmol) 40 (30 µmol) 40 (100 µmol)

IICR 70 (10 µmol) 30 (30 µmol) 30 (100 µmol)

Example 300

2-(N-phenethyl)aminoethyl-2-furylketone 8745

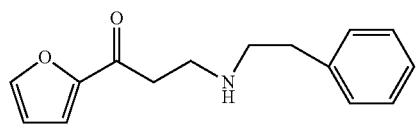 [SMILES: O=C(CCNCCc1ccccc1)c1ccco1]

NMR (CDCl$_3$) 2.48 (m, 2H), 2.74 (m, 4H), 3.45 (m, 2H), 6.53 (1H), 7.21 (m, 5H), 7.58 (s, 1H)

TG 105 (3 µmol) 90.5 (30 µmol)

SOCE 20 (30 µmol) 40 (100 µmol)

IICR 30 (10 µmol) 0 (30 µmol) 10 (100 µmol)

Example 301

2-(N-ethylbenzyl)aminoethyl-5-bromo-2-thienylketone 8779

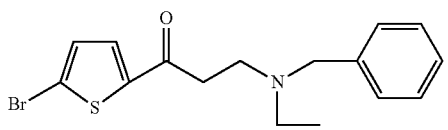

NMR (CDCl$_3$) 1.0 (m, 3H), 2.64 (m, 2H), 2.9 (m, 2H), 3.6 (m, 2H), 3.7 (m, 2H), 7.0-7.4 (m, 7H)

TG 74 (0.3 µmol) 33 (1 µmol) 2 (3 µmol) 3.1 (10 µmol) 0.8 (30 µmol)

SOCE 20 (10 µmol) 30 (30 µmol) 40 (100 µmol)

IICR 70 (10 µmol) 70 (30 µmol) 90 (100 µmol)

Example 302

2-(N-t-butylbenzyl)aminoethyl-4-cyanophenylketone 8789

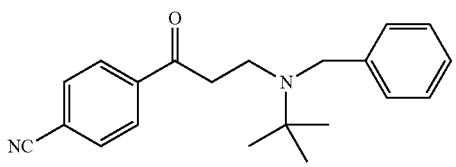 [SMILES: CC(C)(C)N(CCC(=O)c1ccc(C#N)cc1)Cc1ccccc1]

NMR (CDCl$_3$) 1.25 (d, 9H), 2.64 (t, 2H), 2.97 (t, 2H), 3.73 (m, 2H), 6.9-7.4 (m, 9H)

TG 12.2 (3 µmol) 5.5 (10 µmol) 6.4 (30 µmol)

SOCE 0 (10 µmol) 0 (30 µmol) 20 (100 µmol)

IICR 60 (10 µmol) 90 (30 µmol) 90 (100 µmol)

Example 303

4-tolyl(N-benzyl-N-t-butyl)aminoethylketone 8793

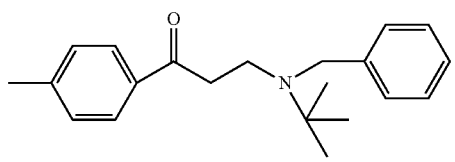 [SMILES: Cc1ccc(C(=O)CCN(Cc2ccccc2)C(C)(C)C)cc1]

NMR (CDCl$_3$) 1.25 (d, 9H), 2.60 (t, 2H), 2.97 (t, 2H), 3.85 (m, 2H), 7.2-7.9 (m, 9H)

TG 45 (3 µmol) 5 (10 µmol) 0.6 (30 µmol)

SOCE 0 (10 µmol) 0 (30 µmol) 0 (100 µmol)

IICR 20 (10 µmol) 20 (30 µmol) 40 (100 µmol)

Example 304

4-cyanophenyl(N-benzyl-N-t-butyl)aminoethylketone 8794

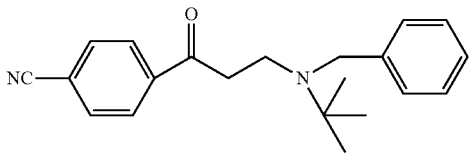 [SMILES: CC(C)(C)N(CCC(=O)c1ccc(C#N)cc1)Cc1ccccc1]

NMR (CDCl$_3$) 1.1 (m, 9H), 2.64 (t, 2H), 2.97 (m, 2H), 3.73 (m, 2H), 6.9-7.4 (m, 9H)

TG 11.4 (3 µmol) 2.1 (10 µmol) 4 (30 µmol)

SOCE 0 (10 µmol) 0 (30 µmol) 10 (100 µmol)

IICR 90 (10 µmol) 100 (30 µmol) 20 (100 µmol)

Example 305

2-(N-t-butyl-N-benzyl)aminoethyl-4-chlorophenylketone 8799

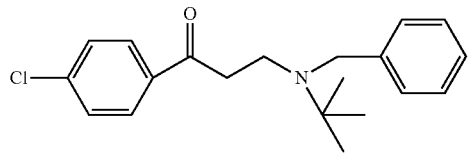 [SMILES: CC(C)(C)N(CCC(=O)c1ccc(Cl)cc1)Cc1ccccc1]

NMR (CDCl$_3$) 1.25 (d, 9H), 2.62 (t, 2H), 2.90 (t, 2H), 3.73 (m, 2H), 6.9-7.4 (m, 9H)

TG 5 (3 μmol) 0 (10 μmol) −3 (30 μmol)

SOCE 20 (10 μmol) 20 (30 μmol) 60 (100 μmol)

IICR 60 (10 μmol) 70 (30 μmol) 50 (100 μmol)

Example 306

2-(N-hydroxyethyl)aminoethyl-5-methyl-2-thienylketone 8801

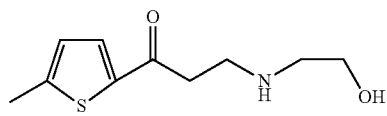

NMR (CDCl$_3$) 2.42 (m, 2H), 2.465 (m, 2H), 3.48 (m, 3H), 3.67 (m, 2H), 6.94 (s, 1H), 7.4 (s, 1H)

TG 100 (3 μmol) 96 (10 μmol) 84 (30 μmol)

SOCE 10 (10 μmol) 20 (30 μmol) 30 (100 μmol)

IICR 50 (10 μmol) 20 (30 μmol) 30 (100 μmol)

Example 307

2-(N-hydroxyethyl)aminoethyl-5-bromo-2-thienylketone 8802

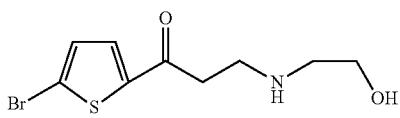

NMR (CDCl$_3$) 2.51 (m, 2H), 2.65 (m, 2H), 3.48 (m, 2H), 3.67 (m, 2H), 7.1 (s, 1H), 7.4 (s, 1H)

TG 93 (3 μmol) 76 (10 μmol) 40 (30 μmol)

SOCE 0 (10 μmol) 10 (30 μmol) 10 (100 μmol)

IICR 30 (10 μmol) 20 (30 μmol) 30 (100 μmol)

Example 308

2-(N-benzylisopropyl)aminoethyl-4-cyanophenylketone 8803

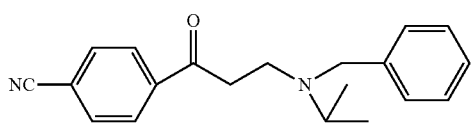 [SMILES: CC(C)N(CCC(=O)c1ccc(C#N)cc1)Cc1ccccc1]

NMR (CDCl$_3$) 0.48 (m, 6H), 2.68 (m, 2H), 2.65 (m, 2H), 3.47 (m, 2H), 7.0-8.0 (m, 9H)

TG 8.9 (3 μmol) 2.1 (10 μmol) 3.8 (30 μmol)

SOCE 0 (10 μmol) 0 (30 μmol) 10 (100 μmol)

IICR 90 (10 μmol) 100 (30 μmol) 95 (100 μmol)

Example 309

2-(N-hydroxylethylisopropyl)aminoethyl-4-cyanophenylketone 8804

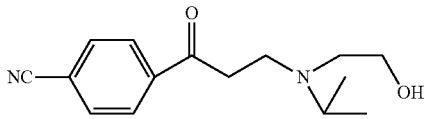 [SMILES: CC(C)N(CCO)CCC(=O)c1ccc(C#N)cc1]

NMR (CDCl$_3$) 1.09 (m, 6H), 1.85 (m, 2H), 2.65 (m, 2H), 3.45 (m, 2H), 7.80-8.2 (m, 4H)

TG 60 (3 μmol) 2.8 (10 μmol) 6 (30 μmol)

SOCE 0 (10 μmol) 0 (30 μmol) 10 (100 μmol)

IICR 0 (10 μmol) 0 (30 μmol) 20 (100 μmol)

Example 310

2-(N-benzylisopropyl)aminoethyl-4-chloro-phenylketone 8805

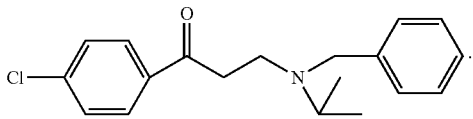 [SMILES: CC(C)N(CCC(=O)c1ccc(Cl)cc1)Cc1ccccc1]

NMR (CDCl$_3$) 1.06 (m, 6H), 2.61 (m, 2H), 2.93 (m, 2H), 3.55 (m, 2H), 7.1-8.0 (m, 9H).

TG 19 (3 μmol) 3.6 (10 μmol) 1.6 (30 μmol)

SOCE 0 (10 μmol) 0 (30 μmol) 10 (100 μmol)

IICR 80 (10 μmol) 80 (30 μmol) 70 (100 μmol)

Example 311

2-(N-hydroxyethylisopropyl)aminoethyl-4-chloro-phenylketone 8806

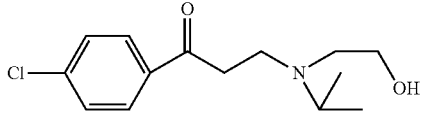

NMR (CDCl$_3$) 1.03 (m, 6H), 2.59 (m, 2H), 2.91 (m, 2H), 3.58 (m, 2H), 3.71 (m, 2H), 7.0-7.4 (m, 6H)

TG 31 (3 µmol) 5.6 (10 µmol) 2 (30 µmol)
SOCE 0 (10 µmol) 0 (30 µmol) 10 (100 µmol)
IICR 50 (10 µmol) 30 (30 µmol) 50 (100 µmol)

Example 312

2-(N-hydroxyethylisopropyl)aminoethylphenylketone 8807

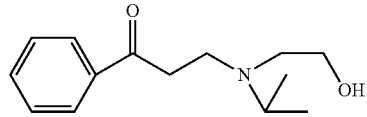

NMR (CDCl$_3$) 2.24 (m, 3H), 2.48 (m, 3H), 2.85 (m, 2H), 3.55 (m, 2H), 6.1 (s, 1H), 7.0-7.4 (m, 6H)

TG 87 (3 µmol) 49 (10 µmol) 12 (30 µmol)
SOCE 0 (10 µmol) 0 (30 µmol) 10 (100 µmol)
IICR 20 (10 µmol) 20 (30 µmol) 80 (100 µmol)

Example 313

2-(N-benzylethyl)aminoethyl-4-fluoro-phenylketone 8808

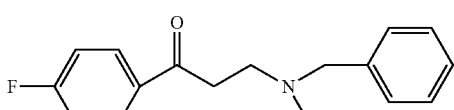

NMR (CDCl$_3$) 2.24 (m, 3H), 2.48 (m, 3H), 2.85 (m, 2H), 3.55 (m, 2H), 6.1 (s, 1H), 7.0-7.4 (m, 6H)

TG 87 (3 µmol) 63 (10 µmol) 12 (30 µmol)
SOCE 0 (10 µmol) 0 (30 µmol) 30 (100 µmol)
IICR 20 (10 µmol) 20 (30 µmol) 30 (100 µmol)

Example 314

2-(N-benzyl-t-butyl)aminoethyl-3-methyl-2-thienylketone 8816

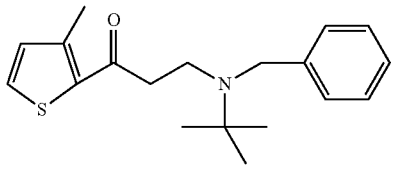 [SMILES: Cc1ccsc1C(=O)CCN(Cc1ccccc1)C(C)(C)C]

NMR (CDCl$_3$) 1.24 (m, 9H), 2.20 (m, 2H), 2.70 (m, 2H), 3.00 (m, 2H), 3.75 (m, 2H), 7.0-7.4 (m, 7H)

TG 11 (3 µmol) 0.4 (10 µmol) −4.3 (30 µmol)
SOCE 0 (10 µmol) 10 (30 µmol) 20 (100 µmol)
IICR 70 (10 µmol) 70 (30 µmol) 100 (100 µmol)

Example 315

2-(N-benzyl-t-butyl)aminoethyl-4-methyl-2-thienylketone 8817

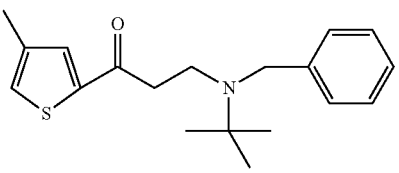 [SMILES: Cc1csc(C(=O)CCN(Cc2ccccc2)C(C)(C)C)c1]

NMR (CDCl$_3$) 1.17 (m, 9H), 2.15 (s, 3H), 2.25 (m, 2H), 2.7 (m, 2H), 3.55 (m, 2H), 6.1 (s, 1H), 6.8-7.4 (m, 7H)

TG 3.4 (3 µmol) −3.9 (10 µmol) −1.5 (30 µmol)
SOCE 0 (10 µmol) 0 (30 µmol) 30 (100 µmol)
IICR 80 (10 µmol) 90 (30 µmol) 100 (100 µmol)

Example 316

2-(N-benzyl-t-butyl)aminoethyl-5-methyl-2-thienylketone 8818

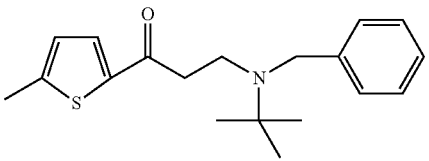 [SMILES: Cc1ccc(C(=O)CCN(Cc2ccccc2)C(C)(C)C)s1]

NMR (CDCl$_3$) 1.17 (m, 9H), 2.48 (m, 3H), 2.6 (m, 2H), 3.0 (m, 2H), 3.7 (m, 2H), 6.1 (s, 1H), 7.0-7.4 (m, 6H)

TG 2.1 (3 µmol) −5.7 (10 µmol) −4.9 (30 µmol)
SOCE 0 (10 µmol) 10 (30 µmol) 20 (100 µmol)
IICR 70 (10 µmol) 80 (30 µmol) 100 (100 µmol)

Example 317

2-(N-benzyl-t-butyl)aminoethyl-5,6-ethylenedioxy-2-phenylketone 8820

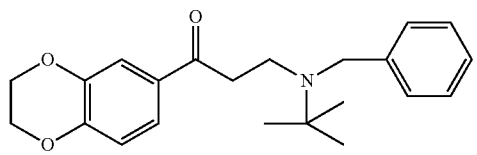 [SMILES: CC(C)(C)N(CCC(=O)c1ccc2c(c1)OCCO2)Cc1ccccc1]

NMR (CDCl$_3$) 1.17 (m, 9H), 2.75 (m, 2H), 2.95 (m, 2H), 3.85 (m, 2H), 7.0-7.6 (m, 8H)
TG 52 (3 μmol) 1.2 (10 μmol) −11.2 (30 μmol)
SOCE 10 (10 μmol) 10 (30 μmol) 30 (100 μmol)
IICR 90 (10 μmol) 95 (30 μmol) 100 (100 μmol)

Example 318

2-(N-benzylisopropyl)aminoethyl-5-methyl-2-thienylketone 8822

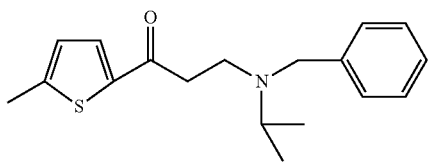 [SMILES: Cc1ccc(C(=O)CCN(Cc2ccccc2)C(C)C)s1]

NMR (CDCl$_3$) 0.9-1.5 (m, 6H), 2.5 (m, 3H), 2.75 (m, 2H), 3.55 (m, 2H), 7.0-7.4 (m, 7H)
TG 17.1 (3 μmol) −12 (10 μmol) 8.8 (30 μmol)
SOCE 10 (10 μmol) 20 (30 μmol) 40 (100 μmol)
IICR 10 (10 μmol) 60 (30 μmol) 80 (100 μmol)

Example 319

2-(N-benzylethyl)aminoethyl-5-methyl-2-thienylketone 8823

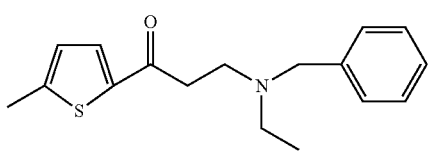 [SMILES: CCN(CCC(=O)c1ccc(C)s1)Cc1ccccc1]

NMR (CDCl$_3$) 0.5 (m, 3H), 1.8-2.2 (m, 4H), 3.2 (m, 2H), 2.85 (m, 2H), 3.55 (m, 2H), 6.0-7.3. (m, 7H)
TG 70 (3 μmol) 28 (10 μmol) −2.9 (30 μmol)
SOCE 0 (10 μmol) 10 (30 μmol) 20 (100 μmol)
IICR 20 (10 μmol) 10 (30 μmol) 70 (100 μmol)

Example 320

2-(N,N-bis-(2-hydroxyethyl)aminoethyl-5-iodo-2-thienylketone 8948

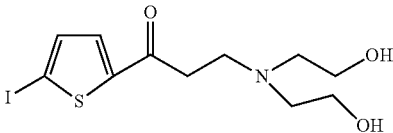 [SMILES: O=C(CCN(CCO)CCO)c1ccc(I)s1]

NMR (CDCl$_3$) 2.53 (m, 3H), 2.73 (m, 2H), 3.02 (m, 2H), 3.66 (m, 2H), 3.75 (m, 2H), 7.32 (m, 2H)
TG 40 (3 μmol) 12 (10 μmol) 5.9 (30 μmol)
SOCE 20 (10 μmol) 40 (30 μmol) 50 (100 μmol)
IICR 0 (10 μmol) 0 (30 μmol) 70 (100 μmol)

Example 321

2-(N-benzylisopropyl)aminoethyl-4-methyl-2-thienylketone 8828

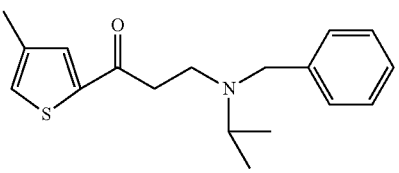 [SMILES: Cc1csc(C(=O)CCN(Cc2ccccc2)C(C)C)c1]

NMR (CDCl$_3$) 0.9-1.1 (m, 6H), 2.48 (m, 3H), 2.55 (m, 2H), 3.2 (m, 2H) 3.55 (m, 2H), 7.0-7.4 (m, 7H)
TG 67 (3 μmol) 27 (10 μmol) −0.4 (30 μmol)
SOCE 0 (10 μmol) 0 (30 μmol) 0 (100 μmol)
IICR 20 (10 μmol) 70 (30 μmol) 100 (100 μmol)

Example 322

2-(N-dibenzyl)aminoethyl-4-methyl-2-thienylketone 8829

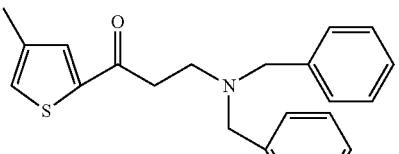

NMR (CDCl$_3$) 2.3 (m, 2H), 2.40 (m, 3H), 2.85 (m, 2H), 3.55 (m, 2H), 3.8 (m, 4H), 7.0-7.4 (m, 12H).
TG 92 (3 μmol) 76 (10 μmol) 25 (30 μmol)
SOCE 0 (10 μmol) 10 (30 μmol) 20 (100 μmol)
IICR 10 (10 μmol) 20 (30 μmol) 30 (100 μmol)

Example 323

2-(N-benzylhydroxyethyl)aminoethyl-4-methyl-2-thienylketone 8830

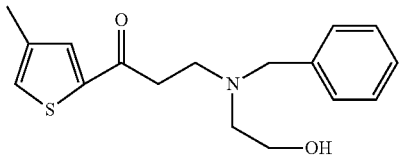 [SMILES: Cc1csc(C(=O)CCN(CCO)Cc2ccccc2)c1]

NMR (CDCl$_3$) 2.29 (m, 2H), 2.48 (s, 3H), 2.85 (m, 2H), 3.0 (m, 2H), 3.8 (m, 2H), 7.0-7.4 (m, 7H)
TG 90 (3 µmol) 88 (10 µmol) 54 (30 µmol)
SOCE 0 (10 µmol) 0 (30 µmol) 30 (100 µmol)
IICR 30 (10 µmol) 50 (30 µmol) 30 (100 µmol)

Example 324

2-(N-benzyl-t-butyl)aminoethyl-4-bromophenylketone 8831

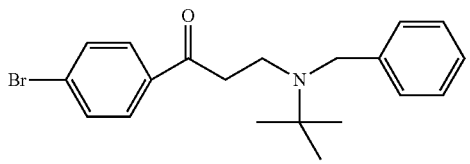 [SMILES: CC(C)(C)N(CCC(=O)c1ccc(Br)cc1)Cc1ccccc1]

NMR (CDCl$_3$) 1.17 (m, 9H), 2.75 (m, 2H), 2.95 (m, 2H), 3.8 (m, 2H), 7.0-7.4 (m, 9H)
TG −6 (3 µmol) −12.2 (10 µmol) −5.7 (30 µmol)
SOCE 20 (10 µmol) 20 (30 µmol) 20 (100 µmol)
IICR 50 (10 µmol) 40 (30 µmol) 40 (100 µmol)

Example 325

2-(N-dibenzyl)aminoethyl-5-bromo-2-thienylketone 8832

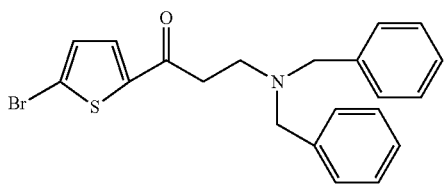 [SMILES: O=C(CCN(Cc1ccccc1)Cc1ccccc1)c1ccc(Br)s1]

NMR (CDCl$_3$) 2.5 (m, 2H), 2.9 (m, 2H), 3.55 (m, 4H), 7.0-7.4 (m, 12H)
TG 43 (3 µmol) 11 (10 µmol) −4 (30 µmol)
SOCE 0 (10 µmol) 20 (30 µmol) 40 (100 µmol)
IICR 20 (10 µmol) 20 (30 µmol) 50 (100 µmol)

Example 326

2-(N-benzylmethyl)aminoethyl-5-bromo-2-thienylketone 8833

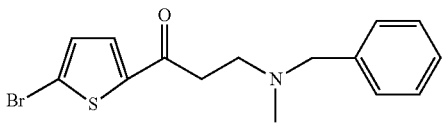 [SMILES: CN(CCC(=O)c1ccc(Br)s1)Cc1ccccc1]

NMR (CDCl$_3$) 2.24 (m, 2H), 2.48 (m, 2H), 2.85 (m, 2H), 3.55 (m, 3H), 7.0-7.4 (m, 7H)
TG 23 (3 µmol) 4.2 (10 µmol) −11.7 (30 µmol)
SOCE 10 (10 µmol) 30 (30 µmol) 60 (100 µmol)
IICR 40 (10 µmol) 10 (30 µmol) 40 (100 µmol)

Example 327

2-(N-benzylhydroxyethyl)aminoethyl-5-bromo-2-thienylketone 8834

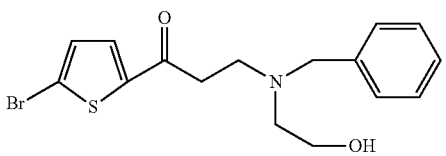 [SMILES: O=C(CCN(CCO)Cc1ccccc1)c1ccc(Br)s1]

NMR (CDCl$_3$) 2.8 (m, 2H), 3.0 (m, 2H), 3.7 (m, 2H), 3.55 (m, 2H), 3.8 (m, 2H) 7.0-7.4 (m, 7H)
TG 31 (3 µmol) 0.7 (10 µmol) 2.8 (30 µmol)
SOCE 20 (10 µmol) 20 (30 µmol) 30 (100 µmol)
IICR 70 (10 µmol) 10 (30 µmol) 40 (100 µmol)

Example 328

2-(N-hydroxyethylmethyl)aminoethyl-5-bromo-2-thienylketone 8835

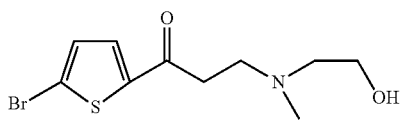

NMR (CDCl$_3$) 2.41 (m, 2H), 2.48 (m, 3H), 2.85 (m, 2H), 3.55 (m, 2H), 3.8 (m, 2H), 7.1 (s, 1H) 7.4 (s, 1H)
TG 57 (3 µmol) 21.1 (10 µmol) 2.1 (30 µmol)
SOCE 10 (10 µmol) 10 (30 µmol) 0 (100 µmol)
IICR 0 (10 µmol) 10 (30 µmol) 80 (100 µmol)

Example 329

2-(N-hydroxyethylisopropyl)aminoethyl-5-bromo-2-thienylketone 8836

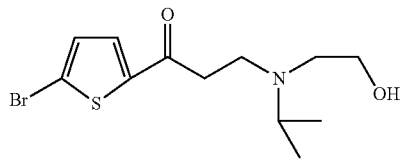 [SMILES: CC(C)N(CCO)CCC(=O)c1ccc(Br)s1]

NMR (CDCl₃) 1.1 (m, 6H), 2.44 (m, 2H), 2.58 (m, 2H), 2.85 (m, 2H), 3.9 (m, 2H), 6.1 (s, 1H), 7.4 (s, 1H)
TG 35 (3 μmol) 9.1 (10 μmol) −13.7 (30 μmol)
SOCE 20 (10 μmol) 20 (30 μmol) 10 (100 μmol)
IICR 0 (10 μmol) 10 (30 μmol) 50 (100 μmol)

Example 330

2-(N-bishydroxyethyl)aminoethyl-5-bromo-2-thienylketone 8837

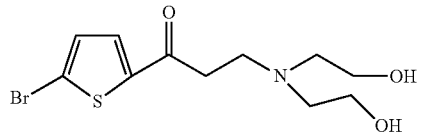 [SMILES: O=C(CCN(CCO)CCO)c1ccc(Br)s1]

NMR (CDCl₃) 2.54 (m, 2H), 2.75 (m, 2H), 3.04 (m, 2H), 3.65-3.8 (m, 6H), 7.1 (s, 1H), 7.4 (s, 1H)
TG 30 (3 μmol) 4.6 (10 μmol) −3.3 (30 μmol)
SOCE 10 (10 μmol) 10 (30 μmol) 20 (100 μmol)
IICR 30 (10 μmol) 40 (30 μmol) 50 (100 μmol)

Example 331

2-(N-2-hydroxyethylethyl)aminoethyl-5-bromo-2-thienylketone 8838

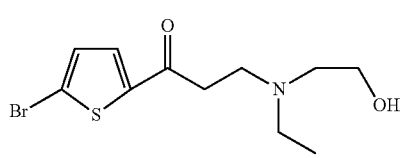 [SMILES: CCN(CCO)CCC(=O)c1ccc(Br)s1]

NMR (CDCl₃), 1.05 (m, 3H), 2.5 (m, 4H), 2.9 (m, 2H), 3.65 (m, 4H), 7.1 (s, 1H), 7.4 (s, 1H)
TG 89 (3 μmol) 64 (10 μmol) 10 (30 μmol)
SOCE 0 (10 μmol) 10 (30 μmol) 20 (100 μmol)
IICR 0 (10 μmol) 10 (30 μmol) 70 (100 μmol)

Example 332

2-(N-hydroxyethyl-t-butyl)aminoethyl-5-bromo-2-thienylketone 8839

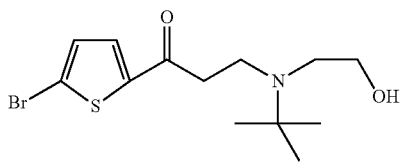

NMR (CDCl₃) 1.16 (m, 9H), 2.48 (m, 2H), 2.85 (m, 2H), 3.55 (m, 4H), 7.1 (s, 1H), 7.4 (s, 1H)
TG 33 (3 μmol) 4.6 (10 μmol) −6.6 (30 μmol)
SOCE 0 (10 μmol) 10 (30 μmol) 20 (100 μmol)
IICR 0 (10 μmol) 10 (30 μmol) 50 (100 μmol)

Example 333

2-(2-hydroxymethylpyrrolidinyl)aminoethyl-5-bromo-2-thienylketone 8842

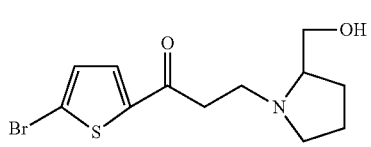

NMR (CDCl₃) 1.73 (m, 4H), 2.48 (m, 2H), 2.60 (m, 2H), 3.70 (m, 2H), 7.1 (s, 1H), 7.4 (s, 1H)
TG 62 (3 μmol) 37 (10 μmol) 2.3 (30 μmol)
SOCE 20 (10 μmol) 30 (30 μmol) 20 (100 μmol)
IICR 0 (10 μmol) 30 (30 μmol) 50 (100 μmol)

Example 334

2-(N-2-hydroxyethyl-N-2-aminoethyl)aminoethyl-5-bromo-2-thienylketone 8843

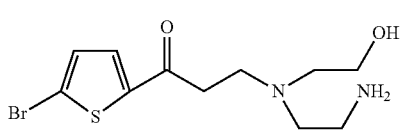 [SMILES: NCCN(CCO)CCC(=O)c1ccc(Br)s1]

NMR (CDCl₃) 2.5 (m, 4H), 2.58 (m, 2H), 2.65 (m, 2H), 3.55-3.7 (m, 4H), 7.1 (s, 1H), 7.4 (s, 1H)
TG 57 (3 μmol) 26 (10 μmol) 9.0 (30 μmol)
SOCE 30 (10 μmol) 30 (30 μmol) 40 (100 μmol)
IICR 20 (10 μmol) 0 (30 μmol) 60 (100 μmol)

Example 335

2-(N-mercaptoethyl)aminoethyl-5-bromo-2-thienylketone 8844

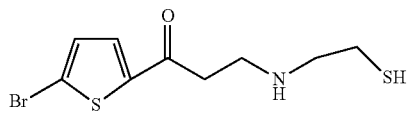 [SMILES: O=C(CCNCCS)c1ccc(Br)s1]

NMR (CDCl₃) 2.1 (m, 2H), 2.48 (m, 4H), 2.85 (m, 2H), 3.55 (m, 2H), 7.1 (s, 1H), 7.4 (s, 1H)

TG 93 (3 µmol) 56 (10 µmol) 12 (30 µmol)
SOCE 20 (10 µmol) 30 (30 µmol) 50 (100 µmol)
IICR 10 (10 µmol) 50 (30 µmol) 70 (100 µmol)

Example 336

2-(N-hydroxyphenyl)aminoethyl-5-bromo-2-thienylketone 8846

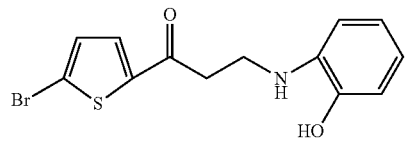 [SMILES: O=C(CCNc1ccccc1O)c1ccc(Br)s1]

NMR (CDCl₃) 1.59 (m, 2H), 2.48 (m, 2H), 2.71 (m, 1H), 7.1-7.4 (m, 6H)

TG 102 (3 µmol) 101 (10 µmol) 100 (30 µmol)
SOCE 10 (10 µmol) 0 (30 µmol) 0 (100 µmol)
IICR 20 (10 µmol) 10 (30 µmol) 60 (100 µmol)

Example 337

2-(N-phenyl-N-n-butyl)aminoethyl-5-bromo-2-thienylketone 8847

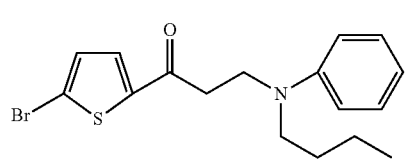 [SMILES: CCCCN(CCC(=O)c1ccc(Br)s1)c1ccccc1]

NMR (CDCl₃), 0.95 (m, 3H), 1.38-1.5 (m, 4H), 245 (m, 2H), 3.33 (m, 2H), 6.5-7.4 (m, 7H)

TG 112 (3 µmol) 84.6 (10 µmol) 54.7 (30 µmol)
SOCE 20 (10 µmol) 30 (30 µmol) 40 (100 µmol)
IICR 50 (10 µmol) 20 (30 µmol) 0 (100 µmol)

Example 338

2-(N,N-di-n-butyl)aminoethyl-5-bromo-2-thienylketone 8848

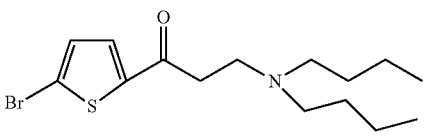 [SMILES: CCCCN(CCCC)CCC(=O)c1ccc(Br)s1]

NMR (CDCl₃), 0.7 (m, 6H), 1.2-1.4 (m, 8H), 2.35 (m, 2H), 2.55 (m, 2H), 2.7 (m, 2H), 7.1 (s, 1H), 7.4 (s, 1H).

TG 22 (3 µmol) 4.4 (10 µmol) 7.0 (30 µmol)
SOCE 0 (10 µmol) 0 (30 µmol) 24 (100 µmol)
IICR 50 (10 µmol) 50 (30 µmol) 60 (100 µmol)

Example 339

2-(N,N-di-sec-butyl)aminoethyl-5-bromo-2-thienylketone 8849

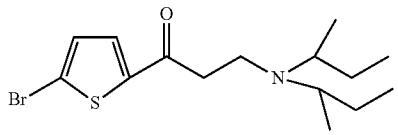 [SMILES: CCC(C)N(CCC(=O)c1ccc(Br)s1)C(C)CC]

NMR (CDCl₃), 0.86-1.0 (m, 16H), 2.48 (m, 2H), 2.85 (m, 2H), 71 (s, 1H), 7.4 (s, 1H)

TG 2.3 (3 µmol) −4.3 (10 µmol −10 (30 µmol)
SOCE 0 (10 µmol) 8 (30 µmol) 61 (100 µmol)
IICR 50 (10 µmol) 80 (30 µmol) 60 (100 µmol)

Example 340

N,N-bis(2-(5-bromo-2-thiophenoyl)ethyl)cystamine 8823

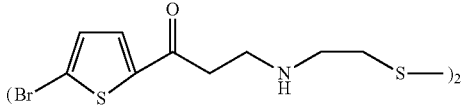

2-acetyl-5-bromothiophene (230 mg), cystamine (122 mg), paraformaldehyde (64 mg), and dioxane (0.4 mL) were heated at 110° C. for 30 minutes.

NMR (CDCl₃) 1.15 (m, 2H), 2.52 (m, 4H), 3.13 (m, 4H), 3.40 (m, 4H), 3.72 (m, 4H), 7.2 (s, 2H), 7.4 (s, 2H)

TG 0.8 (3 µmol) 2.5 (10 µmol) 4.3 (30 µmol)
SOCE 0 (10 µmol) 18 (30 µmol) 65 (100 µmol)
IICR 0 (10 µmol) 40 (30 µmol) 60 (100 µmol)

Example 341

N-2-furoyl-piperadinoethyl-5-bromo-2-thienylketone 8851

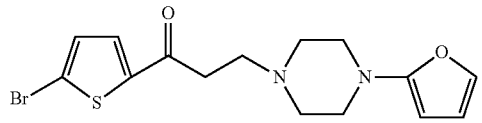 [SMILES: O=C(CCN1CCN(c2ccco2)CC1)c1ccc(Br)s1]

NMR (CDCl$_3$) 2.54-2.9 (m, 4H), 3.7-3.79 (m, 8H), 6.48 (s, 1H), 6.99 (s, 1H), 7.1 (s, 1H), 7.46 (m, 2H)

TG 101 (3 µmol) 96 (10 µmol) 55 (30 µmol)

SOCE 0 (10 µmol) 0 (30 µmol) 21 (100 µmol)

IICR 0 (10 µmol) 10 (30 µmol) 30 (100 µmol)

Example 342

2-(N-1-phenyl-2-hydroxyethyl)aminoethyl-5-bromo-2-thienylketone 8852

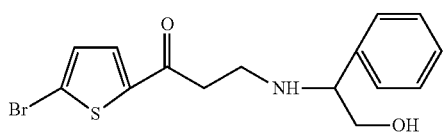 [SMILES: O=C(CCNC(CO)c1ccccc1)c1ccc(Br)s1]

NMR (CDCl$_3$) 3.61 (m, 2H), 3.7 (m, 2H), 3.9 (m, 2H), 4.2 (m, 2H), 7.0-7.4 (m, 7H)

TG 120 (3 µmol) 105 (10 µmol) 94 (30 µmol)

SOCE 0 (10 µmol) 0 (30 µmol) 34 (100 µmol)

IICR 0 (10 µmol) 20 (30 µmol) 40 (100 µmol)

Example 343

2-(N-2-hydroxy-3-aminopropyl)aminoethyl-5-bromo-2-thienylketone 8853

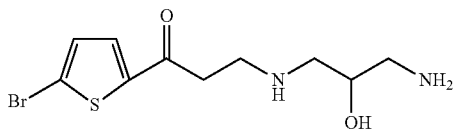 [SMILES: NCC(O)CNCCC(=O)c1ccc(Br)s1]

NMR (CDCl$_3$) 2.16 (m, 2H), 2.51 (m, 2H), 2.85 (m, 2H), 3.55 (m, 4H), 6.8-7.6 (m, 4H)

TG 37 (3 µmol) 20 (10 µmol) –4.3 (30 µmol)

SOCE 0 (10 µmol) 0 (30 µmol) 26 (100 µmol)

IICR 50 (10 µmol) 70 (30 µmol) 80 (100 µmol)

Example 344

2-(N-4-aminobutyl-N-3-aminopropyl)aminoethyl-5-bromo-2-thienylketone 8854

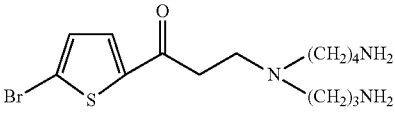

NMR (CDCl$_3$), 1.50 (m, 2H), 1.61 (m, 4H), 2.1-2.8 (m, 4H), 3.22-3.36 (m, 4H), 6.1 (s, 1H), 7.4 (s, 1H)

TG 82 (3 µmol) 48 (10 µmol) 30 (30 µmol)

SOCE 0 (10 µmol) 2 (30 µmol) 6 (100 µmol)

IICR 10 (10 µmol) 40 (30 µmol) 30 (100 µmol)

Example 345

2-(N-2-hydroxypyrrolidino)aminoethyl-5-bromo-2-thienylketone 8855

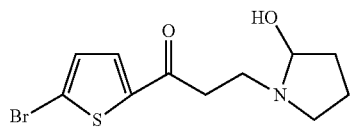 [SMILES: O=C(CCN1CCCC1O)c1ccc(Br)s1]

NMR (CDCl$_3$) 2.1-2.48 (m, 2H), 2.85 (m, 2H), 37 (m, 2H), 7.1 (s, 1H), 7.4 (s, 1H)

TG 75 (3 µmol) 44 (10 µmol) 12.9 (30 µmol)

SOCE 0 (10 µmol) 0 (30 µmol) 10 (100 µmol)

IICR 0 (10 µmol) 20 (30 µmol) 70 (100 µmol)

Example 346

2-(N-hydroxypropyl-N-5-bromo-thienoylethyl)aminoethyl-5-bromo-2-thienylketone 8856

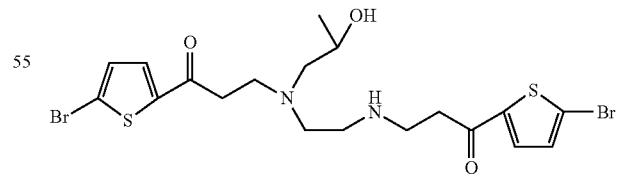

NMR (CDCl$_3$) 1.16 (m, 3H), 2.8 (m, 2H), 2.8-4.0 (m, 12H), 7.1-7.4 (m, 4H)

TG 51 (3 µmol) 24 (10 µmol) 10 (30 µmol)

SOCE 0 (10 µmol) 1 (30 µmol) 35 (100 µmol)

IICR 10 (10 µmol) 30 (30 µmol) 90 (100 µmol)

Example 347

2-(N-2-mercaptophenyl)aminoethyl-5-bromo-2-thienylketone 8857

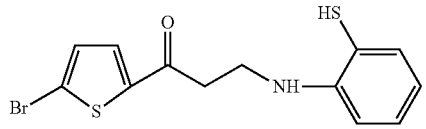

NMR (CDCl$_3$) 1.59 (m, 1H), 2.51 (m, 2H), 2.71 (m, 2H), 3.55 (m, 2H), 7.1-7.4 (m, 6H)
TG 95 (3 µmol) 102 (10 µmol) 86 (30 µmol)
SOCE 0 (10 µmol) 0 (30 µmol) 0 (100 µmol)
IICR 0 (10 µmol) 20 (30 µmol) 50 (100 µmol)

Example 348

2-piperidinoethyl-5-bromo-2-thienylketone 8858

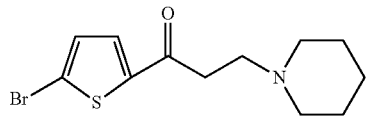 [SMILES: O=C(CCN1CCCCC1)c1ccc(Br)s1]

NMR (CDCl$_3$) 1.43 (m, 6H), 2.38 (m, 6H), 3.62 (m, 2H), 7.1 (m, 1H), 7.4 (s, 1H)
TG 82 (3 µmol) 63 (10 µmol) 26 (30 µmol)
SOCE 0 (10 µmol) 0 (30 µmol) 16 (100 µmol)
IICR 20 (10 µmol) 0 (30 µmol) 20 (100 µmol)

Example 349

2-(2-hydroxy-2-phenylethyl)aminoethyl-5-bromo-2-thienylketone 8859

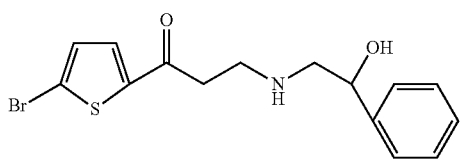 [SMILES: O=C(CCNCC(O)c1ccccc1)c1ccc(Br)s1]

NMR (CDCl$_3$) 2.51 (m, 2H), 2.86 (m, 2H), 3.65 (m, 2H), 7.1-7.4 (m, 7H)
TG 99 (3 µmol) 96 (10 µmol) 78 (30 µmol)
SOCE 46 (10 µmol) 0 (30 µmol) 0 (100 µmol)
IICR 20 (10 µmol) 0 (30 µmol) 50 (100 µmol)

Example 350

2-(N-hydroxymethylpiperidinoethyl-5-bromo-2-thienylketone 8860

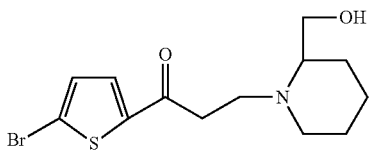 [SMILES: O=C(CCN1CCCCC1CO)c1ccc(Br)s1]

NMR (CDCl$_3$) 1.47 (m, 2H), 1.68 (m, 2H), 1.85 (m, 2H), 2.15 (m, 2H), 2.52 (m, 2H), 3.50 (m, 2H), 7.1-7.4 (m, 2H)
TG 46 (3 µmol) 17.4 (10 µmol) 6.6 (30 µmol)
SOCE 10 (10 µmol) 2 (30 µmol) 3 (100 µmol)
IICR 60 (10 µmol) 50 (30 µmol) 70 (100 µmol)

Example 351

2-phenethylaminoethyl-5-bromo-2-thienylketone 8861

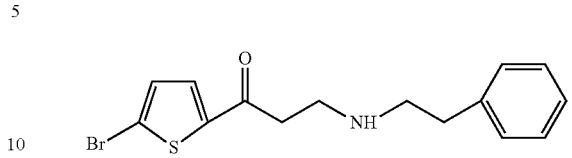

NMR (CDCl$_3$) 2.51 (m, 2H), 2.74 (m, 4H), 3.4 (m, 2H), 7.21-7.4 (m, 7H)
TG 92 (3 µmol) 73 (10 µmol) 26 (30 µmol)
SOCE 0 (10 µmol) 9 (30 µmol) 32 (100 µmol)
IICR 30 (10 µmol) 0 (30 µmol) 0 (100 µmol)

Example 352

2-(3-hydroxypropyl)aminoethyl-5-bromo-2-thienylketone 8862

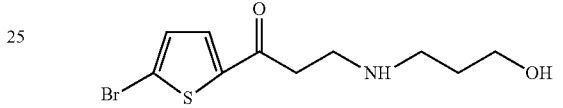

NMR (CDCl$_3$) 1.62 (m, 2H), 2.51 (m, 2H), 2.99 (m, 2H), 3.86 (m, 2H), 4.39 (m, 2H), 7.11 (s, 1H), 7.4 (s, 1H)
TG 110 (3 µmol) 107 (10 µmol) 98 (30 µmol)
SOCE 0 (10 µmol) 0 (30 µmol) 34 (100 µmol)
IICR 30 (10 µmol) 0 (30 µmol) 0 (100 µmol)

Example 353

2-(1-hydroxy-1-phenylmethyl)aminoethyl-5-bromo-2-thienylketone 8863

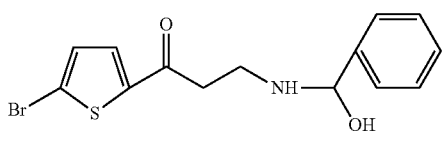 [SMILES: O=C(CCNC(O)c1ccccc1)c1ccc(Br)s1]

NMR (CDCl$_3$) 2.5 (m, 2H), 2.9 (m, 2H), 3.55 (m, 2H), 4.7 (m, 2H), 7.1-7.4 (m, 6H)
TG 109 (3 µmol) 107 (10 µmol) 96 (30 µmol)
SOCE 0 (10 µmol) 0 (30 µmol) 7 (100 µmol)
IICR 60 (10 µmol) 0 (30 µmol) 20 (100 µmol)

Example 354

2-(N-5-bromothionylethylaminoethyl-N-hydroxyethyl)aminoethyl-5-bromo-2-thienylketone 8864

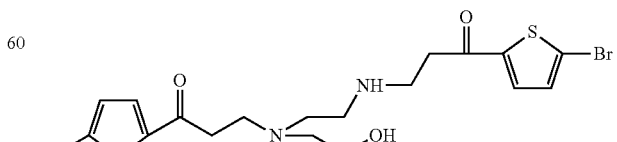

NMR (CDCl$_3$) 1.8 (m, 1H), 2.3 (m, 2H), 2.6 (m, 6H), 3.0 (m, 4H), 7.1-7.4 (m, 4H)

TG 66 (3 μmol) 32.6 (10 μmol) 13.6 (30 μmol)
SOCE 0 (10 μmol) 10 (30 μmol) 10 (100 μmol)
IICR 0 (10 μmol) 0 (30 μmol) 60 (100 μmol)

Example 355

2-(2-hydroxy-1,2-diphenyl-ethyl)aminoethyl-5-bromo-2-thienylketone 8865

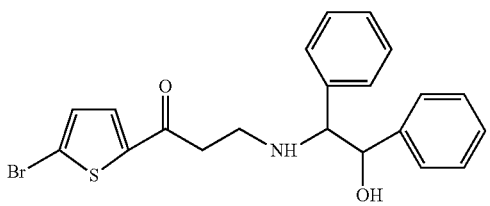 [SMILES: O=C(CCNC(c1ccccc1)C(O)c1ccccc1)c1ccc(Br)s1]

NMR (CDCl$_3$) 1.9 (m, 2H), 2.48 (m, 2H), 3.37 (m, 1H), 3.70 (m, 1H), 3.9 (m, 2H), 6.9-7.4 (m, 12H)
TG 109 (3 μmol) 99 (10 μmol) 79 (30 μmol)
SOCE 0 (10 μmol) 16 (30 μmol) 16 (100 μmol)
IICR 0 (10 μmol) 0 (30 μmol) 50 (100 μmol)

Example 356

N,N-bis(5-bromo-2-thienoylethyl)tetramethylenediamine 8866

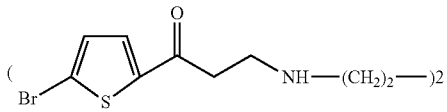

NMR (CDCl$_3$) 1.64 (m, 4H), 2.51 (m, 4H), 3.35 (m, 4H), 3.7 (m, 4H), 6.8-7.4 (m, 4H)
TG 93 (3 μmol) 22.6 (10 μmol) 3.6 (30 μmol)
SOCE 0 (10 μmol) 3 (30 μmol) 10 (100 μmol)
IICR 0 (10 μmol) 0 (30 μmol) 10 (100 μmol)

Example 357

2-(N-hydroxy-1-benzylethyl)aminoethyl-5-bromo-2-thienylketone 8867

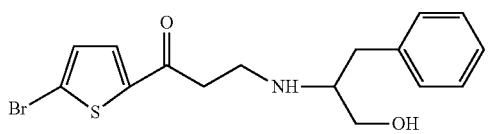 [SMILES: O=C(CCNC(CO)Cc1ccccc1)c1ccc(Br)s1]

NMR (CDCl$_3$) 2.51 (m, 2H), 2.476 (m, 2H), 3.24 (m, 2H), 3.71 (m, 2H), 4.34 (m, 2H), 6.5-7.4 (m, 7H)
TG 102 (3 μmol) 77 (10 μmol) 4 (30 μmol)
SOCE 0 (10 μmol) 9 (30 μmol) 47 (100 μmol)
IICR 0 (10 μmol) 0 (30 μmol) 70 (100 μmol)

Example 358

2-(N-hydroxyethyl)aminoethyl-5-bromo-2-thienylketone 8868

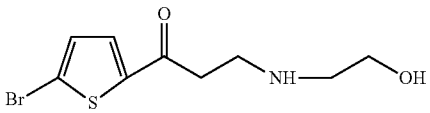 [SMILES: O=C(CCNCCO)c1ccc(Br)s1]

NMR (CDCl$_3$) 2.67 (m, 2H), 3.12 (m, 2H), 3.70 (m, 2H), 4.32 (m, 2H), 7.1 (s, 1H), 7.4 (s, 1H)
TG 95 (3 μmol) 72 (10 μmol) 31 (30 μmol)
SOCE 0 (10 μmol) 4 (30 μmol) 23 (100 μmol)
IICR 0 (10 μmol) 0 (30 μmol) 70 (100 μmol)

Example 359

2-(N-hydroxyethyl-N-phenyl)aminoethyl-5-bromo-2-thienylketone 8869

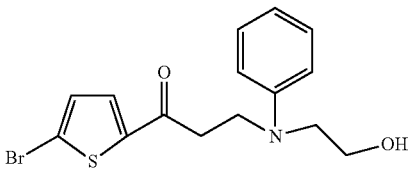 [SMILES: O=C(CCN(CCO)c1ccccc1)c1ccc(Br)s1]

NMR (CDCl$_3$), 2.51 (m, 2H), 3.42 (m, 2H), 4.17 (m, 2H), 4.57 (m, 2H), 6.1-7.7 (m, 7H)
TG 113 (3 μmol) 105 (10 μmol) 94 (30 μmol)
SOCE 0 (10 μmol) 24 (30 μmol) 57 (100 μmol)
IICR 0 (10 μmol) 0 (30 μmol) 70 (100 μmol)

Example 360

2-(N-2-hydroxypropyl)aminoethyl-5-bromo-2-thienylketone 8870

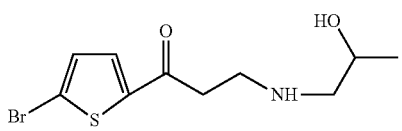

NMR (CDCl$_3$), 1.21 (m, 3H), 1.60 (m, 2H), 2.51 (m, 2H), 3.540 (m, 2H), 4.43 (m, 2H), 7.1 (s, 1H), 7.4 (s, 1H)
TG 99 (3 μmol) 76 (10 μmol) 46 (30 μmol)
SOCE 10 (10 μmol) 0 (30 μmol) 20 (100 μmol)
IICR 0 (10 μmol) 0 (30 μmol) 70 (100 μmol)

Example 361

2-(4-hydroxyethylpiperadino)ethyl-5-bromo-2-thienylketone 8871

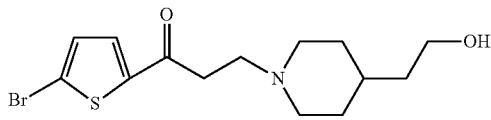 [SMILES: O=C(CCN1CCC(CCO)CC1)c1ccc(Br)s1]

NMR (CDCl$_3$), 1.35 (m, 2H), 1.65 (m, 4H), 2.50 (m, 2H), 3.50 (m, 2H), 3.66 (m, 2H), 4.03 (m, 2H), 4.33 (m, 2H), 7.1 (s, 1H), 7.4 (s, 1H)

TG 103 (3 μmol) 75 (10 μmol) 38 (30 μmol)
SOCE 22 (10 μmol) 2 (30 μmol) 19 (100 μmol)
IICR 22 (10 μmol) 0 (30 μmol) 19 (100 μmol)

Example 362

2-(N-hydroxymethyl-N-ethyl)aminoethyl-5-bromo-2-thienylketone 8872

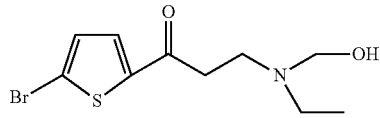

NMR (CDCl$_3$), 0.9 (m, 3H), 1.51 (m, 2H), 3.28 (m, 2H), 4.49 (m, 2H), 7.1 (s, 1H), 7.4 (s, 1H)

TG 109 (3 μmol) 96 (10 μmol) 72 (30 μmol)
SOCE 11 (10 μmol) 13 (30 μmol) 23 (100 μmol)
IICR 0 (10 μmol) 0 (30 μmol) 70 (100 μmol)

Example 363

2-(N-methylpiperadino)ethyl-5-bromo-2-thienylketone 8873

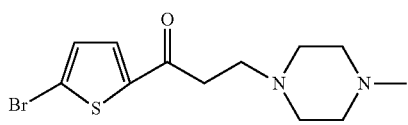 [SMILES: CN1CCN(CCC(=O)c2ccc(Br)s2)CC1]

NMR (CDCl$_3$), 2.29 (m, 2H), 2.3-2.7 (m, 10H), 7.1 (s, 1H), 7.4 (s, 1H)

TG 80 (3 μmol) 42 (10 μmol) 16 (30 μmol)
SOCE 0 (10 μmol) 0 (30 μmol) 14 (100 μmol)
IICR 0 (10 μmol) 0 (30 μmol) 70 (100 μmol)

Example 364

2-(4-imidazolylethyl)aminoethyl-5-bromo-2-thienylketone 8874

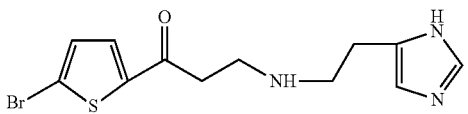 [SMILES: O=C(CCNCCc1cnc[nH]1)c1ccc(Br)s1]

NMR (CDCl$_3$), 1.56 (m, 2H), 2.51 (m, 2H), 7.1 (s, 1H), 7.26 (m, 2H), 7.4 (s, 1H),

TG 102 (3 μmol) 66 (10 μmol) 3.6 (30 μmol)
SOCE 24 (10 μmol) 49 (30 μmol) 70 (100 μmol)
IICR 0 (10 μmol) 0 (30 μmol) 40 (100 μmol)

Example 365

2-(N-1,1-bishydroxymethylpropyl)aminoethyl-5-bromo-2-thienylketone 8875

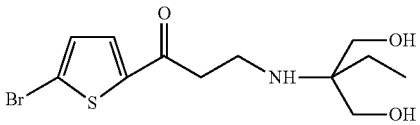 [SMILES: CCC(CO)(CO)NCCC(=O)c1ccc(Br)s1]

NMR (CDCl$_3$), 0.93 (m, 3H), 1.50 (m, 2H), 2.17 (m, 2H), 2.50 (m, 2H), 3.50 (m, 2H), 4.45 (m, 2H), 7.1 (s, 1H), 7.4 (s, 1H)

TG 55.9 (3 μmol) 22.6 (10 μmol) 3.6 (30 μmol)
SOCE 0 (10 μmol) 0 (30 μmol) 10 (100 μmol)
IICR 0 (10 μmol) 0 (30 μmol) 70 (100 μmol)

Example 366

N,N-bis(2-(5-chloro-2-thiophenoyl)ethyl)cystamine 8876

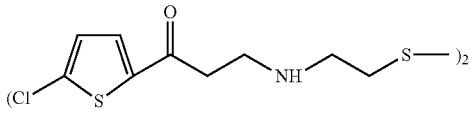

NMR (CDCl$_3$) 1.75 (m, 2H), 2.50 (m, 2H), 3.50-3.67 (m, 4H), 7.0 (s, 2H), 7.4 (s, 2H)

TG 5 (3 μmol) 6.3 (30 μmol)
SOCE 6 (10 μmol) 0 (30 μmol) 90 (100 μmol)
IICR 0 (10 μmol) 0 (30 μmol) 70 (100 μmol)

Example 367

N,N-bis(2-(4-bromo-benzoyl)ethyl)cystamine 8877

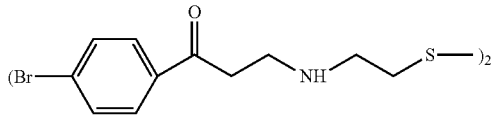

NMR (CDCl$_3$) 1.61 (m, 4H), 2.6 (m, 4H), 3.43 (m, 4H), 3.71 (m, 4H), 7.4-8.0 (m, 8H)
TG 18 (3 µmol) 9.1 (30 µmol)
SOCE 0 (10 µmol) 17 (30 µmol) 96 (100 µmol)
IICR 0 (10 µmol) 0 (30 µmol) 70 (100 µmol)

Example 368

N,N-bis(2-(benzoyl)ethyl)cystamine 8878

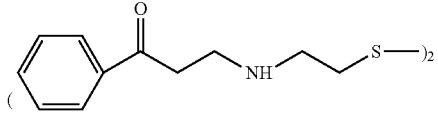

NMR (CDCl$_3$) 1.78 (m, 4H), 3.45 (m, 8H), 3.71 (m, 4H), 7.3-8.0 (m, 10H)
TG 63 (3 µmol) 10 (30 µmol)
SOCE 0 (10 µmol) 0 (30 µmol) 90 (100 µmol)
IICR 0 (10 µmol) 50 (30 µmol) 81 (100 µmol)

Example 369

N,N-bis(2-(2-thiophenoyl)ethyl)cystamine 8879

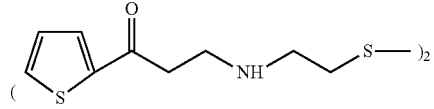

NMR (CDCl$_3$) 1.56 (m, 8H), 2.58 (m, 4H), 3.71 (m, 4H), 7.14-7.70 (m, 6H)
TG 95.1 (3 µmol) −64.9 (30 µmol)
SOCE 20 (10 µmol) 40 (30 µmol) 50 (100 µmol)
IICR 0 (10 µmol) 0 (30 µmol) 70 (100 µmol)

Example 370

N,N-bis(2-naphthoylethyl)cystamine 8881

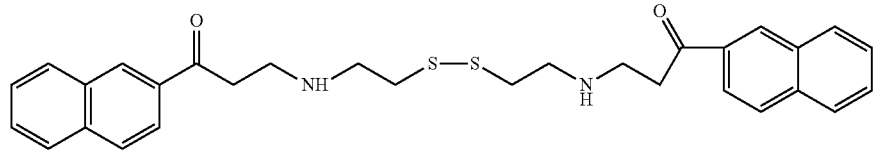 [SMILES: O=C(CCNCCSSCCNCCC(=O)c1ccc2ccccc2c1)c1ccc2ccccc2c1]

NMR (CDCl$_3$) 2.0 (m, 2H), 2.74 (m, 8H), 3.5-4.0 (m, 8H), 7.3-8.4 (m, 14H)
TG 36 (3 µmol) 1.6 (30 µmol)
SOCE 0 (10 µmol) 0 (30 µmol) 3 (100 µmol)
IICR 0 (10 µmol) 0 (30 µmol) 29 (100 µmol)

Example 371

N,N-bis(3-pyridinoylethyl)cystamine 8882

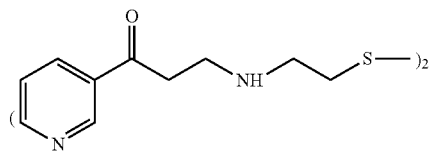

NMR (CDCl$_3$) 1.57 (m, 2H), 2.64 (m, 8H), 3.5 (m, 4H), 3.67 (m, 4H), 7.4-9.2 (m, 8H)
TG 24 (3 µmol) 3.3 (30 µmol)
SOCE 5 (10 µmol) 0 (30 µmol) 71 (100 µmol)
IICR 0 (10 µmol) 0 (30 µmol) 21 (100 µmol)

Example 372

N,N-bis(2-furoylethyl)cystamine 8883

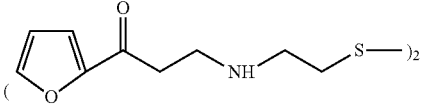

NMR (CDCl$_3$) 1.56 (m, 4H), 2.49 (m, 4H), 3.71 (m, 8H), 6.5 (m, 2H), 7.26 (m, 2H), 7.58 (m, 2H),
TG 13 (3 µmol) −1.5 (30 µmol)
SOCE 0 (10 µmol) 0 (30 µmol) 15 (100 µmol)
IICR 0 (10 µmol) 54 (30 µmol) 58 (100 µmol)

Example 373

2-(N-butyl-N-benzyl)aminoethyl-5-bromo-2-thienylketone 8884

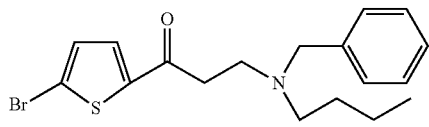 [SMILES: CCCCN(CCC(=O)c1ccc(Cl)s1)Cc1ccccc1]

NMR (CDCl$_3$) 0.84 (m, 3H), 1.82 (m, 4H), 2.51 (m, 4H), 2.7 (m, 2H), 3.53 (m, 2H), 7.0-7.8 (m, 2H)

TG 11 (3 µmol) 4.7 (30 µmol)

SOCE 100 (10 µmol) 28 (30 µmol) 65 (100 µmol)

IICR 0 (10 µmol) 36 (30 µmol) 0 (100 µmol)

Example 374

2-(N-butyl-N-benzyl)aminoethyl-5-chloro-2-thienylketone 8885

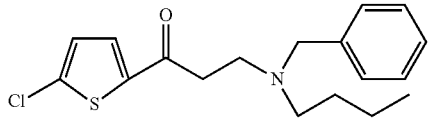

NMR (CDCl$_3$) 0.91.09 (m, 3H), 1.3-1.4 (m, 4H), 2.3 (m, 2H), 2.4 (m, 2H), 3.6 (m, 2H), 3.9 (m, 2H), 7.0-7.5 (m, 7H)

TG 12 (3 µmol) 0 (30 µmol)

SOCE 0 (10 µmol) 0 (30 µmol) 53 (100 µmol)

IICR 0 (10 µmol) 8 (30 µmol) 0 (100 µmol)

Example 375

2-(N-butyl-N-benzyl)aminoethyl-4-bromophenylketone 8886

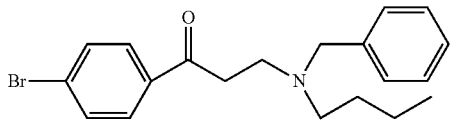 [SMILES: CCCCN(CCC(=O)c1ccc(Br)cc1)Cc1ccccc1]

NMR (CDCl$_3$) 0.8 (m, 3H), 1.3-1.5 (m, 4H), 2.3 (m, 2H), 2.6 (m, 2H), 3.0 (m, 2H), 3.6 (m, 2H), 7.0-7.8 (m, 9H)

TG 54 (3 µmol) 9.8 (30 µmol)

SOCE 4 (10 µmol) 0 (30 µmol) 40 (100 µmol)

IICR 0 (10 µmol) 33 (30 µmol) 0 (100 µmol)

Example 376

2-(N-butyl-N-benzyl)aminoethyl-4-pyridylketone 8887

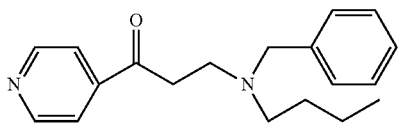 [SMILES: CCCCN(CCC(=O)c1ccncc1)Cc1ccccc1]

NMR (CDCl$_3$) 0.9 (m, 3H), 1.2-1.4 (m, 4H), 2.3 (m, 2H), 2.5 (m, 2H), 2.8 (m, 2H), 3.5 (m, 2H), 6.8-7.5 (m, 9H)

TG 19 (3 µmol) 0.2 (30 µmol)

SOCE 21 (10 µmol) 0 (30 µmol) 27 (100 µmol)

IICR 18 (10 µmol) 84 (30 µmol) 51 (100 µmol)

Example 377

2-(N-butyl-N-benzyl)aminoethyl-2-furylketone 8888

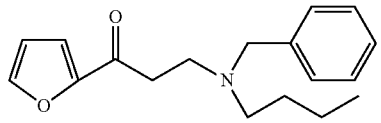 [SMILES: CCCCN(CCC(=O)c1ccco1)Cc1ccccc1]

NMR (CDCl$_3$) 0.9 (m, 3H), 1.2-1.4 (m, 4H), 2.5 (m, 2H), 2.9 (m, 2H), 3.6 (m, 2H), 3.83 (m, 2H), 7.0-7.5 (m, 8H)

TG 27 (3 µmol) 0.2 (30 µmol)

SOCE 21 (10 µmol) 0 (30 µmol) 27 (100 µmol)

IICR 22 (10 µmol) 20 (30 µmol) 36 (100 µmol)

Example 378

2-(N-butyl-N-benzyl)aminoethyl-2-naphthylketone 8889

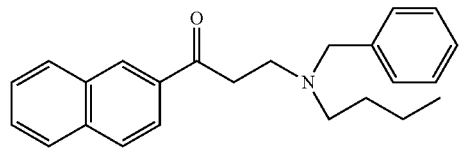 [SMILES: CCCCN(CCC(=O)c1ccc2ccccc2c1)Cc1ccccc1]

NMR (CDCl$_3$) 0.9 (m, 3H), 1.3-1.4 (m, 4H), 2.5 (m, 2H), 2.7 (m, 2H), 3.7 (m, 2H), 7.1-8.0 (m, 12H)

TG 93 (3 µmol) 7.6 (30 µmol)

SOCE 0 (10 µmol) 0 (30 µmol) 41 (100 µmol)

IICR 50 (10 µmol) 24 (30 µmol) 46 (100 µmol)

Example 379

2-(N-2-hydroxyethyl-N-benzyl)aminoethyl-5-iodo-2-thienylketone 8947

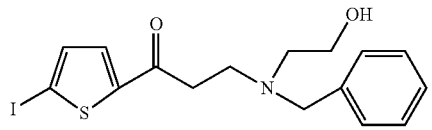 [SMILES: O=C(CCN(CCO)Cc1ccccc1)c1ccc(I)s1]

NMR (CDCl$_3$) 2.5 (m, 2H), 2.98 (m, 2H), 3.71 (m, 2H), 3.81 (m, 2H), 4.31 (m, 2H), 7.2-7.4 (m, 8H)

TG 81 (3 µmol) 71 (10 µmol) 56 (30 µmol)

SOCE 20 (10 µmol) 40 (30 µmol) 50 (100 µmol)

IICR 50 (10 µmol) 24 (30 µmol) 46 (100 µmol)

Example 380

N,N-bis(2-(3-thiophenoyl)ethyl)cystamine 8891

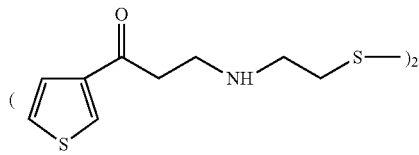

NMR (CDCl$_3$) 2.60 (m, 4H), 3.4 (m, 4H), 3.6-3.8 (m, 8H), 7.4-8.0 (m, 7H)
TG 25 (3 µmol) 4.2 (30 µmol)
SOCE 4 (10 µmol) 31 (30 µmol) 70 (100 µmol)
IICR 10 (10 µmol) 76 (30 µmol) 81 (100 µmol)

Example 381

N,N-bis(2-(2,5-dichloro-3-thiophenoyl)ethyl)cystamine 8892

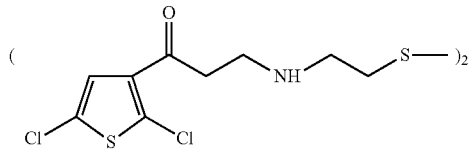

NMR (CDCl$_3$) 1.57 (m, 8H) 2.68 (m, 4H), 7.28 (s, 2H)
TG 60 (3 µmol) 27 (30 µmol)
SOCE 6 (10 µmol) 0 (30 µmol) 39 (100 µmol)
IICR 51 (10 µmol) 51 (30 µmol) 74 (100 µmol)

Example 382

2-N-benzylaminoethyl-5-bromo-2-thienylketone 8840

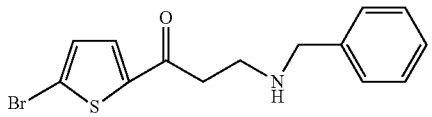 [SMILES: O=C(CCNCc1ccccc1)c1ccc(Br)s1]

NMR (CDCl$_3$) 2.5 (m, 2H), 3.4 (m, 2H), 3.7 (m, 2H), 7.0-7.4 (m, 7H)
TG 86 (3 µmol) 14.1 (30 µmol)
SOCE 0 (10 µmol) 10 (30 µmol) 20 (100 µmol)
IICR 0 (10 µmol) 10 (30 µmol) 50 (100 µmol)

Example 383

2-(N,N-dihexyl)aminoethyl-5-bromo-2-thienylketone 8900

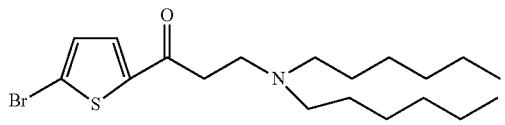 [SMILES: CCCCCCN(CCCCCC)CCC(=O)c1ccc(Br)s1]

NMR (CDCl$_3$) 0.87 (m, 6H), 1.22 (m, 2H), 3.7 (m, 2H), 7.0-7.4 (m, 7H)
TG 27 (3 µmol) 11.2 (10 µmol) 4.2 (30 µmol)
SOCE 25 (10 µmol) 16 (30 µmol) 46 (100 µmol)
IICR 0 (10 µmol) 5 (30 µmol) 0 (100 µmol)

Example 384

2-(N,N-diisobutyl)aminoethyl-5-bromo-2-thienylketone 8901

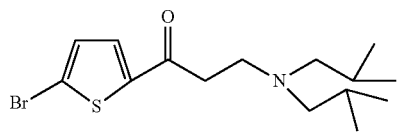 [SMILES: CC(C)CN(CCC(=O)c1ccc(Br)s1)CC(C)C]

NMR (CDCl$_3$) 2.5 (m, 2H), 3.4 (m, 2H), 3.7 (m, 2H), 7.0-7.4 (m, 7H)
TG 16 (3 µmol) 4.9 (10 µmol) 4.2 (30 µmol)
SOCE 0 (10 µmol) 10 (30 µmol) 100 (100 µmol)
IICR 0 (10 µmol) 35 (30 µmol) 70 (100 µmol)

Example 385

2-(N,N-dihexyl)aminoethyl-5-chloro-2-thienylketone 8902

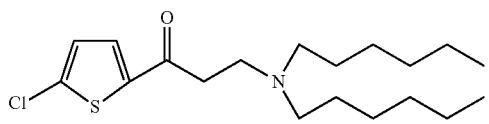 [SMILES: CCCCCCN(CCCCCC)CCC(=O)c1ccc(Cl)s1]

NMR (CDCl$_3$) 0.98 (m, 6H), 1.25 (m, 16H), 2.1-2.38 (m, 6H), 6.96 (s, 1H), 7.47 (s, 1H)
TG 13 (3 µmol) 6.1 (10 µmol) 6.3 (30 µmol)
SOCE 0 (10 µmol) 95 (30 µmol) 53 (100 µmol)
IICR 0 (10 µmol) 14 (30 µmol) 0 (100 µmol)

Example 386

N,N-bis(2-(5-bromo-2-thiophenoyl)ethyl)cystinemethylester 8904

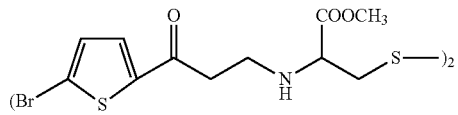

2-acetyl-5-bromothiophene (34.3 mg), cystinedimethylester (23.3 mg), paraformaldehyde (6.7 mg), and dioxane (0.2 mL) were heated for 30 minutes to 110° C.

NMR (CDCl$_3$) 2.02 (m, 2H), 2.51 (m, 4H), 2.93 (m, 4H), 3.15 (m, 4H), 3.4 (m, 2H), 3.79 (m, 6H), 7.1 (s, 2H), 7.4 (s, 2H).
TG 4.6 (3 µmol) 2.9 (10 µmol) 14 (30 µmol)
SOCE 20 (10 µmol) 40 (30 µmol) 50 (100 µmol)
IICR 44 (10 µmol) 72 (30 µmol) 77 (100 µmol)

Example 387

N,N-bis(2-(5-chloro-2-thiophenoyl)ethyl)cystine 8905

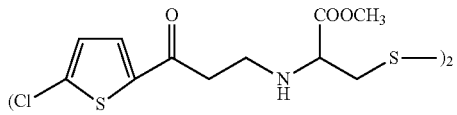

NMR (CDCl$_3$) 2.25 (m, 2H), 3.4 (m, 2H), 3.7 (m, 3H), 5.31 (m, 2H) 7.0-7.4 (m, 2H)
TG 4.6 (3 µmol) 11 (10 µmol) 18 (30 µmol)
SOCE 20 (10 µmol) 40 (30 µmol) 50 (100 µmol)
IICR 0 (10 µmol) 0 (30 µmol) 70 (100 µmol)

Example 388

N,N-bis(4-iodobenzoylethyl)cystamine 8906

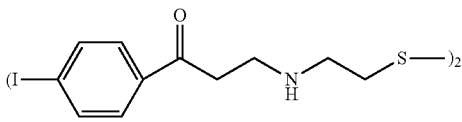

NMR (CDCl$_3$) 2.0 (m, 2H), 2.0 (m, 2H) 2.60 (m, 2H), 2.9 (m, 2H), 5.30-5.31 (m, 2H), 1 (m, 2H), 7.1-7.34 (m, 4H)
TG 14 (3 µmol) 10 (10 µmol) 13 (30 µmol)
SOCE 20 (10 µmol) 40 (30 µmol) 50 (100 µmol)
IICR 0 (10 µmol) 0 (30 µmol) 70 (100 µmol)

Example 389

N,N-bis(2-thiophenoylethyl)cystinemethylester 8908

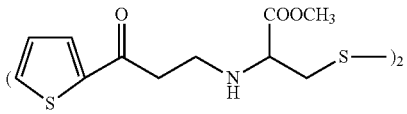

NMR (CDCl$_3$) 3.1 (m, 4H), 3.7 (m, 8H), 3.9 (m, 4H), 6.57 (m, 2H), 7.25 (m, 2H), 7.67 (m, 2H),
TG 9.7 (3 µmol) 2.7 (10 µmol) −3.8 (30 µmol)
SOCE 20 (10 µmol) 40 (30 µmol) 50 (100 µmol)
IICR 22 (10 µmol) 45 (30 µmol) 54 (100 µmol)

Example 390

2-(N-isopropyl-N-benzyl)aminoethyl-5-iodo-2-thienylketone 8946

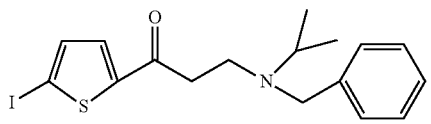 [SMILES: CC(C)N(CCC(=O)c1ccc(I)s1)Cc1ccccc1]

NMR (CDCl$_3$) 0.9-12 (m, 6H), 2.5 (m, 2H), 2.8 (m, 2H), 3.6 (m, 2H), 7.0-7.5 (m, 7H)

TG 16 (3 µmol) 4.6 (10 µmol) 1.6 (30 µmol)
SOCE 20 (10 µmol) 40 (30 µmol) 50 (100 µmol)
IICR 0 (10 µmol) 0 (30 µmol) 70 (100 µmol)

Example 391

N,N-bis(2-naphthoylethyl)cystinemethylester 8910

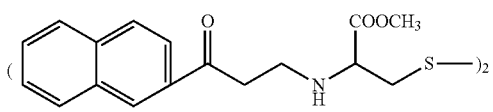 [SMILES: COC(=O)C(CSC)NCCC(=O)c1ccc2ccccc2c1]

NMR (CDCl$_3$) 2.74 (m, 2H), 3.71 (m, 2H), 3.81 (m, 2H), 7.59-8.4 (m, 7H),
TG 33 (3 µmol) 6.4 (10 µmol) 29 (30 µmol)
SOCE 20 (10 µmol) 40 (30 µmol) 50 (100 µmol)
IICR 6 (10 µmol) 37 (30 µmol) 41 (100 µmol)

Example 392

N,N-bis(2-(4-bromobenzoyl)ethyl)cystinemethylester 8911

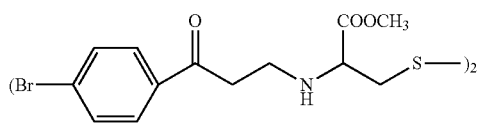

NMR (CDCl$_3$) 2.59 (m, 4H), 3.5 (m, 4H), 3.71 (m, 4H), 3.88 (m, 6H), 7.6 (m, 4H), 7.84 (m, 4H),
TG 25 (3 µmol) 3.7 (10 µmol) 2.3 (30 µmol)
SOCE 20 (10 µmol) 40 (30 µmol) 50 (100 µmol)
IICR 58 (10 µmol) 61 (30 µmol) 76 (100 µmol)

Example 393

N,N-bis(2-(4-pyridinoyl)ethyl)cystinemethylester 8912

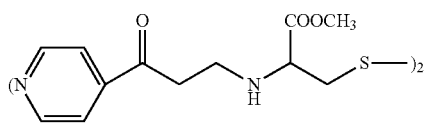

NMR (CDCl$_3$) 2.34 (m, 2H), 2.54 (m, 2H), 2.6 (m, 3H), 7.74 (m, 2H), 8.82 (m, 2H),
TG 54 (3 µmol) 16 (10 µmol) 3.5 (30 µmol)
SOCE 20 (10 µmol) 40 (30 µmol) 50 (100 µmol)
IICR 44 (10 µmol) 42 (30 µmol) 21 (100 µmol)

Example 394

N,N-bis(2-(benzothiophenoyl)ethyl)cystinemethyl-ester 8913

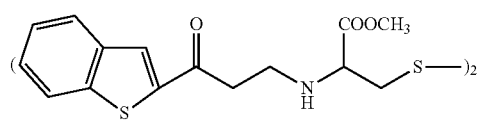 [SMILES: COC(=O)C(CSC)NCCC(=O)c1cc2ccccc2s1]

NMR (CDCl$_3$) 2.67 (m, 3H), 3.26 (m, 2H), 3.74 (m, 4H), 7.44 (m, 2H), 7.94 (m, 3H),
TG 94 (3 µmol) 82 (10 µmol) 60 (30 µmol)
SOCE 20 (10 µmol) 40 (30 µmol) 50 (100 µmol)
IICR 0 (10 µmol) 0 (30 µmol) 70 (100 µmol)

Example 395

2-diisopropylaminoethyl-5-bromo-2-thienylketone 8925

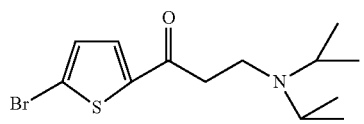 [SMILES: CC(C)N(CCC(=O)c1ccc(Br)s1)C(C)C]

NMR (CDCl$_3$) 0.88 (m, 9H), 2.5 (m, 2H), 3.7 (m, 2H), 7.11 (m, 1H), 7.27 (m, 1H),
TG 22 (3 µmol) 12 (10 µmol) 4.7 (30 µmol)
SOCE 20 (10 µmol) 40 (30 µmol) 50 (100 µmol)
IICR 14 (10 µmol) 67 (30 µmol) 83 (100 µmol)

Example 396

2-diisopropylaminoethyl-5-chloro-2-thienylketone 8926

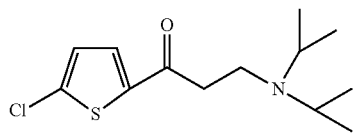 [SMILES: CC(C)N(CCC(=O)c1ccc(Cl)s1)C(C)C]

NMR (CDCl$_3$) 0.85-1.03 (m, 9H), 2.51 (m, 2H), 2.96 (m, 2H), 6.96 (m, 1H), 7.47 (m, 1H),
TG 41 (3 µmol) 18 (10 µmol) 6.7 (30 µmol)
SOCE 20 (10 µmol) 40 (30 µmol) 50 (100 µmol)
IICR 2 (10 µmol) 72 (30 µmol) 83 (100 µmol)

Example 397

2-diisopropylaminoethyl-4-pyridylketone 8927

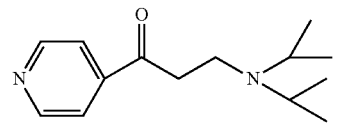 [SMILES: CC(C)N(CCC(=O)c1ccncc1)C(C)C]

NMR (CDCl$_3$) 1.03 (m, 12H), 3.7 (m, 2H), 3.9 (m, 2H), 7.74 (m, 2H), 8.8 (m, 2H),
TG 103 (3 µmol) 96 (10 µmol) 75 (30 µmol)
SOCE 20 (10 µmol) 40 (30 µmol) 50 (100 µmol)
IICR 0 (10 µmol) 0 (30 µmol) 10 (100 µmol)

Example 398

N,N-bis(4-cyanobenzoylethyl)cystamine 8928

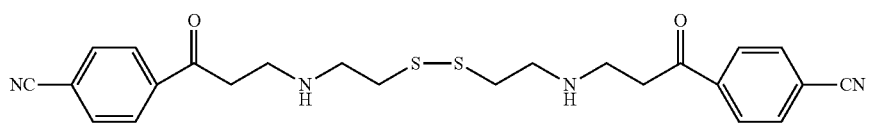 [SMILES: N#Cc1ccc(C(=O)CCNCCSSCCNCCC(=O)c2ccc(C#N)cc2)cc1]

NMR (CDCl$_3$) 1.56 (m, 4H), 2.65 (m, 4H), 3.7 (m, 4H), 7.78 (s, 4H), 8.03 (s, 4H),
TG 33 (3 µmol) 12 (10 µmol) 2.6 (30 µmol)
SOCE 20 (10 µmol) 40 (30 µmol) 50 (100 µmol)
IICR 1 (10 µmol) 44 (30 µmol) 80 (100 µmol)

Example 399

N,N-bis(4-cyanobenzoylethyl)cystinemethylester 8929

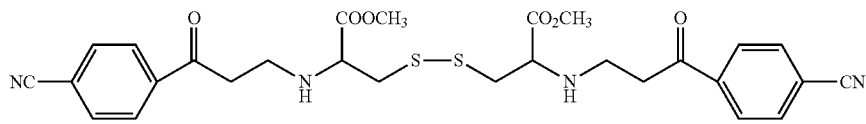 [SMILES: COC(=O)C(CSSCC(NCCC(=O)c1ccc(C#N)cc1)C(=O)OC)NCCC(=O)c1ccc(C#N)cc1]

NMR (CDCl₃) 2.64 (m, 4H), 3.69 (m, 8H), 3.75 (m, 8H), 7.27 (m, 4H), 8.03 (m, 4H),
TG 36 (3 µmol) 13 (10 µmol) 2.9 (30 µmol)
SOCE 20 (10 µmol) 40 (30 µmol) 50 (100 µmol)
IICR 0 (10 µmol) 0 (30 µmol) 70 (100 µmol)

Example 400

N,N-bis(2-thiazolylethyl)cystinemethylester 8930

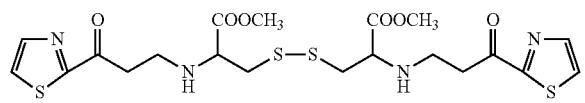 [SMILES: COC(=O)C(CSSCC(NCCC(=O)c1nccs1)C(=O)OC)NCCC(=O)c1nccs1]

NMR (CDCl₃) 2.73 (m, 4H), 3.59 (m, 4H), 3.70 (m, 6H), 3.9 (m, 4H), 7.68 (m, 2H), 8.01 (m, 2H),
TG 73 (3 µmol) 52 (10 µmol) 25 (30 µmol)
SOCE 20 (10 µmol) 40 (30 µmol) 50 (100 µmol)
IICR 19 (10 µmol) 0 (30 µmol) 13 (100 µmol)

Example 401

N,N-bis(2-furoylethyl)cystinemethylester 8931

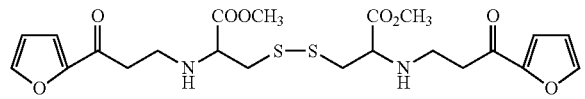 [SMILES: COC(=O)C(CSSCC(NCCC(=O)c1ccco1)C(=O)OC)NCCC(=O)c1ccco1]

NMR (CDCl₃) 2.46 (m, 4H), 3.3 (m, 4H), 3.7 (m, 14H), 6.53 (m, 2H), 7.26 (m, 2H), 7.57 (m, 2H),
TG 17 (3 µmol) 7.9 (10 µmol) 3.7 (30 µmol)
SOCE 20 (10 µmol) 40 (30 µmol) 50 (100 µmol)
IICR 31 (10 µmol) 1 (30 µmol) 57 (100 µmol)

Example 402

N,N-bis(2-pyrazinoylethyl)cystinemethylester 8933

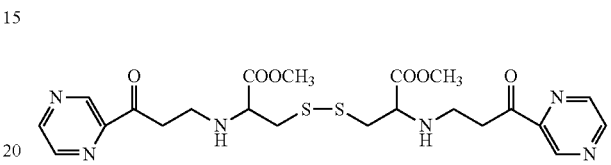

NMR (CDCl₃) 2.73 (m, 4H), 3.35 (m, 4H), 3.46 (m, 4H), 7.26 (m, 2H), 8.65 (m, 2H), 8.76 (m, 2H),
TG 67 (3 µmol) 34 (10 µmol) 10 (30 µmol)
SOCE 20 (10 µmol) 40 (30 µmol) 50 (100 µmol)
IICR 39 (10 µmol) 12 (30 µmol) 28 (100 µmol)

Example 403

N,N-bis(2-(5-methyl-2-thiophenoyl)ethyl)cystinem-ethylester 8932

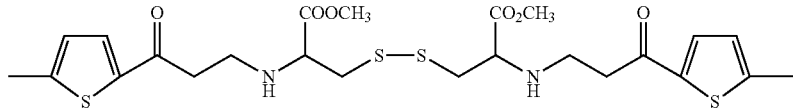

NMR (CDCl₃) 2.54 (m, 4H), 2.67 (m, 4H), 3.71 (m, 6H), 3.85 (m, 4H), 6.94 (m, 2H), 7.52 (m, 2H),
TG 17 (3 µmol) 4.4 (10 µmol) 2 (30 µmol)
SOCE 20 (10 µmol) 40 (30 µmol) 50 (100 µmol)
IICR 57 (10 µmol) 17 (30 µmol) 83 (100 µmol)

Example 404

N,N-bis(2-fluorenylethyl)cystinemethylester 8936

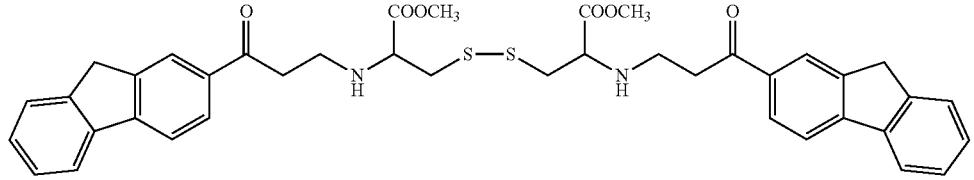 [SMILES: COC(=O)C(CSSCC(NCCC(=O)c1ccc2c(c1)Cc1ccccc1-2)C(=O)OC)NCCC(=O)c1ccc2c(c1)Cc1ccccc1-2]

NMR (CDCl$_3$) 2.67 (m, 4H), 3.71 (m, 6H), 3.80 (m, 4H), 3.97 (m, 8H), 7.4-8.05 (m, 16H)

TG 60 (3 μmol) 16 (10 μmol) 0.3 (30 μmol)

SOCE 20 (10 μmol) 40 (30 μmol) 50 (100 μmol)

IICR 54 (10 μmol) 84 (30 μmol) 94 (100 μmol)

Example 405

2-(N-t-butyl-N-benzyl)aminoethyl-5-iodo-2-thienylketone 8937

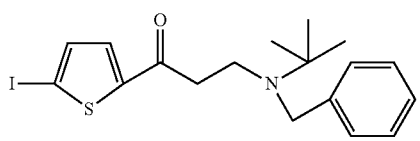 [SMILES: CC(C)(C)N(CCC(=O)c1ccc(I)s1)Cc1ccccc1]

NMR (CDCl$_3$) 1.17 (m, 9H), 2.53 (m, 2H), 2.96 (m, 2H), 3.71 (m, 2H), 7.1-7.5 (m, 7H)

TG 2.6 (3 μmol) 0.8 (10 μmol) −3.3 (30 μmol)

SOCE 20 (10 μmol) 40 (30 μmol) 50 (100 μmol)

IICR 78 (10 μmol) 73 (30 μmol) 35 (100 μmol)

Example 406

N,N-bis(5-iodo-2-thiophenoylethyl)cystinemethylester 8938

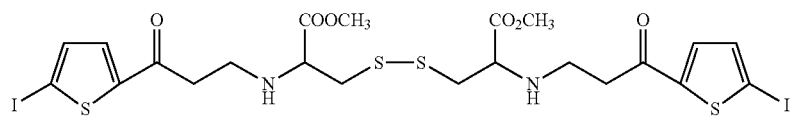 [SMILES: COC(=O)C(CSSCC(NCCC(=O)c1ccc(I)s1)C(=O)OC)NCCC(=O)c1ccc(I)s1]

NMR (CDCl$_3$) 2.52 (m, 8H), 3.71 (m, 6H), 3.9 (m, 4H), 7.3 (m, 4H)

TG 35 (3 μmol) 14 (10 μmol) 7.1 (30 μmol)

SOCE 20 (10 μmol) 40 (30 μmol) 50 (100 μmol)

IICR 49 (10 μmol) 43 (30 μmol) 62 (100 μmol)

Example 407

2-(N-t-butyl-N-benzyl)aminoethyl-3-bromo-2-thienylketone 8939

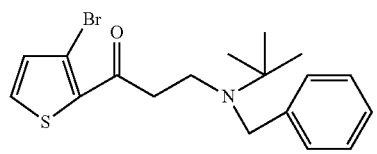 [SMILES: CC(C)(C)N(CCC(=O)c1sccc1Br)Cc1ccccc1]

NMR (CDCl$_3$) 1.17 (s, 9H), 2.93 (m, 2H), 3.0 (m, 2H), 3.73 (m, 2H), 6.9-7.5 (m, 7H)

TG 9.4 (3 μmol) 2.5 (10 μmol) 2.1 (30 μmol)

SOCE 20 (10 μmol) 40 (30 μmol) 50 (100 μmol)

IICR 89 (10 μmol) 83 (30 μmol) 77 (100 μmol)

Example 408

2-(N-t-butyl-N-benzyl)aminoethyl-3-bromo-2-pyridylketone 8940

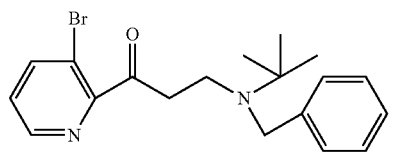 [SMILES: CC(C)(C)N(CCC(=O)c1ncccc1Br)Cc1ccccc1]

NMR (CDCl$_3$) 1.1 (m, 9H), 3.0 (m, 2H), 3.1 (m, 2H), 3.75 (m, 2H), 7.0-8.1 (m, 8H)

TG 2.8 (3 μmol) 4.1 (10 μmol) 3.3 (30 μmol)

SOCE 20 (10 μmol) 40 (30 μmol) 50 (100 μmol)

IICR 76 (10 μmol) 83 (30 μmol) 77 (100 μmol)

Example 409

N,N-bis(2-(5-bromo-2-thiophenoyl)ethyl)cystinemethylester 8941

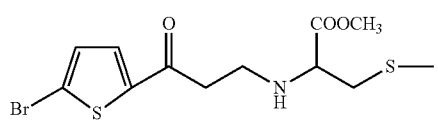 [SMILES: COC(=O)C(CSC)NCCC(=O)c1ccc(Br)s1]

NMR (CDCl$_3$) 2.15 (m, 2H), 2.5 (m, 3H), 2.67 (m, 2H), 2.8 (m, 2H), 3.6 (m, 2H), 3.83 (m, 3H), 7.0-7.5 (m, 2H)

TG 9.3 (3 μmol) 6.1 (10 μmol) 7.9 (30 μmol)

SOCE 20 (10 μmol) 40 (30 μmol) 50 (100 μmol)

IICR 26 (10 μmol) 76 (30 μmol) 81 (100 μmol)

Example 410

N,N-bis-(2-(5-iodo-2-thiophenoyl)ethyl)cystamine
8942

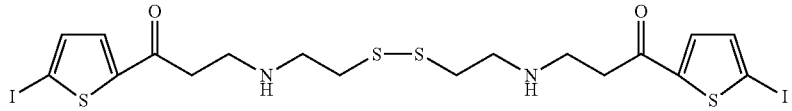 [SMILES: O=C(CCNCCSSCCNCCC(=O)c1ccc(I)s1)c1ccc(I)s1]

NMR (CDCl$_3$) 2.5 (m, 4H), 3.5 (m, 4H), 3.6 (m, 2H), 7.25 (m, 2H)
TG 11 (3 µmol) 5.6 (10 µmol) 3.3 (30 µmol)
SOCE 20 (10 µmol) 40 (30 µmol) 50 (100 µmol)
IICR 59 (10 µmol) 65 (30 µmol) 88 (100 µmol)

Example 411

2-(N,N-diisobutyl)aminoethyl-5-iodo-2-thienylketone 8943

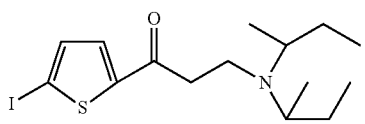 [SMILES: CCC(C)N(CCC(=O)c1ccc(I)s1)C(C)CC]

NMR (CDCl$_3$) 0.9-1.4 (m, 16H), 2.55 (m, 2H), 2.8 (m, 2H), 2.9 (m, 2H), 7.2-7.4 (m, 2H)
TG 3.9 (3 µmol) 5.6 (10 µmol) −4.4 (30 µmol)
SOCE 20 (10 µmol) 40 (30 µmol) 50 (100 µmol)
IICR 76 (10 µmol) 80 (30 µmol) 82 (100 µmol)

Example 412

2-(N,N-isobutyl)aminoethyl-6-bromo-2-pyridylketone 8944

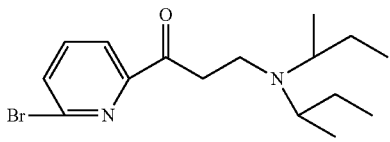 [SMILES: CCC(C)N(CCC(=O)c1cccc(Br)n1)C(C)CC]

NMR (CDCl$_3$) 0.9-1.0 (m, 16H), 2.2-2.5 (m, 4H), 7.6-7.9 (m, 3H)
TG 16 (3 µmol) 8.4 (10 µmol) 2.7 (30 µmol)
SOCE 20 (10 µmol) 40 (30 µmol) 50 (100 µmol)
IICR 44 (10 µmol) 58 (30 µmol) 79 (100 µmol)

Example 413

2-(N,N-isobutyl)aminoethyl-3-bromo-2-thienylketone 8945

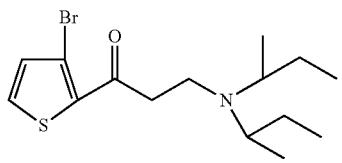 [SMILES: CCC(C)N(CCC(=O)c1sccc1Br)C(C)CC]

NMR (CDCl$_3$) 0.6-1.2 (m, 16H), 2.69 (m, 2H), 3.08 (m, 2H), 4.22 (m, 2H), 7.1-7.5 (m, 2H)
TG 24 (3 µmol) 11 (10 µmol) 13 (30 µmol)
SOCE 20 (10 µmol) 40 (30 µmol) 50 (100 µmol)
IICR 48 (10 µmol) 81 (30 µmol) 78 (100 µmol)

INDUSTRIAL APPLICABILITY

The aforementioned compounds of the present invention have transglutaminase-inhibiting activity or protein-crosslinking-inhibiting activity and further have intracellular calcium modulatory activity. Therefore, the compounds can be used for prevention or treatment of protein-crosslinking causative diseases and diseases associated with an increase in intracellular calcium concentration.

All publications, patents, and patent applications cited herein are incorporated herein by reference in their entirety.

The invention claimed is:

1. A compound represented by the following Formula (3):

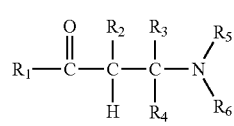

wherein:
$R_1$ is pyridyl, which is optionally substituted with C1-C4 alkyl or halogen;
$R_2$, $R_3$, and $R_4$ are hydrogen atoms;
$R_5$ is benzyl; and
$R_6$ is hydrogen, C1-C4 alkyl, or hydroxyl C1-C4 alkyl.

2. The compound according to claim 1, wherein the compound is selected from the group consisting of:

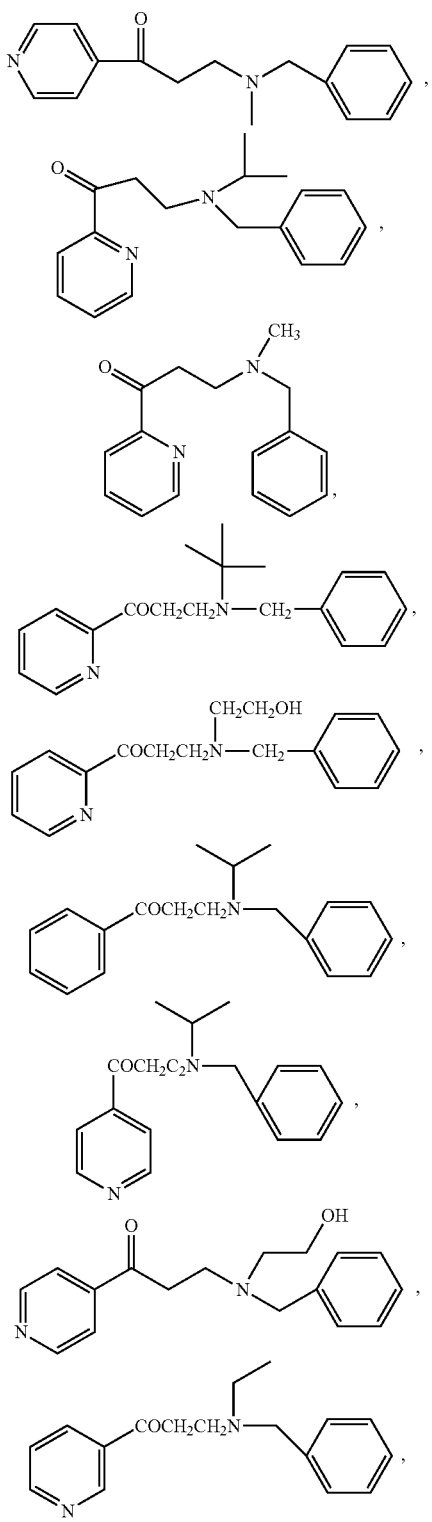
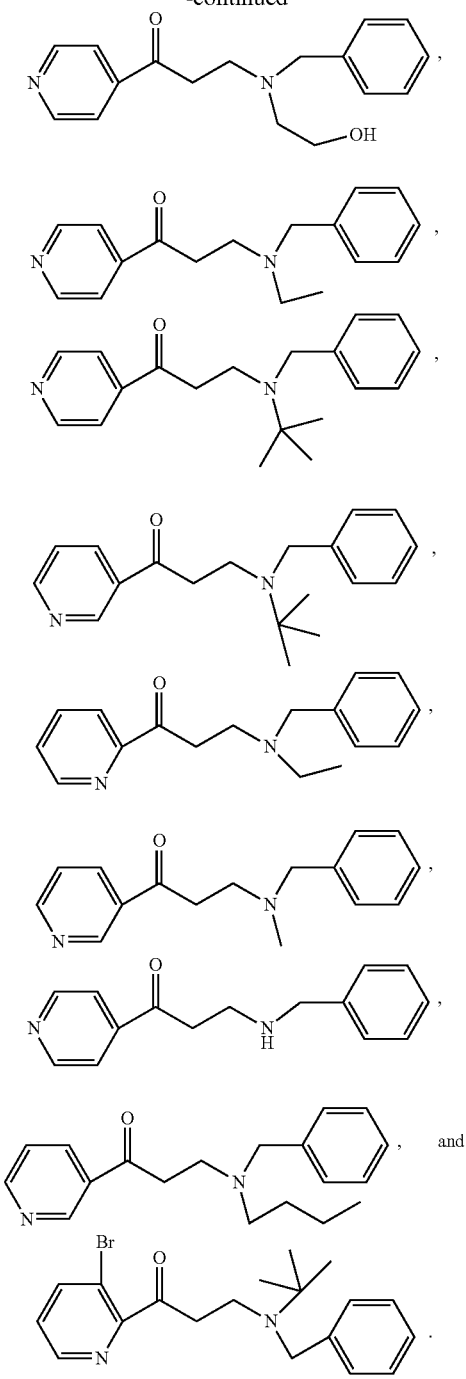
-continued
3. A pharmaceutical composition, comprising at least one of the compounds of claim 1 and a pharmaceutically acceptable carrier.
* * * * *

UNITED STATES PATENT AND TRADEMARK OFFICE
CERTIFICATE OF CORRECTION

PATENT NO.        : 8,937,091 B2                                    Page 1 of 1
APPLICATION NO.   : 13/508247
DATED             : January 20, 2015
INVENTOR(S)       : Katsuhiko Mikoshiba et al.

It is certified that error appears in the above-identified patent and that said Letters Patent is hereby corrected as shown below:

In the Claims
Col. 177, claim 2, seventh formula at lines 40-45,

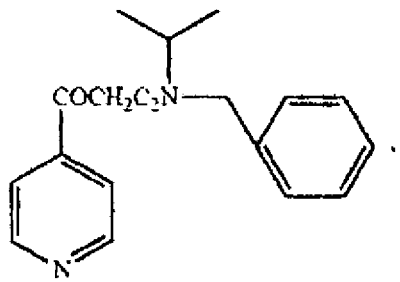

should be:

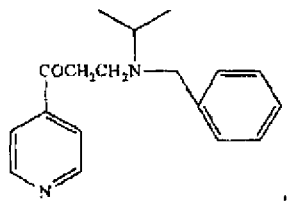

Signed and Sealed this
Fourteenth Day of July, 2015

Michelle K. Lee
*Director of the United States Patent and Trademark Office*